US012163142B2

(12) United States Patent
Van Rooijen et al.

(10) Patent No.: US 12,163,142 B2
(45) Date of Patent: Dec. 10, 2024

(54) METHODS FOR MANUFACTURING PLANT MESSENGER PACKS

(71) Applicant: Flagship Pioneering Innovations VI, LLC, Cambridge, MA (US)

(72) Inventors: Maria Helena Christine Van Rooijen, Cambridge, MA (US); Hok Hei Tam, Newton, MA (US); Barry Andrew Martin, Boston, MA (US); Daniel Garcia Cabanillas, Boston, MA (US); Simon Schwizer, Boston, MA (US); Nataliya Vladimirovna Nukolova, Cambridge, MA (US); Yajie Niu, Lexington, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 642 days.

(21) Appl. No.: 17/270,121

(22) PCT Filed: Aug. 24, 2019

(86) PCT No.: PCT/US2019/048047
§ 371 (c)(1),
(2) Date: Feb. 22, 2021

(87) PCT Pub. No.: WO2020/041784
PCT Pub. Date: Feb. 27, 2020

(65) Prior Publication Data

US 2021/0180081 A1 Jun. 17, 2021

Related U.S. Application Data

(60) Provisional application No. 62/722,613, filed on Aug. 24, 2018.

(51) Int. Cl.
*C12N 15/82* (2006.01)
*A01G 31/02* (2006.01)

(52) U.S. Cl.
CPC ......... *C12N 15/8279* (2013.01); *A01G 31/02* (2013.01)

(58) Field of Classification Search
None
See application file for complete search history.

(56) References Cited

U.S. PATENT DOCUMENTS

| | | | |
|---|---|---|---|
| 4,241,046 A | 12/1980 | Papahadjopoulos et al. | |
| 4,666,747 A | 5/1987 | Quinn | |
| 9,790,490 B2 | 10/2017 | Zhang et al. | |
| 10,799,457 B2 | 10/2020 | Zhang | |
| 11,827,897 B2 * | 11/2023 | Van Rooijen | A01G 31/02 |
| 2005/0198706 A1 | 9/2005 | McCutchen et al. | |
| 2012/0283094 A1 | 11/2012 | Meng et al. | |
| 2014/0044778 A1 | 2/2014 | Kogure et al. | |
| 2014/0194288 A1 | 7/2014 | Grobler | |
| 2014/0308212 A1 | 10/2014 | Zhang | |
| 2016/0045448 A1 | 2/2016 | Zhang | |
| 2016/0208243 A1 | 7/2016 | Zhang et al. | |
| 2016/0270400 A1 | 9/2016 | Watkin | |
| 2017/0367349 A1 | 12/2017 | Gruver et al. | |
| 2018/0271773 A1 | 9/2018 | Lee et al. | |
| 2018/0362974 A1 | 12/2018 | Zhang | |
| 2019/0098895 A1 | 4/2019 | Schroeder et al. | |
| 2019/0380962 A1 | 12/2019 | Zhang | |
| 2021/0196632 A1 | 7/2021 | Van Rooijen et al. | |
| 2021/0219550 A1 | 7/2021 | Van Rooijen et al. | |
| 2021/0228736 A1 | 7/2021 | Van Rooijen et al. | |
| 2021/0254085 A1 | 8/2021 | Rooijen et al. | |
| 2022/0064661 A1 | 3/2022 | Van Rooijen et al. | |
| 2022/0152139 A1 | 5/2022 | Van Rooijen et al. | |
| 2022/0192201 A1 | 6/2022 | Van Rooijen et al. | |
| 2022/0273565 A1 | 9/2022 | Van Rooijen et al. | |
| 2022/0288150 A1 | 9/2022 | Van Rooijen et al. | |
| 2022/0304930 A1 | 9/2022 | Van Rooijen et al. | |
| 2023/0248649 A1 | 8/2023 | Zhang | |
| 2023/0355525 A1 | 11/2023 | Zhang | |

FOREIGN PATENT DOCUMENTS

| | | |
|---|---|---|
| CA | 2999340 A1 | 5/2017 |
| CN | 1944651 A | 4/2007 |
| CN | 107893050 A | 4/2018 |
| CN | 108271340 A | 7/2018 |
| ES | 2375361 T3 | 2/2012 |
| JP | 2002-535268 A | 10/2002 |
| JP | 2014-185090 A | 10/2014 |
| JP | 2017-526388 A | 9/2017 |
| JP | 2018-518183 A | 7/2018 |
| JP | 2018-531932 A | 11/2018 |
| KR | 100842420 B1 | 7/2008 |
| TW | 201639453 A | 11/2016 |
| WO | WO-2000/042990 A1 | 7/2000 |
| WO | WO-2008100016 A1 | 8/2008 |

(Continued)

OTHER PUBLICATIONS

"Doxorubicin," Wikipedia, <https://en.wikipedia.org/w/index.php?title=Doxorubicin&oldid=801276513>, retrieved on Aug. 28, 2019 (10 pages).

"Pseudomonas aeruginosa," Wikipedia, <https://en.wikipedia.org/w/index.php?title=Pseudomonas_aeruginosa&oldid=821925775>, retrieved Oct. 7, 2019 (15 pages).

Cai et al., "Plants send small RNAs in extracellular vesicles to fungal pathogen to silence virulence genes," Science. 360(6393):1126-1129 (May 2018) (5 pages).

Dettenmaier, "Measuring and Modeling of Plant Root Uptake of Organic Chemicals," Utah State University. All Graduate Theses and Dissertations. 18 (2008) (204 pages).

Didiot et al., "Exosome-mediated Delivery of Hydrophobically Modified siRNA for Huntingtin mRNA Silencing," Mol Ther. 24(10):1836-1847 (2016).

(Continued)

*Primary Examiner* — Medina A Ibrahim
(74) *Attorney, Agent, or Firm* — Clark & Elbing LLP

(57) ABSTRACT

Disclosed herein are methods, and related bioreactors, for manufacturing plant messenger packs (PMPs), which can be formulated for use in a variety of agricultural and therapeutic methods.

12 Claims, 13 Drawing Sheets

Specification includes a Sequence Listing.

(56) References Cited

FOREIGN PATENT DOCUMENTS

| | | |
|---|---|---|
| WO | WO-2011097480 A1 | 8/2011 |
| WO | WO-2013/070324 A1 | 5/2013 |
| WO | WO-2015/039983 A1 | 3/2015 |
| WO | WO-2015/048566 A1 | 4/2015 |
| WO | WO-2016/033695 A1 | 3/2016 |
| WO | WO-2016/185564 A1 | 11/2016 |
| WO | WO-2017/052267 A1 | 3/2017 |
| WO | WO-2017/153993 A1 | 9/2017 |
| WO | WO-2018/096057 A1 | 5/2018 |
| WO | WO-2018/107061 A1 | 6/2018 |
| WO | WO-2019/222379 A1 | 11/2019 |
| WO | WO-2019/222390 A1 | 11/2019 |
| WO | WO-2020/041782 A1 | 2/2020 |
| WO | WO-2020/041783 A1 | 2/2020 |
| WO | WO-2020214542 A1 | 10/2020 |
| WO | WO-2020219927 A1 | 10/2020 |
| WO | WO-2021041301 A1 | 3/2021 |
| WO | WO-2022266096 A1 | 12/2022 |

OTHER PUBLICATIONS

García-Manrique et al., "Therapeutic biomaterials based on extracellular vesicles: classification of bio-engineering and mimetic preparation routes," J Extracell Vesicles. 7(1):1422676 (Jan. 17, 2018) (19 pages).
Israeli Office Action for Application No. 280848, dated Jul. 9, 2023 (4 pages).
Luan et al., "Engineering Exosomes as Refined Biological Nanoplatforms for Drug Delivery," Acta Pharmacol Sin. 38(6):754-63 (2017).
Nakase et al., "Combined treatment with a pH-sensitive fusogenic peptide and cationic lipids achieves enhanced cytosolic delivery of exosomes," Sci Rep. 5:10112 (2015) (13 pages).
Notice of Allowance for U.S. Appl. No. 17/470,025, date mailed Jul. 21, 2023 (8 pages).
Notice of Reasons for Rejection for Japanese Patent Application No. 2021-509170, dated Oct. 3, 2023 (8 pages).
Rutter et al. "Extracellular vesicles as key mediators of plant-microbe interactions." Current opinion in plant biology, vol. 44, (Aug. 2018) (14 pages).
Samuel et al., "Extracellular Vesicles Including Exosomes in Cross Kingdom Regulation: A Viewpoint From Plant-Fungal Interactions," Front Plant Sci. 6:766 (2015) (5 pages).
Shtam et al., "Exosomes are natural carriers of exogenous siRNA to human cells in vitro," Cell Commun Signal. 11:88 (2013) (10 pages).
Wallheimer, "*E. coli* thrives near plant roots, can contaminate young produce crops," <http://www.purdue.edu/newsroom/research/2020/101103TurcoEcoli.html>, retrieved on Oct. 7, 2019 (2 pages).
Yu et al., "Characterization of three different types of extracellular vesicles and their impact on bacterial growth," manuscript accepted Aug. 14, 2018, published in final edited form as: Food Chem. 272:372-378 (Jan. 30, 2019) (31 pages).
Zhang et al., "Exosome-Mediated Small RNA Delivery: A Novel Therapeutic Approach for Inflammatory Lung Responses," Mol Ther. 26(9):2119-2130 (Sep. 2018).
Rutter et al., "Isolation and Quantification of Plant Extracellular Vesicles," Bio Protoc. 7(17):e2533 (Sep. 2017) (13 pages).
Rutter et al., "Extracellular Vesicles Isolated from the Leaf Apoplast Carry Stress-Response Proteins," Plant Physiol. 173(1):728-741 (2017).
International Search Report and Written Opinion for PCT/US2019/048047, mailed Nov. 8, 2019 (14 pages).
International Preliminary Report on Patentability for International application No. PCT/US2019/048047, issued Mar. 2, 2021 (7 pages).
Tripathi et al., "An overview on manufactured nanoparticles in plants: Uptake, translocation, accumulation and phytotoxicity," Plant Physiol Biochem. 110:2-12 (2017).

McCrady et al., "The Transport and Affinty of Substituted Benzenes in Soybean Stems," J Exp Bot. 38(196):1875-1890 (1987) (17 pages).
Hsu et al., "Study of root uptake and xylem translocation of cinmethylin and related compounds in detopped soybean roots using a pressure chamber technique," Plant Physiol. 93(4):1573-8 (1990).
Dettenmaier, "Measuring and Modeling of Plant Root Uptake of Organic Chemicals," Utah State University. All Graduate Theses and Dissertations. 18 (2018) (204 pages).
Schriever et al., "Lipophilicity matters—A new look at experimental plant uptake data from literature," Sci Total Environ. 713:136667 (2020) (10 pages).
Wang et al., "Systemic Uptake of Fluorescent Tracers by Soybean (*Glycine max* (L.) Merr.) Seed and Seedlings," Agriculture. 10:248 (2020) (13 pages).
Halperin et al., "Ultrastructural Changes during Growth and Embryogenesis in Carrot Cell Cultures," J Ultrastructure Research. 18(3):428-443 (1967).
Alatorre-Cobos et al., "An improved, low-cost, hydroponic system for growing Arabidopsis and other plant species under aseptic conditions," BMC Plant Biol. 14:69 (2014) (13 pages).
Razaji et al., "The effects of seed priming by ascorbic acid on some morphological and biochemical aspects of rapeseed (*Brassica napus* L.) under drought stress condition," Int J Biosci. 4(1):432-442 (2014).
Cui et al., "Plant extracellular vesicles," 257(1):3-12 (2020).
Théry et al., "Isolation and Characterization of Exosomes from Cell Culture Supernatants and Biological Fluids," Current Protocols in Cell Biology. 3.22.1-3.22.29 (2006) (29 pages).
Sanzari et al., "Nanotechnology in Plant Science: To Make a Long Story Short," Front Bioeng Biotechnol. 7:120 (May 2019) (12 pages).
Woith et al., "Plant Extracellular Vesicles and Nanovesicles: Focus on Secondary Metabolites, Proteins and Lipids with Perspectives on Their Potential and Sources," Int J Mol Sci. 22(7):3719 (2021) (20 pages).
Chen et al., "Systemicity of chlorantraniliprole in velvetleaf (Abutilon theophrasti)," J AOAC Int. 96(1):1-6 (2013).
Mozafari, "Chapter 2. Nanoliposomes: Preparation and Analysis,". Weissig (ed.), Liposomes, Methods in Molecular Biology, vol. 605, pp. 29-50 (2010).
Lowry et al., "Opportunities and challenges for nanotechnology in the agri-tech revolution," Nat Nanotechnol. 14(6):517-522 (Jun. 2019).
Kah et al., "Nano-enabled strategies to enhance crop nutrition and protection," Nat Nanotechnol. 14(6):532-540 (Jun. 2019).
Alfieri et al., "Plant-Derived Nano and Microvesicles for Human Health and Therapeutic Potential in Nanomedicine," Pharmaceutics. 13(4):498 (2021) (21 pages).
Di Gioia et al., "Biological properties and therapeutic effects of plant-derived nanovesicles," Open Med (Wars). 15(1):1096-1122 (2020).
De Palma et al., "Plant Roots Release Small Extracellular Vesicles with Antifungal Activity," Plants (Basel). 9(12):1777 (14 pages) (2020).
Nair et al., "Nanoparticulate material delivery to plants," Plant Sci. 179:154-163 (2010).
Karny et al., "Therapeutic nanoparticles penetrate leaves and deliver nutrients to agricultural crops," 8(1):7589 (May 2018) (10 pages).
Ma et al., "Interactions between engineered nanoparticles (ENPs) and plants: phytotoxicity, uptake and accumulation," Sci Total Environ. 408(16):3053-3061 (2010).
Regente et al., "Vesicular fractions of sunflower apoplastic fluids are associated with potential exosome marker proteins," FEBS Lett. 583(20):3363-6 (2009).
Holden et al., "$Cu^{2+}$ Reduction by Tomato Root Plasma Membrane Vesicles," Plant Physiol. 108(3):1093-1098 (1995).
Regente et al., "Plant extracellular vesicles are incorporated by a fungal pathogen and inhibit its growth," J Exp Bot. 68(20):5485-5495 (2017).

(56) References Cited

OTHER PUBLICATIONS

Buckhout et al., "Iron-Stress Induced Redox Activity in Tomato (Lycopersicum esculentum Mill.) Is Localized on the Plasma Membrane," Plant Physiol. 90(1):151-6 (1989).

Holden et al., "$Fe^{3+}$-Chelate Reductase Activity of Plasma Membranes Isolated from Tomato (Lycopersicon esculentum Mill.) Roots : Comparison of Enzymes from Fe-Deficient and Fe-Sufficient Roots," Plant Physiol. 97(2):537-44 (1991).

Amended claim set filed Jan. 18, 2024 in U.S. Appl. No. 18/382,237 (6 pages).

\* cited by examiner

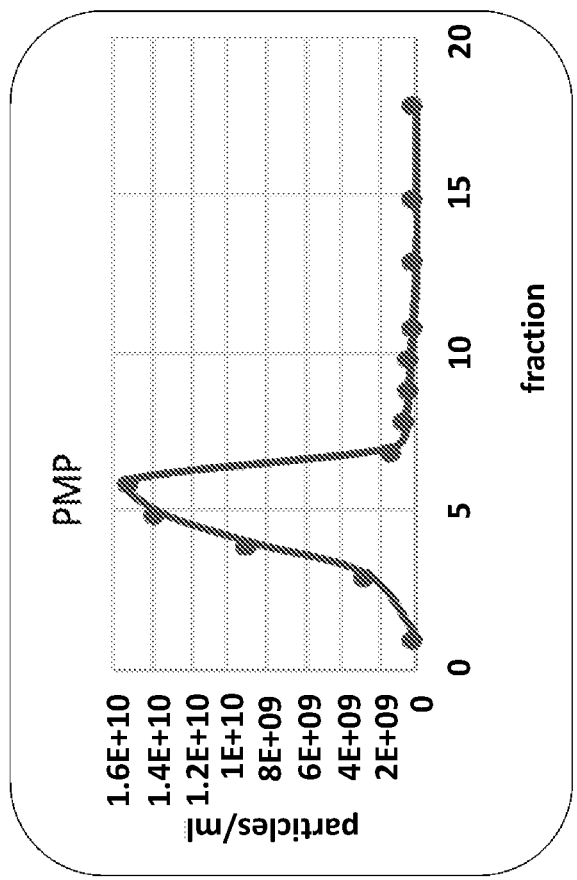

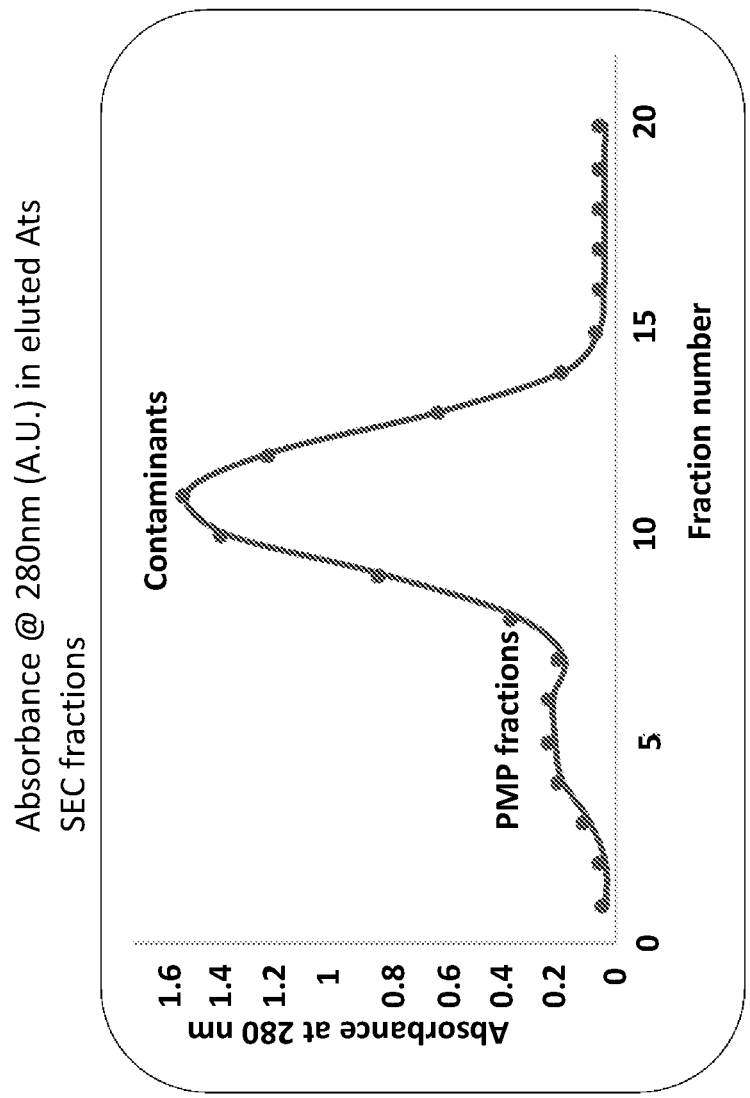

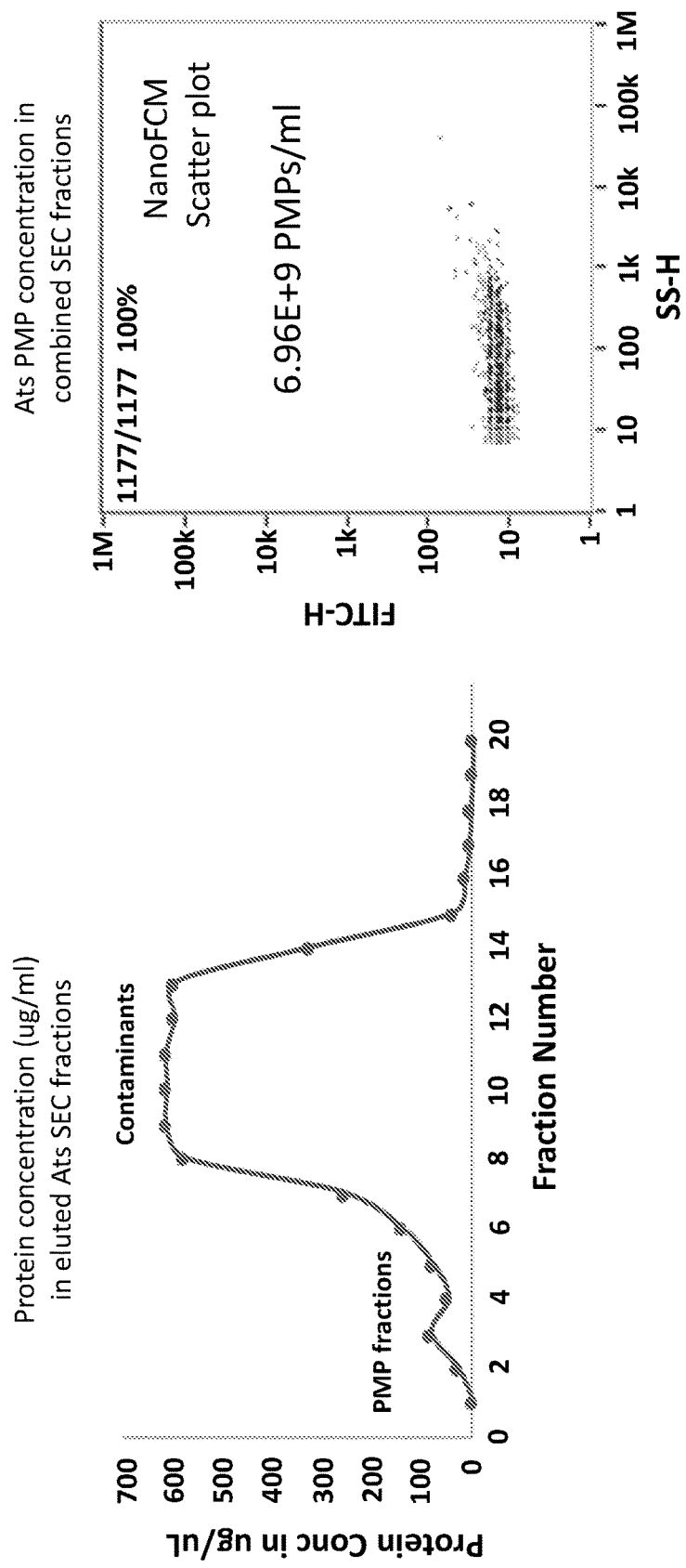

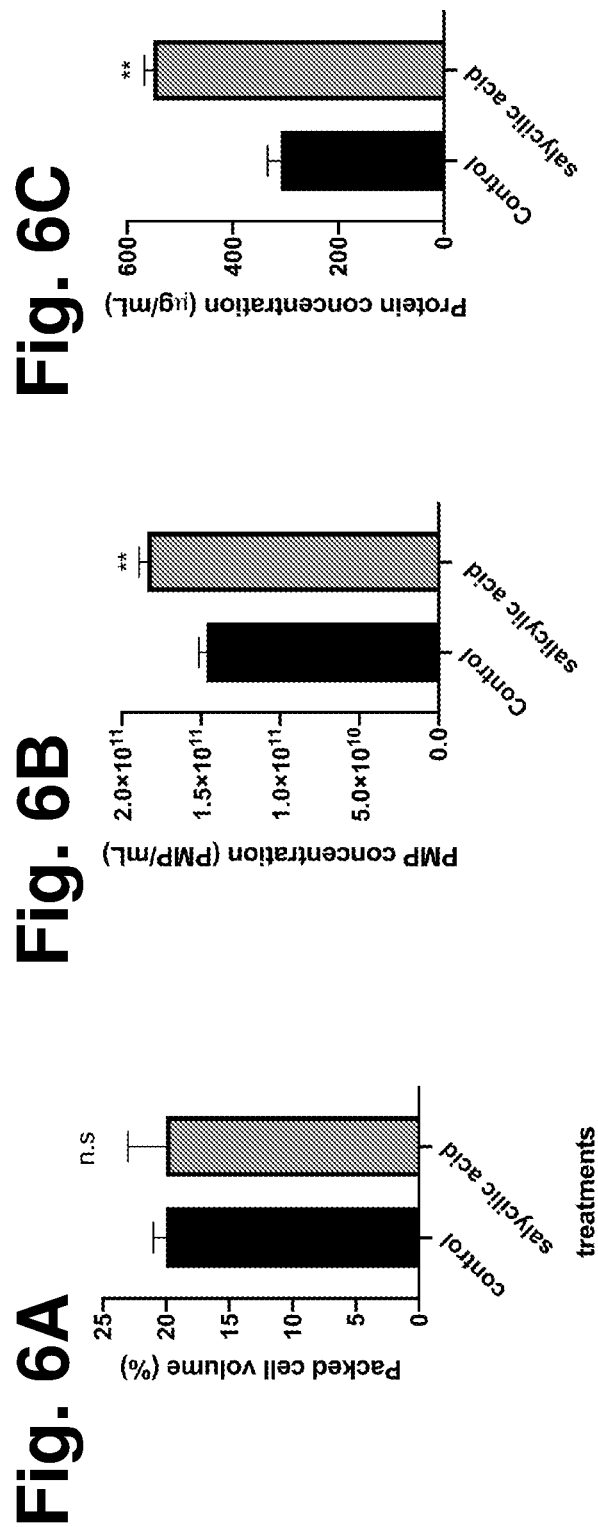

```
                        SEQUENCE LISTING

<160> NUMBER OF SEQ ID NOS: 13

<210> SEQ ID NO 1
<211> LENGTH: 3
<212> TYPE: DNA
<213> ORGANISM: Streptococcus pyogenes
<220> FEATURE:
<221> NAME/KEY: misc_feature
<222> LOCATION: (1)..(1)
<223> OTHER INFORMATION: n is a, c, g, or t

<400> SEQUENCE: 1 ngg                                                                        3

<210> SEQ ID NO 2
<211> LENGTH: 6
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 2 nnagaa                                                                     6

<210> SEQ ID NO 3
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 3 nggng                                                                      5

<210> SEQ ID NO 4
<211> LENGTH: 7
<212> TYPE: DNA
<213> ORGANISM: Neisseria meningitidis
```

```
<220> FEATURE:
<221> NAME/KEY: misc_feature
<222> LOCATION: (1)..(3)
<223> OTHER INFORMATION: n is a, c, g, or t

<400> SEQUENCE: 4 nnngatt                                                                    7

<210> SEQ ID NO 5
<211> LENGTH: 3
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: n is a, c, g, or t

<400> SEQUENCE: 5 ttn                                                                        3

<210> SEQ ID NO 6
<211> LENGTH: 3
<212> TYPE: DNA
<213> ORGANISM: Artificial Sequence
<220> FEATURE:
<223> OTHER INFORMATION: Synthetic Construct

<400> SEQUENCE: 6 cta                                                                        3

<210> SEQ ID NO 7
<211> LENGTH: 22
<212> TYPE: PRT
<213> ORGANISM: Artificial Sequence
<220> FEATURE:
<223> OTHER INFORMATION: Synthetic Construct

<400> SEQUENCE: 7

Gln Arg Leu Ser Thr Gly Ser Arg Ile Asn Ser Ala Lys Asp Asp Ala
1               5                   10                  15

Ala Gly Leu Gln Ile Ala
            20

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION

<400> SEQUENCE: 8

Ser Lys Glu Lys Phe Glu Arg Thr Lys Pro His Val Asn Val Gly Thr
1               5                   10                  15

Ile Gly

<210> SEQ ID NO 9
<211> LENGTH: 1937
<212> TYPE: DNA
<213> ORGANISM: Artificial Sequence
<220> FEATURE:
<223> OTHER INFORMATION: Synthetic Construct
```

<400> SEQUENCE: 9

```
acgaccatgg accatggccg tcgatagccg aatggatctg ctcagcgaaa gagctgtgct      60
gatgagagag tctctccaga agagtcaaac catcaccgat aatgtcgtct ccatcctcgg     120
ctccttcgat agccgtctct ctgctcttga atccgccatg cgtcccactc agattagaac     180
gcatgcgata aggaaagctc acgagaatat cgataagact ctcaaatccg ctgaggttat     240
tctctctcag tttgatctcc tccgtcaggc agagactaaa gtactcaagg gccacatga     300
ggacctggag agttatttgg aggcaatagc tcaactcaga aaagttattc gttattttag     360
cagcaacaaa ggctttaaga acagtgatgg agtcctcaac catgcaaata gcttgcttgc     420
caaagctcag tcgaagctgg aggaggagtt taaacagttg ctagcttctt acagcaaagc     480
tgtggagcct gatcgccttt ttgatggcct tcctaactca ctgagaccat ccgctgacgg     540
tgagggtaat ggaaaagccc acggaggaca ccataacgat gactcagaaa ctgctgctta     600
tacacttcca gtcctcattc catcaagggt attgccactt ttgcatgatt tggctcagca     660
aatggttcag gctggtcacc agcaactgct gctacaaatt tatagagaaa cacgtacttt     720
tgtattggaa gagagcttaa gaaaattggg agttgaaaaa cttagcaaag aggatgttca     780
gaggatgcag tgggaagttt tggaggccaa aattggaaat tggatccatt tcatgcgcat     840
tgctgttaaa ttgctctttg ctggagaaag gcaagtatgt gaccagatat tccgaggctt     900
cgattctctt agtgatcagt gttttgcaga agttacagtg agcagtgtct caatgctact     960
tagctttggg gatgccatag ctaggagcaa gagatctcca gaaaagttgt ttgtactctt    1020
agacatgtat gaaataatgc gggagcttca ttcagagatt gagacaattt tcaaaggtaa    1080
agcatgcctt gaaattagaa actctgctac ggggttgaca aagcggctgg cgcagactgc    1140
tcaggaaaca tttggtgact tcgaagaagc tgtagaaaaa gatgctacaa agactgctgt    1200
tctagatggg actgtccacc cactaacaag ctatgttatc aattatgtca agttcttatt    1260
tgactaccaa gcgactttga agcaactttt ctcggaattt ggaaatggag atgactcgaa    1320
ctctcagctt gcatccgtaa caatgaggat aatgcaggcg cttcaaaaca acctggaggg    1380
aaaatcgaaa cagtacaaag atcaagcact gacacacttg ttcttgatga acaacataca    1440
ttacatggtt agatctgtgc gcaggtcaga agccaaggat tgttaggcg atgattgggt     1500
tcaaaggcac aggcgtgtcg ttcagcaaca tgcaaaccta tacaaaagga ctgcttggac    1560
aaagatatta caaacctcgt cggcgcaagg gttgacctca tccggaggag gaagtgtaga    1620
gggaggaaac agcagcggag tttcgagagg gttactgaaa gagaggttca agatgttcaa    1680
tatgcaattt gatgagttgc atcagagaca atcacaatgg acagttccgg acacagagct    1740
aagagagtca ctaagacttg ctgttgctga agtattattg cctgcttaca gatcattcct    1800
caaacgcttt gggcctctgg ttgagagtgg gaagaattct cagagataca taagtatac     1860
agctgaagat cttgagagat tgttgggtga gttgtttgaa ggaaagtcta tgaacgaacc    1920
acgacggcca tggacga                                                   1937
```

<210> SEQ ID NO 10  
<211> LENGTH: 27  
<212> TYPE: DNA  
<213> ORGANISM: Artificial Sequence  
<220> FEATURE:  
<223> OTHER INFORMATION: Synthetic Construct

```
<400> SEQUENCE: 10
cgcccgggat ggccgtcgat agccgaa                                          27

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct

<400> SEQUENCE: 11
cgcgggccct taccgtcgtg gttcattcat                                       30

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
ggctgatggt gaagatattc a                                                21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
caagcacaat accagtagta c                                                21
```

METHODS FOR MANUFACTURING PLANT MESSENGER PACKS

SEQUENCE LISTING

The instant application contains a Sequence Listing which has been submitted electronically in ASCII format and is hereby incorporated by reference in its entirety. Said ASCII copy, created on Aug. 22, 2019, is named 51296-007Wo3_Sequence_Listing_8.22.19_ST25 and is 5,825 bytes in size.

BACKGROUND

There is need in the art for methods of manufacturing plant messenger packs for use in a variety of agricultural, therapeutic, or commercial applications.

SUMMARY OF THE INVENTION

Disclosed herein are methods of manufacturing plant messenger packs (PMPs) and related articles (e.g., PMP bioreactors). The PMPs manufactured using the methods and articles herein are useful in a variety of agricultural and therapeutic compositions and methods.

In a first aspect, provided herein is a method for producing plant messenger packs (PMPs), the method comprising (a) culturing a plant or plant part in a culture medium in a hydroponic system; (b) harvesting the culture medium; and (c) purifying PMPs from the culture medium.

In some embodiments, the plant or plant part is a tomato plant or a tomato plant part; a seedling, or a root.

In some embodiments, the culture medium is a liquid culture medium or a gel culture medium. In some embodiments, the culture medium comprises one or more of a macronutrient, a micronutrient, a salt, an enzyme, an antibiotic, an antifungal agent, or a plant growth factor.

In some embodiments, the hydroponic system has a capacity of at least 1 L, at least 100 L, or at least 500 L.

In some embodiments, the harvesting comprises separating the culture medium from the plant or plant part. In some embodiments, the harvesting does not comprise disruption of the plant or plant part.

In some embodiments, the culturing is performed for at least 1 week.

In another aspect, the invention features a method for producing plant messenger packs (PMPs), the method including: (a) obtaining a culture medium in which a plant, a plant part, or a plant cell has been cultured; and (b) purifying PMPs from the culture medium.

In yet another aspect, the invention features a method for producing plant PMPs, the method including: (a) culturing a plant, a plant part, or a plant cell in a culture medium; (b) harvesting the culture medium or a portion thereof; and (c) purifying PMPs from the culture medium.

In some embodiments, the culture medium is a liquid culture medium. In some embodiments, the liquid culture medium is in a hydroponic system.

In some embodiments, the culture medium is a gel culture medium, e.g., agar or agarose.

In some embodiments, the culture medium is a semi-solid or solid culture medium, e.g., a sterile natural soil or a sterile synthetic soil.

In some embodiments, the culture medium includes one or more of a macronutrient, a micronutrient, a salt, an enzyme, an antibiotic, an antifungal agent, or a plant growth factor.

In some embodiments, the culturing is performed in a bioreactor. In some embodiments, the bioreactor is a vessel having a capacity of at least 1 L, 10 L, 50 L, 100 L, or 500 L.

In some embodiments, the harvesting includes separating the plant, plant part, or plant cell and the plant culture medium, e.g., using one or more of gravity sedimentation, centrifugation, a spin filter, and a membrane system. In some embodiments, the harvesting does not include disruption of the plant, plant part, or plant cell.

In some embodiments, the harvesting includes centrifugation of the plant, plant part, or plant cell and the culture medium; juicing the culture medium; or washing the culture medium.

In some embodiments, the culture medium is periodically harvested and replaced.

In some embodiments, the culture medium is provided at a volume of at least 1 L.

In some embodiments, the plant is a seedling. In some embodiments, the seedling is germinated in the culture medium.

In some embodiments, the plant part is a radicle or a root. In some embodiments, the root is not attached to a plant shoot.

In some embodiments, the plant part is a pollen grain or a callus.

In some embodiments, the plant is a dicot or a monocot or the plant part is a part of a dicot or a monocot.

In some embodiments, the plant or plant part is a soybean plant or a part thereof, a fava bean plant or a part thereof, an *Arabidopsis* plant or a part thereof, a tomato plant or a part thereof, a barley plant or a part thereof, or an oat plant or a part thereof.

In some embodiments, the plant cell is a tobacco BY-2 cell.

In some embodiments, the plant, plant part, or plant cell has been grown for at least 24 hours or at least one week.

In some embodiments, the plant, plant part, or plant cell is genetically modified, e.g., contains a genetic modification that is effective to increase the production of PMPs from the plant, plant part, or plant cell relative to an unmodified plant, plant part, or plant cell, e.g., a genetic modification that is effective to increase expression of EXO70a1 or EXO84 in the plant, plant part, or plant cell relative to an unmodified plant, plant part, or plant cell. In some embodiments, the genetic modification is stable integration of an EXO70a1 or an EXO84 transgene.

In some embodiments, the method further includes exposing the plant, plant part, or plant cell to an effective amount of a stimulant to increase PMP production.

In some embodiments, the stimulant is a biotic stimulant, e.g., a microbial stimulant, e.g., a bacterial polypeptide, a bacterial saccharide, a bacterial nucleic acid, or a bacterial small molecule. In some embodiments, the bacterial polypeptide is Elongation Factor Tu 18 (EFT18).

In some embodiments, the microbial stimulant is a fungal polypeptide (e.g., Flagellin2), a fungal saccharide, a fungal nucleic acid, or a fungal small molecule In some embodiments, the microbial stimulant is a microorganism, e.g., a bacterium, a virus or a protozoan, or a fungus.

In some embodiments, the plant stimulant is an abiotic stimulant, e.g., osmotic stress, drought, water deprivation, flood, high light intensity, very high light intensity, high temperature, low temperature, salinity, heavy metal toxicity, anaerobiosis, nutrient deficiency, nutrient excess, UV irradiation, atmospheric pollution, or a chemical that induces production of reactive oxygen species (ROS).

In some embodiments, the plant stimulant is a chemical elicitor, e.g., salicylic acid, benzothiadiazole, or 2,6-dichloroisonicotinic acid.

In some embodiments, the stimulant is a heterologous nucleic acid that increases gene expression of EXO70a1 or EXO84.

In some embodiments, the stimulant is added at least 24 hours before the harvesting of the culture medium.

In some embodiments of the above methods, the purifying step includes isolating a crude PMP fraction, wherein the crude PMP fraction has a decreased level of at least one contaminant or undesired component from the plant or part thereof relative to a level in an initial sample.

In some embodiments, the purifying step further includes purifying the crude PMP fraction, thereby producing a plurality of pure PMPs, wherein the plurality of pure PMPs have a decreased level of at least one contaminant or undesired component from the plant or part thereof relative to a level in the crude PMP fraction.

In some embodiments, the method further includes determining the purity of the PMPs and collecting PMPs identified as pure.

In some embodiments, the method further includes formulating the PMPs with a carrier, thereby generating a PMP composition. In some embodiments, the carrier is an agriculturally acceptable carrier. In some embodiments, the PMP composition is formulated for delivery to a plant. In some embodiments, the carrier is a pharmaceutically acceptable carrier. In some embodiments, the composition is formulated for administration to a human. In some embodiments, the composition is formulated as a liquid, a solid, an aerosol, a paste, a gel, or a gas composition.

In some embodiments, the PMP composition is stable for at least 24 hours, 48 hours, seven days, or 30 days. In some embodiments, the PMP composition is stable at a temperature of at least 4° C., 20° C., 24° C., or 37° C.

In some embodiments, the method further includes loading the PMPs with a heterologous functional agent, e.g., a heterologous agricultural agent. In some embodiments, the heterologous agricultural agent is a pesticidal agent, a fertilizing agent, an herbicidal agent, a plant-modifying agent, or a heterologous therapeutic agent. In some embodiments, the heterologous therapeutic agent includes an antifungal agent, an antibacterial agent, a virucidal agent, an anti-viral agent, an insecticidal agent, a nematicidal agent, an antiparasitic agent, or an insect repellent.

In another aspect, the invention features a method for producing PMPs, the method including: (a) culturing a plant, plant part, or a plant cell in a bioreactor; (b) exposing the plant, plant part, or plant cell to an effective amount of a stimulant to increase PMP production; (c) harvesting the culture medium; and (d) purifying PMPs from the culture medium.

In another aspect, the invention features a PMP composition including a plurality of PMPs, wherein the PMPs are produced by a process including the steps of: (a) obtaining a culture medium in which a plant, a plant part, or a plant cell has been cultured; and (b) purifying PMPs from the culture medium.

In another aspect, the invention features a PMP composition including a plurality of PMPs, wherein the PMPs are produced by a process including the steps of: (a) culturing a plant, a plant part, or a plant cell in a culture medium; (b) harvesting the culture medium; and (c) purifying PMPs from the culture medium.

In some embodiments, the PMP composition further includes exposing the plant, plant part, or plant cell to an effective amount of a stimulant to increase PMP production. In some embodiments, the stimulant is a biotic stimulant, an abiotic stimulant, or a chemical elicitor.

In some embodiments, the purifying step includes isolating a crude PMP fraction, wherein the crude PMP fraction has a decreased level of at least one contaminant or undesired component from the plant or part thereof relative to a level in an initial sample. In some embodiments, the purifying step further includes purifying the crude PMP fraction, thereby producing a plurality of pure PMPs, wherein the plurality of pure PMPs have a decreased level of at least one contaminant or undesired component from the plant or part thereof relative to a level in the crude PMP fraction.

In some embodiments, the PMP composition further includes formulating the PMPs with a carrier.

In some embodiments, the carrier is an agriculturally acceptable carrier. In some embodiments, the carrier is a pharmaceutically acceptable carrier.

In some embodiments, the PMP composition is formulated for delivery to a plant. In some embodiments, the PMP composition is formulated for administration to a human.

In some embodiments, the PMP composition is formulated as a liquid, a solid, an aerosol, a paste, a gel, or a gas composition.

In some embodiments, the PMP composition is stable for at least 24 hours, 48 hours, seven days, or 30 days. In some embodiments, the PMP composition is stable at a temperature of at least 4° C., 20° C., 24° C., or 37° C.

In another aspect, the invention features a PMP bioreactor including a bioreactor containing a plant culture and optionally containing an effective amount of a stimulant to increase PMP production.

In some embodiments, the plant culture is a culture including entire plants, plant parts, or plant cells. In some embodiments, the plant is a seedling. In some embodiments, the plant part is a radicle, a root, a pollen grain, or a callus. In some embodiments, the root is not attached to a plant shoot. In some embodiments, the plant is a dicot or a monocot or the plant part is a part of a dicot or a monocot. In some embodiments, the plant or plant part is a soybean plant or a part thereof, a fava bean plant or a part thereof, an *Arabidopsis* plant or a part thereof, a tomato plant or a part thereof, a barley plant or a part thereof, or an oat plant or a part thereof. In some embodiments, the plant cell is a tobacco BY-2 cell.

In some embodiments, the plant, plant part, or plant cell has been grown for at least 24 hours or at least 1 week In some embodiments, the plant, plant part, or plant cell is genetically modified.

In some embodiments, the genetically modified plant, plant part, or plant cell contains a genetic modification that is effective to increase the production of PMPs from the plant, plant part, or plant cell relative to an unmodified plant, plant part, or plant cell or to increase expression of EXO70a1 or EXO84 in the plant, plant part, or plant cell relative to an unmodified plant, plant part, or plant cell. In some embodiments, the genetic modification is stable integration of an EXO70a1 or an EXO84 transgene.

In some embodiments, the stimulant is a biotic stimulant. In some embodiments, the biotic stimulant is a microbial stimulant or a plant stimulant. In some embodiments, the microbial stimulant is a bacterial polypeptide, a bacterial saccharide, a bacterial nucleic acid, bacterial small molecule, fungal polypeptide, a fungal saccharide, a fungal nucleic acid, a fungal small molecule, a microorganism, a bacterium, a virus, a protozoan, or a fungus. In some embodiments, the bacterial polypeptide is Elongation Factor Tu 18 (EFT18). In some embodiments, the fungal polypeptide is Flagellin2.

In some embodiments, the plant stimulant is an abiotic stimulant or a chemical elicitor. In some embodiments, the abiotic stimulant is osmotic stress, drought, water deprivation, flood, high light intensity, very high light intensity, high temperature, low temperature, salinity, heavy metal toxicity, anaerobiosis, nutrient deficiency, nutrient excess, UV irradiation, atmospheric pollution, or a chemical that induces production of reactive oxygen species (ROS). In some embodiments, the chemical elicitor is salicylic acid, benzothiadiazole, or 2,6-dichloroisonicotinic acid.

In some embodiments, the stimulant is a heterologous nucleic acid that increases gene expression of EXO70a1 or EXO84.

In some embodiments, the stimulant is added at least 24 hours before the harvesting of the culture medium.

In another aspect, the invention features a method of increasing the fitness of a plant, the method including delivering to the plant an effective amount of the PMP composition of the aforementioned embodiments, wherein the method increases the fitness of the plant relative to an untreated plant.

In another aspect, the invention features a method of decreasing the fitness of a plant pest, the method including delivering to the plant pest an effective amount of the PMP composition of the aforementioned embodiments, wherein the method decreases the fitness of the plant pest relative to an untreated plant pest.

In another aspect, the invention features a method of treating an infection in an animal in need thereof, the method including administering to the animal an effective amount of the PMP composition of the aforementioned embodiments.

In another aspect, the invention features a method of decreasing the fitness of a pathogen, the method including delivering to the pathogen an effective amount of the PMP composition of the aforementioned embodiments, wherein the method is effective to decrease the fitness of the pathogen relative to an untreated pathogen.

In another aspect, the invention features a method of decreasing the fitness of an animal pathogen vector, the method including delivering to the vector an effective amount of the PMP composition of the aforementioned embodiments, wherein the method decreases the fitness of the vector relative to an untreated vector.

Other features and advantages of the invention will be apparent from the following Detailed Description and the Claims.

Definitions

As used herein, the term "plant" refers to whole plants (e.g., whole seedlings or whole adult plants), plant organs, plant parts, plant tissues, seeds, plant cells, seeds, and progeny of the same. Plant cells include, without limitation, cells from seeds, suspension cultures, embryos, meristematic regions, callus tissue, cambial tissue, hypocotyl, leaves, roots, radicles, shoots, gametophytes, sporophytes, pollen, and microspores. Plant cells also include single-celled plants, e.g., single-celled plastid-containing organisms such as algae. Plant parts include differentiated and undifferentiated tissues including, but not limited to the following: roots, radicles, flowers, pistils, stamens, stems, hypocotyls, cambial tissue, shoots, leaves, pollen, seeds, fruit, harvested produce, tumor tissue, sap (e.g., xylem sap and phloem sap), and various forms of cells and culture (e.g., single cells, protoplasts, embryos, and callus tissue).

As used herein, the term "plant culture" refers to a plant or a plurality of plants, plant parts, plant cells, or plant tissue that is propagated in or on a medium, e.g., a liquid, gaseous, gel, semi-solid, or solid medium. Plant culture includes, but is not limited to, culture of naturally occurring plants, plant parts, plant cells, or plant tissue or genetically modified plants, plant parts, plant cells, or plant tissues. Plant cultures can be classified, for example, as unorganized cultures (e.g., plant cell cultures such as callus, suspension, or protoplast cultures) or organized cultures (such as root, seedling, embryo, or entire plant cultures) depending on the tissue source and the level of differentiation of the cultured plant material. The plant culture may be a hydroponic culture. As used herein, the term "hydroponic" refers to a hydrated growth system for a plant or plant part (e.g., a plant root) that does not include a natural soil. Such hydroponic growth systems include, e.g., a plant growth system comprising a liquid or semi-liquid (e.g., aqueous), gel, semi-solid, or hydrated solid culture medium. Hydroponic cultures may include aquaponic, hydroculture, or aquaculture growth systems.

As used herein, the term "untreated plant culture" refers to a plant culture (e.g., a culture comprising a plant, plant cell, or plant part) that has not been contacted with or delivered a stimulant herein (e.g., a separate plant culture that has not been delivered the stimulant or the same plant culture assessed at a time point prior to delivery of the stimulant).

As used herein, the term "bioreactor" refers to a culture vessel with a capacity of at least 1 L (e.g., at least 5 L, at least 10 L, at least 50 L, at least 100 L, at least 500 L, or at least 1000 L) that allows for culturing, propagating, cultivating, maintaining, or storing of a plant, a plant part (e.g., a plant tissue), or a plant cell under controlled conditions (e.g., one or more of controlled sterility, mixing rate, temperature, light, oxygen supply, and/or nutrient medium). A bioreactor may contain entire plants or plant parts (e.g., may comprise a hydroponic system) or plant cells (e.g., may contain a plant cell culture). A bioreactor may contain any suitable substrate for plant, plant part, or plant cell growth, a liquid, solid, semi-solid, or gel substrate.

As used herein, the term "stimulant" refers to an agent (e.g., an abiotic stimulant, a biotic stimulant, a chemical elicitor, a nucleic acid stimulant, or a polypeptide stimulant) that, upon contact with a plant, a plant part, or a plant cell (e.g., a plant culture) (e.g., in an effective amount and duration), increases the biogenesis (e.g., intracellular production or secretion, e.g., secretion into culture medium) of extracellular vesicles by the plant culture relative to an untreated plant culture, and/or increases the amount of PMPs that can be derived from the plant culture relative to an untreated culture.

As used herein, the term "abiotic stimulant" refers to a non-living chemical and/or a physical factor that stimulates production of extracellular vesicles (EVs) by and/or increases the amount of PMPs that can be derived from a plant, a plant part, or a plant cell (e.g., a plant culture, e.g., a plant cell culture or tissue culture or a culture comprising plant parts or entire plants (e.g., a hydroponic culture)), e.g., by osmotic stress, drought, water deprivation, flood, high light intensity, very high light intensity, high temperature, low temperature, salinity, heavy metal toxicity, anaerobiosis, nutrient deficiency (e.g., nitrogen or phosphorus deficiency), nutrient excess, UV irradiation, atmospheric pollution (e.g., ozone), or exposure to a chemical (e.g., paraquat) that induce production of reactive oxygen species (ROS).

As used herein, the term "biotic stimulant" refers to a biological agent (e.g., a plant pest, e.g., a fungus, a bacterium, a virus, a protozoan, a nematode, or an insect herbivore), or a component thereof (e.g., a protein or polypeptide, a nucleic acid, a saccharide, or a small molecule), that stimulates production of extracellular vesicles by and/or increases the amount of PMPs that can be derived from a plant, a plant part, or a plant cell (e.g., a plant culture, e.g., a plant cell culture or tissue culture, a culture comprising plant parts, or a culture comprising entire plants). The term "microbial stimulant" refers to a biotic stimulant including a microorganism (e.g., a fungus, a bacterium, or a virus) or a component thereof (e.g., a protein or polypeptide, a nucleic acid, a saccharide, or a small molecule capable of being produced by the microorganism). Exemplary microbial stimulants include, but are not limited to the bacterial polypeptide Elongation Factor Tu 18 (EFT18) and the fungal polypeptide Flagellin2.

As used herein, the term "chemical elicitor" refers to a natural or synthetic compound that stimulates production of extracellular vesicles by and/or increases the amount of PMPs that can be derived from a plant, a plant part, or a plant cell (e.g., a plant culture, e.g., a plant cell culture or tissue culture, a culture comprising plant parts, or a culture comprising entire plants). Exemplary chemical elicitors include, but are not limited to salicylic acid, benzothiadiazole, and 2,6-dichloroisonicotinic acid. In some examples, the chemical elicitor induces a defense response in a plant similar to a response induced by a plant pathogen (e.g., a bacterial pathogen or a fungal pathogen), or a compound released from a plant when induced by a plant pathogen (e.g., endogenous elicitors). The defense response may include, e.g., increased production of EVs.

As used herein, the term "formulated for delivery to a plant or a plant pest" refers to a plant messenger pack (PMP) composition that includes an agriculturally acceptable carrier. As used herein, an "agriculturally acceptable" carrier or excipient is one that is suitable for use in agriculture, e.g., for use on plants. In certain embodiments the agriculturally acceptable carrier or excipient does not have undue adverse side effects to the plants, the environment, or to humans or animals who consume the resulting agricultural products derived therefrom commensurate with a reasonable benefit/risk ratio.

As used herein, "decreasing the fitness of a plant pest" refers to any disruption to pest physiology, or any activity carried out by said pest, as a consequence of administration of a PMP composition described herein, including, but not limited to, any one or more of the following desired effects: (1) decreasing a population of a pest by about 10%, 20%, 30%, 40%, 50%, 60%, 70%, 80%, 90%, 95%, 99%, 100% or more; (2) decreasing the reproductive ability or rate of a pest (e.g., insect) by about 10%, 20%, 30%, 40%, 50%, 60%, 70%, 80%, 90%, 95%, 99%, 100% or more; (3) decreasing the mobility of a pest by about 10%, 20%, 30%, 40%, 50%, 60%, 70%, 80%, 90%, 95%, 99%, 100% or more; (4) decreasing the body weight of a pest by about 10%, 20%, 30%, 40%, 50%, 60%, 70%, 80%, 90%, 95%, 99%, 100% or more; (5) decreasing the metabolic rate or activity of a pest by about 10%, 20%, 30%, 40%, 50%, 60%, 70%, 80%, 90%, 95%, 99%, 100% or more; or (6) decreasing plant infestation by a pest by about 10%, 20%, 30%, 40%, 50%, 60%, 70%, 80%, 90%, 95%, 99%, 100% or more. A decrease in pest fitness can be determined in comparison to a pest to which the pest control (e.g., biopesticide or biorepellent) composition has not been administered.

As used herein "decreasing the fitness of a pathogen" refers to any disruption to pathogen physiology as a consequence of administration of a PMP composition described herein, including, but not limited to, any one or more of the following desired effects: (1) decreasing a population of a pathogen by about 10%, 20%, 30%, 40%, 50%, 60%, 70%, 80%, 90%, 95%, 99%, 100% or more; (2) decreasing the reproductive ability or rate of a pathogen by about 10%, 20%, 30%, 40%, 50%, 60%, 70%, 80%, 90%, 95%, 99%, 100% or more; (3) decreasing the mobility of a pathogen by about 10%, 20%, 30%, 40%, 50%, 60%, 70%, 80%, 90%, 95%, 99%, 100% or more; (4) decreasing the body weight or mass of a pathogen by about 10%, 20%, 30%, 40%, 50%, 60%, 70%, 80%, 90%, 95%, 99%, 100% or more; (5) decreasing the metabolic rate or activity of a pathogen by about 10%, 20%, 30%, 40%, 50%, 60%, 70%, 80%, 90%, 95%, 99%, 100% or more; or (6) decreasing pathogen transmission (e.g., vertical or horizontal transmission of a pathogen from one insect to another) by a pathogen by about 10%, 20%, 30%, 40%, 50%, 60%, 70%, 80%, 90%, 95%, 99%, 100% or more. A decrease in pathogen fitness can be determined, e.g., in comparison to an untreated pathogen.

As used herein "decreasing the fitness of a vector" refers to any disruption to vector physiology, or any activity carried out by said vector, as a consequence of administration of a PMP composition described herein, including, but not limited to, any one or more of the following desired effects: (1) decreasing a population of a vector by about 10%, 20%, 30%, 40%, 50%, 60%, 70%, 80%, 90%, 95%, 99%, 100% or more; (2) decreasing the reproductive ability or rate of a vector (e.g., insect, e.g., mosquito, tick, mite, louse) by about 10%, 20%, 30%, 40%, 50%, 60%, 70%, 80%, 90%, 95%, 99%, 100% or more; (3) decreasing the mobility of a vector (e.g., insect, e.g., mosquito, tick, mite, louse) by about 10%, 20%, 30%, 40%, 50%, 60%, 70%, 80%, 90%, 95%, 99%, 100% or more; (4) decreasing the body weight of a vector (e.g., insect, e.g., mosquito, tick, mite, louse) by about 10%, 20%, 30%, 40%, 50%, 60%, 70%, 80%, 90%, 95%, 99%, 100% or more; (5) increasing the metabolic rate or activity of a vector (e.g., insect, e.g., mosquito, tick, mite, louse) by about 10%, 20%, 30%, 40%, 50%, 60%, 70%, 80%, 90%, 95%, 99%, 100% or more; (6) decreasing vector-vector pathogen transmission (e.g., vertical or horizontal transmission of a vector from one insect to another) by a vector (e.g., insect, e.g., mosquito, tick, mite, louse) by about 10%, 20%, 30%, 40%, 50%, 60%, 70%, 80%, 90%, 95%, 99%, 100% or more; (7) decreasing vector-animal pathogen transmission by about 10%, 20%, 30%, 40%, 50%, 60%, 70%, 80%, 90%, 95%, 99%, 100% or more; (8) decreasing vector (e.g., insect, e.g., mosquito, tick, mite, louse) lifespan by about 10%, 20%, 30%, 40%, 50%, 60%, 70%, 80%, 90%, 95%, 99%, 100% or more; (9) increasing vector (e.g., insect, e.g., mosquito, tick, mite, louse) susceptibility to pesticides (e.g., insecticides) by about 10%, 20%, 30%, 40%, 50%, 60%, 70%, 80%, 90%, 95%, 99%, 100% or more; or (10) decreasing vector competence by a vector (e.g., insect, e.g., mosquito, tick, mite, louse) by about 10%, 20%, 30%, 40%, 50%, 60%, 70%, 80%, 90%, 95%, 99%, 100% or more. A decrease in vector fitness can be determined, e.g., in comparison to an untreated vector.

As used herein, "increase the fitness of a plant" refers to an increase in the fitness of the plant directly resulting from contact with a PMP composition described herein and includes, for example, an improved yield, improved vigor of the plant, or improved quality or amount of a harvested product from the plant, an improvement in pre- or post-harvest traits deemed desirable for agriculture or horticulture (e.g., taste, appearance, shelf life), or for an improvement of traits that otherwise benefit humans (e.g., decreased allergen production). An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional plant-modifying agents (e.g., plant-modifying agents delivered without a PMP). For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. An increase in the fitness of plant can also be measured in other ways, such as by an increase or improvement of the vigor rating, increase in the stand (the number of plants per unit of area), increase in plant height, increase in stalk circumference, increase in plant canopy, improvement in appearance (such as greener leaf color as measured visually), improvement in root rating, increase in seedling emergence, protein content, increase in leaf size, increase in leaf number, fewer dead basal leaves, increase in tiller strength, decrease in nutrient or fertilizer requirements, increase in seed germination, increase in tiller productivity, increase in flowering, increase in seed or grain maturation or seed maturity, less plant lodging, increased shoot growth, or any combination of these factors, by a measurable or noticeable amount over the same factor of the plant produced under the same conditions, but without the administration of the instant compositions or with application of conventional agricultural agents.

As used herein, the term "effective amount," "effective concentration," or "concentration effective to" refers to an amount of a PMP, or a composition thereof, sufficient to effect the recited resultor to reach a target level (e.g., a predetermined or threshold level) in or on a target organism.

As used herein, the term "heterologous" refers to an agent that is either (1) exogenous to the plant (e.g., originating from a source that is not the plant or plant part from which the PMP is produced) (e.g., added the PMP using loading approaches described herein) or (2) endogenous to the plant cell or tissue from which the PMP is produced, but present in the PMP (e.g., added to the PMP using loading approaches described herein, genetic engineering, in vitro or in vivo approaches) at a concentration that is higher than that found in nature (e.g., higher than a concentration found in a naturally-occurring plant extracellular vesicle).

As used herein, the term "functional agent" refers to an agent (e.g., an agricultural agent (e.g., pesticidal agent, fertilizing agent, herbicidal agent, plant-modifying agent) or a therapeutic agent (e.g., an antifungal agent, an antibacterial agent, a virucidal agent, an anti-viral agent, an insecticidal agent, a nematicidal agent, an antiparasitic agent, or an insect repellent)) that is or can be associated with PMPs (e.g., loaded into or onto PMPs, (e.g., encapsulated by, embedded in, or conjugated to PMPs)) using in vivo or in vitro methods and is capable of effecting the recited result (e.g., increasing or decreasing the fitness of a plant, plant pest, plant symbiont, animal (e.g., human) pathogen, or animal pathogen vector) in accordance with the present compositions or methods.

As used herein, the term "agricultural agent" refers to an agent that can act on a plant, a plant pest, or a plant symbiont, such as a pesticidal agent, pest repellent, fertilizing agent, herbicidal agent, plant-modifying agent, or plant-symbiont modifying agent.

As used herein, the term "fertilizing agent" refers to an agent that is capable of increasing the fitness of a plant (e.g., a plant nutrient or a plant growth regulator) or a plant symbiont (e.g., a nucleic acid or a peptide).

As used herein, the term "pesticidal agent" refers to an agent, composition, or substance therein, that controls or decreases the fitness of (e.g., kills or inhibits the growth, proliferation, division, reproduction, or spread of) an agricultural, environmental, or domestic/household pest, such as an insect, mollusk, nematode, fungus, bacterium, weed, or virus. Pesticides are understood to include naturally occurring or synthetic insecticides (larvicides or adulticides), insect growth regulators, acaricides (miticides), molluscicides, nematicides, ectoparasiticides, bactericides, fungicides, or herbicides. The term "pesticidal agent" may further encompass other bioactive molecules such as antibiotics, antivirals, pesticides, antifungals, antihelminthics, nutrients, and/or agents that stun or slow insect movement.

As used herein, the term "plant-modifying agent" refers to an agent that can alter the genetic properties (e.g., increase gene expression, decrease gene expression, or alter the nucleotide sequence of DNA or RNA) or biochemical properties of a plant in a manner that results in an increase in plant fitness.

As used herein, the term "therapeutic agent" refers to an agent that can act on an animal (e.g., a human), an animal pathogen, or a pathogen vector, such as an antifungal agent, an antibacterial agent, a virucidal agent, an anti-viral agent, an insecticidal agent, a nematicidal agent, an antiparasitic agent, or an insect repellent.

As used herein, the terms "genetically modified" "genetically modified plant", "genetically modified plant part", or 'genetically modified plant cell" refer to a plant, plant part, or plant cell (e.g., a plant culture) that has been genetically altered (e.g., to have increased or decreased expression of an endogenous nucleic acid, to modify the nucleotide sequence of an endogenous nucleic acid, or to express an exogenous gene) using any methods known in the art (e.g., delivery of a nucleic acid or (e.g., a heterologous DNA or RNA) or a gene editing protein system (e.g., a CRISPR-Cas system, TALEN, or zinc finger)). In certain instances, the genetically modified plant, plant part, or plant cell contains a genetic modification that is effective to increase plant EV production in the plant culture relative to an unmodified plant culture and/or increases the amount of PMPs that can be derived from the plant culture relative to an unmodified plant culture.

As used herein, the term "nucleic acid" and "polynucleotide" are interchangeable and refer to RNA or DNA that is linear or branched, single or double stranded, or a hybrid thereof, regardless of length (e.g., at least 2, 3, 4, 5, 6, 7, 8, 9, 10, 20, 30, 40, 50, 100, 150, 200, 250, 500, 1000, or more nucleic acids). The term also encompasses RNA/DNA hybrids. Nucleotides are typically linked in a nucleic acid by phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The nucleic acids may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5 hydroxymethylcytosine).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, the term "pest" refers to organisms that cause damage to plants or other organisms, are present where they are not wanted, or otherwise are detrimental to humans, for example, by impacting human agricultural methods or products. Pests may include, for example, invertebrates (e.g., insects, nematodes, or mollusks), microorganisms (e.g., phytopathogens, endophytes, obligate parasites, facultative parasites, or facultative saprophytes), such as bacteria, fungi, or viruses; or weeds.

As used herein, the term "formulated for delivery to an animal" refers to a PMP composition that includes a pharmaceutically acceptable carrier. As used herein, a "pharmaceutically acceptable" carrier or excipient is one that is suitable for administration to an animal (e.g., human), e.g., without undue adverse side effects to the animal (e.g., human).

As used herein, the term "repellent" refers to an agent, composition, or substance therein, that deters pests from approaching or remaining on a plant or a pathogen vector (e.g., insects, e.g., mosquitos, ticks, mites, or lice) from approaching or remaining on an animal. A repellent may, for example, decrease the number of pests on or in the vicinity of a plant, but may not necessarily kill or decrease the fitness of the pest.

As used herein, the term "plant extracellular vesicle", "plant EV", or "EV" refers to an enclosed lipid-bilayer structure naturally occurring in a plant. Optionally, the plant EV includes one or more plant EV markers. As used herein, the term "plant EV marker" refers to a component that is naturally associated with a plant EV, such as a plant protein, a plant nucleic acid, a plant small molecule, a plant lipid, or a combination thereof, including but not limited to any of the plant EV markers listed in the Appendix. In some instances, the plant EV marker is an identifying marker of a plant EV but is not a pesticidal agent. In some instances, the plant EV marker is an identifying marker of a plant EV and also a pesticidal agent (e.g., either associated with or encapsulated by the plurality of PMPs, or not directly associated with or encapsulated by the plurality of PMPs).

As used herein, the term "plant messenger pack" or "PMP" refers to a lipid structure (e.g., a lipid bilayer, unilamellar, multilamellar structure; e.g., a vesicular lipid structure), that is about 5-2000 nm (e.g., at least 5-1000 nm, at least 5-500 nm, at least 400-500 nm, at least 25-250 nm, at least 50-150 nm, or at least 70-120 nm) in diameter that is derived from (e.g., enriched, isolated or purified from) a plant source or segment, portion, or extract thereof, including lipid or non-lipid components (e.g., peptides, nucleic acids, or small molecules associated therewith and that has been enriched, isolated or purified from a plant, a plant part, or a plant cell or from a culture medium in which a plant, plant part, or plant cell has been cultured (e.g., a culture medium of a plant cell culture or a hydroponic culture, e.g., secreted PMPs), the enrichment or isolation removing one or more contaminants or undesired components originating from the source plant, plant part, or plant cell or from the culture medium. In some examples, the isolation comprises removing an intact plant or plant part from the culture medium (e.g., a culture medium of a hydroponic system), e.g., removing the plant or plant part without disrupting (e.g., physically damaging) the plant or plant part. PMPs may be highly purified preparations of naturally occurring EVs. Preferably, at least 1% of contaminants or undesired components from the source plant are removed (e.g., at least 2%, 5%, 10%, 15%, 20%, 25%, 30%, 40%, 45%, 50%, 55%, 60%, 70%, 80%, 90%, 95%, 96%, 98%, 99%, or 100%) of one or more contaminants or undesired components from the source plant, e.g., plant cell wall components; pectin; plant organelles (e.g., mitochondria; plastids such as chloroplasts, leucoplasts or amyloplasts; and nuclei); plant chromatin (e.g., a plant chromosome); or plant molecular aggregates (e.g., protein aggregates, nucleic acids, proteins, protein-nucleic acid aggregates, lipoprotein aggregates, lipido-proteic structures, or sugars). Preferably, a PMP is at least 30% pure (e.g., at least 40% pure, at least 50% pure, at least 60% pure, at least 70% pure, at least 80% pure, at least 90% pure, at least 99% pure, or 100% pure) relative to the one or more contaminants or undesired components from the source plant as measured by weight (w/w), spectral imaging (% transmittance), or conductivity (S/m).

PMPs may optionally include additional agents, such as heterologous functional agents, e.g., pesticidal agents, fertilizing agents, plant-modifying agents, therapeutic agents, polynucleotides, polypeptides, or small molecules. The PMPs can carry or associate with additional agents (e.g., heterologous functional agents) in a variety of ways to enable delivery of the agent to a target plant, e.g., by encapsulation of the agent, incorporation of the agent in the lipid bilayer structure, or association of the agent (e.g., by conjugation) with the surface of the lipid bilayer structure. Heterologous functional agents can be incorporated into the PMPs either in vivo (e.g., in planta) or in vitro (e.g., in tissue culture, in cell culture, or synthetically incorporated).

As used herein, the term "stable PMP composition" (e.g., a composition including loaded or non-loaded PMPs) refers to a PMP composition that over a period of time (e.g., at least 24 hours, at least 48 hours, at least 1 week, at least 2 weeks, at least 3 weeks, at least 4 weeks, at least 30 days, at least 60 days, or at least 90 days) retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of the initial number of PMPs (e.g., PMPs per mL of solution) relative to the number of PMPs in the PMP composition (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)); or retains at least 5% (e.g., at least 5%, 10%, 15%, 20%, 25%, 30%, 35%, 40%, 45%, 50%, 55%, 60%, 65%, 70%, 75%, 80%, 85%, 90%, 95%, or 100%) of its activity (e.g., pesticidal and/or repellent activity) relative to the initial activity of the PMP (e.g., at the time of production or formulation) optionally at a defined temperature range (e.g., a temperature of at least 24° C. (e.g., at least 24° C., 25° C., 26° C., 27° C., 28° C., 29° C., or 30° C.), at least 20° C. (e.g., at least 20° C., 21° C., 22° C., or 23° C.), at least 4° C. (e.g., at least 5° C., 10° C., or 15° C.), at least −20° C. (e.g., at least −20° C., −15° C., −10° C., −5° C., or 0° C.), or −80° C. (e.g., at least −80° C., −70° C., −60° C., −50° C., −40° C., or −30° C.)).

As used herein, the term "symbiont" or "plant symbiont" refers to an organism (e.g., an insect) or a microorganism (e.g., bacterium or fungus) that confers benefits to a plant (e.g., increases the fitness of a plant (e.g., increases biomass production (i.e., yield), increases plant nutrition, increases pollination, or increases tolerance to stress (e.g., drought and/or pests)).

BRIEF DESCRIPTION OF THE DRAWINGS

FIG. 3A is a graph showing particle concentration (particles/ml) in eluted *Arabidopsis thaliana* seedling (Ats) hydroponic culture SEC fractions, as measured by nano-flow cytometry (NanoFCM). PMPs were eluted in SEC fractions 4-6.

FIG. 3B is a graph showing absorbance at 280 nm (A.U.) in eluted Ats SEC fractions, measured on a SpectraMax® spectrophotometer. PMPs were eluted in fractions 4-6; fractions 9-13 contained contaminants.

FIG. 3C is a graph showing protein concentration (μg/ml) in eluted Ats SEC fractions, as determined by BCA analysis. PMPs were eluted in fractions 4-6; fractions 9-13 contained contaminants.

FIG. 3D is a scatter plot showing particles in the combined Ats PMP-containing SEC fractions as measured by nano-flow cytometry (NanoFCM). PMP concentration (particles/ml) was determined using a bead standard according to NanoFCM's instructions.

FIG. 6A is a graph showing packed cell volume (PCV; expressed in percentage) in control *Zea mays* Black Mexican Sweet (BMS) cell culture and BMS cell culture treated with 100 μM salicylic acid (SA).

FIG. 6B is a graph showing concentration of PMPs in control BMS cell culture and BMS cell culture treated with 100 UM SA as measured using NanoFCM.

FIG. 6C is is a graph showing protein concentration in control BMS cell culture and BMS cell culture treated with 100 μM SA as measured using a BCA assay.

DETAILED DESCRIPTION

Figure 1B:
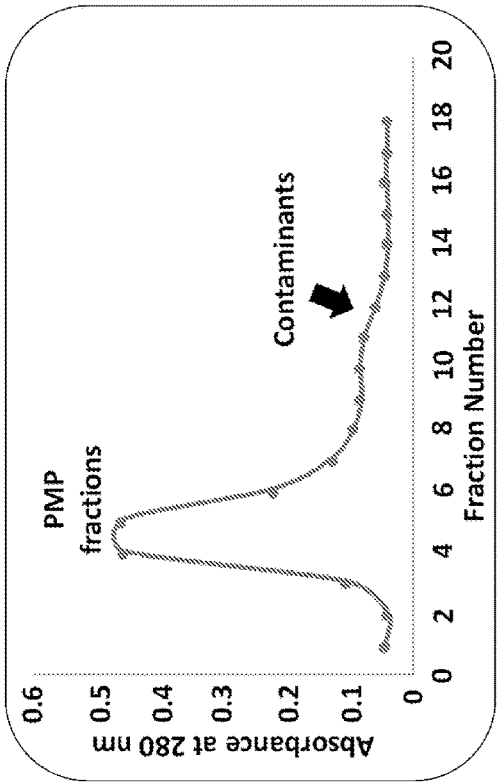
FIG. 1B is a graph showing absorbance at 280 nm (A.U.) in eluted BMS SEC fractions, measured on a SpectraMax® spectrophotometer. PMPs were eluted in fractions 4-6; fractions 9-13 contained contaminants.

Featured herein are methods and related bioreactors for manufacturing plant messenger packs (PMPs), lipid assemblies produced wholly or in part from plant extracellular vesicles (EVs), or segments, portions, or extracts thereof. The manufacturing methods and bioreactors herein permit industrial and/or large-scale production of PMPs. The PMPs can optionally include additional agents (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)). Accordingly, the PMP compositions and formulations described herein can be formulated in compositions for use in a range of agricultural or therapeutic methods.

I. Plant Messenger Pack Manufacturing

The following sections under this heading describe exemplary methods for producing, manufacturing, and obtaining PMPs.

A PMP is a lipid (e.g., lipid bilayer, unilamellar, or multilamellar structure) structure that includes a plant EV, or segment, portion, or extract (e.g., lipid extract) thereof. Plant EVs refer to an enclosed lipid-bilayer structure that naturally occurs in a plant and that is about 5-2000 nm in diameter. Plant EVs can originate from a variety of plant biogenesis pathways. In nature, plant EVs can be found in the intracellular and extracellular compartments of plants, such as the plant apoplast, the compartment located outside the plasma membrane and formed by a continuum of cell walls and the extracellular space. Alternatively, PMPs can be enriched from plant culture medium (e.g., cell culture medium or a culture medium in a hydroponic system) following secretion by plants, plant parts, or plant cells. Plant EVs can be separated from plants, plant parts, or plant cultures (e.g., plant cell cultures), thereby producing PMPs, by a variety of methods further described herein. Further, the PMPs can optionally include a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)), which can be introduced in vivo or in vitro.

PMPs can include plant EVs, or segments, portions, or extracts, thereof. Optionally, PMPs can also include exogenous lipids in addition to lipids derived from plant EVs. In some embodiments, plant EVs are about 5-2000 nm in diameter. For example, the PMP can include a plant EV, or segment, portion, or extract thereof, that has a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1250 nm, about 1250-1500 nm, about 1500-1750 nm, or about 1750-2000 nm. In some instances, the PMP includes a plant EV, or segment, portion, or extract thereof, that has a mean diameter of about 5-950 nm, about 5-900 nm, about 5-850 nm, about 5-800 nm, about 5-750 nm, about 5-700 nm, about 5-650 nm, about 5-600 nm, about 5-550 nm, about 5-500 nm, about 5-450 nm, about 5-400 nm, about 5-350 nm, about 5-300 nm, about 5-250 nm, about 5-200 nm, about 5-150 nm, about 5-100 nm, about 5-50 nm, or about 5-25 nm. In certain instances, the plant EV, or segment, portion, or extract thereof, has a mean diameter of about 50-200 nm. In certain instances, the plant EV, or segment, portion, or extract thereof, has a mean diameter of about 50-300 nm. In certain instances, the plant EV, or segment, portion, or extract thereof, has a mean diameter of about 200-500 nm. In certain instances, the plant EV, or segment, portion, or extract thereof, has a mean diameter of about 30-150 nm.

In some instances, the PMP may include a plant EV, or segment, portion, or extract thereof, that has a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, or at least 1000 nm. In some instances, the PMP includes a plant EV, or segment, portion, or extract thereof, that has a mean diameter less than 1000 nm, less than 950 nm, less than 900 nm, less than 850 nm, less than 800 nm, less than 750 nm, less than 700 nm, less than 650 nm, less than 600 nm, less than 550 nm, less than 500 nm, less than 450 nm, less than 400 nm, less than 350 nm, less than 300 nm, less than 250 nm, less than 200 nm, less than 150 nm, less than 100 nm, or less than 50 nm. A variety of methods (e.g., a dynamic light scattering method) standard in the art can be used to measure the particle diameter of the plant EV or segment, portion, or extract thereof.

In some instances, the PMP may include a plant EV, or segment, portion, or extract thereof, that has a mean surface area of 77 $nm^2$ to 3.2×10$^6$ $nm^2$ (e.g., 77-100 $nm^2$, 100-1000 $nm^2$, 1000-1×10$^4$ $nm^2$, 1×10$^4$-1×10$^5$ $nm^2$, 1×10$^5$-1×10$^6$ $nm^2$, or 1×10$^6$-3.2×10$^6$ $nm^2$). In some instances, the PMP may include a plant EV, or segment, portion, or extract thereof, that has a mean volume of 65 $nm^3$ to 5.3×10$^8$ $nm^3$ (e.g., 65-100 $nm^3$, 100-1000 $nm^3$, 1000-1×10$^4$ $nm^3$, 1×10$^4$-1×10$^5$ $nm^3$, 1×10$^5$-1×10$^6$ $nm^3$, 1×10$^6$-1×10$^7$ $nm^3$, 1×10$^7$-1×10$^8$ $nm^3$, 1×10$^8$-5.3×10$^8$ $nm^3$). In some instances, the PMP may include a plant EV, or segment, portion, or extract thereof, that has a mean surface area of at least 77 $nm^2$, (e.g., at least 77 $nm^2$, at least 100 $nm^2$, at least 1000 $nm^2$, at least 1×10$^4$ $nm^2$, at least 1×10$^5$ $nm^2$, at least 1×10$^6$ $nm^2$, or at least 2×10$^6$ $nm^2$). In some instances, the PMP may include a plant EV, or segment, portion, or extract thereof, that has a mean volume of at least 65 $nm^3$ (e.g., at least 65 $nm^3$, at least 100 $nm^3$, at least 1000 $nm^3$, at least 1×10$^4$ $nm^3$, at least 1×10$^5$ $nm^3$, at least 1×10$^6$ $nm^3$, at least 1×10$^7$ $nm^3$, at least 1×10$^8$ $nm^3$, at least 2×10$^8$ $nm^3$, at least 3×10$^8$ $nm^3$, at least 4×10$^8$ $nm^3$, or at least 5×10$^8$ $nm^3$).

In some instances, the PMP can have the same size as the plant EV or segment, extract, or portion thereof. Alternatively, the PMP may have a different size than the initial plant EV from which the PMP is produced. For example, the PMP may have a diameter of about 5-2000 nm. For example, the PMP can have a mean diameter of about 5-50 nm, about 50-100 nm, about 100-150 nm, about 150-200 nm, about 200-250 nm, about 250-300 nm, about 300-350 nm, about 350-400 nm, about 400-450 nm, about 450-500 nm, about 500-550 nm, about 550-600 nm, about 600-650 nm, about 650-700 nm, about 700-750 nm, about 750-800 nm, about 800-850 nm, about 850-900 nm, about 900-950 nm, about 950-1000 nm, about 1000-1200 nm, about 1200-1400 nm, about 1400-1600 nm, about 1600-1800 nm, or about 1800-2000 nm. In some instances, the PMP may have a mean diameter of at least 5 nm, at least 50 nm, at least 100 nm, at least 150 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1000 nm, at least 1200 nm, at least 1400 nm, at least 1600 nm, at least 1800 nm, or about 2000 nm. A variety of methods (e.g., a dynamic light scattering method) standard in the art can be used to measure the particle diameter of the PMPs. In some instances, the size of the PMP is determined following loading of heterologous functional agents, or following other modifications to the PMPs.

In some instances, the PMP may have a mean surface area of 77 $nm^2$ to $1.3 \times 10^7$ $nm^2$ (e.g., 77-100 $nm^2$, 100-1000 $nm^2$, 1000-$1 \times 10^4$ $nm^2$, $1 \times 10^4$-$1 \times 10^5$ $nm^2$, $1 \times 10^5$-$1 \times 10^6$ $nm^2$, or $1 \times 10^6$-$1.3 \times 10^7$ $nm^2$). In some instances, the PMP may have a mean volume of 65 $nm^3$ to $4.2 \times 10^9$ $nm^3$ (e.g., 65-100 $nm^3$, 100-1000 $nm^3$, 1000-$1 \times 10^4$ $nm^3$, $1 \times 10^4$-$1 \times 10^5$ $nm^3$, $1 \times 10^5$-$1 \times 10^6$ $nm^3$, $1 \times 10^6$-$1 \times 10^7$ $nm^3$, $1 \times 10^7$-$1 \times 10^8$ $nm^3$, $1 \times 10^8$-$1 \times 10^9$ $nm^3$, or $1 \times 10^9$-$4.2 \times 10^9$ $nm^3$). In some instances, the PMP has a mean surface area of at least 77 $nm^2$, (e.g., at least 77 $nm^2$, at least 100 $nm^2$, at least 1000 $nm^2$, at least $1 \times 10^4$ $nm^2$, at least $1 \times 10^5$ $nm^2$, at least $1 \times 10^6$ $nm^2$, or at least $1 \times 10^7$ $nm^2$). In some instances, the PMP has a mean volume of at least 65 $nm^3$ (e.g., at least 65 $nm^3$, at least 100 $nm^3$, at least 1000 $nm^3$, at least $1 \times 10^4$ $nm^3$, at least $1 \times 10^5$ $nm^3$, at least $1 \times 10^6$ $nm^3$, at least $1 \times 10^7$ $nm^3$, at least $1 \times 10^8$ $nm^3$, at least $1 \times 10^9$ $nm^3$, at least $2 \times 10^9$ $nm^3$, at least $3 \times 10^9$ $nm^3$, or at least $4 \times 10^9$ $nm^3$).

In some instances, the PMP may include an intact plant EV. Alternatively, the PMP may include a segment, portion, or extract of the full surface area of the vesicle (e.g., a segment, portion, or extract including less than 100% (e.g., less than 90%, less than 80%, less than 70%, less than 60%, less than 50%, less than 40%, less than 30%, less than 20%, less than 10%, less than 10%, less than 5%, or less than 1%) of the full surface area of the vesicle) of a plant EV. The segment, portion, or extract may be any shape, such as a circumferential segment, spherical segment (e.g., hemisphere), curvilinear segment, linear segment, or flat segment. In instances where the segment is a spherical segment of the vesicle, the spherical segment may represent one that arises from the splitting of a spherical vesicle along a pair of parallel lines, or one that arises from the splitting of a spherical vesicle along a pair of non-parallel lines. Accordingly, the plurality of PMPs can include a plurality of intact plant EVs, a plurality of plant EV segments, portions, or extracts, or a mixture of intact and segments of plant EVs. One skilled in the art will appreciate that the ratio of intact to segmented plant EVs will depend on the particular isolation method used. For example, grinding or blending a plant, or part thereof, may produce PMPs that contain a higher percentage of plant EV segments, portions, or extracts than a non-destructive extraction method, such as vacuum-infiltration.

In instances where, the PMP includes a segment, portion, or extract of a plant EV, the EV segment, portion, or extract may have a mean surface area less than that of an intact vesicle, e.g., a mean surface area less than 77 $nm^2$, 100 $nm^2$, 1000 $nm^2$, $1 \times 10^4$ $nm^2$, $1 \times 10^5$ $nm^2$, $1 \times 10^6$ $nm^2$, or $3.2 \times 10^6$ $nm^2$). In some instances, the EV segment, portion, or extract has a surface area of less than 70 $nm^2$, 60 $nm^2$, 50 $nm^2$, 40 $nm^2$, 30 $nm^2$, 20 $nm^2$, or 10 $nm^2$). In some instances, the PMP may include a plant EV, or segment, portion, or extract thereof, that has a mean volume less than that of an intact vesicle, e.g., a mean volume of less than 65 $nm^3$, 100 $nm^3$, 1000 $nm^3$, $1 \times 10^4$ $nm^3$, $1 \times 10^5$ $nm^3$, $1 \times 10^6$ $nm^3$, $1 \times 10^7$ $nm^3$, $1 \times 10^8$ $nm^3$, or $5.3 \times 10^8$ $nm^3$).

In instances where the PMP includes an extract of a plant EV, e.g., in instances where the PMP includes lipids extracted (e.g., with chloroform) from a plant EV, the PMP may include at least 1%, 2%, 5%, 10%, 20%, 30%, 40%, 50%, 60% or more, of lipids extracted (e.g., with chloroform) from a plant EV. The PMPs in the plurality may include plant EV segments and/or plant EV-extracted lipids or a mixture thereof.

Further outlined herein are details regarding methods of manufacturing PMPs, PMP bioreactors, plant EV markers that can be associated with PMPs, and formulations for compositions including PMPs.

A. Production Methods

The production methods and bioreactors described herein permit industrial and/or large-scale production of PMPs. PMPs may be manufactured using plant EVs, or a segment, portion or extract (e.g., lipid extract) thereof, that have been released from cultures of plants, plant parts, plant tissues, or plant cells (e.g., in a plant cell culture or a hydroponic culture in a bioreactor). For example, PMPs may be manufactured by a method involving (a) obtaining a culture medium in which a plant, a plant part, or a plant cell has been cultured; and (b) purifying PMPs from the culture medium. In another example, PMPs may be manufactured by a method involving (a) culturing a plant, a plant part, or a plant cell in a culture medium; (b) harvesting the culture medium; and (c) purifying PMPs from the culture medium.

Each manufacturing step is discussed in further detail, below.

PMPs can be produced from plants, plant parts, or plant cells or tissues using a variety of methods. Any method that allows release of the EVs from the intracellular region of a plant cell, from the EV-containing apoplastic fraction of a plant (e.g., plant tissue or plant part), or an otherwise extracellular fraction that contains secreted EVs (e.g., a culture medium) is suitable in the present methods. EVs can be released by either destructive (e.g., grinding or blending of a plant, or any plant part (e.g., cell or tissue)) or non-destructive (washing or vacuum infiltration of a plant or any plant part (e.g., cell or tissue)) methods. For instance, the plant, or part thereof (e.g., cell or tissue), can be vacuum-infiltrated, ground, blended, or a combination thereof to release EVs from the plant or plant part (e.g., cell or tissue). For instance, the releasing step may involve (b) providing a plant, or a part thereof (e.g., cell or tissue), wherein the releasing step involves vacuum infiltrating the plant (e.g., with a vesicle isolation buffer) to release and collect the apoplastic fraction. Alternatively, the releasing step may involve (b) providing a plant, or a part thereof (e.g., cell or tissue), wherein the releasing step involves grinding or blending the plant to release the EVs.

Exemplary methods regarding the isolation and purification of PMPs is found, for example, in Rutter and Innes, *Plant Physiol.* 173 (1): 728-741, 2017; Rutter et al, *Bio. Protoc.* 7 (17): e2533, 2017; Regente et al, *J of Exp. Biol.* 68 (20): 5485-5496, 2017; Mu et al, *Mol. Nutr. Food Res.*, 58, 1561-1573, 2014, and Regente et al, *FEBS Letters.* 583: 3363-3366, 2009, each of which is herein incorporated by reference.

The crude PMP fraction can be further purified by additional purification methods to produce a PMP composition. For example, the crude PMP fraction can be separated from other plant components by ultracentrifugation, e.g., using a density gradient (iodixanol or sucrose) and/or use of other approaches to remove aggregated components (e.g., precipitation or size-exclusion chromatography). The resulting pure plant PMP fractions may have a decreased level of contaminants (e.g., one or more non-PMP components, such as protein aggregates, nucleic acid aggregates, protein-nucleic acid aggregates, free lipoproteins, lipido-proteic structures), nuclei, cell wall components, cell organelles, or a combination thereof) relative to one or more fractions generated during the earlier separation steps, or relative to a pre-established threshold level, e.g., a commercial release specification. For example, the pure PMPs may have a decreased level (e.g., by about 5%, 10%, 15%, 20%, 30%, 40%, 50%, 60%, 70%, 80%, 90%, 100%, or more than 100%; or by about 2-fold, 4-fold, 5-fold, 10-fold, 20-fold, 25-fold, 50-fold, 75-fold, 100-fold, or more than 100-fold) of plant organelles or cell wall components relative to the level in the initial sample. In some instances, the pure PMP fraction is substantially free (e.g., has undetectable levels) of one or more non-PMP components, such as protein aggregates, nucleic acid aggregates, protein-nucleic acid aggregates, free lipoproteins, lipido-proteic structures), nuclei, cell wall components, cell organelles, or a combination thereof. Further examples of the releasing and separation steps can be found in Example 1. The PMPs may be at a concentration of, e.g., $1\times10^9$ PMPs/mL, $5\times10^9$, $1\times10^{10}$, $5\times10^{10}$, $5\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, or more than $1\times10^{13}$ PMPs/mL.

Protein aggregates may also be removed from PMPs. For example, the PMPs can be taken through a range of pHs (e.g., as measured using a pH probe) to precipitate protein aggregates in solution. The pH can be adjusted to, e.g., pH 3, pH 5, pH 7, pH 9, or pH 11 with the addition of, e.g., sodium hydroxide or hydrochloric acid. Once the solution is at the specified pH, it can be filtered to remove particulates. Alternatively, the PMPs can be flocculated using the addition of charged polymers, such as Polymin-P or Praestol 2640. Briefly, Polymin-P or Praestol 2640 is added to the solution and mixed with an impeller. The solution can then be filtered to remove particulates. Alternatively, aggregates can be solubilized by increasing salt concentration. For example, NaCl can be added to the PMPs until it is at, e.g., 1 mol/L. The solution can then be filtered to isolate the PMPs. Alternatively, aggregates are solubilized by increasing the temperature. For example, the PMPs can be heated under mixing until the solution has reached a uniform temperature of, e.g., 50° C. for 5 minutes. The PMP mixture can then be filtered to isolate the PMPs. Alternatively, soluble contaminants from PMP solutions can be separated by size-exclusion chromatography column according to standard procedures, where PMPs elute in the first fractions, whereas proteins and ribonucleoproteins and some lipoproteins are eluted later. The efficiency of protein aggregate removal can be determined by measuring and comparing the protein concentration before and after removal of protein aggregates, for example, via BCA/Bradford protein quantification.

Any of the production methods described herein can be supplemented with any quantitative or qualitative methods known in the art to characterize or identify the PMPs at any step of the production process. PMPs may be characterized by a variety of analysis methods to estimate PMP yield, PMP concentration, PMP purity, PMP composition, or PMP sizes. PMPs can be evaluated by a number of methods known in the art that enable visualization, quantitation, or qualitative characterization (e.g., identification of the composition) of the PMPs, such as microscopy (e.g., transmission electron microscopy), dynamic light scattering, nanoparticle tracking, spectroscopy (e.g., Fourier transform infrared analysis), or mass spectrometry (protein and lipid analysis). In certain instances, methods (e.g., mass spectroscopy) may be used to identify plant EV markers present on the PMP, such as markers disclosed in the Appendix. To aid in analysis and characterization, of the PMP fraction, the PMPs can additionally be labelled or stained. For example, the EVs can be stained with 3,3'-dihexyloxacarbocyanine iodide ($DIOC_6$), a fluorescent lipophilic dye. In the absence of sophisticated forms of nanoparticle tracking, this relatively simple approach quantifies the total membrane content and can be used to indirectly measure the concentration of PMPs (Rutter and Innes, *Plant Physiol.* 173 (1): 728-741, 2017; Rutter et al, *Bio. Protoc.* 7 (17): e2533, 2017). For more precise measurements, and to assess the size distributions of PMPs, nanoparticle tracking can be used.

During the production process, the PMPs can optionally be prepared such that the PMPs are at an increased concentration (e.g., by about 5%, 10%, 15%, 20%, 30%, 40%, 50%, 60%, 70%, 80%, 90%, 100%, or more than 100%; or by about 2-fold, 4-fold, 5-fold, 10-fold, 20-fold, 25-fold, 50-fold, 75-fold, 100-fold, or more than 100-fold) relative to the PMP level in a control or initial sample. The PMPs may make up about 0.1% to about 100% of the PMP composition, such as any one of about 0.01% to about 100%, about 1% to about 99.9%, about 0.1% to about 10%, about 1% to about 25%, about 10% to about 50%, or about 50% to about 99%. In some instances, the composition includes at least any of 0.1%, 0.5%, 1%, 5%, 10%, 20%, 30%, 40%, 50%, 60%, 70%, 80%, 90%, 95%, or more PMPs, e.g., as measured by wt/vol, percent PMP protein composition, and/or percent lipid composition (e.g., by measuring fluorescently labelled lipids); See, e.g., Example 3). In some instances, the concentrated agents are used as commercial products, e.g., the final user may use diluted agents, which have a substantially lower concentration of active ingredient. In some embodiments, the composition is formulated as an agricultural concentrate formulation, e.g., an ultra-low-volume concentrate formulation.

As illustrated by Example 1, PMPs can be produced using a variety of plant cell cultures.

As illustrated by Example 2, PMPs can be purified by a variety of methods, for example, by using a density gradient (iodixanol or sucrose) in conjunction with ultracentrifugation and/or methods to remove aggregated contaminants, e.g., precipitation or size-exclusion chromatography. For instance, Example 2 illustrates purification of PMPs that have been purified via the separation steps outlined in Example 1. Further, PMPs can be characterized in accordance with the methods illustrated in Example 3.

The PMP can be modified or loaded with a heterologous agent prior to use, as outlined further herein.

B. Plant Cultures

PMPs may be obtained from a variety of plant cultures, e.g., a plant cell culture or tissue culture or a culture comprising entire plants or plant parts (e.g., a hydroponic culture).

As used herein, the term "plant culture" refers to a plurality of plant cells, plant parts, plants (e.g., entire plants), or plant tissue that is propagated in or on a liquid, gel, semi-solid, or solid medium. Plant cultures include, but are not limited to, cultures of naturally occurring plants, plant parts, plant cells, or plant tissue or genetically modified plants, plant parts, plant cells, or plant tissues.

i. Sources of Plant Cultures

Plant cultures can be obtained from many plant species, e.g., tobacco, corn, wheat, soybean, crop wild relatives (e.g., teosinte), tropical species, tomato, rice, grapefruit, *ginseng*, carrot, sunflower, ginger, potato, moss, grasses, green algae, common vetch, medicinal plants, and extremophiles. For example, PMPs may be produced from a plant culture obtained from any genera of plants (vascular or nonvascular), including but not limited to angiosperms (monocotyledonous and dicotyledonous plants), gymnosperms, ferns, selaginellas, horsetails, psilophytes, lycophytes, algae (e.g., unicellular or multicellular, e.g., Archaeplastida, *Botryococcus*, or *Chlorella*), or bryophytes. In certain instances, PMPs can be produced using a plant culture obtained from a vascular plant, for example monocotyledons or dicotyledons or gymnosperms. For example, PMPs can be produced from plant cell culture, tissue culture, or cultured plants or plant parts obtained from alfalfa, apple, *Arabidopsis*, banana, barley, canola, castor bean, chicory, *chrysanthemum*, clover, cocoa, coffee, cotton, cottonseed, corn, *crambe*, cranberry, cucumber, dendrobium, *dioscorea, eucalyptus*, fescue, flax, *gladiolus*, Liliaceae, linseed, millet, muskmelon, mustard, oat, oil palm, oilseed rape, *papaya*, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat or vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, *crambe*, flax, linseed, mustard, oil palm, oilseed rape, peanut, potato, rice, safflower, sesame, soybean, sugarbeet, sunflower, tobacco, tomato, or wheat. In some examples, PMPs are produced from plant culture (e.g., cultured plants, plant parts, or plant cells) obtained from a member of the Brassicaceae (such as *Arabidopsis* or *Brassica napus*), tomato, tobacco (e.g., tobacco BY-2 cells), rice, *Setaria viridis* (Indian goosegrass), soybean, fava bean, barley, or oat.

PMPs may be produced using plant culture consisting of or obtained from entire plants or from one or more plant parts (e.g., leaf, seed, root, radicle, root hair, shoot, stem, hypocotyl, flower, fruit, vegetable, pollen), including shoot vegetative organs/structures (e.g., leaves, stems, hypocotyls, rhizomes, or tubers), roots (e.g., primary roots, secondary roots, radicles, root hairs, or root nodules), flowers and floral organs/structures (e.g., pollen, bracts, sepals, petals, stamens, carpels, anthers, or ovules), seed (including embryo, endosperm, or seed coat), spores, fruit (including mature ovaries and associated tissues, e.g., receptacle, hypanthium, or perianth), sap (e.g., phloem or xylem sap), vascular tissue, ground tissue, tumor tissue, single cells, protoplasts, embryos, callus tissue, guard cells, egg cells, or progeny of same.

Further examples of plants that grow readily in culture (e.g., as whole plant, plant parts, or plant cell lines) include *Arabidopsis thaliana* (cress), *Allium sativum* (garlic) *Taxus chinensis, T. cuspidata, T. baccata, T. brevifolia, T. mairei* (yew), Catharanthus *roseus* (periwinkle), *Nicotiana benthamiana* (Solanaceae), *N. tabacum* (tobacco) including tobacco cells lines such as NT-I or BY-2 (NT-I cells are available from ATCC, No. 74840, see also U.S. Pat. No. 6,140,075), *Oryza sativa* (rice), *Lycopersicon esculentum* (tomato), *Medicago sativa* (alfalfa), *Glycine max* (soybean), *Medicago truncatula* and *M. sativa* (clovers), *Phaseolus vulgaris* (bean), *Solanum tuberosum* (potato), *Beta vulgaris* (beet), *Saccharum* spp. (sugarcane), *Tectona grandis* (teak), *Musa* spp. (banana), *Phyllostachys nigra* (bamboo), *Vitis vinifera* or *V. gamay* (grape), *Populus alba* (poplar), *Elaeis guineensis* (oil palm), *Ulmus* spp. (elm), *Thalictrum minus* (meadow rue), *Tinospora cordifolia, Vinca rosea* (vinca), *Sorghum* spp., *Lolium perenne* (ryegrass), *Cucumis sativus* (cucumber), *Asparagus officinalis*, Bruceajavanica (Yadanxi), Doritaenopsis or *Phalaenopsis* (orchids), *Rubus chamaemorus* (cloudberry), Cojfea *arabica, Triticum timopheevii* (wheat), *Actinidia deliciosa* (kiwi), *Typha latifolia* (cattail), *Azadirachta indica* (neem), *Uncaria tomentosa* or *U. guianensis* (cat's claw), *Platycodon grandiflorum* (balloon flower), *Calotropis gigantea* (mikweed), *Kosteletzkya virginica* (mallow), *Pyrus malus* (apple), *Papaver somniferum* (opium poppy), *Citrus* ssp., *Choisya ternata* (mock orange), *Galium mollugo* (madder), *Digitalis lanata* or *D. purpurea* (foxglove), *Stevia rebaudiana* (sweetleaf), *Stizolobium hassjoo* (purselane), *Panicum virgatum* (switchgrass), *Rudgea jasminoides, Panax quinquefolius* (American *ginseng*), *Cupressus macrocarpa* or *C. arizonica* (cypress), *Vetiveria zizanioides* (vetiver grass), *Withania somnifera* (Indian *ginseng*), *Vigna unguiculata* (cowpea), *Phyllanthus niruri* (spurge), *Pueraria tuberosa* or *P. lobata* (kudzu), *Glycyrrhiza echinata* (liquorice), *Cicer arietinum* (chick pea), *Silybum marianum* (milk thistle), *Callistemon citrinus* (bottle brush tree), *Astragalus chrysochlorus* (cuckoo flower), *Coronilla vaginalis*, such as cell line 39 RAR (crown vetch), *Salvia miltiorrhiza* (red sage), *Vigna radiata* (mung bean), *Gisekia pharnaceoides, Datura tatula* or *D. stramonium* (devil's trumpet), and *Zea mays* spp. (maize/corn).

The plants, plant parts, plant cells, or plant tissue can be genetically modified. As used herein, the term "genetically modified plant culture" refers to a plant culture in which the plant, plant part, plant cell, or plant tissue has been genetically altered (e.g., to have increased or decreased expression of an endogenous nucleic acid, to modify the nucleotide sequence of an endogenous nucleic acid, or to express an exogenous gene) using any methods known in the art (e.g., delivery a nucleic acid or (e.g., a heterologous DNA or RNA) or a gene editing protein system (e.g., CRISPR-Cas system, TALEN, or zinc finger)). In certain instances, the genetically modified plant, plant part, plant cell, or plant tissue contains a genetic modification that is effective to increase plant EV production in the plant, plant part, plant cell, or plant tissue relative to an unmodified plant, plant part, plant cell, or plant tissue. Technology for introducing nucleic acids into plants or plant cellsis well-known to those of skill in the art, and includes *Agrobacterium*-mediated techniques as well as other techniques involving the uptake of exogenous genetic material by the plant, such as PEG- or electroporation-mediated uptake, particle bombardment-mediated delivery, and/or microinjection.

ii. Cultures Comprising Plants

Plant cultures include cultures comprising entire plants, e.g., entire embryos, seedlings, juvenile plants, or adult plants of any of the plant species described herein. Cultures comprising entire plants may be grown in or on any suitable medium, e.g., a liquid, gaseous, gel, semi-solid, or solid medium. In some examples, seedlings, juvenile plants, or adult plants (e.g., tomato plants, *Arabidopsis thaliana* plants, rice plants, or *Setaria viridis* plants) are cultured in a hydroponic system, as described herein. Cultures comprising entire plants may be grown in a bioreactor. The plants may be germinated in the hydroponic system, or may be introduced to the hydroponic system at any stage of growth. The entire plant or only a portion of the plant (e.g., a root system of the plant) may be exposed to the culture medium.

iii. Cultures Comprising Plant Parts

Plant cultures include cultures comprising plant parts. Plant parts include, but are not limited to leaves (e.g., leaf blade, leaflet, phyllode, or petiole), seeds (including embryo, endosperm, or seed coat), roots (e.g., primary roots, secondary roots, radicles, root hairs, or root nodules), shoot vegetative organs/structures (e.g., leaves, stems, hypocotyls, rhizomes, or tubers), flowers and floral organs/structures (e.g., pollen, bracts, sepals, petals, stamens, carpels, anthers, or ovules), fruits (including mature ovaries and associated tissues, e.g., receptacle, hypanthium, or perianth), vegetables, pollen, seeds, spores, sap (e.g., phloem or xylem sap), or plant tissues (e.g., vascular tissue, ground tissue, parenchyma, sclerenchyma, collenchyma, or tumor tissue). Cultures comprising plant parts may be grown in or on any suitable medium, e.g., a liquid, gaseous, gel, semi-solid, or solid medium. In some examples, plant parts are cultured in a hydroponic system, as described herein. Cultures comprising plant parts may be grown in a bioreactor. In some examples, roots (e.g., *Arabidopsis thaliana* roots) are cultured in a liquid culture medium (e.g., root culture). In some examples, the roots are not associated with a shoot portion of a plant. The root culture may be a hairy root culture, e.g., a root culture that has been induced to have indefinite growth by contacting with a root-inducing (Ri) plasmid of *Rhizobium rhizogenes*.

iv. Plant Cell Cultures

Plant cell cultures include unorganized cell cultures, in which a plurality of the cultured cells are not organized into a tissue or organ of a multicellular plant, such as a leaf, root, shoot, or reproductive structure of a multicellular plant. Exemplary unorganized cell cultures include callus culture, cell suspension culture, and protoplast culture. Plant cell cultures also include single-celled plants, e.g., single-celled plastid-containing organisms such as algae. In some examples, the plant cell culture is a tobacco BY-2 cell culture, e.g., a tobacco BY-2 cell culture in a liquid culture medium. In some instances, plant cell cultures are derived from callus tissue. A callus refers to an unorganized cell mass containing a plurality of undifferentiated cells (e.g., parenchyma cells) or cells derived therefrom. Several classes of callus exist. Calli that display some degree of organ regeneration are termed embryonic callus, rooty callus, or shooty callus depending on the organs regenerated. Calli that do not display organ regeneration may be compact callus (cells are densely aggregated) or friable callus (cells are easily separated from one another).

In some instances, callus tissues are derived from plant tissue explants (e.g., excised plant parts). Explants may be entire or partial plant parts including embryos, somatic embryos, meristematic regions, root tips, axillary buds, callus tissue, single cells, filaments, leaves, stems, flowers, stigmas, roots, rhizomes, tubers, shoots, gametophytes, sporophytes, pollen, seeds, microspores, megaspores, fruit, and tumor tissue. Explants can be surface sterilized (e.g. by rinsing, wiping, or immersion) using agents such as sodium hypochlorite, mercuric chloride, and alcohol. Aseptically grown seedlings (e.g., seedlings grown in sterile conditions from surface-sterilized seeds) may also be used as explants for the production of callus.

In instances in which plant cell cultures are derived from explants, said explants are induced to form callus. Those skilled in the art will recognize that the conditions favoring callus formation differ among species, genotypes, or plant tissues. Methods for inducing callus include the application of plant hormones. Often, an auxin (e.g., 2,4-D, IAA, NAA, IBA) and a cytokinin (e.g., kinetin, BA, zeatin, 2iP) are used in combination. Brassinosteroids and abscisic acid may also be used. Plant hormones that induce callus are often delivered to the plant by inclusion in callus-inducing medium (CIM). This medium often also contains inorganic salts and vitamins (e.g., Millipore Sigma Murashige and Skoog basal salt mixture), a carbohydrate source (e.g., sucrose, glucose, fructose, sorbitol, mannitol), and a support matrix, e.g., agar, filter paper, cotton, vermiculite. Antibiotics, such as fungicides and bactericides, may also be included in the medium. Other conditions that may affect the formation of callus include temperature, light conditions, and orientation of the explant. Alternately, callus may be induced by wounding and or pathogen infection (e.g., crown gall tumors induced by the bacterium *Agrobacterium tumefaciens*). Callus that has been induced from an explant may be separated from the explant, e.g., by cutting away explant tissue or by transplanting all or a subset (one or more cells) of the callus tissue to a separate substrate, to provide callus for use in plant cell culture. In instances in which friable callus cells are grown in liquid media, these cells may be shaken or agitated in said liquid media to disperse the callus structure into single cells or small cell aggregates (homogenization). A sieve may be used to remove large cell aggregates.

C. Methods of Plant Cell Culture i. Growth Substrates

In some instances, plant cultures (e.g., plant cell cultures, cultures comprising plant parts, or cultures comprising entire plants) may be grown on solid, semi-solid, or gel substrates. Solid substrates for plant cultures may include agar, agarose, filter paper, cotton, vermiculite, sterile natural soils, or sterile synthetic soils. Plant cultures on solid substrate may be exposed to a medium by methods including soaking, spraying, or direct incorporation of the medium into the substrate (e.g., agar). Plant cultures are generally maintained in sterile (aseptic) conditions. Those of skill in the art will be familiar with techniques to maintain sterility, including the use of laminar flow cabinets and sterilization (e.g. autoclaving, flame sterilization) of equipment.

In other instances, plant cultures (e.g., plant cell cultures, cultures comprising plant parts, or cultures comprising entire plants) may be grown in liquid culture medium, as described herein. Plant cultures in a liquid medium may be contained in a variety of vessels including flasks, tubes, and bottles. Plant cultures may be contained in a bioreactor, as described herein.

ii. Bioreactor Vessels

As used herein, the term "bioreactor" refers to a culture vessel with a capacity of at least 1 L (e.g., at least 2 L, 3 L, 4 L, 5 L, at least 10 L, at least 20 L, 30 L, 50 L, at least 100 L, at least 200 L, 250 L, 500 L, 750 L, or at least 1000 L) that allows for culturing, propagating, cultivating, maintaining, or storing of plants, e.g., entire plants, plant parts, plant cells, or plant tissue, under controlled conditions (e.g., one or more of: controlled sterility, mixing rate, temperature, light, oxygen supply, and/or nutrient medium). Any of the plant, plant part, or plant cell culture methods described herein may be performed in a bioreactor. Typically, bioreactors are useful for culturing plant cells or callus.

A variety of bioreactors may be used to manufacture PMPs. Such a bioreactor may include a vessel that may be a closed or open system having several possible shapes, such as a vat, tank, flask, tube, jar, or bag. The vessel may be composed of a suitable material (e.g., glass, plastic, or metal). In some instances, the vessel may be reusable, e.g., an Eppendorf BioFlo® 120 vessel. Reusable vessels may be sterilized between uses by, for example, autoclaving or the use of heated steam. Alternatively, the vessel may be single-use (e.g., CELL-tainer® Single-use Bioreactor Bag, WAVE® Bioreactor System 200, Flexsafe® RM Bag). The vessel may be a fermenter.

Bioreactors with a variety of volume capacities may be used to culture a plant culture to manufacture PMPs. For example, the bioreactor may have a capacity of at least 1 L (e.g., at least 1 L, at least 2 L, at least 5 L, at least 10 L, at least 50 L, at least 100 L, at least 200 L, at least 300 L, at least 400 L, at least 500 L, at least 600 L, at least 700 L, at least 800 L, at least 900 L, at least 1000 L, at least 2000 L, at least 3000 L, at least 4000 L, at least 5000 L, at least 6000 L, at least 7000 L, at least 8000 L, at least 9000 L, at least 10,000 L, or more than 10,000 L). In some instances, the bioreactor has a capacity of about 1 L to about 10 L, about 10 L to about 50 L, about 50 L to about 100 L, about 100 L to about 500 L, about 500 L to about 1000 L, about 1000 L to about 5000 L, about 5000 L to about 10,000 L.

The bioreactor vessel may include sterile components for adding and/or removing culture medium and/or cultured plants, plant parts, or plant cells, such as sterile feeder vessels aseptically connected to the bioreactor vessel, sterile filter sampling probes (e.g., FISP® in-situ Ceramic Membrane Bioreactor Sampling Probes), and addition ports for use with sterile needles. Those of skill in the art are familiar with techniques to maintain sterility. Alternatively, samples can be taken directly from the bioreactor vessel by opening the bioreactor in a sterile environment, e.g., a laminar flow hood.

iii. Hydroponic Systems

In some instances, the plant culture (e.g., plant cultures comprising plant parts or cultures comprising entire plants) is grown in a hydroponic system. For some applications, the hydroponic system may be a bioreactor. A hydroponic system provides nutrients to plants via a culture medium other than a natural soil. Exemplary hydroponic systems expose the roots of a plant to a culture medium (e.g., a liquid culture medium) comprising nutrients, e.g., defined nutrients. Plants or plant parts may be suspended or supported such that only a portion of the plant or plant part, e.g. a root or a radicle, is contacted by the culture medium. The hydroponic system may be, e.g., a static solution culture, a continuous-flow solution culture, a culture using a nutrient film technique, an aeroponic culture, a fogponic culture, a passive sub-irrigation culture, a, ebb and flow sub-irrigated culture, a deep water culture, or a rotary culture. Hydroponic systems include hydroculture systems (e.g., passive hydroponic (i.e., wick) systems engineered according to standard methods). The hydroponic system may comprise an inert growing medium, e.g., clay, lightweight expanded clay aggregates (LECA), vermiculite, gravel, perlite, or rock wool.

The hydroponic system may have a capacity of at least 1 L (e.g., at least 1 L, at least 2 L, at least 5 L, at least 10 L, at least 50 L, at least 100 L, at least 200 L, at least 300 L, at least 400 L, at least 500 L, at least 600 L, at least 700 L, at least 800 L, at least 900 L, at least 1000 L, at least 2000 L, at least 3000 L, at least 4000 L, at least 5000 L, at least 6000 L, at least 7000 L, at least 8000 L, at least 9000 L, at least 10,000 L, or more than 10,000 L). In some instances, the hydroponic system has a capacity of about 1 L to about 10 L, about 10 L to about 50 L, about 50 L to about 100 L, about 100 L to about 500 L, about 500 L to about 1000 L, about 1000 L to about 5000 L, about 5000 L to about 10,000 L.

In one aspect, included herein is a method for producing plant messenger packs, the method including (a) culturing a plant or plant part in a hydroponic system; (b) harvesting the culture medium, and (c) purifying PMPs from the culture medium.

In another aspect, included herein is a method for producing plant messenger packs, the method including (a) culturing a plant or plant part in a hydroponic system; (b) exposing the plant or plant part to an effective amount of a stimulant to increase PMP production; (c) harvesting the culture medium, and (d) purifying PMPs from the culture medium.

iv. Culture Medium

The bioreactor vessel (e.g., the vessel containing a plant cell culture or a hydroponic culture) may further contain a culture medium. The culture medium may be a liquid, gel, semi-solid, solid, or aerosolized solution containing factors involved in plant cell growth. The culture medium may contain a support matrix, e.g., agar, agarose, or gellan gum. The culture medium may contain one or more carbon sources, e.g., sucrose, glucose, fructose, sorbitol, or mannitol. Concentration of the carbon source may vary between 0 and greater than 50 grams per liter (e.g., greater than 0 grams per liter, 10 grams per liter, 20 grams per liter, 30 grams per liter, 40 grams per liter, or 50 grams per liter). The culture medium may contain one or more macronutrients, e.g., carbon (C), hydrogen (H), oxygen (O), nitrogen (N), phosphorus (P), potassium (K), calcium (Ca), magnesium (Mg), or sulfur(S). The culture medium may contain one or more micronutrients, such as iron (Fe), manganese (Mn), zinc (Zn), copper (Cu), molybdenum (Mo), iodine (I), boron (B), cobalt (Co), aluminum (Al), nickel (Ni), sodium(S), silicon (Si), or chlorine (Cl). The culture medium may contain one or more organic supplements, possibly including amino acids (e.g., Ala, Arg, Asn, Cys, His, Ile, Leu, or Met), vitamins, and other cofactors (e.g., myo-Inositol, thiamine, pyridoxine, folic acid, ascorbic acid, tocopherol, yeast extracts, or peptone). The culture medium may contain one or more salts. An exemplary culture medium is Millipore Sigma Murashige and Skoog basal salt mixture. In some instances, the culture medium may contain one or more plant growth factors, e.g., phytohormones and/or artificial growth regulators, e.g., IAA, 2,4-D, NAA, IBA, 2,4,5-T, kinetin, BAP, zeatin, purine, adenine, GA3, GA4, GA7, or ABA. The culture medium may also contain negative regulators of growth, such as paclobutrazol or anzymidrol. In some examples, the culture medium includes one or more enzymes. In some examples, the culture medium includes one or more pesticidal agents, e.g., one or more of the antibiotic or antifungal agents described in Section IIIA herein. The culture medium may be a fully defined medium, e.g., a medium wherein all its chemical components are known.

Further, the culture medium may include one or more stimulants, such as those outlined in Section ID herein. Additionally or alternatively, the culture medium may contain one or more heterologous functional agents to be incorporated into the PMPs, such as those described in Section III herein. In some instances, the culture medium includes one or more plant EV stimulants and one or more heterologous functional agents, wherein the heterologous functional agents are incorporated into the PMPs.

v. Culture Conditions and Modes of Culture

A plant, plant cell, or plant part may be cultured in a bioreactor (e.g., in plant cell culture or in a hydroponic system) for any suitable period of time, e.g., less than one day, at least one day, two days, three days, four days, five days, six days, seven days, one week, two weeks, three weeks, one month, two months, three months, four months, five months, six months, one year, or more than one year. In some examples, a plant is cultured in a bioreactor (e.g., a hydroponic system) for all or a part of its life cycle (e.g., one, more than one, or all of germination, a seedling phase, a juvenile phase, phase change, an adult phase, flowering, fruiting, or senescence).

In some instances, plants, plant parts, or plant cells may be continuously immersed in the culture medium (e.g., a liquid phase bioreactor or a submerged bioreactor). In other instances, immersion of plants, plant parts, or plant cells in the culture medium may be intermittent (e.g., ebb and flood bioreactors, ebb and flow bioreactors (e.g., ebb and flow hydroponic systems)). In such bioreactors, the plants, plant parts, or plant cells are alternately immersed in a medium and exposed to a gas composition. The duration and frequency of immersion may vary. In other instances, cells may be exposed to a medium in the form of a fog, mist, spray or aerosol (e.g., nutrient spray bioreactors, mist bioreactors).

Several modes of culture may be used in the bioreactor. For example, the bioreactor may be used to grow a batch culture, a fed-batch culture, a continuous culture, or a semi-continuous culture (e.g., culture in which the culture medium is periodically harvested and replaced). In batch culture, plants, plant parts, or plant cells are allowed to grow in a fixed volume of culture medium for the duration of growth. In fed-batch culture, plants, plant parts, or plant cells are started in a given volume of culture medium, and more medium is added over time (continuously or in stepwise increments). In continuous culture, culture volume is held constant because fresh growth medium is added and plant culture and/or culture medium is discarded at commensurate volumes.

During semi-continuous culture, plants, plant parts, or plant cells are retained in the bioreactor while all or a portion of the culture medium is removed (e.g., harvested) and replaced. The culture medium may be removed (e.g., harvested) and replaced at any appropriate interval, e.g., once every day, every two days, every three days, every four days, every five days, every six days, every week, every two weeks, every month, or at intervals of greater than a month. Alternatively, the culture medium may be harvested and replaced when the culture is at a particular condition, e.g., when the density of the culture reaches a threshold level. When designing a medium exchange device for plant cultures, long-term (3-4 months) operation with repeated cycles is considered.

In some instances, the culture may be aerated. The gas composition used in aeration may include $O_2$, $CO_2$, N, Ar, and $C_2H_4$. Oxygen concentration in the gas composition may be 10-100% (v/v), e.g., 10%, 20%, 30%, 40%, 50%, 60%, 70%, 80%, 90%, or 100%. The culture may be aerated, for example, by gas spargers positioned in the bioreactor vessel (e.g., ring, pipe, plate, or frit spargers, ceramic porous spargers, sintered steel porous spargers). Aeration rates can range from, e.g., greater than 0.001 vvm (volume of air (e.g. liter) per unit of medium (e.g. liter) per unit of time (e.g. minute)) to greater than 2 vvm, e.g., greater than 0.001 vvm, 0.01 vvm, 0.1 vvm, 1 vvm, 2 vvm. In other instances, the culture may be aerated by exposure to ambient air, e.g. via a gas-permeable material exposed to a headspace above the culture.

In some instances, the culture may be mixed. Methods of mixing may include mechanical stirring (e.g., marine impellers, helical ribbon impellers, anchor impellers, pitched blade impellers, Rushton impellers, spiral stirrers, magnetic stirrers, vibrating perforated plates), the use of bubble columns (i.e., gas sparging of a column-shaped vessel), the use of airlift reactors (i.e., gas sparging in a vessel with channels that are physically separated, e.g. by a baffle, concentric cylinder, or external loop, creating upward and downward flow of gas and liquid), external agitation (e.g., placement on a shaking or rocking plate) and combinations thereof. Mixing may be intermittent or continuous.

In some instances, the culture contained in the bioreactor vessel may be periodically or continuously exposed to light. Light intensity may be between 0 and 20 kilolux (Klux), e.g., greater than 0 Klux, 5 Klux, 10 Klux, 15 Klux, or 20 Klux. Wavelengths of light may include 100 nm-100 µm (ultraviolet, visible, and infrared light). Sources of light may be external (e.g. fluorescent lamps, halogen bulbs, metal halide bulbs, light-emitting diodes, solid-state lamps, or sunlight) or internal to the reactor (e.g. encapsulated lamps, or fiber optic cables). Photoperiod (duration of illumination per 24-hour day) may be between 0 hours (no light exposure) and 24 hours (continuous light exposure), e.g., 0 hours, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours).

The bioreactor can be set at a variety of temperatures. In some instances, the temperature may be controlled such that the culture medium and/or ambient temperature is a temperature optimal for growth or viability of a particular plant, plant part, or plant cell. For example, in some instances, the temperature of the culture in the bioreactor vessel is 21-30° C., e.g., 21° C., 22° C., 23° C., 24° C., 25° C., 26° C., 27° C., 28° C., 29° C., 30° C. One skilled in the art will appreciate that the optimal temperature for growth will depend on the type of plant or plant part, type of plant cell, or type of plant tissue. In other instances, the temperature can be set at a temperature optimal for stimulation of the production or secretion of EVs from the plant tissues and cells or optimal for maximizing the amount of PMPs that can be derived from the plant culture, as described in the section entitled "Stimulants." The temperature in the bioreactor can be regulated in a variety of ways, such as by a temperature control element contained in the vessel, a fluid-circulating jacket surrounding the vessel, or a heated pad underneath the vessel.

Further, the pH of the culture medium in the bioreactor may be set at any desired pH. In some instances, the pH may be controlled such that the culture medium is at a pH optimal for growth or viability of a particular plant, plant part, or plant cell. For example, in some instances, the pH of the culture may range from pH 3.5 to pH 7.5, e.g., greater than pH 3.5, 4.5, 5.5, 6.5, or 7.5). In other instances, the pH can be set at a pH optimal for stimulation of the production or secretion of EVs from the plant tissues and cells or optimal for maximizing the amount of PMPs that can be derived from the plant culture, as described in the section entitled "Stimulants." pH may evolve with the age and nutritional uptake of the culture. pH may be manually adjusted by the addition of pH-altering reagents (e.g., acids, bases).

Components to measure conditions of the culture may be present and may include thermometers, pH sensors, dissolved oxygen sensors, and dissolved $CO_2$ sensors. Measurements may be taken online (within the bioreactor vessel) or offline (in samples removed from the bioreactor vessel). The presence or absence of metabolites in the medium (e.g., sugars, nitrogen) may also be measured. One of skill in the art may use these measurements to assess the status of the culture.

In some cases, the growth of plant culture, e.g., plant cell culture, can be described as a sigmoid growth curve. Such a growth curve consists of a lag phase in which the plant, plant part, or plant cells proliferate slowly, a logarithmic growth phase in which the plant, plant part, or plant cells proliferate more quickly, a stationary or plateau phase at which nutrient availability limits growth rate, and a decline phase in which cell death predominates. Growth of plant cultures (e.g., plant cell cultures) may be measured as, for example, settled volume (e.g., settled cell volume), packed volume (e.g., packed cell volume), fresh weight (e.g., fresh cell weight), dry weight (e.g., dry cell weight), medium conductivity, or optical density.

The growth of plants, plant parts, or plant cells in the bioreactor can be determined in many different ways. For example, plant, plant part, or plant cell growth in culture can be determined by measuring the fractional volume of settled plants, plant parts, or plant cells (e.g., fractional settled cell volume (FSCV)), the fractional packed volume of plants, plant parts, or plant cells (e.g., fractional packed cell volume (FPCV)), or the biomass concentration. Fractional settled volume (e.g., FSCV) can be determined, e.g., by removing a sample of culture medium comprising plants, plant parts, or plant cells from the bioreactor vessel, allowing the plants, plant parts, or plant cells to settle in a container (e.g., for about ten minutes), and recording the volume of the settled plant, plant part, or plant cell phase. Alternatively, the fractional settled volume (e.g., FSCV) can be measured, e.g., directly in the bioreactor once agitation and aeration are turned off and the plants, plant parts, or plant cells are given time to settle through gravitational forces, if the interface between the clarified liquid and the settled plant, plant part, or plant phase can be visualized or measured. Fractional packed volume (e.g., FPCV) can be measured, e.g., by removing a sample of culture medium comprising plants, plant parts, or plant cells from the bioreactor vessel, centrifuging the sample, and recording the volume of packed plants, plant parts, or plant cells. Biomass concentration can be determined, e.g., by the grams of dry weight of plants, plant parts, or plant cells per liter of culture. Dry weight of plants, plant parts, or plant cells can be determined, e.g., by placing a sample containing plants, plant parts, or plant cells from the bioreactor vessel onto pre-weighed filter paper, removing medium by suction, washing the plants, plant parts, or plant cells with water, drying the plants, plant parts, or plant, and weighing them. In addition, one of skill can use a variety of methods to determine plant, plant part, or plant cell viability, e.g., by using oxygen uptake measurements or dye exclusion assays. For example, those of skill in the art can count viable cells in a plant cell culture using an appropriate dye and a hemocytometer.

A stimulant, such as those described in Section ID herein, can be introduced into the bioreactor (e.g., at any stage of the plant culture, e.g., at a lag phase, a logarithmic growth phase, or a stationary or plateau phase). For example, agents that are abiotic or biotic EV stimulants can be introduced in the plant culture medium at any point during plant cell or tissue growth. Additionally or alternatively, the conditions in the bioreactor (e.g., temperature, $CO_2$, or $O_2$) can be altered to expose the plant culture to an environmental condition that is a stimulant. Examples of stimulants useful in the present methods and bioreactors are further described in Section ID below.

vi. Scaling Up Cultures

In some cases, the plant culture may be scaled up in volume: in these cases, an initial volume of plant culture grown in a liquid, gel, or solid medium ("pre-culture"), (e.g., 0.25 L pre-culture, 0.5 L pre-culture, 1 L pre-culture, 2 L pre-culture, 3 L pre-culture, 4 L pre-culture, 5 L pre-culture, 6 L pre-culture, 7 L pre-culture, 8 L pre-culture, 9 L pre-culture, 10 L pre-culture) at a given density (e.g., cell density or density of a plant or plant part) (e.g., 10 g fw/L, 50 g fw/L, 100 g fw/L, 200 g fw/L, 400 g fw/L, 600 g fw/L) is added to a larger volume of growth medium (e.g., 5 L, 10 L, 20 L, 50 L, 100 L, 1000 L, 2000 L) and allowed to grow to a given density (e.g., 10 g fw/L, 50 g fw/L, 100 g fw/L, 200 g fw/L, 400 g fw/L, 600 g fw/L). This scaling-up step may be performed once in some instances. Alternatively, the culture may be scaled up in several steps, e.g., into progressively larger volumes of medium.

In instances where plant cultures are contained in a bioreactor, several modes of culture may be used, as described below. In batch culture, plants, plant parts, or plant cells are allowed to grow in a fixed volume of culture medium for the duration of growth. In fed-batch culture, plants, plant parts, or plant cells are started in a given volume of culture medium, and more medium is added over time (continuously or in stepwise increments). In continuous culture, culture volume is held constant because fresh growth medium is added and growth medium and/or plant culture is discarded at commensurate volumes.

vii. Exchanging and Harvesting Culture Medium

Culture medium can be exchanged or removed from the bioreactor vessel for a variety of reasons, including to induce EV production or secretion (e.g., by introducing a medium containing a stimulant), to harvest the culture medium or a portion thereof, or to restart growth of the plant, plant part, or plant cells after nutrient depletion. One of skill in the art will understand that medium exchange can be carried out in a variety of ways. For example, sterile medium can be added by filtration through a sterile filter. Culture medium can be removed from the bioreactor vessel by using a peristaltic pump to draw medium through a sterile tube welder from the bioreactor into flexible tubing, for example.

Removing culture medium from the bioreactor, e.g., harvesting culture medium, may comprise separating the culture medium from the plant, plant part, or plant cell. In some examples, the harvesting does not comprise disruption, e.g., mechanical disruption, lysis, or damage, of the plant, plant part, or plant cell. The separating may occur in the bioreactor, or may occur after culture medium comprising plants, plant parts, or plant cells has been removed from the bioreactor. Methods for separating culture medium from plants, plant parts, or plant cells include gravity sedimentation, centrifugation, spin filters, and membrane systems. Alternatively, plants, plant parts, or plant cells may be manually removed from the culture medium.

Since plant cells in culture medium typically grow as aggregates, rather than single cells, and have relatively low metabolic rates compared with microbial or mammalian cells, gravity sedimentation is a useful option for cell retention (e.g., separating cells from culture medium). Gravity sedimentation is a simple and reliable cell retention technique that minimizes contamination potential because it can be performed entirely within the bioreactor. When agitation and aeration cease, a clarified zone propagates from the liquid surface downward as the cell aggregates settle, leaving a clarified liquid phase on top of a settled-cell phase. This clarified liquid phase can then be drawn off and replaced with a different medium. Gravity sedimentation may also be used to separate entire plants or plant parts from culture medium.

In some examples, harvesting the culture medium involves juicing the culture medium, e.g., pressing (e.g., cold pressing) or centrifuging the culture medium, e.g., a gel, semi-solid, or solid culture medium. In other examples, harvesting the culture medium involves washing the culture medium (e.g., a gel, semi-solid, or solid culture medium), e.g., washing the culture medium with a solution or buffer to release PMPs from the culture medium. Plants, plant parts, or plant cells may be removed from the culture medium prior to harvesting, e.g., removed using any of the methods described herein.

In some examples, the culture medium is harvested continually or periodically throughout the culturing process. In other examples, the culture medium is harvested at one or more specific stages in the culturing process. For example, a culture medium of a plant cell culture may be harvested when the plant cell culture is at an exponential growth phase or a non-exponential growth phase, e.g., a lag phase, stationary phase, or death phase. In another example, a culture medium of a hydroponic system (e.g., a culture medium comprising a plant or plant part) may be harvested when the plant or plant part is undergoing germination, is at a seedling phase, a juvenile phase, phase change, or an adult phase, is flowering, is fruiting, is senescent, or has senesced.

D. Stimulants

In some examples, the PMP manufacturing methods described herein involve use of a stimulant. A stimulant is an agent (e.g., an abiotic stimulant, a biotic stimulant, a chemical elicitor, a nucleic acid stimulant, or a polypeptide stimulant) that, upon contact with a plant culture (e.g., in an effective amount and duration), increases the biogenesis (e.g., intracellular production or secretion, e.g., secretion into culture medium) of extracellular vesicles in the plant cell culture relative to an untreated plant cell culture, and/or increases the amount of PMPs that can be derived from the plant culture relative to an untreated culture. For example, the stimulant may increase biogenesis (e.g., intracellular production or secretion of extracellular vesicles) by about 1%, 2%, 3%, 4%, 5%, 10%, 15%, 20%, 30%, 40%, 50%, 60%, 70%, 80%, 90%, 100%, or more than 100%; or by about 2-fold, 4-fold, 5-fold, 10-fold, 20-fold, 25-fold, 50-fold, 75-fold, 100-fold, or more than 100-fold in the plant culture relative to an untreated plant culture. In another example, the stimulant may increase the amount of PMPs that can be derived from the plant culture, e.g., derived by the PMP purification methods described herein, by about 1%, 2%, 3%, 4%, 5%, 10%, 15%, 20%, 30%, 40%, 50%, 60%, 70%, 80%, 90%, 100%, or more than 100%; or by about 2-fold, 4-fold, 5-fold, 10-fold, 20-fold, 25-fold, 50-fold, 75-fold, 100-fold, or more than 100-fold in the plant culture relative to an untreated plant culture.

The plant culture may be exposed to the stimulant for any duration (e.g., at least 1 min, 5 min, 15 min, 30 min, 1 hr, 2 hr, 3 hr, 4 hr, 5 hr, 10 hr, 12 hr, 24 hr, 2 days, 3 days, 4 days, 6 days, 1 week, 2 weeks, 3 weeks, 1 month, or more than one month) and amount sufficient to promote EV biogenesis (e.g., intracellular production or secretion of extracellular vesicles) and/or increase the amount of PMPs that can be derived from the plant culture. One skilled in the art will appreciate that the amount of the stimulant with which the plant culture is contacted or exposed will depend on the specific stimulant used. The plant culture can be exposed to any number of different stimulants (e.g., at least 2, 3, 4, 5, 6, 7, 8, 9, or at least 10 kinds of stimulants).

The stimulant can be an abiotic stimulant, a biotic stimulant, and/or a chemical elicitor, such as those further described herein.

i. Abiotic Stimulant

In some instances, the stimulant is an abiotic stimulant. An abiotic stimulant refers to a non-living chemical and/or a physical factor that stimulates production of extracellular vesicles in a plant or part thereof (e.g., a plant culture, e.g., a plant cell culture or tissue culture, a culture comprising plant parts, or a culture comprising entire plants), e.g., by osmotic stress, drought, water deprivation, flood, high light intensity, very high light intensity, high temperature, low temperature, salinity, heavy metal toxicity, anaerobiosis, nutrient deficiency (e.g., nitrogen or phosphorus), nutrient excess, UV irradiation, atmospheric pollution (e.g., ozone), or exposure to chemicals (e.g., paraquat) that induce production of reactive oxygen species (ROS). The abiotic stimulant, in some instances, may be considered an environmental condition or stressor that can have an adverse effect on metabolism, growth, or viability of a plant culture, a plant cell, a plant tissue, a plant seed, a plant organ, or a whole plant. As such, in some instances, the abiotic stimulant may be a condition or agent that exerts abiotic stress on the plant culture.

In one aspect, included herein is a method for producing plant messenger packs, the method including (a) culturing a plant, plant part, or plant cell in a bioreactor; (b) exposing the plant, plant part, or plant cell to an effective amount of a stimulant to increase PMP production; (c) harvesting the culture medium, and (d) purifying PMPs from the culture medium.

Accordingly, in another aspect, provided herein is a PMP bioreactor comprising a bioreactor containing a plant culture and an effective amount of a stimulant to increase PMP production.

In some instances, the abiotic stimulant is a high culturing temperature (i.e., heat stress) or a low culturing temperature (e.g., cold stress). For example, the plant culture may be exposed to (e.g., a bioreactor including the plant culture may be set at) a temperature that, after a sufficient duration, can cause increased plant EV biogenesis or release by the plant cell culture, e.g., can increase the amount of PMPs that can be derived from the plant culture. For example, heat stress may occur when the plant culture is subjected to temperatures at least about 5° C., 10° C., 15° C., 20° C., 25° C., 30° C., 35° C., or 40° C. higher than the normal plant culture growing temperatures (e.g., temperature ranges suggested for optimal growth and yield, which for most species are known in the art). In contrast, cold stress may occur when the plant culture is subjected to temperatures at least about 5° C., 10° C., 15° C., 20° C., 25° C., 30° C., 35° C., or 40° C. lower than the normal plant culture growing temperatures (e.g., temperature ranges suggested for optimal growth and yield, which for most species are known in the art). In certain instances, the abiotic stimulant is a temperature of equal to or less than 20° C., 15° C., 10° C., 5° C., or 0° C. In other instances, the abiotic stimulant is a temperature of equal to or greater than 20° C., 25° C., 30° C., or 35° C. In some instances, the plant culture can be exposed to the high or low temperature for at least 1 min, 5 min, 15 min, 30 min, 1 hr, 2 hr, 3 hr, 4 hr, 5 hr, 10 hr, 12 hr, or 24 hr.

In some instances, the abiotic stimulant is low pH or high pH. High pH or low pH are relative terms that vary according to the plant species, and the normal plant soil conditions (e.g., soil conditions suggested for optimal growth and yield, which for most species are known in the art). For example, low pH may be a pH about 0.1, 0.2, 0.5, 1, 2, 3, 4, or 5 units lower than the normal plant culture growing pH (e.g., a pH suggested for optimal growth and yield, which for most species are known in the art). In contrast, high pH may be a pH about 0.1, 0.2, 0.5, 1, 2, 3, 4, or 5 units higher than the normal plant culture growing pH (e.g., pH suggested for optimal growth and yield, which for most species are known in the art). In certain instances, the abiotic stimulant is a high pH equal to or greater than pH 7, 7.5, 8, 8.5, 9, 9.5, or 10. In other instances, the abiotic stimulant is a low pH, e.g., a pH less than or equal to pH 7, 6.5, 6, 5.5, 5, 4.5, or 4. In some instances, the plant culture can be exposed to the high or low pH for at least 1 min, 5 min, 15 min, 30 min, 1 hr, 2 hr, 3 hr, 4 hr, 5 hr, 10 hr, 12 hr, or 24 hr.

In some instances, the abiotic stimulant is high light intensity, high irradiance, or light stress (e.g., light intensities that can cause increased plant EV biogenesis or release by the plant cell culture, e.g., can increase the amount of PMPs that can be derived from the plant culture, when delivered for a sufficient intensity and duration). In certain instances, the high light intensity may also be sufficient to cause photoinhibition damage to the plant, plant part, or plant cell. In some instances, the high light intensity can be at least 250 µE, 300 µE, 350 µE, 400 µE, 450 µE, 500 µE, 550 µE, or 600 µE. In some instances, the duration for the high light intensity stress can be at least 1 min, 5 min, 15 min, 30 min, 1 hr, 2 hr, 3 hr, 4 hr, 5 hr, 10 hr, 12 hr, or 24 hr.

In some instances, the abiotic stimulant is osmotic stress. Osmotic stress can be associated with or induced by elevated concentrations of osmolytes, which result in a perturbation in the osmotic potential of the intracellular or extracellular environment of a plant, plant part, or plant cell. For example, one or more solutes or osmolytes can be contacted with the plant culture in an amount and for a duration to cause osmotic stress and thereby increase plant EV biogenesis or release, e.g., increase the amount of PMPs that can be derived from the plant culture. The terms "solute" and "osmolyte" are used interchangeably and refer to substances that lower the water potential. Examples of such substances include, but are not limited to, ionic osmolytes and nonionic osmolytes that can be included into the culture medium.

Ionic solutes can be water soluble inorganic solutes such as sodium chloride (NaCl). Examples of water soluble inorganic solutes include, but are not limited to, NaCl, KCl (potassium chloride), LiCl (lithium chloride), CsCl (cesium chloride), RbCl (Rubidium chloride) and $CaCl_2$ (calcium chloride), sodium sulfate, magnesium sulfate, calcium sulfate, sodium chloride, magnesium chloride, calcium chloride, potassium chloride, etc., salts of agricultural fertilizers, and salts associated with alkaline or acid soil conditions (Werner J. E. et al. (1995) Physiologia Plantarum 93:659-666; U.S. Pat. No. 7,253,338). In general, the cell culture medium can include any water soluble inorganic salt that can increase sodium, magnesium, calcium, chlorides, sulfates, carbonates, or bicarbonates in the culture medium, such as sodium sulfate, magnesium sulfate, calcium sulfate, sodium chloride, magnesium chloride, calcium chloride, potassium chloride, salts of agricultural fertilizers, or and salts associated with alkaline or acid soil conditions. For example, the culture medium may have high salinity (e.g., culture medium with electrical conductivity of at least 2 ds/m, 4 ds/m, 5 ds/m, 6 ds/m, 7 ds/m, 8 ds/m, 9 ds/m, 10 ds/m, 12 ds/m, 14 ds/m, 16 ds/m, 18 ds/m, 20 ds/m, 22 ds/m, 24 ds/m, 26 ds/m, 28 ds/m or more than 28 ds/m.

Examples of non-ionic osmolytes include, but are not limited to, sugars, sugar alcohols, and high molecular weight polymeric osmolytes. Any sugar alcohol that is mostly metabolically inert can be used as an osmolyte, including but are not limited to, mannitol, sorbitol, xylitol, lactitol, or maltitol. A combination of two or more sugar alcohols may also be used. Examples of other sugars that can be used as an osmolyte include, but are not limited to, melibiose and sucrose.

The osmolyte may also be a high-molecular weight polymeric solute, referring to a class of polymeric solutes that largely do not permeate into plant cells. Examples of high-molecular weight polymeric solutes that can be used for lowering the water potential, include, but are not limited to, polyethylene glycol (PEG), polypropylene glycols, and dextran. Polyethylene glycol (PEG) is a polymer produced in a range of molecular weights. PEG of molecular weight 6000 or above largely cannot enter the pores of plant cells. Accordingly, PEG of higher molecular weight (e.g., greater than or equal to a molecular weight of 3000) can be used for the methods described herein. In some instances, PEG having a molecular weight between 3000 and 35000 (e.g., 3000, 5000, 10000, 15000, 20000, 25000, 30000, or 35000) can be used herein.

Further, an increase in the osmotic pressure of the culture medium may be induced by other conditions that cause an increase in osmotic potential, thereby inducing osmotic stress. Examples of conditions that induce osmotic stress include, but are not limited to, salinity, drought, heat, chilling, and/or freezing. For example, the osmotic pressure of the plant culture medium may be from 0.4-1.23 MPa. In other instances, the osmotic pressure of the culture medium is at least 0.4 MPa, 0.5 MPa, 0.6 MPa, 0.7 MPa, 0.8 MPa, 0.9 MPa, 1 MPa, 1.1 MPa, 1.2 MPa, 1.23 MPa, or more than 1.23 MPa.

In some instances, the abiotic stimulant is drought, drought stress, or low water availability, referring to reduced water availability that is low enough for a sufficient time to cause increased plant EV release by the plant cell culture, e.g., increase the amount of PMPs that can be derived from the plant culture. In certain instances, the drought stress may be sufficient to cause reduced growth or viability of the plant, plant part, or plant cell. In some instances, the plant culture can be exposed to the drought stress for at least 1 min, 5 min, 15 min, 30 min, 1 hr, 2 hr, 3 hr, 4 hr, 5 hr, 10 hr, 12 hr, or 24 hr.

In some instances, the abiotic stimulant is an agent or condition that causes oxidative stress in plants, plant parts, or plant cells. Adverse environmental conditions such as drought, salt stress, and use of herbicides promote the overproduction of reactive oxygen species (ROS) in plants, plant parts, and plant cells. For example, in some instances the abiotic stimulant is paraquat. Paraquat is an herbicide that exerts oxidative stress on plants (e.g., at a concentration of 0.03 to 0.3 µM). Paraquat, a bipyridylium herbicide, acts by intercepting electrons from the electron transport chain at PSI. This reaction results in the production of bipyridyl radicals that readily react with dioxygen, thereby producing superoxide.

In some instances, the abiotic stimulant is a condition or agent that causes a nutrient deficiency in plants, plant parts, or plant cells. For example, the plant culture may be provided a culture medium that is a nitrogen limiting medium (e.g., a medium where the amount of total available nitrogen (e.g., from nitrates, ammonia, or other known sources of nitrogen) is not sufficient to sustain optimal plant growth and development). One skilled in the art would recognize conditions where total available nitrogen is sufficient to sustain optimal plant growth and development (e.g., optimal plant, plant part, or plant cell growth and development). One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to the particular plant culture and environmental conditions.

ii. Chemical Elicitors

The stimulant can be a chemical elicitor. As used herein, the term "chemical elicitor" refers to a natural or synthetic compound that induces a defense response in plants similar to the response induced by a plant pathogen (e.g., a bacterial pathogen or a fungal pathogen), or compounds released from plants as induced by a plant pathogen (e.g., endogenous elicitors).

In one aspect, included herein is a method for producing PMPs, the method including (a) culturing a plant, plant part, or plant cell in a bioreactor; (b) exposing the plant, plant part, or plant cell to an amount of a chemical elicitor effective to increase PMP production; (c) harvesting the culture medium, and (d) purifying PMPs from the culture medium.

Accordingly, in another aspect, provided herein is a PMP bioreactor comprising a bioreactor (e.g., a plant cell culture system or a hydroponic system) containing a plant culture and a chemical elicitor in an amount sufficient effective to increase PMP production by the plant culture.

Examples of chemical elicitors useful as stimulants include salicylic acid, benzothiadiazole, 2,6-dichloroisonicotinic acid, jasmonic acid, methyl jasmonate, nitric oxide, benzoic acid, β-amino butyric acid, methionine, tryptophan, humic acid, heavy metals (e.g., iron, copper, chromium, cobalt, cadmium, nickel, manganese, zinc, mercury, arsenic, or lead), acetic acid, or nano-oxides. In certain instances, the chemical elicitor is salicylic acid. In other instances, the chemical elicitor is benzothiadiazole. In yet other instances, the chemical elicitor is 2,6-dichloroisonicotinic acid.

The amount of the chemical elicitor and duration of exposure to the plant culture necessary to increase EV production or release by the plant culture, e.g., increase the amount of PMPs that can be derived from the plant culture, will vary depending on the type of plant, plant part, or plant cell, the density of the plant culture, and growth conditions, but can be determined using standard techniques in the art.

iii. Biotic Stimulant

In some instances, the stimulant is a biotic stimulant. As used herein, the term "biotic stimulant" refers to a biological agent (e.g., a plant pest, e.g., a fungus, a bacterium, a virus, a protozoan, a nematode, or an insect herbivore), or a component thereof (e.g., a protein, a polypeptide, a nucleic acid, or a small molecule), that stimulates production of extracellular vesicles in a plant or part thereof (e.g., cell culture or tissue culture), e.g., increases the amount of PMPs that can be derived from the plant culture.

In one aspect, included herein is a method for producing PMPs, the method including (a) culturing a plant, plant part, or plant cell in a bioreactor; (b) exposing the plant, plant part, or plant cell to an amount of a biotic stimulant effective to increase PMP production; (c) harvesting the culture medium, and (d) purifying PMPs from the culture medium.

Accordingly, in another aspect, provided herein is a PMP bioreactor comprising a bioreactor (e.g., a plant cell culture system or a hydroponic system) containing a plant culture and a biotic stimulant in an amount sufficient effective to increase PMP production by the plant culture.

The biotic stimulant may be, for example, a fungus, a bacterium, a virus, a protozoan, a nematode, or an insect herbivore. In some instances, the biotic stimulant is a microbial stimulant, referring to a composition including a microorganism (e.g., a bacterium, a virus, or a fungus) or an isolated component thereof. The microbial agent may include live cells, dead cells, cell lysates, or isolated components thereof (e.g., polypeptides, nucleic acids, small molecules, saccharides). In some instances, the microbial stimulant is a microorganism (e.g., a live or dead cell), such as a bacterium, a virus, a protozoan, or a fungus.

In some instances, the microbial stimulant is a bacterial polypeptide, a bacterial saccharide (e.g., a polysaccharide or an oligosaccharide), a bacterial nucleic acid, or a bacterial nucleic acid. In some instances, the microbial stimulant is a bacterial polypeptide. In certain instances, the bacterial polypeptide is Elongation Factor Tu 18 (EFT18). In some instances, the bacterial polypeptide includes an amino acid sequence having at least 30%, 40%, 50%, 60%, 70%, 80%, 90%, 95%, 98%, 99%, or 100% sequence identity to EFT18. In some instances, the bacterial peptide is glutathione. In some embodiments, the microbial stimulant is a bacterial cell wall component or a lipopolysaccharide.

In other instances, the microbial stimulant may be a fungal polypeptide, a fungal saccharide (e.g., a polysaccharide or an oligosaccharide), a fungal nucleic acid, or a fungal nucleic acid. In certain instances, the fungal polypeptide is Flagellin2. In some instances, the microbial stimulant is yeast cell wall, mycelia cell wall, or fungal spores.

In some instances, the microbial stimulant is a viral polypeptide, a viral saccharide (e.g., a polysaccharide or an oligosaccharide), a viral nucleic acid, or a viral nucleic acid. In some instances, the viral polypeptide is a viral coat protein hairpin (e.g., from tobacco mosaic virus).

In some instances, the microbial stimulant is a protozoal polypeptide, a protozoal saccharide (e.g., a polysaccharide or an oligosaccharide), a protozoal nucleic acid, or a protozoal nucleic acid In some instances, the biotic stimulant is a polysaccharide (e.g., alginate, chitin, dextran, pectin, or chitosan). In some instance the biotic stimulant is an oligosaccharide (e.g., mannuronate, guluronate, mannan, and galacturonides). In some instances, the biotic stimulant is a polypeptide (e.g., cellulase or oligandrin). In some instances, the biotic stimulant is a glycoprotein. In some instances, the biotic stimulant is a lipid (e.g., a lipopolysaccharide). In some instances, the biotic stimulant is an oligogalacturonide.

In certain instances, the microbial stimulant is a plant pathogen or a plant pest, or a component (e.g., nucleic acid, small molecule, or polypeptide) thereof. Examples of plant pathogens or plant pests that can be used as biotic stimulants include those described in the section entitled "Delivery to a Plant Pest" herein, or as further described, below.

Bacterial Stimulants

In some instances, the biotic stimulant is a bacterium, or component thereof (e.g., nucleic acid, small molecule, or polypeptide), e.g., a bacterium that causes disease in plants, including, but not limited to, any bacteria described herein. For example, the bacteria may be one belonging to Actinobacteria or Proteobacteria, such as bacteria in the families of the Burkholderiaceae, Xanthomonadaceae, Pseudomonadaceae, Enterobacteriaceae, Microbacteriaceae, and Rhizobiaceae.

In some instances, the bacteria is an *Acidovorax avenae* subsp., including e.g., *Acidovorax avenae* subsp. *avenae* (=*Pseudomonas avenae* subsp. *avenae*), *Acidovorax avenae* subsp. *cattleyae* (=*Pseudomonas cattleyae*), or *Acidovorax avenae* subsp. *citrulli* (=*Pseudomonas pseudoalcaligenes* subsp. *citrulli*, *Pseudomonas avenae* subsp. *citrulli*)).

In some instances, the bacteria is a *Burkholderia* spp., including e.g., *Burkholderia andropogonis* (=*Pseudomonas andropogonis*, *Pseudomonas woodsii*), *Burkholderia caryophylli* (=*Pseudomonas caryophylli*), *Burkholderia cepacia* (=*Pseudomonas cepacia*), *Burkholderia gladioli* (=*Pseudomonas gladioli*), *Burkholderia gladioli* pv. *agaricicola* (=Pseudomnas *gladioli* pv. *agaricicola*), *Burkholderia gladioli* pv. *alliicola* (i.e., *Pseudomonas gladioli* pv. *alliicola*), *Burkholderia gladioli* pv. *gladioli* (i.e., *Pseudomonas gladioli*, *Pseudomonas gladioli* pv. *gladioli*), *Burkholderia glumae* (i.e., *Pseudomonas glumae*), *Burk-*

*holderia plantarii* (i.e., *Pseudomonas plantarii*), *Burkholderia solanacearum* (i.e., *Ralstonia solanacearum*), or *Ralstonia* spp.

In some instances, the bacteria is a *Liberibacter* spp., including *Candidatus Liberibacter* spec., including e.g., *Candidatus Liberibacter asiaticus*, *Liberibacter africanus* (Laf), *Liberibacter americanus* (Lam), *Liberibacter asiaticus* (Las), *Liberibacter europaeus* (Leu), *Liberibacter psyllaurous*, or *Liberibacter solanacearum* (Lso).

In some instances, the bacteria is a *Corynebacterium* spp. including e.g., *Corynebacterium fascians*, *Corynebacterium flaccumfaciens* pv. *flaccumfaciens*, *Corynebacterium michiganensis*, *Corynebacterium michiganense* pv. *tritici*, *Corynebacterium michiganense* pv. *nebraskense*, or *Corynebacterium sepedonicum*.

In some instances, the bacteria is an *Erwinia* spp. including e.g., *Erwinia amylovora*, *Erwinia ananas*, *Erwinia carotovora* (i.e., *Pectobacterium carotovorum*), *Erwinia carotovora* subsp. *atroseptica*, *Erwinia carotovora* subsp. *carotovora*, *Erwinia chrysanthemi*, *Erwinia chrysanthemi* pv. *zeae*, *Erwinia dissolvens*, *Erwinia herbicola*, *Erwinia rhapontic*, *Erwinia stewartiii*, *Erwinia tracheiphila*, or *Erwinia uredovora*.

In some instances, the bacteria is a *Pseudomonas syringae* subsp., including e.g., *Pseudomonas syringae* pv. *actinidiae* (Psa), *Pseudomonas syringae* pv. *atrofaciens*, *Pseudomonas syringae* pv. *coronafaciens*, *Pseudomonas syringae* pv. *glycinea*, *Pseudomonas syringae* pv. *lachrymans*, *Pseudomonas syringae* pv. *maculicola* *Pseudomonas syringae* pv. *papulans*, *Pseudomonas syringae* pv. *striafaciens*, *Pseudomonas syringae* pv. *syringae*, *Pseudomonas syringae* pv. *tomato*, or *Pseudomonas syringae* pv. *tabaci*.

In some instances, the bacteria is a *Streptomyces* spp., including e.g., *Streptomyces acidiscabies*, *Streptomyces albidoflavus*, *Streptomyces candidus* (i.e., *Actinomyces candidus*), *Streptomyces caviscabies*, *Streptomyces collinus*, *Streptomyces europaeiscabiei*, *Streptomyces intermedius*, *Streptomyces ipomoeae*, *Streptomyces luridiscabiei*, *Streptomyces niveiscabiei*, *Streptomyces puniciscabiei*, *Streptomyces retuculiscabiei*, *Streptomyces scabiei*, *Streptomyces scabies*, *Streptomyces setonii*, *Streptomyces steliiscabiei*, *Streptomyces turgidiscabies*, or *Streptomyces wedmorensis*.

In some instances, the bacteria is a *Xanthomonas axonopodis* subsp., including e.g., *Xanthomonas axonopodis* pv. *alfalfae* (=*Xanthomonas alfalfae*), *Xanthomonas axonopodis* pv. *aurantifolii* (=*Xanthomonas fuscans* subsp. *aurantifolii*), *Xanthomonas axonopodis* pv. *allii* (=*Xanthomonas campestris* pv. *allii*), *Xanthomonas axonopodis* pv. *axonopodis*, *Xanthomonas axonopodis* pv. *bauhiniae* (=*Xanthomonas campestris* pv. *bauhiniae*), *Xanthomonas axonopodis* pv. *begoniae* (=*Xanthomonas campestris* pv. *begoniae*), *Xanthomonas axonopodis* pv. *betlicola* (=*Xanthomonas campestris* pv. *betlicola*), *Xanthomonas axonopodis* pv. *biophyti* (=*Xanthomonas campestris* pv. *biophyti*), *Xanthomonas axonopodis* pv. *cajani* (=*Xanthomonas campestris* pv. *cajani*), *Xanthomonas axonopodis* pv. *cassavae* (=*Xanthomonas cassavae*, *Xanthomonas campestris* pv. *cassavae*), *Xanthomonas axonopodis* pv. *cassiae* (=*Xanthomonas campestris* pv. *cassiae*), *Xanthomonas axonopodis* pv. *citri* (=*Xanthomonas citri*), *Xanthomonas axonopodis* pv. *citrumelo* (=*Xanthomonas alfalfae* subsp. *citrumelonis*), *Xanthomonas axonopodis* pv. *clitoriae* (=*Xanthomonas campestris* pv. *clitoriae*), *Xanthomonas axonopodis* pv. *coracanae* (=*Xanthomonas campestris* pv. *coracanae*), *Xanthomonas axonopodis* pv. *cyamopsidis* (=*Xanthomonas campestris* pv. *cyamopsidis*), *Xanthomonas axonopodis* pv. *desmodii* (=*Xanthomonas campestris* pv. *desmodii*), *Xanthomonas axonopodis* pv. *desmodiigangetici* (=*Xanthomonas campestris* pv. *desmodiigangetici*), *Xanthomonas axonopodis* pv. *desmodiilaxiflori* (=*Xanthomonas campestris* pv. *desmodiilaxiflori*), *Xanthomonas axonopodis* pv. *desmodiirotundifolii* (=*Xanthomonas campestris* pv. *desmodiirotundifolii*), *Xanthomonas axonopodis* pv. *dieffenbachiae* (=*Xanthomonas campestris* pv. *dieffenbachiae*), *Xanthomonas axonopodis* pv. *erythrinae* (=*Xanthomonas campestris* pv. *erythrinae*), *Xanthomonas axonopodis* pv. *fascicularis* (=*Xanthomonas campestris* pv. *fasciculari*), *Xanthomonas axonopodis* pv. *glycines* (=*Xanthomonas campestris* pv. *glycines*), *Xanthomonas axonopodis* pv. *khayae* (=*Xanthomonas campestris* pv. *khayae*), *Xanthomonas axonopodis* pv. *lespedezae* (=*Xanthomonas campestris* pv. *lespedezae*), *Xanthomonas axonopodis* pv. *maculifoliigardeniae* (=*Xanthomonas campestris* pv. *maculifoliigardeniae*), *Xanthomonas axonopodis* pv. *malvacearum* (=*Xanthomonas citri* subsp. *malvacearum*), *Xanthomonas axonopodis* pv. *manihotis* (=*Xanthomonas campestris* pv. *manihotis*), *Xanthomonas axonopodis* pv. *martyniicola* (=*Xanthomonas campestris* pv. *martyniicola*), *Xanthomonas axonopodis* pv. *melhusii* (=*Xanthomonas campestris* pv. *melhusii*), *Xanthomonas axonopodis* pv. *nakataecorchori* (=*Xanthomonas campestris* pv. *nakataecorchori*), *Xanthomonas axonopodis* pv. *passiflorae* (=*Xanthomonas campestris* pv. *passiflorae*), *Xanthomonas axonopodis* pv. *patelii* (=*Xanthomonas campestris* pv. *patelii*), *Xanthomonas axonopodis* pv. *pedalii* (=*Xanthomonas campestris* pv. *pedalii*), *Xanthomonas axonopodis* pv. *phaseoli* (=*Xanthomonas campestris* pv. *phaseoli*, *Xanthomonas phaseoli*), *Xanthomonas axonopodis* pv. *phaseoli* var. *fuscans* (=*Xanthomonas fuscans*), *Xanthomonas axonopodis* pv. *phyllanthi* (=*Xanthomonas campestris* pv. *phyllanthi*), *Xanthomonas axonopodis* pv. *physalidicola* (=*Xanthomonas campestris* pv. *physalidicola*), *Xanthomonas axonopodis* pv. *poinsettiicola* (=*Xanthomonas campestris* pv. *poinsettiicola*), *Xanthomonas axonopodis* pv. *punicae* (=*Xanthomonas campestris* pv. *punicae*), *Xanthomonas axonopodis* pv. *rhynchosiae* (=*Xanthomonas campestris* pv. *rhynchosiae*), *Xanthomonas axonopodis* pv. *ricini* (=*Xanthomonas campestris* pv. *ricini*), *Xanthomonas axonopodis* pv. *sesbaniae* (=*Xanthomonas campestris* pv. *sesbaniae*), *Xanthomonas axonopodis* pv. *tamarindi* (=*Xanthomonas campestris* pv. *tamarindi*), *Xanthomonas axonopodis* pv. *vasculorum* (=*Xanthomonas campestris* pv. *vasculorum*), *Xanthomonas axonopodis* pv. *vesicatoria* (=*Xanthomonas campestris* pv. *vesicatoria*, *Xanthomonas vesicatoria*), *Xanthomonas axonopodis* pv. *vignaeradiatae* (=*Xanthomonas campestris* pv. *vignaeradiatae*), *Xanthomonas axonopodis* pv. *vignicola* (=*Xanthomonas campestris* pv. *vignicola*), or *Xanthomonas axonopodis* pv. *vitians* (=*Xanthomonas campestris* pv. *vitians*).

In some instances, the bacteria is *Xanthomonas campestris* pv. *musacearum*, *Xanthomonas campestris* pv. *pruni* (=*Xanthomonas arboricola* pv. *pruni*), or *Xanthomonas fragariae*.

In some instances, the bacteria is a *Xanthomonas translucens* supsp. (=*Xanthomonas campestris* pv. *hordei*) including e.g., *Xanthomonas translucens* pv. *arrhenatheri* (=*Xanthomonas campestris* pv. *arrhenatheri*), *Xanthomonas translucens* pv. *cerealis* (=*Xanthomonas campestris* pv. *cerealis*), *Xanthomonas translucens* pv. *graminis* (=*Xanthomonas campestris* pv. *graminis*), *Xanthomonas translucens* pv. *phlei* (=*Xanthomonas campestris* pv. *phlei*), *Xanthomonas translucens* pv. *phleipratensis* (=*Xanthomonas campestris* pv. *phleipratensis*), *Xanthomonas translu-* cens pv. poae (=*Xanthomonas campestris* pv. *poae*), *Xanthomonas translucens* pv. *secalis* (=*Xanthomonas campestris* pv. *secalis*), *Xanthomonas translucens* pv. *translucens* (=*Xanthomonas campestris* pv. *translucens*), or *Xanthomonas translucens* pv. *undulosa* (=*Xanthomonas campestris* pv. *undulosa*).

In some instances, the bacteria is a *Xanthomonas oryzae* supsp., *Xanthomonas oryzae* pv. *oryzae* (=*Xanthomonas campestris* pv. *oryzae*), or *Xanthomonas oryzae* pv. *oryzicola* (=*Xanthomonas campestris* pv. *oryzicola*).

In some instances, the bacteria is a Xylella fastidiosa from the family of Xanthomonadaceae.

Table 7 shows further examples of bacterial pests that can be used as biotic stimulants in the production methods and bioreactors described herein.

Fungal Stimulants

In some instances, the biotic stimulant is a fungus, or component thereof (e.g., nucleic acid, small molecule, or polypeptide), e.g., a fungus that causes a disease in plants, including any fungus described herein. For example, the biotic stimulant may be a fungus that causes diseases in plants such as powdery mildew pathogens, for example Blumeria species, for example *Blumeria graminis; Podosphaera* species, for example *Podosphaera leucotricha; Sphaerotheca* species, for example *Sphaerotheca fuliginea; Uncinula* species, for example *Uncinula necator*; diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia* recondite, *P. triticina, P. graminis* or *P. striiformis* or *P. hordei; Uromyces* species, for example *Uromyces appendiculatus*; diseases caused by pathogens from the group of the Oomycetes, for example Albugo species, for example Algubo *candida; Bremia* species, for example *Bremia lactucae; Peronospora* species, for example *Peronospora pisi, P. parasitica* or *P. brassicae; Phytophthora* species, for example *Phytophthora infestans; Plasmopara* species, for example *Plasmopara* viticola; *Pseudoperonospora* species, for example *Pseudoperonospora humuli* or *Pseudoperonospora cubensis; Pythium* species, for example *Pythium ultimum*; leaf blotch diseases and leaf wilt diseases caused, for example, by *Alternaria* species, for example *Alternaria solani; Cercospora* species, for example *Cercospora beticola*; Cladiosporium species, for example Cladiosporium *cucumerinum; Cochliobolus* species, for example *Cochliobolus sativus* (conidia form: *Drechslera*, Syn: *Helminthosporium*), *Cochliobolus miyabeanus; Colletotrichum* species, for example *Colletotrichum* lindemuthanium; *Cycloconium* species, for example *Cycloconium* oleaginum; *Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans, Leptosphaeria nodorum; Magnaporthe* species, for example *Magnaporthe grisea; Microdochium* species, for example *Microdochium nivale; Mycosphaerella* species, for example *Mycosphaerella graminicola, M. arachidicola* and M. fifiensis; Phaeosphaeria species, for example *Phaeosphaeria nodorum; Pyrenophora* species, for example *Pyrenophora teres, Pyrenophora tritici* repentis; *Ramularia* species, for example *Ramularia* collo-*cygni, Ramularia areola; Rhynchosporium* species, for example *Rhynchosporium secalis; Septoria* species, for example *Septoria apii, Septoria* lycopersii; *Typhula* species, for example *Typhula incarnata; Venturia* species, for example *Venturia inaequalis*; root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola*; ear and panicle diseases (including corn cobs) caused, for example, by *Alternaria* species, for example *Alternaria* spp.; *Aspergillus* species, for example *Aspergillus flavus; Cladosporium* species, for example *Cladosporium* cladosporioides; *Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum*; diseases caused by smut fungi, for example *Sphacelotheca* species, for example *Sphacelotheca reiliana; Tilletia* species, for example *Tilletia* caries, *T. controversa; Urocystis* species, for example *Urocystis occulta; Ustilago* species, for example *Ustilago nuda, U. nuda tritici*; fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum*; Verticilium species, for example Verticilium *alboatrum*; seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma* lingam; *Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnata; Verticillium* species, caused for example by *Verticillium dahliae*; cancers, galls and witches' broom caused, for example, by *Nectria* species, for example *Nectria galligena*; wilt diseases caused, for example, by *Monilinia* species, for example *Monilinia laxa*; leaf blister or leaf curl diseases caused, for example, by *Exobasidium* species, for example *Exobasidium vexans*; Taphrina species, for example *Taphrina deformans*; decline diseases of wooden plants caused, for example, by Esca disease, caused for example by Phaemoniella clamydospora, *Phaeoacremonium aleophilum* and *Fomitiporia mediterranea*; Eutypa dyeback, caused for example by *Eutypa lata*; Ganoderma diseases caused for example by *Ganoderma boninense*; Rigidoporus diseases caused for example by *Rigidoporus lignosus*; diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*; Club root caused, for example, by Plasmodiophora species, for example Plamodiophora *brassicae*; diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Table 6 provides further examples of fungal plant pests that can be used as biotic stimulants in the production methods and bioreactors described herein.

Viral Stimulants

In some instances, the biotic stimulant is a virus, or component thereof (e.g., nucleic acid, small molecule, or polypeptide), e.g., a virus that causes disease in plants, including, but not limited to, any viruses described herein.

Table 10 provides further examples of viral plant pests that can be used as biotic stimulants in the production methods and bioreactors described herein.

Insect Stimulants

In some instances, the biotic stimulant is an insect, or component thereof (e.g., nucleic acid, small molecule, or polypeptide), e.g., an insect that is a plant pest, including, but not limited to, any insects described herein. For example, the biotic stimulant may be an insect, or component thereof, of the order Acari, Araneae, Anoplura, Coleoptera, Collembola, Dermaptera, Dictyoptera, Diplura, Diptera (e.g., spotted-wing *Drosophila*), Embioptera, Ephemeroptera, Grylloblatodea, Hemiptera (e.g., aphids, Greenhouse whitefly), Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, or Zoraptera.

Table 8 provides further examples of insect plant pests that can be used as biotic stiumlants in the manufacturing methods and bioreactors described herein.

Mollusk Stimulants

In some instances, the biotic stimulant is a mollusk, or component thereof (e.g., nucleic acid, small molecule, or polypeptide), e.g., a mollusk that causes disease in plants, including, but not limited to, any mollusks described herein, e.g., terrestrial slugs and snails which mostly occur as polyphagous pests on agricultural and horticultural crops. For example, the mollusk may belong to the family Achatinidae, Agriolimacidae, Ampullariidae, Arionidae, Bradybaenidae, Helicidae, Hydromiidae, Lymnaeidae, Milacidae, Urocyclidae, or Veronicellidae.

For example, in some instances, the mollusk is *Achatina* spp., *Archachatina* spp. (e.g., *Archachatina marginata*), *Agriolimax* spp., *Arion* spp. (e.g., *A. ater*, *A. circumscriptus*, *A. distinctus*, *A. fasciatus*, *A. hortensis*, *A. intermedius*, *A. rufus*, *A. subfuscus*, *A. silvaticus*, A. *lusitanicus*), Arliomax spp. (e.g., Arliomax *columbianus*), *Biomphalaria* spp., *Bradybaena* spp. (e.g., B. *fruticum*), *Bulinus* spp., *Cantareus* spp. (e.g., *C.* asperses), *Cepaea* spp. (e.g., *C. hortensis*, *C.* nemoralis, *C. hortensis*), *Cernuella* spp., *Cochlicella* spp., *Cochlodina* spp. (e.g., *C. laminata*), *Deroceras* spp. (e.g., *D. agrestis*, *D. empiricorum*, *D. laeve*, D. panornimatum, *D. reticulatum*), *Discus* spp. (e.g., *D. rotundatus*), *Euomphalia* spp., *Galba* spp. (e.g., G. *trunculata*), *Helicella* spp. (e.g., *H. itala*, *H. obvia*), *Helicigona* spp. (e.g., H. *arbustorum*), *Helicodiscus* spp., *Helix* spp. (e.g., *H. aperta*, *H. aspersa*, *H. pomatia*), *Limax* spp. (e.g., *L. cinereoniger*, *L. flavus*, *L. marginatus*, *L. maximus*, *L. tenellus*), *Limicolaria* spp. (e.g., *Limicolaria* aurora), *Lymnaea* spp. (e.g., *L. stagnalis*), Mesodon spp. (e.g., Meson thyroidus), *Monadenia* spp. (e.g., *Monadenia fidelis*), *Milax* spp. (e.g., *M. gagates*, *M. marginatus*, *M. sowerbyi*, M. *budapestensis*), *Oncomelania* spp., Neohelix spp. (e.g., Neohelix *albolabris*), *Opeas* spp., *Otala* spp. (e.g., *Otala lacteal*), *Oxyloma* spp. (e.g., *O. pfeifferi*), *Pomacea* spp. (e.g., *P. canaliculata*), *Succinea* spp., *Tandonia* spp. (e.g., *T. budapestensis*, *T. sowerbyi*), *Theba* spp., *Vallonia* spp., or *Zonitoides* spp. (e.g., *Z. nitidus*).

Nematode Stimulants

In some instances, the biotic stimulant is a nematode, or component thereof (e.g., nucleic acid, small molecule, or polypeptide), e.g., a nematode that causes disease in plants, including, but not limited to, any nematodes described herein, for example, *Meloidogyne* spp. (root-knot), *Heterodera* spp., *Globodera* spp., *Pratylenchus* spp., *Helicotylenchus* spp., *Radopholus similis*, *Ditylenchus dipsaci*, *Rotylenchulus reniformis*, *Xiphinema* spp., *Aphelenchoides* spp. and *Belonolaimus longicaudatus*. In some instances, the nematode is a plant parasitic nematode or a nematode living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and Scutellonema spp.; sedentary parasites such as *Heterodera* spp., *Globodera* spp., and *Meloidogyne* spp., and stem and leaf endoparasites such as *Ditylenchus* spp., *Aphelenchoides* spp., and Hirshmaniella spp. Especially harmful root parasitic soil nematodes are such as cystforming nematodes of the genera *Heterodera* or *Globodera*, and/or root knot nematodes of the genus *Meloidogyne*. Harmful species of these genera are for example *Meloidogyne incognita*, *Heterodera glycines* (soybean cyst nematode), *Globodera pallida* and *Globodera rostochiensis* (potato cyst nematode), which species are effectively controlled with the PMP compositions described herein. However, the use of the PMP compositions described herein is in no way restricted to these genera or species, but also extends in the same manner to other nematodes.

Other examples of nematodes that can be used as biotic stimulants include but are not limited to e.g. Aglenchus *agricola*, *Anguina tritici*, *Aphelenchoides arachidis*, *Aphelenchoides fragaria* and the stem and leaf endoparasites *Aphelenchoides* spp. in general, *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus*, *Bursaphelenchus mucronatus*, and *Bursaphelenchus* spp. in general, Cacopaurus *pestis*, *Criconemella curvata*, Criconemella *onoensis*, Criconemella ornata, Criconemella rusium, Criconemella xenoplax (=Mesocriconema xenoplax) and Criconemella spp. in general, Criconemoides femiae, Criconemoides *onoense*, Criconemoides *ornatum* and Criconemoides spp. in general, *Ditylenchus destructor*, *Ditylenchus dipsaci*, *Ditylenchus* myceliophagus and the stem and leaf endoparasites *Ditylenchus* spp. in general, Dolichodorus *heterocephalus*, *Globodera pallida* (=*Heterodera pallida*), Globodera rostochiensis (potato cyst nematode), *Globodera solanacearum*, *Globodera tabacum*, *Globodera virginia* and the sedentary, cyst forming parasites *Globodera* spp. in general, *Helicotylenchus* digonicus, *Helicotylenchus dihystera, Helicotylenchus erythrine, Helicotylenchus multicinctus, Helicotylenchus nannus, Helicotylenchus pseudorobustus* and *Helicotylenchus* spp. in general, Hemicriconemoides, Hemicycliophora *arenaria*, Hemicycliophora *nudata*, Hemicycliophora *parvana, Heterodera avenae, Heterodera cruciferae, Heterodera glycines* (soybean cyst nematode), *Heterodera oryzae, Heterodera schachtii, Heterodera zeae* and the sedentary, cyst forming parasites *Heterodera* spp. in general, Hirschmaniella *gracilis*, Hirschmaniella *oryzae* Hirschmaniella *spinicaudata* and the stem and leaf endoparasites Hirschmaniella spp. in general, Hoplolaimus aegyptii, Hoplolaimus *califomicus*, Hoplolaimus *columbus*, Hoplolaimus *galeatus*, Hoplolaimus *indicus*, Hoplolaimus magnistylus, Hoplolaimus *pararobustus, Longidorus africanus, Longidorus breviannulatus, Longidorus elongatus, Longidorus laevicapitatus, Longidorus* vineacola and the ectoparasites *Longidorus* spp. in general, *Meloidogyne* acronea, *Meloidogyne africana, Meloidogyne arenaria, Meloidogyne arenaria* thamesi, *Meloidogyne artiella, Meloidogyne* chitwoodi, *Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne* thamesi and the sedentary parasites *Meloidogyne* spp. in general, Meloinema spp., Nacobbus *aberrans*, Neotylenchus vigissi, Paraphelenchus pseudoparietinus, Paratrichodorus allius, Paratrichodorus *lobatus*, Paratrichodorus *minor*, Paratrichodorus *nanus*, Paratrichodorus *porosus*, Paratrichodorus *teres* and Paratrichodorus spp. in general, Paratylenchus *hamatus*, *Paratylenchus minutus*, Paratylenchus *projectus* and Paratylenchus spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus* giibbicaudatus, *Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, Pseudohalenchus *minutus*, Psilenchus *magnidens*, Psilenchus *tumidus*, Punctodera *chalcoensis*, Quinisulcius *acutus, Radopholus citrophilus, Radopholus similis*, the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, Scutellonema *brachyurum*, Scutellonema bradys, Scutellonema clathricaudatum and the migratory endoparasites Scutellonema spp. in general, *Subanguina* radiciola, Tetylenchus *nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Other examples of nematode pests include species belonging to the family Criconematidae, Belonolaimidae, Hoploaimidae, Heteroderidae, Longidoridae, Pratylenchidae, Trichodoridae, or Anguinidae.

Table 9 provides further examples of nematode plant pests that can be used as biotic stimulants in the production methods and bioreactors described herein.

iv. Nucleic Acid or Polypeptide Stimulants

In some instances, the stimulant is a heterologous polypeptide, a heterologous nucleic acid, or a heterologous small molecule.

For example, the heterologous nucleic acid may be a DNA, an RNA, a PNA, or a hybrid DNA-RNA molecule. In some instances, the RNA is a messenger RNA (mRNA), a guide RNA (gRNA), or an inhibitory RNA. In some instance, the inhibitory RNA is RNAi, shRNA, or miRNA. In some instances, the inhibitory RNA inhibits gene expression in a plant, plant part, or plant cell. In some instances, the nucleic acid is an mRNA, a modified mRNA, or a DNA molecule that, in the plant, plant part, or plant cell, increases expression of an enzyme, a pore-forming protein, a signaling ligand, a cell penetrating peptide, a transcription factor, a receptor, an antibody, a nanobody, a gene editing protein (e.g., CRISPR-Cas system, TALEN, or zinc finger), a riboprotein, a protein aptamer, or a chaperone. In certain instances, the heterologous nucleic acid alters gene expression in pathways involved in EV biogenesis or secretion in the cell. For example, the heterologous nucleic acid may increase gene expression of EXO70a1 and/or EXO84 in the plant cell, thereby stimulating EV secretion from the plant cell and increasing the amount of PMPs that can be derived from the plant culture.

Examples of polypeptides that can be used herein can include a gene editing protein (e.g., CRISPR-Cas system, TALEN, or zinc finger). In certain instances, the heterologous polypeptide alters gene expression or otherwise edits the sequence of a gene involved in EV biogenesis or secretion in the cell. For example, the heterologous polypeptide may increase gene expression of EXO70a1 and/or EXO84 in the plant cell, thereby stimulating EV secretion from the plant cell and/or increasing the amount of PMPs that can be derived from the plant culture.

E. Plant EV Markers

The PMPs manufactured in accordance with the methods or bioreactors herein may have a range of markers that identify the PMPs as being produced using a plant EV, and/or including a segment, portion, or extract thereof. As used herein, the term "plant EV marker" refers to a component that is naturally associated with a plant and incorporated into or onto the plant EV in planta, such as a plant protein, a plant nucleic acid, a plant small molecule, a plant lipid, or a combination thereof. Examples of plant EV markers can be found, for example, in Rutter and Innes, *Plant Physiol.* 173 (1): 728-741, 2017; Raimondo et al., *Oncotarget.* 6 (23): 19514, 2015; Ju et al., *Mol. Therapy.* 21 (7): 1345-1357, 2013; Wang et al., *Molecular Therapy.* 22 (3): 522-534, 2014; and Regente et al, *J of Exp. Biol.* 68 (20): 5485-5496, 2017; each of which is incorporated herein by reference. Additional examples of plant EV markers are listed in the Appendix, and are further outlined herein.

In some instances, the plant EV marker can include a plant lipid. Examples of plant lipid markers that may be found in the PMPs include phytosterol, campesterol, β-sitosterol, stigmasterol, avenasterol, glycosyl inositol phosphoryl ceramides (GIPCs), glycolipids (e.g., monogalactosyldiacylglycerol (MGDG) or digalactosyldiacylglycerol (DGDG)), or a combination thereof. For instance, the PMP may include GIPCs, which represent the main sphingolipid class in plants and are one of the most abundant membrane lipids in plants. Other plant EV markers may include lipids that accumulate in plants in response to abiotic or biotic stressors (e.g., bacterial or fungal infection), such as phosphatidic acid (PA) or phosphatidylinositol-4-phosphate (PI4P).

Alternatively, the plant EV marker may include a plant protein. In some instances, the protein plant EV marker may be an antimicrobial protein naturally produced by plants, including defense proteins that plants secrete in response to abiotic or biotic stressors (e.g., bacterial or fungal infection). Plant pathogen defense proteins include soluble N-ethylmalemide-sensitive factor association protein receptor protein (SNARE) proteins (e.g., Syntaxin-121 (SYP121; GenBank Accession No.: NP_187788.1 or NP_974288.1), Penetration1 (PEN1; GenBank Accession No: NP_567462.1)) or ABC transporter Penetration3 (PEN3; GenBank Accession No: NP_191283.2). Other examples of plant EV markers includes proteins that facilitate the long-distance transport of RNA in plants, including phloem proteins (e.g., Phloem protein2-A1 (PP2-A1), GenBank Accession No: NP_193719.1), calcium-dependent lipid-binding proteins, or lectins (e.g., Jacalin-related lectins, e.g., *Helianthus annuus* jacalin (Helja; GenBank: AHZ86978.1). For example, the RNA binding protein may be Glycine-Rich RNA Binding Protein-7 (GRP7; GenBank Accession Number: NP_179760.1). Additionally, proteins that regulate plasmodesmata function can in some instances be found in plant EVs, including proteins such as Synap-Totgamin A (GenBank Accession No: NP_565495.1). In some instances, the plant EV marker can include a protein involved in lipid metabolism, such as phospholipase C or phospholipase D. In some instances, the plant protein EV marker is a cellular trafficking protein in plants. In certain instances where the plant EV marker is a protein, the protein marker may lack a signal peptide that is typically associated with secreted proteins. Unconventional secretory proteins seem to share several common features like (i) lack of a leader sequence, (ii) absence of post-translational modifications (PTMs) specific for ER or Golgi apparatus, and/or (iii) secretion not affected by brefeldin A which blocks the classical ER/Golgi-dependent secretion pathway. One skilled in the art can use a variety of tools freely accessible to the public (e.g., SecretomeP Database; SUBA3 (SUBcellular localization database for *Arabidopsis* proteins)) to evaluate a protein for a signal sequence, or lack thereof.

In instances where the plant EV marker is a protein, the protein may have an amino acid sequence having at least 35%, 40%, 45%, 50%, 55%, 60%, 65%, 70%, 75%, 80%, 85%, 90%, 95%, 98%, 99%, or 100% sequence identity to a plant EV marker, such as any of the plant EV markers listed in the Appendix. For example, the protein may have an amino acid sequence having at least 35%, 40%, 45%, 50%, 55%, 60%, 65%, 70%, 75%, 80%, 85%, 90%, 95%, 98%, 99%, or 100% sequence identity to PEN1 from *Arabidopsis thaliana* (GenBank Accession Number: NP_567462.1).

In some instances, the plant EV marker includes a nucleic acid encoded in plants, e.g., a plant RNA, a plant DNA, or a plant PNA. For example, the PMP may include dsRNA, mRNA, a viral RNA, a microRNA (miRNA), or a small interfering RNA (siRNA) encoded by a plant. In some instances, the nucleic acid may be one that is associated with a protein that facilitates the long-distance transport of RNA in plants, as discussed herein. In some instances, the nucleic acid plant EV marker may be one involved in host-induced gene silencing (HIGS), which is the process by which plants silence foreign transcripts of plant pests (e.g., pathogens such as fungi). For example, the nucleic acid may be one that silences bacterial or fungal genes. In some instances, the nucleic acid may be a microRNA, such as miR159 or miR166, which target genes in a fungal pathogen (e.g., *Verticillium dahliae*). In some instances, the protein may be one involved in carrying plant defense compounds, such as proteins involved in glucosinolate (GSL) transport and metabolism, including Glucosinolate Transporter-1-1 (GTR1; GenBank Accession No: NP_566896.2), Glucosinolate Transporter-2 (GTR2; NP_201074.1), or Epithiospecific Modifier 1 (ESM1; NP_188037.1).

In instances where the plant EV marker is a nucleic acid, the nucleic acid may have a nucleotide sequence having at least 35%, 40%, 45%, 50%, 55%, 60%, 65%, 70%, 75%, 80%, 85%, 90%, 95%, 98%, 99%, or 100% sequence identity to a plant EV marker, e.g., such as those encoding the plant EV markers listed in the Appendix. For example, the nucleic acid may have a polynucleotide sequence having at least 35%, 40%, 45%, 50%, 55%, 60%, 65%, 70%, 75%, 80%, 85%, 90%, 95%, 98%, 99%, or 100% sequence identity to miR159 or miR166.

In some instances, the plant EV marker includes a compound produced by plants. For example, the compound may be a defense compound produced in response to abiotic or biotic stressors, such as secondary metabolites. One such secondary metabolite that be found in PMPs are glucosinolates (GSLs), which are nitrogen and sulfur-containing secondary metabolites found mainly in Brassicaceae plants. Other secondary metabolites may include allelochemicals.

In some instances, the PMPs may also be identified as being produced using a plant EV based on the lack of certain markers (e.g., lipids, polypeptides, or polynucleotides) that are not typically produced by plants, but are generally associated with other organisms (e.g., markers of animal EVs, bacterial EVs, or fungal EVs). For example, in some instances, the PMP lacks lipids typically found in animal EVs, bacterial EVs, or fungal EVs. In some instances, the PMP lacks lipids typical of animal EVs (e.g., sphingomyelin). In some instances, the PMP does not contain lipids typical of bacterial EVs or bacterial membranes (e.g., LPS). In some instances, the PMP lacks lipids typical of fungal membranes (e.g., ergosterol).

Plant EV markers can be identified using any approaches known in the art that enable identification of small molecules (e.g., mass spectroscopy, mass spectrometry), lipids (e.g., mass spectroscopy, mass spectrometry), proteins (e.g., mass spectroscopy, immunoblotting), or nucleic acids (e.g., PCR analysis). In some instances, a PMP composition described herein includes a detectable amount, e.g., a predetermined threshold amount, of a plant EV marker described herein.

F. Modified PMPs

The PMPs produced in accordance with the methods or bioreactors herein may be modified. In one aspect, PMPs may be loaded with a heterologous agent (e.g., a plant cell wall-penetrating agent) that is capable of increasing plant cell uptake relative to an unmodified PMP. For example, the modified PMPs may include a plant cell wall-penetrating agent, such as an enzyme, detergent, or lipid. This agent may be added at any step during the manufacturing process effective to introduce the agent into the manufactured PMPs.

In some instances, the cell wall-penetrating agent is an enzyme. For example, the enzyme may be a bacterial, fungal, protozoal, mammalian, or plant enzyme that is capable of degrading plant cell walls. In some instances, the enzyme is a bacterial enzyme capable of degrading plant cell walls. In some instances, the enzyme has at least 30%, 40%, 50%, 60%, 70%, 80%, 90%, 95%, 98%, or 100% identity to all or a portion of the sequence of a bacterial enzyme capable of degrading plant cell walls. In some instances, the enzyme is a fungal enzyme capable of degrading plant cell walls. In some instances, the enzyme has at least 30%, 40%, 50%, 60%, 70%, 80%, 90%, 95%, 98%, or 100% identity to all or a portion of the sequence of a fungal enzyme capable of degrading plant cell walls. In some instances, the enzyme is a plant enzyme capable of degrading plant cell walls. In some instances, the cell wall-degrading enzyme has at least 30%, 40%, 50%, 60%, 70%, 80%, 90%, 95%, 98%, or 100% identity to all or a portion of the sequence of a plant enzyme capable of degrading plant cell walls. In some instances, the enzyme is a protozoal enzyme capable of degrading plant cell walls. In some instances, the cell wall-degrading enzyme has at least 30%, 40%, 50%, 60%, 70%, 80%, 90%, 95%, 98%, or 100% identity to all or a portion of the sequence of a protozoal enzyme capable of degrading plant cell walls.

In some instances, the enzyme is a cellulase. For example, the cellulase may have at least 30%, 40%, 50%, 60%, 70%, 80%, 90%, 95%, 98%, or 100% identity to all or a portion of the sequence of a bacterial cellulase. In some instances, the cellulase has at least 30%, 40%, 50%, 60%, 70%, 80%, 90%, 95%, 98%, or 100% identity to all or a portion of the sequence of a fungal cellulase. In some instances, the cellulase has at least 30%, 40%, 50%, 60%, 70%, 80%, 90%, 95%, 98%, or 100% identity to all or a portion of a protozoal cellulase.

In some instances, the cell wall-penetrating agent is a detergent. In some embodiments, the detergent is saponin.

In some instances, the cell wall-penetrating agent includes a cationic lipid. In some embodiments, the cationic lipid is 1,2-dioleoyl-sn-glycero-3-phosphatidylcholine (DOPC). In some embodiments, the cationic lipid is 1,2-dierucoyl-sn-glycero-3-phosphocholine (DEPC).

The agent may increase uptake of the PMP as a whole or may increase uptake of a portion or component of the PMP, such as a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)) carried by the PMP. The degree to which plant cell uptake is increased may vary depending on the plant or plant part to which the composition is delivered, the PMP formulation, and other modifications made to the PMP, For example, the modified PMPs may have an increased plant cell uptake of at least 1%, 2%, 5%, 10%, 15%, 20%, 30%, 40%, 50%, 60%, 70%, 80%, 90%, or 100% relative to an unmodified PMP. In some instances, the increased plant cell uptake is an increased plant cell uptake of at least 2-fold, 4-fold, 5-fold, 10-fold, 100-fold, or 1000-fold relative to an unmodified PMP.

In another aspect, the PMPs can be modified with other components (e.g., lipids, e.g., sterols, e.g., cholesterol; or small molecules) to alter the functional and structural characteristics of the PMP. For example, the PMPs can be modified with stabilizing molecules that increase the stability of the PMPs (e.g., for at least one day at room temperature, and/or stable for at least one week at 4° C.).

Plant cell uptake of the modified PMPs can be measured by a variety of methods well known in the art. For example, the PMPs, or a component thereof, can be labelled with a marker (e.g., a fluorescent marker) that can be detected in isolated plant cells to confirm uptake. Alternatively, plant cell uptake can be detected based on measures of plant fitness. For example, efficacy of the present compositions and methods can be determined by comparing fitness changes in plants treated with the presently modified PMPs relative to treatment of compositions lacking modified PMPs.

G. Loading of Agents

PMPs produced in accordance with the methods or bioreactors herein can be modified to include a heterologous functional agent (e.g., a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent)), such as those described herein. The PMPs can carry or associate with such agents in a variety of ways to enable delivery of the agent to a target plant, e.g., by encapsulating the agent, incorporation of the component in the lipid bilayer structure, or association of the component (e.g., by conjugation) with the surface of the lipid bilayer structure of the PMP.

The heterologous functional agent can be incorporated or loaded into or onto the PMPs by any methods known in the art that allow association, directly or indirectly, between the PMPs and agent. Heterologous functional agent agents can be incorporated into the PMPs by an in vivo method (e.g., in planta, e.g., through production of PMPs from a transgenic plant that includes the heterologous agent), or in vitro (e.g., in tissue culture, or in cell culture), or both in vivo and in vitro methods.

In instances where the PMPs are loaded with a heterologous functional agent in vivo, PMPs may be produced using EVs, or a segments or portions thereof, or an extract containing EVs that has been loaded in planta. In planta methods include expression of the heterologous functional agent in a plant, plant cell culture, or plant tissue that has been genetically modified to express the heterologous functional agent for loading into EVs. In some instances, the heterologous functional agent is exogenous to the plant. Alternatively, the heterologous functional agent may be naturally found in the plant, but engineered to be expressed at an elevated level relative to level of that found in a non-genetically modified plant.

In some instances, the PMPs can be loaded in vitro. The substance may be loaded onto or into (e.g., may be encapsulated by) the PMPs using, but not limited to, physical, chemical, and/or biological methods (e.g., in tissue culture or in cell culture). For example, the heterologous functional agent may be introduced into PMPs by one or more of electroporation, sonication, passive diffusion, stirring, lipid extraction, or extrusion. Loaded PMPs can be assessed to confirm the presence or level of the loaded agent using a variety of methods, such as HPLC (e.g., to assess small molecules); immunoblotting (e.g., to assess proteins); and quantitative PCR (e.g., to assess nucleotides). However, it should be appreciated by those skilled in the art that the loading of a substance of interest into PMPs is not limited to the above-illustrated methods.

In some instances, the heterologous functional agent can be conjugated to the PMP, in which the heterologous functional agent is connected or joined, indirectly or directly, to the PMP. For instance, one or more heterologous functional agents can be chemically-linked to a PMP, such that the one or more heterologous functional agents are joined (e.g., by covalent or ionic bonds) directly to the lipid bilayer of the PMP. In some instances, the conjugation of various heterologous functional agents to the PMPs can be achieved by first mixing the one or more heterologous functional agents with an appropriate cross-linking agent (e.g., N-ethylcarbodiimide ("EDC"), which is generally utilized as a carboxyl activating agent for amide bonding with primary amines and also reacts with phosphate groups) in a suitable solvent. After a period of incubation sufficient to allow the heterologous functional agent to attach to the cross-linking agent, the cross-linking agent/heterologous functional agent mixture can then be combined with the PMPs and, after another period of incubation, subjected to a sucrose gradient (e.g., and 8, 30, 45, and 60% sucrose gradient) to separate the free heterologous functional agent and free PMPs from the heterologous functional agent conjugated to the PMPs. As part of combining the mixture with a sucrose gradient, and an accompanying centrifugation step, the PMPs conjugated to the heterologous functional agent are then seen as a band in the sucrose gradient, such that the conjugated PMPs can then be collected, washed, and dissolved in a suitable solution for use as described herein.

In some instances, the PMPs are stably associated with the heterologous functional agent prior to and following delivery of the PMP, e.g., to a plant. In other instances, the PMPs are associated with the heterologous functional agent such that the heterologous functional agent becomes dissociated from the PMPs following delivery of the PMP, e.g., to a plant.

The PMPs can be loaded with various concentrations of the heterologous functional agent, depending on the particular agent or use. For example, in some instances, the PMPs are loaded such that the PMP composition disclosed herein includes about 0.001, 0.01, 0.1, 1.0, 2, 3, 4, 5, 6, 7, 8, 9, 10, 15, 20, 30, 40, 50, 60, 70, 80, 90, or 95 (or any range between about 0.001 and 95) or more wt % of a heterologous functional agent. In some instances, the PMPs are loaded such that the PMP composition includes about 95, 90, 80, 70, 60, 50, 40, 30, 20, 15, 10, 9, 8, 7, 6, 5, 4, 3, 2, 1.0, 0.1, 0.01, 0.001 (or any range between about 95 and 0.001) or less wt % of a heterologous functional agent. For example, the PMP composition can include about 0.001 to about 0.01 wt %, about 0.01 to about 0.1 wt %, about 0.1 to about 1 wt %, about 1 to about 5 wt %, or about 5 to about 10 wt %, about 10 to about 20 wt % of the heterologous functional agent. In some instances, the PMP can be loaded with about 1, 5, 10, 50, 100, 200, or 500, 1,000, 2,000 (or any range between about 1 and 2,000) or more µg/ml of a heterologous functional agent. A PMP of the invention can be loaded with about 2,000, 1,000, 500, 200, 100, 50, 10, 5, 1 (or any range between about 2,000 and 1) or less µg/ml of a heterologous functional agent.

in some instances, the PMPs are loaded such that the PMP composition disclosed herein includes at least 0.001 wt %, at least 0.01 wt %, at least 0.1 wt %, at least 1.0 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 30 wt %, at least 40 wt %, at least 50 wt %, at least 60 wt %, at least 70 wt %, at least 80 wt %, at least 90 wt %, or at least 95 wt % of a heterologous functional agent. In some instances, the PMP can be loaded with at least 1 µg/ml, at least 5 µg/ml, at least 10 µg/ml, at least 50 µg/ml, at least 100 µg/ml, at least 200 µg/ml, at least 500 µg/ml, at least 1,000 g/ml, at least 2,000 µg/ml of a heterologous functional agent.

Examples of particular heterologous functional agents that can be loaded into the PMPs are further outlined in the section entitled "Heterologous Functional Agents."

II. PMP Formulations

A. Agricultural Formulations

To allow ease of application, handling, transportation, storage, and effective activity, PMPs (e.g., produced in accordance with the methods or bioreactors herein), can be formulated with other substances for use in agriculture, e.g., formulated for delivery to a plant, plant pest, plant symbiont. PMPs can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

PMP compositions can be applied as aqueous suspensions or emulsions prepared from concentrated formulations of such agents. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the PMP composition, a carrier, and surfactants. The carrier is usually selected from among the attapulgite clays, the montmorillonite clays, the diatomaceous earths, or the purified silicates. Effective surfactants, including from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates can comprise a suitable concentration of PMPs, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble PMP compositions dispersed in an aqueous carrier at a concentration in the range from about 5% to about 50% by weight. Suspensions are prepared by finely grinding the composition and vigorously mixing it into a carrier comprised of water and surfactants. Ingredients, such as inorganic salts and synthetic or natural gums may also be added, to increase the density and viscosity of the aqueous carrier.

PMP compositions may also be applied as granular compositions that are particularly useful for applications to the soil. Granular compositions usually contain from about 0.5% to about 10% by weight of the PMP composition, dispersed in a carrier that comprises clay or a similar substance. Such compositions are usually prepared by dissolving the formulation in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing the present PMP formulation are prepared by intimately mixing PMPs in powdered form with a suitable dusty agricultural carrier, such as kaolin clay, ground volcanic rock, and the like. Dusts can suitably contain from about 1% to about 10% of the packets. They can be applied as a seed dressing or as a foliage application with a dust blower machine.

It is equally practical to apply the present formulation in the form of a solution in an appropriate organic solvent, usually petroleum oil, such as the spray oils, which are widely used in agricultural chemistry.

PMPs can also be applied in the form of an aerosol composition. In such compositions the packets are dissolved or dispersed in a carrier, which is a pressure-generating propellant mixture. The aerosol composition is packaged in a container from which the mixture is dispensed through an atomizing valve.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer including: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007. For ease of use, this embodiment will be referred to as "OIWE."

Additionally, generally, when the molecules disclosed above are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO (ethylene oxide-propylene oxide) block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the PMP composition on the target. The types of surfactants used for bioenhancement depend generally on the nature and mode of action of the PMP composition. However, they are often non-ionics such as: alkyl ethoxylates; linear aliphatic alcohol ethoxylates; aliphatic amine ethoxylates.

A carrier or diluent in an agricultural formulation is a material added to the PMP composition to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of PMP composition when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g., plant and animal sources. Specific examples are: vegetable oils, seed oils, and esters thereof, also alkoxylated alkyl polyglucosides.

In some instances, PMPs can be freeze-dried or lyophilized. See U.S. Pat. No. 4,311,712. The PMPs can later be reconstituted on contact with water or another liquid. Other components can be added to the lyophilized or reconstituted PMPs, for example, other heterologous functional agents, agriculturally acceptable carriers, or other materials in accordance with the formulations described herein.

Other optional features of the composition include carriers or delivery vehicles that protect the PMP composition against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

For further information on agricultural formulations, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

B. Pharmaceutical Formulations

The PMPs produced herein that can be formulated into pharmaceutical compositions, e.g., for administration to an animal (e.g., a human). The pharmaceutical composition may be administered to an animal (e.g., human) with a pharmaceutically acceptable diluent, carrier, and/or excipient. Depending on the mode of administration and the dosage, the pharmaceutical composition of the methods described herein will be formulated into suitable pharmaceutical compositions to permit facile delivery. The single dose may be in a unit dose form as needed.

A pathogen control composition may be formulated for e.g., oral administration, intravenous administration (e.g., injection or infusion), or subcutaneous administration to an animal. For injectable formulations, various effective pharmaceutical carriers are known in the art (See, e.g., Remington: The Science and Practice of Pharmacy, $22^{nd}$ ed., (2012) and ASHP Handbook on Injectable Drugs, $18^{th}$ ed., (2014)).

Pharmaceutically acceptable carriers and excipients in the present compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. The compositions may be formulated according to conventional pharmaceutical practice. The concentration of the compound in the formulation will vary depending upon a number of factors, including the dosage of the active agent (e.g., PMP) to be administered, and the route of administration.

For oral administration to an animal, the pathogen control composition can be prepared in the form of an oral formulation. Formulations for oral use can include tablets, caplets, capsules, syrups, or oral liquid dosage forms containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Formulations for oral use may also be provided in unit dosage form as chewable tablets, non-chewable tablets, caplets, capsules (e.g., as hard gelatin capsules wherein the active ingredient is mixed with an inert solid diluent, or as soft gelatin capsules wherein the active ingredient is mixed with water or an oil medium). The compositions disclosed herein may also further include an immediate-release, extended release or delayed-release formulation.

For parenteral administration to an animal, the pathogen control compositions may be formulated in the form of liquid solutions or suspensions and administered by a parenteral route (e.g., subcutaneous, intravenous, or intramuscular). The pharmaceutical composition can be formulated for injection or infusion. Pharmaceutical compositions for parenteral administration can be formulated using a sterile solution or any pharmaceutically acceptable liquid as a vehicle. Pharmaceutically acceptable vehicles include, but are not limited to, sterile water, physiological saline, or cell culture media (e.g., Dulbecco's Modified Eagle Medium (DMEM), α-Modified Eagles Medium (α-MEM), F-12 medium). Formulation methods are known in the art, see e.g., Gibson (ed.) Pharmaceutical Preformulation and Formulation (2nd ed.) Taylor & Francis Group, CRC Press (2009).

III. Heterologous Functional Agents

The PMPs produced herein can further include a heterologous functional agent, such as a heterologous agricultural agent (e.g., pesticidal agent, fertilizing agent, herbicidal agent, plant-modifying agent) or a heterologous therapeutic agent (e.g., an antifungal agent, an antibacterial agent, a virucidal agent, an anti-viral agent, an insecticidal agent, a nematicidal agent, an antiparasitic agent, or an insect repellent). For example, the PMP may encapsulate the heterologous functional agent. Alternatively, the heterologous functional agent can be embedded on or conjugated to the surface of the PMP. In some instances, the PMPs include two or more (e.g., 2, 3, 4, 5, 6, 7, 8, 9, 10, or more than 10) different heterologous functional agents. Heterologous functional agents may be added at any step during the manufacturing process effective to introduce the agent into the manufactured PMPs.

In certain instances, the heterologous functional agent (e.g., a heterologous agricultural agent (e.g., pesticidal agent, fertilizing agent, herbicidal agent, plant-modifying agent, a heterologous nucleic acid, a heterologous polypeptide, or a heterologous small molecule) or a heterologous therapeutic agent (e.g., an antifungal agent, an antibacterial agent, a virucidal agent, an anti-viral agent, a nematicidal agent, an antiparasitic agent, or an insect repellent)) can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), or a cation moiety.

Examples of heterologous functional agents that can be loaded into the PMPs manufactured herein are outlined below.

A. Heterologous Agricultural Agents

The PMPs produced herein can include a heterologous agricultural agent (e.g., an agent that effects a plant or an organism that associates with a plant and can be loaded into a PMP), such as a pesticidal agent, herbicidal agent, fertilizing agent, or a plant-modifying agent.

For example, in some instances, the PMPs may include a pesticidal agent. The pesticidal agent can be an antifungal agent, an antibacterial agent, an insecticidal agent, a molluscicidal agent, a nematicidal agent, a virucidal agent, or a combination thereof. The pesticidal agent can be a chemical agent, such as those well known in the art. Alternatively or additionally, the pesticidal agent can be a peptide, a polypeptide, a nucleic acid, a polynucleotide, or a small molecule. The pesticidal agent may be an agent that can decrease the fitness of a variety of plant pests or can be one that targets one or more specific target plant pests (e.g., a specific species or genus of plant pests).

In some instances, the PMPs may include one or more heterologous fertilizing agents. Examples of heterologous fertilizing agents include plant nutrients or plant growth regulators, such as those well known in the art. Alternatively, or additionally, the fertilizing agent can be a peptide, a polypeptide, a nucleic acid, or a polynucleotide that can increase the fitness of a plant symbiont. The fertilizing agent may be an agent that can increase the fitness of a variety of plants or plant symbionts or can be one that targets one or more specific target plants or plant symbionts (e.g., a specific species or genera of plants or plant symbionts).

In other instances, the PMPs may include one or more heterologous plant-modifying agents. In some instances, the plant-modifying agent can include a peptide or a nucleic acid.

i. Antibacterial Agents

The PMP compositions described herein can further include an antibacterial agent. In some instances, the PMP compositions include two or more (e.g., 2, 3, 4, 5, 6, 7, 8, 9, 10, or more than 10) different antibacterial agents. For example, the antibacterial agent can decrease the fitness of (e.g., decrease growth or kill) a bacterial plant pest (e.g., a bacterial plant pathogen). A PMP composition including an antibiotic as described herein can be contacted with a target pest, or plant infested thereof, in an amount and for a time sufficient to: (a) reach a target level (e.g., a predetermined or threshold level) of antibiotic concentration inside or on the target pest; and (b) decrease fitness of the target pest. The antibacterials described herein may be formulated in a PMP composition for any of the methods described herein, and in certain instances, may be associated with the PMP thereof.

As used herein, the term "antibacterial agent" refers to a material that kills or inhibits the growth, proliferation, division, reproduction, or spread of bacteria, such as phytopathogenic bacteria, and includes bactericidal (e.g., disinfectant compounds, antiseptic compounds, or antibiotics) or bacteriostatic agents (e.g., compounds or antibiotics). Bactericidal antibiotics kill bacteria, while bacteriostatic antibiotics only slow their growth or reproduction.

Bactericides can include disinfectants, antiseptics, or antibiotics. The most used disinfectants can comprise: active chlorine (i.e., hypochlorites (e.g., sodium hypochlorite), chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called carbolic acid), cresols (called Lysole in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, etc. Heavy metals and their salts are the most toxic, and environment-hazardous bactericides and therefore, their use is strongly oppressed or canceled; further, also properly concentrated strong acids (phosphoric, nitric, sulfuric, amidosulfuric, toluenesulfonic acids) and alkalis (sodium, potassium, calcium hydroxides).

As antiseptics (i.e., germicide agents that can be used on human or animal body, skin, mucoses, wounds and the like), few of the above mentioned disinfectants can be used, under proper conditions (mainly concentration, pH, temperature and toxicity toward man/animal). Among them, important are: properly diluted chlorine preparations (i.e., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds, such as hexachlorophene, triclosan and Dibromol, and cation-active compounds, such as 0.05-0.5% benzalkonium, 0.5-4% chlorhexidine, 0.1-2% octenidine solutions.

The PMP composition described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside (e.g., kasugamycin). In some instances, the antibiotic is a bacteriostatic antibiotic. In some instances the bacteriostatic antibiotic targets protein synthesis (e.g., macrolides, lincosamides, and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include rifampicin, ciprofloxacin, doxycycline, ampicillin, and polymyxin B. The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

Other non-limiting examples of antibiotics are found in Table 1. One skilled in the art will appreciate that a suitable concentration of each antibiotic in the composition depends on factors such as efficacy, stability of the antibiotic, number of distinct antibiotics, the formulation, and methods of application of the composition.

TABLE 1

Examples of Antibiotics

| Antibiotics | Action |
| --- | --- |
| Penicillins, cephalosporins, vancomycin | Cell wall synthesis |
| Polymixin, gramicidin | Membrane active agent, disrupt cell membrane |
| Tetracyclines, macrolides, chloramphenicol, clindamycin, spectinomycin | Inhibit protein synthesis |
| Sulfonamides | Inhibit folate-dependent pathways |
| Ciprofloxacin | Inhibit DNA-gyrase |
| Isoniazid, rifampicin, pyrazinamide, ethambutol, (myambutol)l, streptomycin | Antimycobacterial agents | ii. Antifungal Agents

The PMP compositions described herein can further include an antifungal agent. In some instances, the PMP compositions include two or more (e.g., 2, 3, 4, 5, 6, 7, 8, 9, 10, or more than 10) different antifungal agents. For example, the antifungal agent can decrease the fitness of (e.g., decrease growth or kill) a fungal plant pest. A PMP composition including an antifungal as described herein can be contacted with a target fungal pest, or plant infested therewith, in an amount and for a time sufficient to: (a) reach a target level (e.g., a predetermined or threshold level) of antibiotic concentration inside or on the target fungus; and (b) decrease fitness of the target fungus. The antifungals described herein may be formulated in a PMP composition for any of the methods described herein, and in certain instances, may be associated with the PMP thereof.

As used herein, the term "fungicide" or "antifungal agent" refers to a substance that kills or inhibits the growth, proliferation, division, reproduction, or spread of fungi, such as phytopathogenic fungi. Many different types of antifungal agent have been produced commercially. Non limiting examples of antifungal agents include: azoxystrobin, mancozeb, prothioconazole, folpet, tebuconazole, difenoconazole, captan, bupirimate, or fosetyl-Al. Further exemplary fungicides include, but are not limited to, strobilurins, azoxystrobin, dimoxystrobin, enestroburin, fluoxastrobin, kresoxim-methyl, metominostrobin, picoxystrobin, pyraclostrobin, trifloxystrobin, orysastrobin, carboxamides, carboxanilides, benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M (mefenoxam), methfuroxam, metsulfovax, ofurace, oxadixyl, oxycarboxin, penthiopyrad, pyracarbolid, salicylanilide, tecloftalam, thifluzamide, tiadinil, N-biphenylamides, bixafen, boscalid, carboxylic acid morpholides, dimethomorph, flumorph, benzamides, flumetover, fluopicolid (picobenzamid), zoxamid, carboxamides, carpropamid, diclocymet, mandipropamid, silthiofam, azoles, triazoles, bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, Imidazoles, cyazofamid, imazalil, pefurazoate, prochloraz, triflumizole, benzimidazoles, benomyl, carbendazim, fuberidazole, thiabendazole, ethaboxam, etridiazole, hymexazol, nitrogen-containing heterocyclyl compounds, pyridines, fuazinam, pyrifenox, pyrimidines, bupirimate, cyprodinil, ferimzone, fenarimol, mepanipyrim, nuarimol, pyrimethanil, piperazines, triforine, pyrroles, fludioxonil, fenpiclonil, morpholines, aldimorph, dodemorph, fenpropimorph, tridemorph, dicarboximides, iprodione, procymidone, vinclozolin, acibenzolar-S-methyl, anilazine, captan, captafol, dazomet, diclomezin, fenoxanil, folpet, fenpropidin, famoxadon, fenamidon, octhilinone, probenazole, proquinazid, pyroquilon, quinoxyfen, tricyclazole, carbamates, dithiocarbamates, ferbam, mancozeb, maneb, metiram, metam, propineb, thiram, zineb, ziram, diethofencarb, flubenthiavalicarb, iprovalicarb, propamocarb, guanidines, dodine, iminoctadine, guazatine, kasugamycin, polyoxins, streptomycin, validamycin A, organometallic compounds, fentin salts, sulfur-containing heterocyclyl compounds, isoprothiolane, dithianone, organophosphorous compounds, edifenphos, fosetyl, fosetyl-aluminum, iprobenfos, pyrazophos, tolclofos-methyl, Organochlorine compounds, thiophanate-methyl, chlorothalonil, dichlofluanid, tolylfluanid, flusulfamide, phthalide, hexachlorobenzene, pencycuron, quintozene, nitrophenyl derivatives, binapacryl, dinocap, dinobuton, spiroxamine, cyflufenamid, cymoxanil, metrafenon, N-2-cyanophenyl-3,4-dichloroisothiazol-5-carboxamide (isotianil), N-(3',4',5'-trifluorobiphenyl-2-yl)-3-difluoromethyl-1-methylpyrazole-4-carboxamide, 3-[5-(4-chlorophenyl)-2,3-dimethylisoxazolidin-3-yl]-pyridine, N-(3',4'-dichloro-4-fluorobiphenyl-2-yl)-3-difluoromethyl-1-methylpyrazol-e-4-carboxamide, 5-chloro-7-(4-methylpiperidin-1-yl)-6-(2,4,6-trifluorophenyl)-[1,2,4]tria-zolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazo-le-1-sulfonamide, methyl-(2-chloro-5-[1-(3-methylbenzyloxyimino)-ethyl]benzyl) carbamate, methyl-(2-chloro-5-[1-(6-methylpyridin-2-ylmethoxyimino)ethyl]benzyl) carbamate, methyl 3-(4-chlorophenyl)-3-(2-isopropoxycarbonylamino-3-methylbutyryl-amino) propionate, 4-fluorophenyl N-(1-(1-(4-cyanophenyl) ethanesulfonyl) but-2-yl) carbamate, N-(2-(4-[3-(4-chlorophenyl) prop-2-ynyloxy]-3-methoxyphenyl)ethyl)-2-metha-nesulfonylamino-3-methylbutyramide, N-(2-(4-[3-(4-chlorophenyl) prop-2-ynyloxy]-3-methoxyphenyl)ethyl)-2-ethan-esulfonylamino-3-methylbutyramide, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylt-hiazol-5-carboxamide, or methyl 2-(ortho-((2,5-dimethylphenyloxy-methylene)phenyl)-3-methoxyacrylate. One skilled in the art will appreciate that a suitable concentration of each antifungal in the composition depends on factors such as efficacy, stability of the antifungal, number of distinct antifungals, the formulation, and methods of application of the composition.

iii. Insecticides

The PMP compositions described herein can further include an insecticide. In some instances, the PMP compositions include two or more (e.g., 2, 3, 4, 5, 6, 7, 8, 9, 10, or more than 10) different insecticide agents. For example, the insecticide can decrease the fitness of (e.g., decrease growth or kill) an insect plant pest. A PMP composition including an insecticide as described herein can be contacted with a target insect pest, or plant infested therewith, in an amount and for a time sufficient to: (a) reach a target level (e.g., a predetermined or threshold level) of insecticide concentration inside or on the target insect; and (b) decrease fitness of the target insect. The insecticides described herein may be formulated in a PMP composition for any of the methods described herein, and in certain instances, may be associated with the PMP thereof.

As used herein, the term "insecticide" or "insecticidal agent" refers to a substance that kills or inhibits the growth, proliferation, reproduction, or spread of insects, such as agricultural insect pests. Non limiting examples of insecticides are shown in Table 2. Additional non-limiting examples of suitable insecticides include biologics, hormones or pheromones such as azadirachtin, *Bacillus* species, *Beauveria* species, codlemone, Metarrhizium species, *Paecilomyces* species, *thuringiensis*, and *Verticillium* species, and active compounds having unknown or non-specified mechanisms of action such as fumigants (such as aluminium phosphide, methyl bromide and sulphuryl fluoride) and selective feeding inhibitors (such as cryolite, flonicamid and pymetrozine). One skilled in the art will appreciate that a suitable concentration of each insecticide in the composition depends on factors such as efficacy, stability of the insecticide, number of distinct insecticides, the formulation, and methods of application of the composition.

TABLE 2

Examples of insecticides

| Class | Compounds |
|---|---|
| chloronicotinyls/ neonicotinoids | acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, acetylcholinesterase (AChE) inhibitors (such as carbamates and organophosphates) |

TABLE 2-continued

Examples of insecticides

| Class | Compounds |
|---|---|
| carbamates | alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb |
| organophosphates | acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion |
| pyrethroids | acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum) |
| oxadiazines | indoxacarb, acetylcholine receptor modulators (such as spinosyns) |
| spinosyns | Spinosad |
| cyclodiene | camphechlor, chlordane, endosulfan, gamma-HCH, HCH, heptachlor, |
| organochlorines | lindane, methoxychlor |
| fiproles | acetoprole, ethiprole, vaniliprole, fipronil |
| mectins | abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene |
| diacylhydrazines | chromafenozide, halofenozide, methoxyfenozide, tebufenozide |
| benzoylureas | bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron |
| organotins | azocyclotin, cyhexatin, fenbutatin oxide |
| pyrroles | Chlorfenapyr |
| dinitrophenols | binapacyrl, dinobuton, dinocap, DNOC |
| METIs | fenazaquin, fenpyroximate, pyrimidifen, pyridaben, tebufenpyrad, tolfenpyrad, rotenone, acequinocyl, fluacrypyrim, microbial disrupters of the intestinal membrane of insects (such as Bacillus thuringiensis strains), inhibitors of lipid synthesis (such as tetronic acids and tetramic acids) |
| tetronic acids | spirodiclofen, spiromesifen, spirotetramat |
| tetramic acids | cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester; CAS Reg. No.: 382608-10-8), carboxamides (such as flonicamid), octopaminergic agonists (such as amitraz), inhibitors of the magnesium-stimulated ATPase (such as propargite), ryanodin receptor agonists (such as phthalamides or rynaxapyr) |
| phthalamides | N2-[1,1-dimethyl-2-(methylsulphonyl)ethyl]-3-iodo-N1-[2-methyl--4-[1,2,2,2-tetrafluoro-1-(trifluoromethyl)ethyl]phenyl]-1,2-benzenedi-carboxamide (i.e., flubendiamide; CAS reg. No.: 272451-65-7) | iv. Nematicide

The PMP compositions described herein can further include a nematicide. In some instances, the PMP compositions include two or more (e.g., 2, 3, 4, 5, 6, 7, 8, 9, 10, or more than 10) different nematicides. For example, the nematicide can decrease the fitness of (e.g., decrease growth or kill) a nematode plant pest. A PMP composition including a nematicide as described herein can be contacted with a target nematode pest, or plant infested therewith, in an amount and for a time sufficient to: (a) reach a target level (e.g., a predetermined or threshold level) of nematicide concentration inside or on the target nematode; and (b) decrease fitness of the target nematode. The nematicides described herein may be formulated in a PMP composition for any of the methods described herein, and in certain instances, may be associated with the PMP thereof.

As used herein, the term "nematicide" or "nematicidal agent" refers to a substance that kills or inhibits the growth, proliferation, reproduction, or spread of nematodes, such as agricultural nematode pests. Non limiting examples of nematicides are shown in Table 3. One skilled in the art will appreciate that a suitable concentration of each nematicide in the composition depends on factors such as efficacy, stability of the nematicide, number of distinct nematicides, the formulation, and methods of application of the composition.

vi. Virucides

The PMP compositions described herein can further include a virucide. In some instances, the PMP compositions include two or more (e.g., 2, 3, 4, 5, 6, 7, 8, 9, 10, or more than 10) different virucides. For example, the virucide can decrease the fitness of (e.g., decrease or eliminate) a viral plant pathogen. A PMP composition including a virucide as described herein can be contacted with a target virus, or plant infested therewith, in an amount and for a time sufficient to: (a) reach a target level (e.g., a predetermined or threshold level) of virucide concentration; and (b) decrease or eliminate the target virus. The virucides described herein may be formulated in a PMP composition for any of the methods described herein, and in certain instances, may be associated with the PMP thereof.

As used herein, the term "virucide" or "antiviral" refers to a substance that kills or inhibits the growth, proliferation, reproduction, development, or spread of viruses, such as agricultural virus pathogens. A number of agents can be employed as a virucide, including chemicals or biological agents (e.g., nucleic acids, e.g., dsRNA). One skilled in the art will appreciate that a suitable concentration of each virucide in the composition depends on factors such as efficacy, stability of the virucide, number of distinct virucides, the formulation, and methods of application of the composition.

TABLE 3

Examples of Nematicides

| | |
|---|---|
| FUMIGANTS | D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, Chloropicrin, |
| CARBAMATES | Aldicarb, Aldoxycarb, Carbofuran, Oxamyl, Cleothocarb |
| ORGANOPHOSPHATES | Ethoprophos, Fenamiphos, Cadusafos, Fosthiazate, Fensulfothion, Thionazin, Isazofos, |
| BIOCHEMICALS | DITERA ®, CLANDOSAN ®, SINCOCIN ® | v. Molluscicide

The PMP compositions described herein can further include a molluscicide. In some instances, the PMP compositions include two or more (e.g., 2, 3, 4, 5, 6, 7, 8, 9, 10, or more than 10) different molluscicides. For example, the molluscicide can decrease the fitness of (e.g., decrease growth or kill) a mollusk plant pest. A PMP composition including a molluscicide as described herein can be contacted with a target mollusk pest, or plant infested therewith, in an amount and for a time sufficient to: (a) reach a target level (e.g., a predetermined or threshold level) of molluscicide concentration inside or on the target mollusk; and (b) decrease fitness of the target mollusk. The molluscicides described herein may be formulated in a PMP composition for any of the methods described herein, and in certain instances, may be associated with the PMP thereof.

As used herein, the term "molluscicide" or "molluscicidal agent" refers to a substance that kills or inhibits the growth, proliferation, reproduction, or spread of mollusks, such as agricultural mollusk pests. A number of chemicals can be employed as a molluscicide, including metal salts such as iron (III) phosphate, aluminium sulfate, and ferric sodium EDTA, [3][4], metaldehyde, methiocarb, or acetylcholinesterase inhibitors. One skilled in the art will appreciate that a suitable concentration of each molluscicide in the composition depends on factors such as efficacy, stability of the molluscicide, number of distinct molluscicides, the formulation, and methods of application of the composition.

vii. Herbicides

The PMP compositions described herein can further include one or more (e.g., 1, 2, 3, 4, 5, 6, 7, 8, 9, 10, or more than 10) herbicide. For example, the herbicide can decrease the fitness of (e.g., decrease or eliminate) a weed. A PMP composition including an herbicide as described herein can be contacted with a target weed in an amount and for a time sufficient to: (a) reach a target level (e.g., a predetermined or threshold level) of herbicide concentration on the plant and (b) decrease the fitness of the weed. The herbicides described herein may be formulated in a PMP composition for any of the methods described herein, and in certain instances, may be associated with the PMP thereof.

As used herein, the term "herbicide" refers to a substance that kills or inhibits the growth, proliferation, reproduction, or spread of weeds. A number of chemicals can be employed as a herbicides, including Glufosinate, Propaquizafop, Metamitron, Metazachlor, Pendimethalin, Flufenacet, Diflufenican, Clomazone, Nicosulfuron, Mesotrione, Pinoxaden, Sulcotrione, Prosulfocarb, Sulfentrazone, Bifenox, Quinmerac, Triallate, Terbuthylazine, Atrazine, Oxyfluorfen, Diuron, Trifluralin, or Chlorotoluron. Further examples of herbicides include, but are not limited to, benzoic acid herbicides, such as dicamba esters, phenoxyalkanoic acid herbicides, such as 2,4-D, MCPA and 2,4-DB esters, aryloxyphenoxypropionic acid herbicides, such as clodinafop, cyhalofop, fenoxaprop, fluazifop, haloxyfop, and quizalofop esters, pyridinecarboxylic acid herbicides, such as aminopyralid, picloram, and clopyralid esters, pyrimidinecarboxylic acid herbicides, such as aminocyclopyrachlor esters, pyridyloxyalkanoic acid herbicides, such as fluoroxypyr and triclopyr esters, and hydroxybenzonitrile herbicides, such as bromoxynil and ioxynil esters, esters of the arylpyridine carboxylic acids, and arylpyrimidine carboxylic acids of the generic structures disclosed in U.S. Pat. Nos. 7,314,849, 7,300,907, and 7,642,220, each of which is incorporated by reference herein in its entirety. In certain embodiments, the herbicide can be selected from the group consisting of 2,4-D, 2,4-DB, acetochlor, acifluorfen, alachlor, ametryn, amitrole, asulam, atrazine, azafenidin, benefin, bensulfuron, bensulide, bentazon, bromacil, bromoxynil, butylate, carfentrazone, chloramben, chlorimuron, chlorproham, chlorsulfuron, clethodim, clomazone, clopyralid, cloransulam, cyanazine, cycloate, DCPA, desmedipham, dichlobenil, diclofop, diclosulam, diethatyl, difenzoquat, diflufenzopyr, dimethenamid-p, diquat, diuron, DSMA, endothall, EPTC, ethalfluralin, ethametsulfuron, ethofumesate, fenoxaprop, fluazifop-P, flucarbazone, flufenacet, flumetsulam, flumiclorac, flumioxazin, fluometuron, fluroxypyr, fluthiacet, fomesafen, foramsulfuron, glufosinate, glyphosate, halosulfuron, haloxyfop, hexazinone, imazamethabenz, imazamox, imazapic, imazaquin, imazethapyr, isoxaben, isoxaflutole, lactofen, linuron, MCPA, MCPB, mesotrione, methazole, metolachlor-s, metribuzin, metsulfuron, molinate, MSMA, napropamide, naptalam, nicosulfuron, norflurazon, oryzalin, oxadiazon, oxasulfuron, oxyfluorfen, paraquat, pebulate, pelargonic acid, pendimethalin, phenmedipham, picloram, primisulfuron, prodiamine, prometryn, pronamide, propachlor, propanil, prosulfuron, pyrazon, pyridate, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, vernolate. One skilled in the art will appreciate that a suitable concentration of each herbicide in the composition depends on factors such as efficacy, stability of the herbicide, number of distinct herbicides, the formulation, and methods of application of the composition.

viii. Repellents

The PMP compositions described herein can further include a repellent. In some instances, the PMP compositions include two or more (e.g., 2, 3, 4, 5, 6, 7, 8, 9, 10, or more than 10) different repellents. For example, the repellent can repel any of the pests described herein (e.g., insects, nematodes, or mollusks); microorganisms (e.g., phytopathogens or endophytes, such as bacteria, fungi, or viruses); or weeds. A PMP composition including a repellent as described herein can be contacted with a target plant, or plant infested therewith, in an amount and for a time sufficient to: (a) reach a target level (e.g., a predetermined or threshold level) of repellent concentration; and (b) decrease the levels of the pest on the plant relative to an untreated plant. The repellent described herein may be formulated in a PMP composition for any of the methods described herein, and in certain instances, may be associated with the PMP thereof.

In some instances, the repellent is an insect repellent. Some examples of well-known insect repellents include: benzil; benzyl benzoate; 2,3,4,5-bis(butyl-2-ene)tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo,endo)-dimethyl bicyclo[2.2.1]hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-menthane-3,8-diol, and normal-propyl N,N-diethylsuccinamate. Other repellents include citronella oil, dimethyl phthalate, normal-butylmesityl oxide oxalate and 2-ethyl hexanediol-1,3 (See, Kirk-Othmer Encyclopedia of Chemical Technology, 2nd Ed., Vol. 11:724-728; and The Condensed Chemical Dictionary, 8th Ed., p 756).

An insect repellent may be a synthetic or nonsynthetic insect repellent. Examples of synthetic insect repellents include methyl anthranilate and other anthranilate-based insect repellents, benzaldehyde, DEET (N,N-diethyl-m-toluamide), dimethyl carbate, dimethyl phthalate, icaridin (i.e., picaridin, Bayrepel, and KBR 3023), indalone (e.g., as used in a "6-2-2" mixture (60% Dimethyl phthalate, 20% Indalone, 20% Ethylhexanediol), IR3535 (3-[N-Butyl-N-acetyl]-aminopropionic acid, ethyl ester), metofluthrin, permethrin, SS220, or tricyclodecenyl allyl ether. Examples of natural insect repellents include beautyberry (Callicarpa) leaves, birch tree bark, bog myrtle (*Myrica* Gale), catnip oil (e.g., nepetalactone), citronella oil, essential oil of the lemon *eucalyptus* (*Corymbia citriodora*; e.g., p-menthane-3,8-diol (PMD)), neem oil, lemongrass, tea tree oil from the leaves of *Melaleuca* alternifolia, tobacco, or extracts thereof.

ix. Fertilizing Agents

The PMP compositions described herein can further include a heterologous fertilizing agent. In some instances, the heterologous fertilizing agent is associated with the PMPs. For example, a PMP may encapsulate the heterologous fertilizing agent. Additionally, or alternatively, the heterologous fertilizing agent can be embedded on or conjugated to the surface of the PMP.

Examples of heterologous fertilizing agents include plant nutrients or plant growth regulators, such as those well known in the art. Alternatively, or additionally, the fertilizing agent can be a peptide, a polypeptide, a nucleic acid, or a polynucleotide that can increase the fitness of a plant symbiont. The fertilizing agent may be an agent that can increase the fitness of a variety of plants or plant symbionts or can be one that targets one or more specific target plants or plant symbionts (e.g., a specific species or genera of plants or plant symbionts).

In some instances, the heterologous fertilizing agent can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), or a cation moiety.

Examples of heterologous fertilizing agents that can be used in the presently disclosed PMP compositions and methods are outlined below.

In some instances, the heterologous fertilizing agent includes any material of natural or synthetic origin that is applied to soils or to plant tissues to supply one or more plant nutrients essential to the growth of plants. The plant nutrient may include a macronutrient, micronutrient, or a combination thereof. Plant macronutrients include nitrogen, phosphorus, potassium, calcium, magnesium, and/or sulfur. Plant micronutrients include copper, iron, manganese, molybdenum, zinc, boron, silicon, cobalt, and/or vanadium. Examples of plant nutrient fertilizers include a nitrogen fertilizer including, but not limited to urea, ammonium nitrate, ammonium sulfate, non-pressure nitrogen solutions, aqua ammonia, anhydrous ammonia, ammonium thiosulfate, sulfur-coated urea, urea-formaldehydes, IBDU, polymer-coated urea, calcium nitrate, ureaform, or methylene urea, phosphorous fertilizers such as diammonium phosphate, monoammonium phosphate, ammonium polyphosphate, concentrated superphosphate and triple superphosphate, or potassium fertilizers such as potassium chloride, potassium sulfate, potassium-magnesium sulfate, potassium nitrate. Such compositions can exist as free salts or ions within the composition. Fertilizers may be designated by the content of one or more of its components, such as nitrogen, phosphorous, or potassium. The content of these elements in a fertilizer may be indicated by the N—P—K value (where N=nitrogen content by weight percentage, P=phosphorous content by weight percentage, and K=potassium content by weight percentage).

Inorganic fertilizers, on the other hand, are manufactured from non-living materials and include, for example, ammonium nitrate, ammonium sulfate, urea, potassium chloride, potash, ammonium phosphate, anhydrous ammonia, and other phosphate salts. Inorganic fertilizers are readily commercially available and contain nutrients in soluble form that are immediately available to the plant. Inorganic fertilizers are generally inexpensive, having a low unit cost for the desired element. One skilled in the art will appreciate that the exact amount of a given element in a fertilizing agent may be calculated and administered to the plant or soil.

Fertilizers may be further classified as either organic fertilizers or inorganic fertilizers. Organic fertilizers include fertilizers having a molecular skeleton with a carbon backbone, such as in compositions derived from living matter. Organic fertilizers are made from materials derived from living things. Animal manures, compost, bonemeal, feather meal, and blood meal are examples of common organic fertilizers. Organic fertilizers, on the other hand, are typically not immediately available to plants and require soil microorganisms to break the fertilizer components down into simpler structures prior to use by the plants.

In addition, organic fertilizers may not only elicit a plant growth response as observed with common inorganic fertilizers, but natural organic fertilizers may also stimulate soil microbial population growth and activities. Increased soil microbial population (e.g., plant symbionts) may have significant beneficial effects on the physical and chemical properties of the soil, as well as increasing disease and pest resistance.

In one aspect, a PMP composition including a plant nutrient as described herein can be contacted with the plant in an amount and for a time sufficient to: (a) reach a target level (e.g., a predetermined or threshold level) of plant nutrient concentration inside or on the plant, and (b) increase the fitness of the plant relative to an untreated plant.

In another aspect, a PMP composition including a plant nutrient as described herein can be contacted with the plant symbiont in an amount and for a time sufficient to: (a) reach a target level (e.g., a predetermined or threshold level) of plant nutrient concentration inside or on the plant symbiont (e.g., a bacterial or fungal endosymbiont), and (b) increase the fitness of the plant symbiont relative to an untreated plant symbiont.

The heterologous fertilizing agent may include a plant growth regulator. Exemplary plant growth regulators include auxins, cytokinins, gibberellins, and abscisic acid. In some instances, the plant growth regulator is abscisic cacid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, flu- thiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapacethyl and uniconazole. Other plant growth regulators that can be incorporated seed coating compositions are described in US 2012/0108431, which is incorporated by reference in its entirety.

x. Plant-Modifying Agents

The PMP compositions described herein include one or more heterologous plant-modifying agents. For example, the PMPs may encapsulate the heterologous plant-modifying agent. Alternatively or additionally, the heterologous plant-modifying agent can be embedded on or conjugated to the surface of the PMP.

In some instances, the plant-modifying agent can include a peptide or a nucleic acid. The plant-modifying agent may be an agent that increases the fitness of a variety of plants or can be one that targets one or more specific plants (e.g., a specific species or genera of plants). Additionally, in some instances, the PMP compositions include two or more (e.g., 2, 3, 4, 5, 6, 7, 8, 9, 10, or more than 10) different plant-modifying agents.

Further, in some instances, the heterologous plant-modifying agent (e.g., an agent including a nucleic acid molecule or peptide) can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), or a cation moiety.

Examples of heterologous plant-modifying agents (e.g., peptides or nucleic acids) that can be used in the presently disclosed PMP compositions and methods are outlined below.

A Polypeptides

The PMP composition (e.g., PMPs) described herein may include a heterologous polypeptide. In some instances, the PMP composition described herein includes a polypeptide or functional fragments or derivative thereof that modifies a plant (e.g., e.g., increases the fitness of the plant). For example, the polypeptide can increase the fitness of a plant. A PMP composition including a polypeptide as described herein can be contacted with a plant in an amount and for a time sufficient to: (a) reach a target level (e.g., a predetermined or threshold level) of polypeptide concentration; and (b) modify the plant (e.g., increase the fitness of the plant).

Examples of polypeptides that can be used herein can include an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone.

Polypeptides included herein may include naturally occurring polypeptides or recombinantly produced variants. In some instances, the polypeptide may be a functional fragments or variants thereof (e.g., an enzymatically active fragment or variant thereof). For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide. In some instances, the polypeptide may have at least 50% (e.g., at least 50%, 60%, 70%, 80%, 90%, 95%, 97%, 99%, or greater) identity to a protein of interest.

The polypeptides described herein may be formulated in a composition for any of the uses described herein. The compositions disclosed herein may include any number or type (e.g., classes) of polypeptides, such as at least about any one of 1 polypeptide, 2, 3, 4, 5, 10, 15, 20, or more polypeptides. A suitable concentration of each polypeptide in the composition depends on factors such as efficacy, stability of the polypeptide, number of distinct polypeptides in the composition, the formulation, and methods of application of the composition. In some instances, each polypeptide in a liquid composition is from about 0.1 ng/ml to about 100 mg/mL. In some instances, each polypeptide in a solid composition is from about 0.1 ng/g to about 100 mg/g.

Methods of making a polypeptide are routine in the art. See, in general, Smales & James (Eds.), Therapeutic Proteins: Methods and Protocols (Methods in Molecular Biology), Humana Press (2005); and Crommelin, Sindelar & Meibohm (Eds.), Pharmaceutical Biotechnology: Fundamentals and Applications, Springer (2013).

Methods for producing a polypeptide involve expression in plant cells, although recombinant proteins can also be produced using insect cells, yeast, bacteria, mammalian cells, or other cells under the control of appropriate promoters. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, Molecular Cloning: A Laboratory Manual (Fourth Edition), Cold Spring Harbor Laboratory Press (2012).

Various mammalian cell culture systems can be employed to express and manufacture a recombinant polypeptide agent. Examples of mammalian expression systems include CHO cells, COS cells, HeLA and BHK cell lines. Processes of host cell culture for production of protein therapeutics are described in, e.g., Zhou and Kantardjieff (Eds.), Mammalian Cell Cultures for Biologics Manufacturing (Advances in Biochemical Engineering/Biotechnology), Springer (2014). Purification of proteins is described in Franks, Protein Biotechnology: Isolation, Characterization, and Stabilization, Humana Press (2013); and in Cutler, Protein Purification Protocols (Methods in Molecular Biology), Humana Press (2010). Formulation of protein therapeutics is described in Meyer (Ed.), Therapeutic Protein Drug Products: Practical Approaches to formulation in the Laboratory, Manufacturing, and the Clinic, Woodhead Publishing Series (2012).

In some instances, the PMP composition includes an antibody or antigen binding fragment thereof. For example, an agent described herein may be an antibody that blocks or potentiates activity and/or function of a component of the plant. The antibody may act as an antagonist or agonist of a polypeptide (e.g., enzyme or cell receptor) in the plant. The making and use of antibodies against a target antigen is known in the art. See, for example, Zhiqiang An (Ed.), Therapeutic Monoclonal Antibodies: From Bench to Clinic, 1st Edition, Wiley, 2009 and also Greenfield (Ed.), Antibodies: A Laboratory Manual, 2nd Edition, Cold Spring Harbor Laboratory Press, 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

B. Nucleic Acids

Numerous nucleic acids are useful in the PMP compositions and methods described herein. The PMP compositions disclosed herein may include any number or type (e.g., classes) of heterologous nucleic acids (e.g., DNA molecule or RNA molecule, e.g., mRNA, guide RNA (gRNA), or inhibitory RNA molecule (e.g., siRNA, shRNA, or miRNA), or a hybrid DNA-RNA molecule), such as at least about 1 class or variant of a nucleic acid, 2, 3, 4, 5, 10, 15, 20, or more classes or variants of nucleic acids. A suitable concentration of each nucleic acid in the composition depends on factors such as efficacy, stability of the nucleic acid, number of distinct nucleic acids, the formulation, and methods of application of the composition. Examples of nucleic acids useful herein include an antisense RNA, a short interfering RNA (siRNA), a short hairpin (shRNA), a microRNA (miRNA), an (asymmetric interfering RNA) aiRNA, a peptide nucleic acid (PNA), a morpholino, a locked nucleic acid (LNA), a piwi-interacting RNA (piRNA), a ribozyme, a deoxyribozymes (DNAzyme), an aptamer (DNA, RNA), a circular RNA (circRNA), a guide RNA (gRNA), or a DNA molecule A PMP composition including a nucleic acid as described herein can be contacted with a plant in an amount and for a time sufficient to: (a) reach a target level (e.g., a predetermined or threshold level) of nucleic acid concentration; and (b) modify the plant (e.g., increase the fitness of the plant).

(a) Nucleic Acid Encoding Peptides

In some instances, the PMP composition includes a heterologous nucleic acid encoding a polypeptide. Nucleic acids encoding a polypeptide may have a length from about 10 to about 50,000 nucleotides (nts), about 25 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, about 5000 to about 6000 nts, about 6000 to about 7000 nts, about 7000 to about 8000 nts, about 8000 to about 9000 nts, about 9000 to about 10,000 nts, about 10,000 to about 15,000 nts, about 10,000 to about 20,000 nts, about 10,000 to about 25,000 nts, about 10,000 to about 30,000 nts, about 10,000 to about 40,000 nts, about 10,000 to about 45,000 nts, about 10,000 to about 50,000 nts, or any range therebetween.

The PMP composition may also include functionally active variants of a nucleic acid sequence of interest. In some instances, the variant of the nucleic acids has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a nucleic acid of interest. In some instances, the invention includes a functionally active polypeptide encoded by a nucleic acid variant as described herein. In some instances, the functionally active polypeptide encoded by the nucleic acid variant has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire amino acid sequence, to a sequence of a polypeptide of interest or the naturally derived polypeptide sequence.

Certain methods for expressing a nucleic acid encoding a protein may involve expression in cells, including insect, yeast, plant, bacteria, or other cells under the control of appropriate promoters. Expression vectors may include non-transcribed elements, such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green et al., Molecular Cloning: A Laboratory Manual, Fourth Edition, Cold Spring Harbor Laboratory Press, 2012.

Genetic modification using recombinant methods is generally known in the art. A nucleic acid sequence coding for a desired gene can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. Expression vectors can be suitable for replication and expression in bacteria. Expression vectors can also be suitable for replication and integration in eukaryotes. Typical cloning vectors contain transcription and translation terminators, initiation sequences, and promoters useful for expression of the desired nucleic acid sequence.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Alternatively, the promoter may be an inducible promoter. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transformed cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., *FEBS Letters* 479:79-82, 2000). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some instances, an organism may be genetically modified to alter expression of one or more proteins. Expression of the one or more proteins may be modified for a specific time, e.g., development or differentiation state of the organism. In one instances, the invention includes a composition to alter expression of one or more proteins, e.g., proteins that affect activity, structure, or function. Expression of the one or more proteins may be restricted to a specific location(s) or widespread throughout the organism.

(b) Synthetic mRNA

The PMP composition may include a synthetic mRNA molecule, e.g., a synthetic mRNA molecule encoding a polypeptide. The synthetic mRNA molecule can be modified, e.g., chemically. The mRNA molecule can be chemically synthesized or transcribed in vitro. The mRNA molecule can be disposed on a plasmid, e.g., a viral vector, bacterial vector, or eukaryotic expression vector. In some examples, the mRNA molecule can be delivered to cells by transfection, electroporation, or transduction (e.g., adenoviral or lentiviral transduction).

In some instances, the modified RNA agent of interest described herein has modified nucleosides or nucleotides. Such modifications are known and are described, e.g., in WO 2012/019168. Additional modifications are described, e.g., in WO 2015/038892; WO 2015/038892; WO 2015/089511; WO 2015/196130; WO 2015/196118 and WO 2015/196128 A2.

In some instances, the modified RNA encoding a polypeptide of interest has one or more terminal modification, e.g., a 5' cap structure and/or a poly-A tail (e.g., of between 100-200 nucleotides in length). The 5' cap structure may be selected from the group consisting of CapO, CapI, ARCA, inosine, NI-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contain a 5' UTR including at least one Kozak sequence, and a 3' UTR. Such modifications are known and are described, e.g., in WO 2012/135805 and WO 2013/052523. Additional terminal modifications are described, e.g., in WO 2014/164253 and WO 2016/011306, WO 2012/045075, and WO 2014/093924. Chimeric enzymes for synthesizing capped RNA molecules (e.g., modified mRNA) which may include at least one chemical modification are described in WO 2014/028429.

In some instances, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular. Such modifications are described, e.g., in WO 2013/151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO 2013/151666, WO 2013/151668, WO 2013/151663, WO 2013/151669, WO 2013/151670, WO 2013/151664, WO 2013/151665, WO 2013/151671, WO 2013/151672, WO 2013/151667 and WO 2013/151736. Methods of purification include purifying an RNA transcript including a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO 2014/152031); using ion (e.g., anion) exchange chromatography that allows for separation of longer RNAs up to 10,000 nucleotides in length via a scalable method (WO 2014/144767); and subjecting a modified mRNA sample to DNAse treatment (WO 2014/152030).

Formulations of modified RNAs are known and are described, e.g., in WO 2013/090648. For example, the formulation may be, but is not limited to, nanoparticles, poly(lactic-co-glycolic acid) (PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Modified RNAs encoding polypeptides in the fields of human disease, antibodies, viruses, and a variety of in vivo settings are known and are disclosed in for example, Table 6 of International Publication Nos. WO 2013/151666, WO 2013/151668, WO 2013/151663, WO 2013/151669, WO 2013/151670, WO 2013/151664, WO 2013/151665, WO 2013/151736; Tables 6 and 7 International Publication No. WO 2013/151672; Tables 6, 178 and 179 of International Publication No. WO 2013/151671; Tables 6, 185 and 186 of International Publication No WO 2013/151667. Any of the foregoing may be synthesized as an IVT polynucleotide, chimeric polynucleotide or a circular polynucleotide, and each may include one or more modified nucleotides or terminal modifications.

(c) Inhibitory RNA

In some instances, the PMP composition includes an inhibitory RNA molecule, e.g., that acts via the RNA interference (RNAi) pathway. In some instances, the inhibitory RNA molecule decreases the level of gene expression in a plant and/or decreases the level of a protein in the plant. In some instances, the inhibitory RNA molecule inhibits expression of a plant gene. For example, an inhibitory RNA molecule may include a short interfering RNA, short hairpin RNA, and/or a microRNA that targets a gene in the plant. Certain RNA molecules can inhibit gene expression through the biological process of RNA interference (RNAi). RNAi molecules include RNA or RNA-like structures typically containing 15-50 base pairs (such as about18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), short hairpin RNAs (shRNA), meroduplexes, dicer substrates, and multivalent RNA interference (U.S. Pat. Nos. 8,084,599, 8,349,809, 8,513,207 and 9,200,276). A shRNA is a RNA molecule including a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 22 nucleotides. MiRNAs bind to target sites on mRNA molecules and silence the mRNA, e.g., by causing cleavage of the mRNA, destabilization of the mRNA, or inhibition of translation of the mRNA. In some instances, the inhibitory RNA molecule decreases the level and/or activity of a negative regulator of function. In other instances, the inhibitor RNA molecule decreases the level and/or activity of an inhibitor of a positive regulator of function. The inhibitory RNA molecule can be chemically synthesized or transcribed in vitro.

In some instances, the nucleic acid is a DNA, a RNA, or a PNA. In some instances, the RNA is an inhibitory RNA. In some instances, the inhibitory RNA inhibits gene expression in a plant. In some instances, the nucleic acid is an mRNA, a modified mRNA, or a DNA molecule that, in the plant, increases expression of an enzyme (e.g., a metabolic recombinase, a helicase, an integrase, a RNAse, a DNAse, or an ubiquitination protein), a pore-forming protein, a signaling ligand, a cell penetrating peptide, a transcription factor, a receptor, an antibody, a nanobody, a gene editing protein (e.g., CRISPR-Cas system, TALEN, or zinc finger), riboprotein, a protein aptamer, or a chaperone. In some instances, the nucleic acid is an mRNA, a modified mRNA, or a DNA molecule that increases the expression of an enzyme (e.g., a metabolic enzyme, a recombinase enzyme, a helicase enzyme, an integrase enzyme, a RNAse enzyme, a DNAse enzyme, or an ubiquitination protein), a pore-forming protein, a signaling ligand, a cell penetrating peptide, a transcription factor, a receptor, an antibody, a nanobody, a gene editing protein (e.g., a CRISPR-Cas system, a TALEN, or a zinc finger), a riboprotein, a protein aptamer, or a chaperone. In some instances, the increase in expression in the plant is an increase in expression of about 5%, 10%, 15%, 20%, 30%, 40%, 50%, 60%, 70%, 80%, 90%, 100%, or more than 100% relative to a reference level (e.g., the expression in an untreated plant). In some instances, the increase in expression in the plant is an increase in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

In some instances, the nucleic acid is an antisense RNA, a siRNA, a shRNA, a miRNA, an aiRNA, a PNA, a morpholino, a LNA, a piRNA, a ribozyme, a DNAzyme, an aptamer (DNA, RNA), a circRNA, a gRNA, or a DNA molecules (e.g., an antisense polynucleotide) to reduces, in the plant, expression of, e.g., an enzyme (a metabolic enzyme, a recombinase enzyme, a helicase enzyme, an integrase enzyme, a RNAse enzyme, a DNAse enzyme, a polymerase enzyme, a ubiquitination protein, a superoxide management enzyme, or an energy production enzyme), a transcription factor, a secretory protein, a structural factor (actin, kinesin, or tubulin), a riboprotein, a protein aptamer, a chaperone, a receptor, a signaling ligand, or a transporter. In some instances, the decrease in expression in the plant is a decrease in expression of about 5%, 10%, 15%, 20%, 30%, 40%, 50%, 60%, 70%, 80%, 90%, 100%, or more than 100% relative to a reference level (e.g., the expression in an untreated plant). In some instances, the decrease in expression in the plant is a decrease in expression of about 2× fold, about 4× fold, about 5× fold, about 10× fold, about 20× fold, about 25× fold, about 50× fold, about 75× fold, or about 100× fold or more, relative to a reference level (e.g., the expression in an untreated plant).

RNAi molecules include a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for a target gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided as ready-to-use RNA synthesized in vitro or as an antisense gene transfected into cells which will yield RNAi molecules upon transcription. Hybridization with mRNA results in degradation of the hybridized molecule by RNAse H and/or inhibition of the formation of translation complexes. Both result in a failure to produce the product of the original gene.

The length of the RNAi molecule that hybridizes to the transcript of interest may be around 10 nucleotides, between about 15 or 30 nucleotides, or about 15, 16, 17, 18, 19, 20, 21, 22, 23, 24, 25, 26, 27, 28, 29, 30 or more nucleotides. The degree of identity of the antisense sequence to the targeted transcript may be at least 75%, at least 80%, at least 85%, at least 90%, or at least 95.

RNAi molecules may also include overhangs, i.e., typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In some instances, both the sense strand and the antisense strand contain 3' and 5' overhangs. In some instances, one or more of the 3' overhang nucleotides of one strand base pairs with one or more 5' overhang nucleotides of the other strand. In other instances, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another instance, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules include a nucleotide sequence that is identical to about 15 to about 25 contiguous nucleotides of the target mRNA. In some instances, the siRNA sequence commences with the dinucleotide AA, includes a GC-content of about 30-70% (about 30-60%, about 40-60%, or about 45%-55%), and does not have a high percentage identity to any nucleotide sequence other than the target in the genome in which it is to be introduced, for example as determined by standard BLAST search.

siRNAs and shRNAs resemble intermediates in the processing pathway of the endogenous microRNA (miRNA) genes (Bartel, Cell 116:281-297, 2004). In some instances, siRNAs can function as miRNAs and vice versa (Zeng et al., *Mol. Cell* 9:1327-1333, 2002; Doench et al., *Genes Dev.* 17:438-442, 2003). Exogenous siRNAs downregulate mRNAs with seed complementarity to the siRNA (Birmingham et al., *Nat. Methods* 3:199-204, 2006). Multiple target sites within a 3' UTR give stronger downregulation (Doench et al., *Genes Dev.* 17:438-442, 2003).

Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al., Nat. Methods 3 (9): 670-676, 2006; Reynolds et al., Nat. Biotechnol. 22 (3): 326-330, 2004; Khvorova et al., Nat. Struct. Biol. 10 (9): 708-712, 2003; Schwarz et al., Cell 115 (2): 199-208, 2003; Ui-Tei et al., Nucleic Acids Res. 32 (3): 936-948, 2004; Heale et al., Nucleic Acids Res. 33 (3): e30, 2005; Chalk et al., Biochem. Biophys. Res. Commun. 319 (1): 264-274, 2004; and Amarzguioui et al., Biochem. Biophys. Res. Commun. 316 (4): 1050-1058, 2004).

The RNAi molecule modulates expression of RNA encoded by a gene. Because multiple genes can share some degree of sequence homology with each other, in some instances, the RNAi molecule can be designed to target a class of genes with sufficient sequence homology. In some instances, the RNAi molecule can contain a sequence that has complementarity to sequences that are shared amongst different gene targets or are unique for a specific gene target. In some instances, the RNAi molecule can be designed to target conserved regions of an RNA sequence having homology between several genes thereby targeting several genes in a gene family (e.g., different gene isoforms, splice variants, mutant genes, etc.). In some instances, the RNAi molecule can be designed to target a sequence that is unique to a specific RNA sequence of a single gene.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that such modifications can increase nuclease resistance and/or serum stability, or decrease immunogenicity.

In some instances, the RNAi molecule is linked to a delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the molecule from the polymer, by cleavage of the physiologically labile linkage, facilitates interaction of the molecule with the appropriate cellular components for activity.

The RNAi molecule-polymer conjugate may be formed by covalently linking the molecule to the polymer. The polymer is polymerized or modified such that it contains a reactive group A. The RNAi molecule is also polymerized or modified such that it contains a reactive group B. Reactive groups A and B are chosen such that they can be linked via a reversible covalent linkage using methods known in the art.

Conjugation of the RNAi molecule to the polymer can be performed in the presence of an excess of polymer. Because the RNAi molecule and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate. Alternatively, the excess polymer can be co-administered with the conjugate.

The making and use of inhibitory agents based on non-coding RNA such as ribozymes, RNAse P, siRNAs, and miRNAs are also known in the art, for example, as described in Sioud, RNA Therapeutics: Function, Design, and Delivery (Methods in Molecular Biology). Humana Press (2010).

(d) Gene Editing

The PMP compositions described herein may include a component of a gene editing system. For example, the agent may introduce an alteration (e.g., insertion, deletion (e.g., knockout), translocation, inversion, single point mutation, or other mutation) in a gene in the plant. Exemplary gene editing systems include the zinc finger nucleases (ZFNs), Transcription Activator-Like Effector-based Nucleases (TALEN), and the clustered regulatory interspaced short palindromic repeat (CRISPR) system. ZFNs, TALENs, and CRISPR-based methods are described, e.g., in Gaj et al., Trends Biotechnol. 31 (7): 397-405, 2013.

In a typical CRISPR/Cas system, an endonuclease is directed to a target nucleotide sequence (e.g., a site in the genome that is to be sequence-edited) by sequence-specific, non-coding guide RNAs that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA (crRNA), and a trans-activating crRNA (tracrRNA). The crRNA contains a guide RNA, i.e., typically an about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The RNAs serve as guides to direct Cas proteins to silence specific DNA/RNA sequences, depending on the spacer sequence. See, e.g., Horvath et al., Science 327:167-170, 2010; Makarova et al., Biology Direct 1:7, 2006; Pennisi, Science 341:833-836, 2013. The target DNA sequence must generally be adjacent to a protospacer adjacent motif (PAM) that is specific for a given Cas endonuclease; however, PAM sequences appear throughout a given genome. CRISPR endonucleases identified from various prokaryotic species have unique PAM sequence requirements; examples of PAM sequences include 5'-NGG (SEQ ID NO: 1) (*Streptococcus pyogenes*), 5'-NNAGAA (SEQ ID NO: 2) (*Streptococcus thermophilus* CRISPR1), 5'-NGGNG (SEQ ID NO: 3) (*Streptococcus thermophilus* CRISPR3), and 5'-NNNGATT (SEQ ID NO: 4) (*Neisseria* meningiditis). Some endonucleases, e.g., Cas9 endonucleases, are associated with G-rich PAM sites, e.g., 5'-NGG (SEQ ID NO: 1), and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN (SEQ ID NO: 5). Cpf1 can also recognize a 5'-CTA PAM motif (SEQ ID NO: 6). Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al., *Cell* 163:759-771, 2015.

For the purposes of gene editing, CRISPR arrays can be designed to contain one or multiple guide RNA sequences corresponding to a desired target DNA sequence; see, for example, Cong et al., *Science* 339:819-823, 2013; Ran et al., *Nature Protocols* 8:2281-2308, 2013. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric single guide RNA (sgRNA), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al., Nature Biotechnol. 985-991, 2015.

Whereas wild-type Cas9 generates double-strand breaks (DSBs) at specific DNA sequences targeted by a gRNA, a number of CRISPR endonucleases having modified functionalities are available, for example: a nickase version of Cas9 generates only a single-strand break; a catalytically inactive Cas9 (dCas9) does not cut the target DNA but interferes with transcription by steric hindrance. dCas9 can further be fused with an effector to repress (CRISPRi) or activate (CRISPRa) expression of a target gene. For example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease (dCas9-FokI) can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene.org/crispr/). A double nickase Cas9 that introduces two separate double-strand breaks, each directed by a separate guide RNA, is described as achieving more accurate genome editing by Ran et al., *Cell* 154:1380-1389, 2013.

CRISPR technology for editing the genes of eukaryotes is disclosed in US Patent Application Publications US 2016/0138008 A1 and US 2015/0344912 A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some instances, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism (homology-directed repair). In such instances, a donor template that encodes the desired nucleotide sequence to be inserted or knocked-in at the double-stranded break is provided to the cell or subject; examples of suitable templates include single-stranded DNA templates and double-stranded DNA templates (e.g., linked to the polypeptide described herein). In general, a donor template encoding a nucleotide change over a region of less than about 50 nucleotides is provided in the form of single-stranded DNA; larger donor templates (e.g., more than 100 nucleotides) are often provided as double-stranded DNA plasmids. In some instances, the donor template is provided to the cell or subject in a quantity that is sufficient to achieve the desired homology-directed repair but that does not persist in the cell or subject after a given period of time (e.g., after one or more cell division cycles). In some instances, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by homology arms or regions of high sequence identity with the targeted nucleotide sequence; in some instances, the regions of high identity include at least 10, at least 50, at least 100, at least 150, at least 200, at least 300, at least 400, at least 500, at least 600, at least 750, or at least 1000 nucleotides on each side of the core sequence. In some instances where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In instances, where the donor template is in the form of a double-stranded DNA, the core sequence is flanked by homology arms including at least 500, at least 600, at least 700, at least 800, at least 900, or at least 1000 nucleotides on each side of the core sequence. In one instance, two separate double-strand breaks are introduced into the cell or subject's target nucleotide sequence with a double nickase Cas9 (see Ran et al., *Cell* 154:1380-1389, 2013), followed by delivery of the donor template.

In some instances, the composition includes a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide the composition to specific DNA sites by one or more RNA sequences (sgRNA) to modulate activity and/or expression of one or more target nucleic acids sequences.

In instances, the agent includes a guide RNA (gRNA) for use in a CRISPR system for gene editing. In some instances, the agent includes a zinc finger nuclease (ZFN), or a mRNA encoding a ZFN, that targets (e.g., cleaves) a nucleic acid sequence (e.g., DNA sequence) of a gene in the plant. In some instances, the agent includes a TALEN, or an mRNA encoding a TALEN, that targets (e.g., cleaves) a nucleic acid sequence (e.g., DNA sequence) in a gene in the plant.

For example, the gRNA can be used in a CRISPR system to engineer an alteration in a gene in the plant. In other examples, the ZFN and/or TALEN can be used to engineer an alteration in a gene in the plant. Exemplary alterations include insertions, deletions (e.g., knockouts), translocations, inversions, single point mutations, or other mutations. The alteration can be introduced in the gene in a cell, e.g., in vitro, ex vivo, or in vivo. In some examples, the alteration increases the level and/or activity of a gene in the plant. In other examples, the alteration decreases the level and/or activity of (e.g., knocks down or knocks out) a gene in the plant. In yet another example, the alteration corrects a defect (e.g., a mutation causing a defect), in a gene in the plant.

In some instances, the CRISPR system is used to edit (e.g., to add or delete a base pair) a target gene in the plant. In other instances, the CRISPR system is used to introduce a premature stop codon, e.g., thereby decreasing the expression of a target gene. In yet other instances, the CRISPR system is used to turn off a target gene in a reversible manner, e.g., similarly to RNA interference. In some instances, the CRISPR system is used to direct Cas to a promoter of a gene, thereby blocking an RNA polymerase sterically.

In some instances, a CRISPR system can be generated to edit a gene in the plant, using technology described in, e.g., U.S. Publication No. 20140068797, Cong, Science 339:819-823, 2013; Tsai, Nature Biotechnol. 32:6 569-576, 2014; U.S. Pat. Nos. 8,871,445; 8,865,406; 8,795,965; 8,771,945; and 8,697,359.

In some instances, the CRISPR interference (CRISPRi) technique can be used for transcriptional repression of specific genes in the plant. In CRISPRi, an engineered Cas9 protein (e.g., nuclease-null dCas9, or dCas9 fusion protein, e.g., dCas9-KRAB or dCas9-SID4X fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression.

In some instances, CRISPR-mediated gene activation (CRISPRa) can be used for transcriptional activation of a gene in the plant. In the CRISPRa technique, dCas9 fusion proteins recruit transcriptional activators. For example, dCas9 can be fused to polypeptides (e.g., activation domains) such as VP64 or the p65 activation domain (p65D) and used with sgRNA (e.g., a single sgRNA or multiple sgRNAs), to activate a gene or genes in the plant. Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1).

The CRISPRi and CRISPRa techniques are described in greater detail, e.g., in Dominguez et al., Nat. Rev. Mol. Cell Biol. 17:5-15, 2016, incorporated herein by reference. In addition, dCas9-mediated epigenetic modifications and simultaneous activation and repression using CRISPR systems, as described in Dominguez et al., can be used to modulate a gene in the plant.

B. Heterologous Therapeutic Agents

The PMPs manufactured herein can include a heterologous therapeutic agent (e.g., an agent that effects an animal (e.g., human), an animal pathogen, or a pathogen vector thereof, and can be loaded into a PMP), such as a pathogen control agent (e.g., antifungal agent, an antibacterial agent, a virucidal agent, an anti-viral agent, an insecticidal agent, a nematicidal agent, an antiparasitic agent, or an insect repellent). PMPs loaded with such agents can be formulated with a pharmaceutically acceptable carrier for delivery to an animal, an animal pathogen, or a pathogen vector thereof.

i. Antibacterial Agents

The PMP compositions described herein can further include an antibacterial agent. For example, a PMP composition including an antibiotic as described herein can be administered to an animal in an amount and for a time sufficient to: reach a target level (e.g., a predetermined or threshold level) of antibiotic concentration inside or on the animal; and/or treat or prevent a bacterial infection in the animal. The antibacterials described herein may be formulated in a PMP composition for any of the methods described herein, and in certain instances, may be associated with the PMP thereof. In some instances, the PMP compositions includes two or more (e.g., 2, 3, 4, 5, 6, 7, 8, 9, 10, or more than 10) different antibacterial agents.

As used herein, the term "antibacterial agent" refers to a material that kills or inhibits the growth, proliferation, division, reproduction, or spread of bacteria, such as phytopathogenic bacteria, and includes bactericidal (e.g., disinfectant compounds, antiseptic compounds, or antibiotics) or bacteriostatic agents (e.g., compounds or antibiotics). Bactericidal antibiotics kill bacteria, while bacteriostatic antibiotics only slow their growth or reproduction.

Bactericides can include disinfectants, antiseptics, or antibiotics. The most used disinfectants can comprise: active chlorine (i.e., hypochlorites (e.g., sodium hypochlorite), chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called carbolic acid), cresols (called Lysole in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, etc. Heavy metals and their salts are the most toxic, and environment-hazardous bactericides and therefore, their use is strongly oppressed or canceled; further, also properly concentrated strong acids (phosphoric, nitric, sulfuric, amidosulfuric, toluenesulfonic acids) and alkalis (sodium, potassium, calcium hydroxides).

As antiseptics (i.e., germicide agents that can be used on human or animal body, skin, mucoses, wounds and the like), few of the above mentioned disinfectants can be used, under proper conditions (mainly concentration, pH, temperature and toxicity toward man/animal). Among them, important are: properly diluted chlorine preparations (i.e., Daquin's solution, 0.5% sodium or potassium hypochlorite solution, pH-adjusted to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds, such as hexachlorophene, triclosan and Dibromol, and cation-active compounds, such as 0.05-0.5% benzalkonium, 0.5-4% chlorhexidine, 0.1-2% octenidine solutions.

The PMP composition described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside (e.g., kasugamycin). In some instances, the antibiotic is a bacteriostatic antibiotic. In some instances the bacteriostatic antibiotic targets protein synthesis (e.g., macrolides, lincosamides, and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include rifampicin, ciprofloxacin, doxycycline, ampicillin, and polymyxin B. The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

Examples of antibacterial agents suitable for the treatment of animals include Penicillins (Amoxicillin, Ampicillin, Bacampicillin, Carbenicillin, Cloxacillin, Dicloxacillin, Flucloxacillin, Mezlocillin, Nafcillin, Oxacillin, Penicillin G, Crysticillin 300 A.S., Pentids, Permapen, Pfizerpen, Pfizerpen-AS, Wycillin, Penicillin V, Piperacillin, Pivampicillin, Pivmecillinam, Ticarcillin), Cephalosporins (Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Ceftobiprole, Ceftaroline, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Cefuracetime, Ceftioxide, Combinations, Ceftazidime/Avibactam, Ceftolozane/Tazobactam), Monobactams (Aztreonam), Carbapenems (Imipenem, Imipenem/cilastatin, Doripenem, Ertapenem, Meropenem, Meropenem/vaborbactam), Macrolide (Azithromycin, Erythromycin, Clarithromycin, Dirithromycin, Roxithromycin, Telithromycin), Lincosamides (Clindamycin, Lincomycin), Streptogramins (Pristinamycin, Quinupristin/dalfopristin), Aminoglycoside (Amikacin, Gentamicin, Kanamycin, Neomycin, Netilmicin, Paromomycin, Streptomycin, Tobramycin), Quinolone (Flumequine, Nalidixic acid, Oxolinic acid, Piromidic acid, Pipemidic acid, Rosoxacin, Second Generation, Ciprofloxacin, Enoxacin, Lomefloxacin, Nadifloxacin, Norfloxacin, Ofloxacin, Pefloxacin, Rufloxacin, Balofloxacin, Gatifloxacin, Grepafloxacin, Levofloxacin, Moxifloxacin, Pazufloxacin, Sparfloxacin, Temafloxacin, Tosufloxacin, Besifloxacin, Delafloxacin, Clinafloxacin, Gemifloxacin, Prulifloxacin, Sitafloxacin, Trovafloxacin), Sulfonamides (Sulfamethizole, Sulfamethoxazole, Sulfisoxazole, Trimethoprim-Sulfamethoxazole), Tetracycline (Demeclocycline, Doxycycline, Minocycline, Oxytetracycline, Tetracycline, Tigecycline), Other (Lipopeptides, Fluoroquinolone, Lipoglycopeptides, Cephalosporin, Macrocyclics, Chloramphenicol, Metronidazole, Tinidazole, Nitrofurantoin, Glycopeptides, Vancomycin, Teicoplanin, Lipoglycopeptides, Telavancin, Oxazolidinones, Linezolid, Cycloserine 2, Rifamycins, Rifampin, Rifabutin, Rifapentine, Rifalazil, Polypeptides, Bacitracin, Polymyxin B, Tuberactinomycins, Viomycin, Capreomycin).

One skilled in the art will appreciate that a suitable concentration of each antibiotic in the composition depends on factors such as efficacy, stability of the antibiotic, number of distinct antibiotics, the formulation, and methods of application of the composition.

ii. Antifungal Agents

The PMP compositions described herein can further include an antifungal agent. For example, a PMP composition including an antifungal as described herein can be administered to an animal in an amount and for a time sufficient to reach a target level (e.g., a predetermined or threshold level) of antifungal concentration inside or on the animal; and/or treat or prevent a fungal infection in the animal. The antifungals described herein may be formulated in a PMP composition for any of the methods described herein, and in certain instances, may be associated with the PMP thereof. In some instances, the PMP compositions includes two or more (e.g., 2, 3, 4, 5, 6, 7, 8, 9, 10, or more than 10) different antifungal agents.

As used herein, the term "fungicide" or "antifungal agent" refers to a substance that kills or inhibits the growth, proliferation, division, reproduction, or spread of fungi, such as fungi that are pathogenic to animals. Many different types of antifungal agent have been produced commercially. Non limiting examples of antifungal agents include: Allylamines (Amorolfin, Butenafine, Naftifine, Terbinafine), Imidazoles ((Bifonazole, Butoconazole, Clotrimazole, Econazole, Fenticonazole, Ketoconazole, Isoconazole, Luliconazole, Miconazole, Omoconazole, Oxiconazole, Sertaconazole, Sulconazole, Tioconazole, Terconazole); Triazoles (Albaconazole, Efinaconazole, Fluconazole, Isavuconazole, Itraconazole, Posaconazole, Ravuconazole, Terconazole, Voriconazole), Thiazoles (Abafungin), Polyenes (Amphotericin B, Nystatin, Natamycin, Trichomycin), Echinocandins (Anidulafungin, Caspofungin, Micafungin), Other (Tolnaftate, Flucytosine, Butenafine, Griseofulvin, Ciclopirox, Selenium sulfide, Tavaborole). One skilled in the art will appreciate that a suitable concentration of each antifungal in the composition depends on factors such as efficacy, stability of the antifungal, number of distinct antifungals, the formulation, and methods of application of the composition.

iii. Insecticides

The PMP compositions described herein can further include an insecticide. For example, the insecticide can decrease the fitness of (e.g., decrease growth or kill) an insect vector of an animal pathogen. A PMP composition including an insecticide as described herein can be contacted with an insect, in an amount and for a time sufficient to: (a) reach a target level (e.g., a predetermined or threshold level) of insecticide concentration inside or on the insect; and (b) decrease fitness of the insect. In some instances, the insecticide can decrease the fitness of (e.g., decrease growth or kill) a parasitic insect. A PMP composition including an insecticide as described herein can be contacted with a parasitic insect, or an animal infected therewith, in an amount and for a time sufficient to: (a) reach a target level (e.g., a predetermined or threshold level) of insecticide concentration inside or on the parasitic insect; and (b) decrease the fitness of the parasitic insect. The insecticides described herein may be formulated in a PMP composition for any of the methods described herein, and in certain instances, may be associated with the PMP thereof. In some instances, the PMP compositions include two or more (e.g., 2, 3, 4, 5, 6, 7, 8, 9, 10, or more than 10) different insecticide agents.

As used herein, the term "insecticide" or "insecticidal agent" refers to a substance that kills or inhibits the growth, proliferation, reproduction, or spread of insects, such as insect vectors of animal pathogens or parasitic insects. Non limiting examples of insecticides are shown in Table 4. Additional non-limiting examples of suitable insecticides include biologics, hormones or pheromones such as azadirachtin, Bacillus species, Beauveria species, codle- mone, Metarrhizium species, Paecilomyces species, thuringiensis, and Verticillium species, and active compounds having unknown or non-specified mechanisms of action such as fumigants (such as aluminium phosphide, methyl bromide and sulphuryl fluoride) and selective feeding inhibitors (such as cryolite, flonicamid and pymetrozine). One skilled in the art will appreciate that a suitable concentration of each insecticide in the composition depends on factors such as efficacy, stability of the insecticide, number of distinct insecticides, the formulation, and methods of application of the composition.

TABLE 4

Examples of insecticides

| Class | Compounds |
|---|---|
| chloronicotinyls/ neonicotinoids | acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, acetylcholinesterase (AChE) inhibitors (such as carbamates and organophosphates) |
| carbamates | alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb |
| organophosphates | acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion |
| pyrethroids | acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum) |
| oxadiazines | indoxacarb, acetylcholine receptor modulators (such as spinosyns) |
| spinosyns | Spinosad |
| cyclodiene | camphechlor, chlordane, endosulfan, gamma-HCH, HCH, heptachlor, |
| organochlorines | lindane, methoxychlor |
| fiproles | acetoprole, ethiprole, vaniliprole, fipronil |
| mectins | abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene |
| diacylhydrazines | chromafenozide, halofenozide, methoxyfenozide, tebufenozide |
| benzoylureas | bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron |

TABLE 4-continued

Examples of insecticides

| Class | Compounds |
|---|---|
| organotins | azocyclotin, cyhexatin, fenbutatin oxide |
| pyrroles | Chlorfenapyr |
| dinitrophenols | binapacyrl, dinobuton, dinocap, DNOC |
| METIs | fenazaquin, fenpyroximate, pyrimidifen, pyridaben, tebufenpyrad, tolfenpyrad, rotenone, acequinocyl, fluacrypyrim, microbial disrupters of the intestinal membrane of insects (such as Bacillus thuringiensis strains), inhibitors of lipid synthesis (such as tetronic acids and tetramic acids) |
| tetronic acids | spirodiclofen, spiromesifen, spirotetramat |
| tetramic acids | cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester; CAS Reg. No.: 382608-10-8), carboxamides (such as flonicamid), octopaminergic agonists (such as amitraz), inhibitors of the magnesium-stimulated ATPase (such as propargite), ryanodin receptor agonists (such as phthalamides or rynaxapyr) |
| phthalamides | N2-[1,1-dimethyl-2-(methylsulphonyl)ethyl]-3-iodo-N1-[2-methyl--4-[1,2,2,2-tetrafluoro-1-(trifluoromethyl)ethyl]phenyl]-1,2-benzenedicarboxamide (i.e., flubendiamide; CAS reg. No.: 272451-65-7) | iv. Nematicides

The PMP compositions described herein can further include a nematicide. In some instances, the PMP composition includes two or more (e.g., 2, 3, 4, 5, 6, 7, 8, 9, 10, or more than 10) different nematicides. For example, the nematicide can decrease the fitness of (e.g., decrease growth or kill) a parasitic nematode. A PMP composition including a nematicide as described herein can be contacted with a parasitic nematode, or an animal infected therewith, in an amount and for a time sufficient to: (a) reach a target level (e.g., a predetermined or threshold level) of nematicide concentration inside or on the target nematode; and (b) decrease fitness of the parasitic nematode. The nematicides described herein may be formulated in a PMP composition for any of the methods described herein, and in certain instances, may be associated with the PMP thereof.

As used herein, the term "nematicide" or "nematicidal agent" refers to a substance that kills or inhibits the growth, proliferation, reproduction, or spread of nematodes, such as a parasitic nematode. Non limiting examples of nematicides are shown in Table 5. One skilled in the art will appreciate that a suitable concentration of each nematicide in the composition depends on factors such as efficacy, stability of the nematicide, number of distinct nematicides, the formulation, and methods of application of the composition.

TABLE 5

Examples of Nematicides

| | |
|---|---|
| FUMIGANTS | D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, Chloropicrin, |
| CARBAMATES | Aldicarb, Aldoxycarb, Carbofuran, Oxamyl, Cleothocarb |
| ORGANOPHOSPHATES | Ethoprophos, Fenamiphos, Cadusafos, Fosthiazate, Fensulfothion, Thionazin, Isazofos, |
| BIOCHEMICALS | DITERA ®, CLANDOSAN ®, SINCOCIN ® | v. Antiparasitic Agent

The PMP compositions described herein can further include an antiparasitic agent. For example, the antiparasitic can decrease the fitness of (e.g., decrease growth or kill) a parasitic protozoan. A PMP composition including an antiparasitic as described herein can be contacted with a protozoan in an amount and for a time sufficient to: (a) reach a target level (e.g., a predetermined or threshold level) of antiparasitic concentration inside or on the protozoan, or animal infected therewith; and (b) decrease fitness of the protozoan. This can be useful in the treatment or prevention of parasites in animals. For example, a PMP composition including an antiparasitic agent as described herein can be administered to an animal in an amount and for a time sufficient to: reach a target level (e.g., a predetermined or threshold level) of antiparasitic concentration inside or on the animal; and/or treat or prevent a parasite (e.g., parasitic nematode, parasitic insect, or protozoan) infection in the animal. The antiparasitic described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different antiparasitic agents.

As used herein, the term "antiparasitic" or "antiparasitic agent" refers to a substance that kills or inhibits the growth, proliferation, reproduction, or spread of parasites, such as parasitic protozoa, parasitic nematodes, or parasitic insects. Examples of antiparasitic agents include Antihelmintics (Bephenium, Diethylcarbamazine, Ivermectin, Niclosamide, Piperazine, Praziquantel, Pyrantel, Pyrvinium, Benzimidazoles, Albendazole, Flubendazole, Mebendazole, Thiabendazole, Levamisole, Nitazoxanide, Monopantel, Emodepside, Spiroindoles), Scabicides (Benzyl benzoate, Benzyl benzoate/disulfiram, Lindane, Malathion, Permethrin), Pediculicides (Piperonyl butoxide/pyrethrins, Spinosad, Moxidectin), Scabicides (Crotamiton), Anticestodes (Niclosamide, Pranziquantel, Albendazole), Antiamoebics (Rifampin, Apmphotericin B); or Antiprotozoals (Melarsoprol, Eflornithine, Metronidazole, Tinidazole, Miltefosine, Artemisinin). In certain instances, the antiparasitic agent may be use for treating or prevening infections in livestock animals, e.g., Levamisole, Fenbendazole, Oxfendazole, Albendazole, Moxidectin, Eprinomectin, Doramectin, Ivermectin, or Clorsulon. One skilled in the art will appreciate that a suitable concentration of each antiparasitic in the composition depends on factors such as efficacy, stability of the antiparasitic, number of distinct antiparasitics, the formulation, and methods of application of the composition.

vi. Antiviral Agent

The PMP compositions described herein can further include an antiviral agent. A PMP composition including an antivirual agent as described herein can be administered to an animal in an amount and for a time sufficient to reach a target level (e.g., a predetermined or threshold level) of antiviral concentration inside or on the animal; and/or to treat or prevent a viral infection in the animal. The antivirals described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different antivirals.

As used herein, the term "antiviral" or "virucide" refers to a substance that kills or inhibits the growth, proliferation, reproduction, development, or spread of viruses, such as viral pathogens that infect animals. A number of agents can be employed as an antiviral, including chemicals or biological agents (e.g., nucleic acids, e.g., dsRNA). Examples of antiviral agents useful herein include Abacavir, Acyclovir (Aciclovir), Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir (Tamiflu), Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), or Zidovudine. One skilled in the art will appreciate that a suitable concentration of each antiviral in the composition depends on factors such as efficacy, stability of the antivirals, number of distinct antivirals, the formulation, and methods of application of the composition.

vii. Repellents

The PMP compositions described herein can further include a repellent. For example, the repellent can repel a vector of animal pathogens, such as insects. The repellent described herein may be formulated in a PMP composition for any of the methods described herein, and in certain instances, may be associated with the PMP thereof. In some instances, the PMP composition includes two or more (e.g., 2, 3, 4, 5, 6, 7, 8, 9, 10, or more than 10) different repellents.

For example, a PMP composition including a repellent as described herein can be contacted with an insect vector or a habitat of the vector in an amount and for a time sufficient to: (a) reach a target level (e.g., a predetermined or threshold level) of repellent concentration; and/or (b) decrease the levels of the insect near or on nearby animals relative to a control. Altneratively, a PMP composition including a repellent as described herein can be contacted with an animal in an amount and for a time sufficient to: (a) reach a target level (e.g., a predetermined or threshold level) of repellent concentration; and/or (b) decrease the levels of the insect near or on the animal relative to an untreated animal.

Some examples of well-known insect repellents include: benzil; benzyl benzoate; 2,3,4,5-bis(butyl-2-ene)tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo,endo)-dimethyl bicyclo[2.2.1]hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-methane-3,8-diol, and normal-propyl N,N-diethylsuccinamate. Other repellents include citronella oil, dimethyl phthalate, normal-butylmesityl oxide oxalate and 2-ethyl hexanediol-1,3 (See, Kirk-Othmer Encyclopedia of Chemical Technology, 2nd Ed., Vol. 11:724-728; and The Condensed Chemical Dictionary, 8th Ed., p 756).

In some instances, the repellent is an insect repellent, including synthetic or nonsynthetic insect repellents. Examples of synthetic insect repellents include methyl anthranilate and other anthranilate-based insect repellents, benzaldehyde, DEET (N,N-diethyl-m-toluamide), dimethyl carbate, dimethyl phthalate, icaridin (i.e., picaridin, Bayrepel, and KBR 3023), indalone (e.g., as used in a "6-2-2" mixture (60% Dimethyl phthalate, 20% Indalone, 20% Ethylhexanediol), IR3535 (3-[N-Butyl-N-acetyl]-aminopropionic acid, ethyl ester), metofluthrin, permethrin, SS220, or tricyclodecenyl allyl ether. Examples of natural insect repellents include beautyberry (Callicarpa) leaves, birch tree bark, bog myrtle (*Myrica* Gale), catnip oil (e.g., nepetalactone), citronella oil, essential oil of the lemon eucalyptus (*Corymbia citriodora*; e.g., p-menthane-3,8-diol (PMD)), neem oil, lemongrass, tea tree oil from the leaves of *Melaleuca* alternifolia, tobacco, or extracts thereof.

IV. Methods of Use

The PMPs produced herein are useful in a variety of agricultural or therapeutic methods. Examples of methods of using PMPs are described further below.

A. Delivery to a Plant

Provided herein are methods of delivering a PMP composition (e.g., manufactured in accordance with the methods or bioreactors herein) to a plant, e.g., by contacting the plant, or part thereof, with the PMP composition. In some instances, plants may be treated with unloaded PMPs. In other instances, the PMPs include a heterologous functional agent, e.g., pesticidal agents (e.g., antibacterial agents, antifungal agents, nematicides, molluscicides, virucides, herbicides), pest control agents (e.g., repellents), fertilizing agents, or plant-modifying agents.

In one aspect, provided herein is a method of increasing the fitness of a plant, the method including delivering to the plant the PMP composition described herein (e.g., in an effective amount and duration) to increase the fitness of the plant relative to an untreated plant (e.g., a plant that has not been delivered the PMP composition).

An increase in the fitness of the plant as a consequence of delivery of a PMP composition can manifest in a number of ways, e.g., thereby resulting in a better production of the plant, for example, an improved yield, improved vigor of the plant or quality of the harvested product from the plant. An improved yield of a plant relates to an increase in the yield of a product (e.g., as measured by plant biomass, grain, seed or fruit yield, protein content, carbohydrate or oil content or leaf area) of the plant by a measurable amount over the yield of the same product of the plant produced under the same conditions, but without the application of the instant compositions or compared with application of conventional agricultural agents. For example, yield can be increased by at least about 0.5%, about 1%, about 2%, about 3%, about 4%, about 5%, about 10%, about 20%, about 30%, about 40%, about 50%, about 60%, about 70%, about 80%, about 90%, about 100%, or more than 100%. Yield can be expressed in terms of an amount by weight or volume of the plant or a product of the plant on some basis. The basis can be expressed in terms of time, growing area, weight of plants produced, or amount of a raw material used. For example, such methods may increase the yield of plant tissues including, but not limited to: seeds, fruits, kernels, bolls, tubers, roots, and leaves.

An increase in the fitness of a plant as a consequence of delivery of a PMP composition can also be measured by other methods, such as an increase or improvement of the vigor rating, the stand (the number of plants per unit of area), plant height, stalk circumference, stalk length, leaf number, leaf size, plant canopy, visual appearance (such as greener leaf color), root rating, emergence, protein content, increased tillering, bigger leaves, more leaves, less dead basal leaves, stronger tillers, less fertilizer needed, less seeds needed, more productive tillers, earlier flowering, early grain or seed maturity, less plant verse (lodging), increased shoot growth, earlier germination, or any combination of these factors, by a measurable or noticeable amount over the same factor of the plant produced under the same conditions, but without the administration of the instant compositions or with application of conventional agricultural agents.

Provided herein is a method of modifying or increasing the fitness of a plant, the method including delivering to the plant an effective amount of a PMP composition provided herein, wherein the method modifies the plant and thereby introduces or increases a beneficial trait in the plant (e.g., by about 1%, 2%, 5%, 10%, 20%, 30%, 40%, 50%, 60%, 70%, 80%, 90%, 100%, or more than 100%) relative to an untreated plant. In particular, the method may increase the fitness of the plant (e.g., by about 1%, 2%, 5%, 10%, 20%, 30%, 40%, 50%, 60%, 70%, 80%, 90%, 100%, or more than 100%) relative to an untreated plant.

In some instances, the increase in plant fitness is an increase (e.g., by about 1%, 2%, 5%, 10%, 20%, 30%, 40%, 50%, 60%, 70%, 80%, 90%, 100%, or more than 100%) in disease resistance, drought tolerance, heat tolerance, cold tolerance, salt tolerance, metal tolerance, herbicide tolerance, chemical tolerance, water use efficiency, nitrogen utilization, resistance to nitrogen stress, nitrogen fixation, pest resistance, herbivore resistance, pathogen resistance, yield, yield under water-limited conditions, vigor, growth, photosynthetic capability, nutrition, protein content, carbohydrate content, oil content, biomass, shoot length, root length, root architecture, seed weight, or amount of harvestable produce.

In some instances, the increase in fitness is an increase (e.g., by about 1%, 2%, 5%, 10%, 20%, 30%, 40%, 50%, 60%, 70%, 80%, 90%, 100%, or more than 100%) in development, growth, yield, resistance to abiotic stressors, or resistance to biotic stressors. An abiotic stress refers to an environmental stress condition that a plant or a plant part is subjected to that includes, e.g., drought stress, salt stress, heat stress, cold stress, and low nutrient stress. A biotic stress refers to an environmental stress condition that a plant or plant part is subjected to that includes, e.g. nematode stress, insect herbivory stress, fungal pathogen stress, bacterial pathogen stress, or viral pathogen stress. The stress may be temporary, e.g. several hours, several days, several months, or permanent, e.g. for the life of the plant.

In some instances, the increase in plant fitness is an increase (e.g., by about 1%, 2%, 5%, 10%, 20%, 30%, 40%, 50%, 60%, 70%, 80%, 90%, 100%, or more than 100%) in quality of products harvested from the plant. For example, the increase in plant fitness may be an improvement in commercially favorable features (e.g., taste or appearance) of a product harvested from the plant. In other instances, the increase in plant fitness is an increase in shelf-life of a product harvested from the plant (e.g., by about 1%, 2%, 5%, 10%, 20%, 30%, 40%, 50%, 60%, 70%, 80%, 90%, 100%, or more than 100%).

Alternatively, the increase in fitness may be an alteration of a trait that is beneficial to human or animal health, such as a reduction in allergen production. For example, the increase in fitness may be a decrease (e.g., by about 1%, 2%, 5%, 10%, 20%, 30%, 40%, 50%, 60%, 70%, 80%, 90%, 100%, or more than 100%) in production of an allergen (e.g., pollen) that stimulates an immune response in an animal (e.g., human).

The modification of the plant (e.g., increase in fitness) may arise from modification of one or more plant parts. For example, the plant can be modified by contacting leaf, seed, pollen, root, fruit, shoot, flower, cells, protoplasts, or tissue (e.g., meristematic tissue) of the plant. As such, in another aspect, provided herein is a method of increasing the fitness of a plant, the method including contacting pollen of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In yet another aspect, provided herein is a method of increasing the fitness of a plant, the method including contacting a seed of the plant with an effective amount of a PMP composition disclosed herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method including contacting a protoplast of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In a further aspect, provided herein is a method of increasing the fitness of a plant, the method including contacting a plant cell of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting meristematic tissue of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In another aspect, provided herein is a method of increasing the fitness of a plant, the method including contacting an embryo of the plant with an effective amount of a PMP composition herein, wherein the method increases the fitness of the plant (e.g., by about 1%, 2%, 5%, 10%, 20%, 30%, 40%, 50%, 60%, 70%, 80%, 90%, 100%, or more than 100%) relative to an untreated plant.

In cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

i. Plants

A variety of plants can be delivered or treated with a PMP composition described herein. Plants that can be delivered a PMP composition (i.e., "treated") in accordance with the present methods include whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, cotyledons, and seed coat) and fruit (the mature ovary), plant tissue (e.g., vascular tissue, ground tissue, and the like) and cells (e.g., guard cells, egg cells, and the like), and progeny of same. Plant parts can further refer parts of the plant such as the shoot, root, stem, seeds, stipules, leaves, petals, flowers, ovules, bracts, branches, petioles, internodes, bark, pubescence, tillers, rhizomes, fronds, blades, pollen, stamen, and the like.

The class of plants that can be treated in a method disclosed herein includes the class of higher and lower plants, including angiosperms (monocotyledonous and dicotyledonous plants), gymnosperms, ferns, horsetails, psilophytes, lycophytes, bryophytes, and algae (e.g., multicellular or unicellular algae). Plants that can be treated in accordance with the present methods further include any vascular plant, for example monocotyledons or dicotyledons or gymnosperms, including, but not limited to alfalfa, apple, *Arabidopsis*, banana, barley, canola, castor bean, *chrysanthemum*, crucifers, clover, cocoa, coffee, cotton, cottonseed, corn, *crambe*, cranberry, cucumber, dendrobium, *dioscorea*, *eucalyptus*, fescue, flax, *gladiolus*, Liliaceae, linseed, millet, muskmelon, mustard, oat, oil palm, oilseed rape, *papaya*, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat and vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes (e.g., a vineyard), kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, *crambe*, flax, linseed, mustard, oil palm, oilseed rape, peanut, potato, rice, safflower, sesame, soybean, sugarbeet, sunflower, tobacco, tomato, and wheat. Plants that can be treated in accordance with the methods of the present invention include any crop plant, for example, forage crop, oilseed crop, grain crop, fruit crop, vegetable crop, fiber crop, spice crop, nut crop, turf crop, sugar crop, beverage crop, and forest crop. In certain instances, the crop plant that is treated in the method is a soybean plant. In other certain instances, the crop plant is wheat. In certain instances, the crop plant is corn. In certain instances, the crop plant is cotton. In certain instances, the crop plant is alfalfa. In certain instances, the crop plant is sugarbeet. In certain instances, the crop plant is rice. In certain instances, the crop plant is potato. In certain instances, the crop plant is tomato.

In certain instances, the plant is a crop. Examples of such crop plants include, but are not limited to, monocotyledonous and dicotyledonous plants including, but not limited to, fodder or forage legumes, ornamental plants, food crops, trees, or shrubs selected from *Acer* spp., *Allium* spp., *Amaranthus* spp., *Ananas comosus*, *Apium graveolens*, *Arachis* spp, *Asparagus officinalis*, *Beta vulgaris*, *Brassica* spp. (e.g., *Brassica napus*, *Brassica rapa* ssp. (canola, oilseed rape, turnip rape), *Camellia sinensis*, *Canna indica*, *Cannabis sativa*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g., *Glycine max*, *Soja hispida* or *Soja* max), *Gossypium hirsutum*, *Helianthus* spp. (e.g., *Helianthus annuus*), Hibiscus spp., *Hordeum* spp. (e.g., *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g., *Lycopersicon* esculenturn, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g., *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum* bicolor, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. In certain embodiments, the crop plant is rice, oilseed rape, canola, soybean, corn (maize), cotton, sugarcane, alfalfa, sorghum, or wheat.

In certain instance, the compositions and methods can be used to treat post-harvest plants or plant parts, food, or feed products. In some instances, the food or feed product is a non-plant food or feed product (e.g., a product edible for humans, veterinary animals, or livestock (e.g., mushrooms)). The plant or plant part for use in the present invention include plants of any stage of plant development. In certain instances, the delivery can occur during the stages of germination, seedling growth, vegetative growth, and reproductive growth. In certain instances, delivery to the plant occurs during vegetative and reproductive growth stages. Alternatively, the delivery can occur to a seed. The stages of vegetative and reproductive growth are also referred to herein as "adult" or "mature" plants.

ii. Weeds

In cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

As used herein, the term "weed" refers to a plant that grows where it is not wanted. Such plants are typically invasive and, at times, harmful, or have the risk of becoming so. Weeds may be treated with the present PMP compositions to reduce or eliminate the presence, viability, or reproduction of the plant. For example, and without being limited thereto, the methods can be used to target weeds known to damage plants. For example, and without being limited thereto, the weeds can be any member of the following group of families: Gramineae, Umbelliferae, Papilionaceae, Cruciferae, Malvaceae, Eufhorbiaceae, Compositae, Chenopodiaceae, Fumariaceae, Charyophyllaceae, Primulaceae, Geraniaceae, Polygonaceae, Juncaceae, Cyperaceae, Aizoaceae, Asteraceae, Convolvulaceae, Cucurbitaceae, Euphorbiaceae, Polygonaceae, Portulaceae, Solanaceae, Rosaceae, Simaroubaceae, Lardizabalaceae, Liliaceae, Amaranthaceae, Vitaceae, Fabaceae, Primulaceae, Apocynaceae, Araliaceae, Caryophyllaceae, Asclepiadaceae, Celastraceae, Papaveraceae, Onagraceae, Ranunculaceae, Lamiaceae, Commelinaceae, Scrophulariaceae, Dipsacaceae, Boraginaceae, Equisetaceae, Geraniaceae, Rubiaceae, Cannabaceae, Hyperiacaceae, Balsaminaceae, Lobeliaceae, Caprifoliaceae, Nyctaginaceae, Oxalidaceae, Vitaceae, Urticaceae, Polypodiaceae, Anacardiaceae, Smilacaceae, Araceae, Campanulaceae, Typhaceae, Valerianaceae, Verbenaceae, Violaceae. For example, and without being limited thereto, the weeds can be any member of the group consisting of *Lolium rigidum, Amaramthus palmeri, Abutilon theopratsi, Sorghum halepense, Conyza canadensis, Setaria verticillata, Capsella pastoris*, and *Cyperus rotundas*. Additional weeds include, for example, Mimosapigra, *salvinia, hyptis, senna*, noogoora, burr, *Jatropha gossypifolia, Parkinsonia* aculeate, *Chromolaena odorata, Cryptoslegia grandiflora*, or *Andropogon gayanus*. Weeds can include monocotyledonous plants (e.g., *Agrostis, Alopecurus, Avena, Bromus, Cyperus, Digitaria, Echinochloa, Lolium, Monochoria, Rottboellia, Sagittaria, Scirpus, Setaria, Sida* or *Sorghum*) or dicotyledonous plants (*Abutilon, Amaranthus, Chenopodium, Chrysanthemum, Conyza, Galium, Ipomoea, Nasturtium, Sinapis, Solanum, Stellaria, Veronica*, Viola or *Xanthium*).

The compositions and related methods can be used to prevent infestation by or reduce the numbers of pathogens or pathogen vectors in any habitats in which they reside (e.g., outside of animals, e.g., on plants, plant parts (e.g., roots, fruits and seeds), in or on soil, water, or on another pathogen or pathogen vector habitat. Accordingly, the compositions and methods can reduce the damaging effect of pathogen vectors by for example, killing, injuring, or slowing the activity of the vector, and can thereby control the spread of the pathogen to animals. Compositions disclosed herein can be used to control, kill, injure, paralyze, or reduce the activity of one or more of any pathogens or pathogen vectors in any developmental stage, e.g., their egg, nymph, instar, larvae, adult, juvenile, or desiccated forms. The details of each of these methods are described further below.

B. Delivery to a Plant Pest

Provided herein are methods of delivering a PMP composition (e.g., manufactured in accordance with the methods or bioreactors herein) to a plant pest, e.g., by contacting the plant pest with the PMP composition. In some instances, plant pest may be treated with unloaded PMPs. In other instances, the PMPs include a heterologous functional agent, e.g., pesticidal agents (e.g., antibacterial agents, antifungal agents, nematicides, molluscicides, virucides, or herbicides) or pest control agents (e.g., repellents). For example, the methods can be useful for decreasing the fitness of a pest, e.g., to prevent or treat a pest infestation as a consequence of delivery of a PMP composition.

In one aspect, provided herein is a method of decreasing the fitness of a pest, the method including delivering to the pest the PMP composition described herein (e.g., in an effective amount and for an effective duration) to decrease the fitness of the pest relative to an untreated pest (e.g., a pest that has not been delivered the PMP composition).

In one aspect, provided herein is a method of decreasing a fungal infection in (e.g., treating) a plant having a fungal infection, wherein the method includes delivering to the plant pest a PMP composition including a plurality of PMPs (e.g., a PMP composition described herein).

In another aspect, provided herein is a method of decreasing a fungal infection in (e.g., treating) a plant having a fungal infection, wherein the method includes delivering to the plant pest a PMP composition including a plurality of PMPs (e.g., a PMP composition described herein), and wherein the plurality of PMPs include an antifungal agent. In some instances, the antifungal agent is a nucleic acid that inhibits expression of a gene (e.g., dcl1 and dcl2 (i.e., dcl1/2) in a fungus that causes the fungal infection. In some instances, the fungal infection is caused be a fungus belonging to a *Sclerotinia* spp. (e.g., *Sclerotinia sclerotiorum*), a *Botrytis* spp. (e.g., *Botrytis cinerea*), an *Aspergillus* spp., a *Fusarium* spp., or a *Penicillium* spp. In some instances, the composition includes a PMP produced from an *Arabidopsis* apoplast EV. In some instances, the method decreases or substantially eliminates the fungal infection.

In another aspect, provided herein is a method of decreasing a bacterial infection in (e.g., treating) a plant having a bacterial infection, wherein the method includes delivering to the plant pest a PMP composition including a plurality of PMPs (e.g., a PMP composition described herein).

In another aspect, provided herein is a method of decreasing a bacterial infection in (e.g., treating) a plant having a bacterial infection, wherein the method includes delivering to the plant pest a PMP composition including a plurality of PMPs, and wherein the plurality of PMPs include an antibacterial agent. In some instances, the antibacterial agent is streptomycin. In some instances, the bacterial infection is caused by a bacterium belonging to a *Pseudomonas* spp (e.g., *Pseudomonas syringae* or Psuedomonas *aeruginosa*). In some instances, the composition includes a PMP produced from an *Arabidopsis* apoplast EV. In some instances, the method decreases or substantially eliminates the bacterial infection.

In another aspect, provided herein is a method of decreasing the fitness of an insect plant pest, wherein the method includes delivering to the insect plant pest a PMP composition including a plurality of PMPs (e.g., a PMP composition described herein).

In another aspect, provided herein is a method of decreasing the fitness of an insect plant pest, wherein the method includes delivering to the insect plant pest a PMP composition including a plurality of PMPs (e.g., a PMP composition described herein), and wherein the plurality of PMPs includes an insecticidal agent. In some instances, the insecticidal agent is a peptide nucleic acid. In some instances, the insect plant pest is an aphid. In some instances, the insect plant pest is a lepidopteran (e.g., *Spodoptera frugiperda*). In some instances, the method decreases the fitness of the insect plant pest relative to an untreated insect plant pest In another aspect, provided herein is a method of decreasing the fitness of a nematode plant pest, wherein the method includes delivering to the nematode plant pest a PMP composition including a plurality of PMPs (e.g., a PMP composition described herein).

In another aspect, provided herein is a method of decreasing the fitness of a nematode plant pest, wherein the method includes delivering to the nematode plant pest a PMP composition including a plurality of PMPs (e.g., a PMP composition described herein), and wherein the plurality of PMPs include a nematicidal agent. In some instances, the nematicidal agent is a neuropeptide (e.g., Mi-NLP-15b). In some instances, the nematode plant pest is a corn root-knot nematode. In some instances, the method decreases the fitness of the nematode plant pest relative to an untreated nematode plant pest.

In another aspect, provided herein is a method of decreasing the fitness of a weed, wherein the method includes delivering to the weed a PMP composition including a plurality of PMPs (e.g., a PMP composition described herein).

In another aspect, provided herein is a method of decreasing the fitness of a weed, wherein the method includes delivering to the weed a PMP composition including a plurality of PMPs (e.g., a PMP composition described herein), and wherein the plurality of PMPs include an herbicidal agent (e.g. Glufosinate). In some instances, the weed is an Indian goosegrass (*Eleusine indica*). In some instances, the method decreases the fitness of the weed relative to an untreated weed.

A decrease in the fitness of the pest as a consequence of delivery of a PMP composition can manifest in a number of ways. In some instances, the decrease in fitness of the pest may manifest as a deterioration or decline in the physiology of the pest (e.g., reduced health or survival) as a consequence of delivery of the PMP composition. In some instances, the fitness of an organism may be measured by one or more parameters, including, but not limited to, reproductive rate, fertility, lifespan, viability, mobility, fecundity, pest development, body weight, metabolic rate or activity, or survival in comparison to a pest to which the PMP composition has not been administered. For example, the methods or compositions provided herein may be effective to decrease the overall health of the pest or to decrease the overall survival of the pest. In some instances, the decreased survival of the pest is about 2%, 5%, 10%, 20%, 30%, 40%, 50%, 60%, 70%, 80%, 90%, 100%, or greater than 100% greater relative to a reference level (e.g., a level found in a pest that does not receive a PMP composition). In some instances, the methods and compositions are effective to decrease pest reproduction (e.g., reproductive rate, fertility) in comparison to a pest to which the PMP composition has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pest fitness may manifest as a decrease in the production of one or more nutrients in the pest (e.g., vitamins, carbohydrates, amino acids, or polypeptides) in comparison to a pest to which the PMP composition has not been administered. In some instances, the methods or compositions provided herein may be effective to decrease the production of nutrients in the pest (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pest fitness may manifest as an increase in the pest's sensitivity to a pesticidal agent and/or a decrease in the pest's resistance to a pesticidal agent in comparison to a pest to which the PMP composition has not been administered. In some instances, the methods or compositions provided herein may be effective to increase the pest's sensitivity to a pesticidal agent by about 2%, 5%, 10%, 20%, 30%, 40%, 50%, 60%, 70%, 80%, 90%, 100%, or greater than 100% relative to a reference level (e.g., a level found in a pest that does not receive a PMP composition). The pesticidal agent may be any pesticidal agent known in the art, including insecticidal agents. In some instances, the methods or compositions provided herein may increase the pest's sensitivity to a pesticidal agent by decreasing the pest's ability to metabolize or degrade the pesticidal agent into usable substrates in comparison to a pest to which the PMP composition has not been administered.

In some instances, the decrease in pest fitness may manifest as an increase in the pest's sensitivity to an allelochemical agent and/or a decrease in the pest's resistance to an allelochemical agent in comparison to a pest to which the PMP composition has not been administered. In some instances, the methods or compositions provided herein may be effective to decrease the pest's resistance to an allelochemical agent by about 2%, 5%, 10%, 20%, 30%, 40%, 50%, 60%, 70%, 80%, 90%, 100%, or greater than 100% relative to a reference level (e.g., a level found in a pest that does not receive a PMP composition). In some instances, the allelochemical agent is caffeine, soyacystatin, fenitrothion, monoterpenes, diterpene acids, or phenolic compounds (e.g., tannins, flavonoids). In some instances, the methods or compositions provided herein may increase the pest's sensitivity to an allelochemical agent by decreasing the pest's ability to metabolize or degrade the allelochemical agent into usable substrates in comparison to a pest to which the PMP composition has not been administered.

In some instances, the methods or compositions provided herein may be effective to decease the pest's resistance to parasites or pathogens (e.g., fungal, bacterial, or viral pathogens or parasites) in comparison to a pest to which the PMP composition has not been administered. In some instances, the methods or compositions provided herein may be effective to decrease the pest's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the methods or compositions provided herein may be effective to decrease the pest's ability to carry or transmit a plant pathogen (e.g., plant virus (e.g., TYLCV) or a plant bacterium (e.g., *Agrobacterium* spp)) in comparison to a pest to which the PMP composition has not been administered. For example, the methods or compositions provided herein may be effective to decrease the pest's ability to carry or transmit a plant pathogen (e.g., a plant virus (e.g., TYLCV) or plant bacterium (e.g., *Agrobacterium* spp)) by about 2%, 5%, 10%, 20%, 30%, 40%, 50%, 60%, 70%, 80%, 90%, 100%, or greater than 100% relative to a reference level (e.g., a level found in a pest that does not receive a PMP composition).

Additionally or alternatively, in cases where an herbicide is included in the PMP, or compositions thereof, the methods may be further used to decrease the fitness of or kill weeds. In such instances, the method may be effective to decrease the fitness of the weed by about 2%, 5%, 10%, 20%, 30%, 40%, 50%, 60%, 70%, 80%, 90%, 100%, or more in comparison to an untreated weed (e.g., a weed to which the PMP composition has not been administered). For example, the method may be effective to kill the weed, thereby decreasing a population of the weed by about 2%, 5%, 10%, 20%, 30%, 40%, 50%, 60%, 70%, 80%, 90%, 100%, or more in comparison to an untreated weed. In some instances, the method substantially eliminates the weed. Examples of weeds that can be treated in accordance with the present methods are further described herein.

In some instances, the decrease in pest fitness may manifest as other fitness disadvantages, such as a decreased tolerance to certain environmental factors (e.g., a high or low temperature tolerance), a decreased ability to survive in certain habitats, or a decreased ability to sustain a certain diet in comparison to a pest to which the PMP composition has not been administered. In some instances, the methods or compositions provided herein may be effective to decrease pest fitness in any plurality of ways described herein. Further, the PMP composition may decrease pest fitness in any number of pest classes, orders, families, genera, or species (e.g., 1 pest species, 2, 3, 4, 5, 6, 7, 8, 9, 10, 15, 20, 30, 40, 50, 60, 70, 80, 90, 100, 150, 200, 200, 250, 500, or more pest species). In some instances, the PMP composition acts on a single pest class, order, family, genus, or species.

Pest fitness may be evaluated using any standard methods in the art. In some instances, pest fitness may be evaluated by assessing an individual pest. Alternatively, pest fitness may be evaluated by assessing a pest population. For example, a decrease in pest fitness may manifest as a decrease in successful competition against other insects, thereby leading to a decrease in the size of the pest population.

i. Fungi

The PMP compositions and related methods can be useful for decreasing the fitness of a fungus, e.g., to prevent or treat a fungal infection in a plant. Included are methods for delivering a PMP composition to a fungus by contacting the fungus with the PMP composition. Additionally or alternatively, the methods include delivering the PMP composition to a plant at risk of or having a fungal infection, by contacting the plant with the PMP composition.

The PMP compositions and related methods are suitable for delivery to fungi that cause fungal diseases in plants, including diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia* recondite, *P. triticina*, *P. graminis* or *P. striiformis* or *P. hordei*; *Uromyces* species, for example *Uromyces appendiculatus*; diseases caused by pathogens from the group of the Oomycetes, for example Albugo species, for example Algubo *candida*; *Bremia* species, for example *Bremia lactucae*; *Peronospora* species, for example *Peronospora pisi*, *P. parasitica* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*; leaf blotch diseases and leaf wilt diseases caused, for example, by *Alternaria* species, for example *Alternaria solani*; *Cercospora* species, for example *Cercospora beticola*; Cladiosporium species, for example Cladiosporium *cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*, *Leptosphaeria nodorum*; *Magnaporthe* species, for example *Magnaporthe grisea*; *Microdochium* species, for example *Microdochium nivale*; *Mycosphaerella* species, for example *Mycosphaerella graminicola*, *M. arachidicola* and *M. fifiensis*; *Phaeosphaeria* species, for example *Phaeosphaeria nodorum*; *Pyrenophora* species, for example *Pyrenophora teres*, *Pyrenophora tritici* repentis; *Ramularia* species, for example *Ramularia* collo-*cygni*, *Ramularia areola*; *Rhynchosporium* species, for example *Rhynchosporium secalis*; *Septoria* species, for example *Septoria apii*, *Septoria* lycopersii; *Typhula* species, for example *Typhula incarnata*; *Venturia* species, for example *Venturia inaequalis*; root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*; ear and panicle diseases (including corn cobs) caused, for example, by *Alternaria* species, for example *Alternaria* spp.; *Aspergillus* species, for example *Aspergillus flavus*; *Cladosporium* species, for example *Cladosporium* cladosporioides; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*; diseases caused by smut fungi, for example *Sphacelotheca* species, for example *Sphacelotheca reiliana*; *Tilletia* species, for example *Tilletia caries*, *T. controversa*; *Urocystis* species, for example *Urocystis occulta*; *Ustilago* species, for example *Ustilago nuda*, *U. nuda tritici*; fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; Verticilium species, for example *Verticilium alboatrum*; seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*; cancers, galls and witches' broom caused, for example, by *Nectria* species, for example *Nectria galligena*; wilt diseases caused, for example, by *Monilinia* species, for example *Monilinia laxa*; leaf blister or leaf curl diseases caused, for example, by *Exobasidium* species, for example *Exobasidium vexans*; Taphrina species, for example *Taphrina deformans*; decline diseases of wooden plants caused, for example, by Esca disease, caused for example by Phaemoniella clamydospora, *Phaeoacremonium aleophilum* and *Fomitiporia mediterranea*; *Eutypa* dyeback, caused for example by *Eutypa lata*; *Ganoderma* diseases caused for example by *Ganoderma boninense*; *Rigidoporus* diseases caused for example by *Rigidoporus lignosus*; diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*; Club root caused, for example, by Plasmodiophora species, for example *Plamodiophora brassicae*; diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Fungal diseases on leaves, stems, pods and seeds caused, for example, by *Alternaria* leaf spot (*Alternaria spec. atrans tenuissima*), Anthracnose (*Colletotrichum gloeosporoides dematium* var. *truncatum*), brown spot (*Septoria glycines*), *cercospora* leaf spot and blight (*Cercospora kikuchii*), choanephora leaf blight (*Choanephora infundibulifera* trispora (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

In certain instances, the fungus is a *Sclerotinia* spp (Scelrotinia *sclerotiorum*). In certain instances, the fungus is a *Botrytis* spp (e.g., *Botrytis cinerea*). In certain instances, the fungus is an *Aspergillus* spp. In certain instances, the fungus is a *Fusarium* spp. In certain instances, the fungus is a *Penicillium* spp.

Compositions of the present invention are useful in various fungal control applications. The above-described compositions may be used to control fungal phytopathogens prior to harvest or post-harvest fungal pathogens. In one embodiment, any of the above-described compositions are used to control target pathogens such as *Fusarium* species, *Botrytis* species, *Verticillium* species, *Rhizoctonia* species, *Trichoderma* species, or *Pythium* species by applying the composition to plants, the area surrounding plants, or edible cultivated mushrooms, mushroom spawn, or mushroom compost. In another embodiment, compositions of the present invention are used to control post-harvest pathogens such as *Penicillium, Geotrichum, Aspergillus niger*, or *Colletotrichum* species.

Table 6 provides further examples of fungi, and plant diseases associated therewith, that can be treated or prevented using the PMP composition and related methods described herein.

TABLE 6

| Fungal pests | |
| --- | --- |
| Disease | Causative Agent |
| Alternaria leaf blight of wheat | Alternaria triticina |
| Alternaria leaf spot of cole crops | Alternaria japonica |
| American soybean rust | Phakopsora meibomiae |
| Ampelopsis rust | Phakopsora ampelopsidis |

TABLE 6-continued

| Fungal pests | |
|---|---|
| Disease | Causative Agent |
| Anemone | Ochropsora ariae |
| Angular leaf spot of Citrus | Pseudocercospora angolensis |
| Arctic Rubus rust | Phragmidium arcticum |
| Ascochyta blight of broad beans | Didymella fabae |
| Ash dieback | Chalara fraxinea |
| Asia mountain Rosa rust | Phragmidium butleri |
| Asian filbert rust | Pucciniastrum coryli |
| Asian Kuehneola rose rust | Kuehneola japonica |
| Asian Mountain Rubus rust | Phragmidium assamense |
| Asian Phragmidium Rubus rust | Phragmidium arisanense |
| Asian pistacio rust | Pileolaria pistaciae |
| Asian rose rust | Gerwasia rosae |
| Asian Rubus rust | Hamaspora hashiokai |
| Asian soybean rust | Phakopsora pachyrhizi |
| Asian sugarcane smut | *Sporisorium sacchari* |
| Asian Wart bark, blister canker, ring rot, Physalospora canker of pear and apple | *Botryosphaeria berengeriana* f. sp. *pyricola* |
| Asian/European brown rot of rosaceae | Monilinia fructigena |
| Asiatic brown fruit rot | Monilia polystroma |
| Barclay's Asian Rubus rust | Phragmidium barclayi |
| Black leaf blight of soybean | Arkoola nigra |
| Blister blight of tea | Exobasidium vexans |
| Blue stain of Mongolian oak | Ophiostoma longicollum |
| Box Rust or Boxwood Rust | *Puccinia buxi* |
| Brown rust of sugarcane | *Puccinia melanocephala* |
| Cherry leaf scorch | Apiognomonia erythrostoma |
| Chocolate spot of Ya Li pears | Alternaria yaliinficiens |
| Chrysanthemum White Rust | *Puccinia horiana* |
| Coffee Leaf Rust | Hemileia vastatrix |
| Common Asian Rubus Rust | Hamaspora acutissima |
| Common larch | Melampsora capraearum |
| Common potato and tomato rust | *Puccinia pittieriana* |
| Crumenulopsis pine dieback | Crumenulopsis sororia |
| Daylily Rust | *Puccinia hemerocallidis* |
| Digitalis Downy Mildew | Peronospora digitalis |
| Downy mildew (Plasmopara) of Impatiens | Plasmopara obducens |
| Eggplant | *Puccinia substriata* var. *substriata* |
| Ergot of pearl millet | Claviceps fusiformis |
| European Larch canker | Lachnellula willkommii |
| Few-loculed Asian Rubus rust | Phragmidium pauciloculare |
| Flag smut of wheat | Urocystis agropyri |
| Gladiolus Rust | *Uromyces transversalis* |
| Goplana dioscoreae | Goplana dioscoreae |
| Grape leaf rust | Phakopsora euvitis |
| Gray Rubus rust | Phragmidium griseum |
| Himalayan rhododendron spruce rust | Chrysomyxa himalensis |
| Hiratsuka Rubus rust | Phragmidium hiratsukanum |
| Horse's tooth or ergot of maize | Claviceps gigantea |
| Japanese apple rust | Gymnosporangium yamadae |
| Japanese Chamaecyparis | Gymnosporangium miyabei |
| Japanese ergot of sorghum | Claviceps sorghicola |
| Kamtschatka rose rust | Phragmidium kamtschatkae |
| Late wilt of maize | *Harpophora maydis* |
| Long-Spored Asian Rubus rust | Hamaspora longissima |
| Mai secco disease of Citrus | *Phoma tracheiphila* |
| Miscanthus | *Puccinia miscanthi* |
| Mulberry rust | Aecidium mori |
| Nambu Rubus rust | Phragmidium nambuanum |
| Neck rot of onion | Ciborinia allii |
| New Zealand Rubus Rust | Hamaspora australis |
| Northern blue stain of pine | Leptographium wingfieldii |
| Northern spruce | Chrysomyxa rhododendri |
| Oak Wilt | Ceratocystis fagacearum |
| Orange rust of sugarcane | *Puccinia kuehnii* |
| Peronospora radii | Peronospora radii |
| Pistachio Rust | Pileolaria terebinthi |
| Poinsettia scab | Sphaceloma poinsettiae |
| Potato smut | *Thecaphora solani* |
| *Puccinia gladioli* on Gladiolus | *Puccinia gladioli* |
| *Puccinia glyceriae* (anam. Aecidium hydrangea | *Puccinia glyceriae* |
| *Puccinia mccleanii* on Gladiolus | *Puccinia mccleanii* |

TABLE 6-continued

Fungal pests

| Disease | Causative Agent |
| --- | --- |
| *Puccinia psidii* | *Puccinia psidii* |
| Pucciniastrum actinidiae on *Actinidia* spp. | Pucciniastrum actinidiae |
| Red Miscanthus rust | *Puccinia erythropus* |
| Rust of European blackberry | Phragmidium bulbosum |
| Rust of Rubus saxitilis | Phragmidium acuminatum |
| Rust on Asian Rubus | Gerwasia rubi |
| Rust on South American Rubus | Gerwasia imperialis |
| Scots stem pine rust | Cronartium flaccidum |
| Shoot blight of boxwood | Calonectria pseudonaviculata |
| Sirex wasp fungus | Amylostereum areolatum |
| Solanum | *Puccinia agrophila* |
| South American Rubus rust | Gerwasia mayorii |
| Sporisorium smut of wild Saccharum | Sporisorium pulverulentum |
| Spruce needle rust | Chrysomyxa abietis |
| Stackburn, seedling blight, leaf spot of rice | Alternaria padwickii |
| Sudden needle drop of Spruce (SNEED) | Setomelanomma holmii |
| Sugary disease or Asian ergot of sorghum | *Claviceps sorghi* |
| Sweet potato rust | Endophyllum kaernbachii |
| Taiwan Rubus rust | Phragmidium formosanum |
| Tar spot of corn | *Phyllachora maydis* |
| Teak Rust | Olivea tectonae |
| Thekopsora areolate | Thekopsora areolata |
| Tip over disease of egglant | Diaporthe vexans |
| Tropical American Kuehneola rust of Rubus | Kuehneola loeseneriana |
| Tropical American Mainsia Rubus rust | Mainsia rubi |
| Tropical Soybean Rust | Aecidium glycines |
| *Uromyces gladioli* on Gladiolus | *Uromyces gladioli* |
| *Uromyces nyikensis* on Gladiolus | *Uromyces nyikensis* |
| Uromycladium tepperianum on *Acacia* spp. | Uromycladium tepperianum |
| Variable Rubus | Gerwasia variabilis |
| Wineberry Rubus rust | *Hamaspora sinica* var. *sinica* |
| Yamada Rubusrust | Phragmidium yamadanum |
| Anthracnose leaf blight and stalk rot | *Colletotrichum graminicola anthracnose* (teleomorph: *Glomerella graminicola*), *Glomerella tucumanensis* (anamorph: *Glomerella falcatum*) |
| *Aspergillus* ear and kernel rot | *Aspergillus* flavus |
| Banded leaf and sheath spot | *Rhizoctonia solani* = *Rhizoctonia microsclerotia* (teleomorph: Thanatephorus cucumeris) |
| Bean rust | *Uromyces appendiculatus* |
| Black bundle disease | Acremonium strictum = Cephalosporium acremonium |
| Black kernel rot | Lasiodiplodia theobromae = Botryodiplodia theobromae |
| Borde bianco | *Marasmiellus* sp. |
| Brown spot (black spot, stalk rot) | *Physoderma maydis* |
| Brown stripe downy mildew | *Sclerophthora rayssiae* var. *zeae* |
| Cephalosporium kernel rot | Acremonium strictum = Cephalosporium acremonium |
| Charcoal rot | Macrophomina phaseolina |
| Corn common rust | *Puccinia sorghi* |
| Corn southern rust | *Puccinia polysora* |
| Corn tropical rust | Physopella pallescens, *P. zeae* = *Angiospora zeae* |
| Corticium ear rot | Thanatephorus cucumeris = Corticium sasakii |
| Cotton rust | *Puccinia schedonnardi* |
| Cotton southwestern rust | *Puccinia cacabata* |
| Cotton tropical rust | Phakopsora gossypii |
| Crazy top downy mildew | *Sclerophthora macrospora* = *S. macrospora* |
| Curvularia leaf spot | Curvularia clavata, C. eragrostidis, = C. maculans (teleomorph: Cochliobolus eragrostidis), Curvularia inaequalis, C. intermedia (teleomorph: Cochliobolus intermedius), Curvularia lunata (teleomorph: Cochliobolus lunatus), Curvularia pallescens (teleomorph: Cochliobolus pallescens), Curvularia senegalensis, C. tuberculata (teleomorph: Cochliobolus tuberculatus) |
| Didymella leaf spot | Didymella exitialis |
| *Diplodia* ear rot and stalk rot | *Diplodia frumenti* (teleomorph: *Botryosphaeria festucae*) |
| *Diplodia* ear rot, stalk rot, seed rot and seedling blight | *Diplodia maydis* = *Stenocarpella maydis* |
| *Diplodia* leaf spot or leaf streak | *Stenocarpella macrospora* = *Diplodia macrospore* |
| Grape leaf Downey mildew | Plasmopara viticola |

TABLE 6-continued

Fungal pests

| Disease | Causative Agent |
|---|---|
| Dry ear rot (cob, kernel and stalk rot) | Nigrospora oryzae (teleomorph: Khuskia oryzae) |
| Ear rots, minor | *Aspergillus glaucus*, A. niger, *Aspergillus* spp., *Cunninghamella* sp., Curvularia pallescens, Doratomyces stemonitis = Cephalotrichum stemonitis, Fusarium culmorum, Gonatobotrys simplex, Pithomyces maydicus, Rhizopus microsporus, R. stolonifer = R. nigricans, Scopulariopsis brumptii |
| epitea | Melampsora larici |
| Ergot (horse's tooth, diente del cabal Io) | Claviceps gigantea (anamorph: *Sphacelia* sp.) |
| Eyespot | *Aureobasidium zeae = Kabatiella zeae* |
| *Fusarium* ear and stalk rot | *Fusarium subglutinans = F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: Fusarium graminearum) |
| Gray ear rot | *Botryosphaeria zeae = Physalospora zeae* (anamorph: Macrophoma zeae) |
| Gray leaf spot (*Cercospora* | *Cercospora sorghi = C. sorghi* var. *maydis, C. zeae-maydis* leaf spot) |
| Green ear downy mildew | Sclerospora graminicola |
| *Helminthosporium* ear rot (race 1) | Bipolaris zeicola = *Helminthosporium carbonum* |
| *Helminthosporium* root rot | *Exserohilum pedicellatum = Helminthosporium pedicellatum* (teleomorph: Setosphaeria) |
| Hormodendrum ear rot (Cladosporium rot) | Cladosporium cladosporioides = Hormodendrum cladosporioides, C. herbarum (teleomorph: Mycosphaerella tassiana) |
| Hyalothyridium leaf spot | *Hyalothyridium maydis* |
| Java downy mildew | *Peronosclerospora maydis = Sclerospora maydis* |
| Late wilt | *Cephalosporium maydis* |
| Leaf (brown) rust | *Puccinia recondita* (anamorph: Aecidium clematitis) |
| Leaf spots, minor | Alternaria alternata, *Ascochyta maydis*, A. tritici, A. zeicola, Bipolaris victoriae = *Helminthosporium victoriae* (teleomorph: Cochliobolus victoriae), C. sativus (anamorph: Bipolaris sorokiniana = H. *Exserohilum maydis, Leptothyrium zeae*, Ophiosphaerella herpotricha, *Setosphaeria prolata*) Graphium penicillioides, Leptosphaeria prolatum = Drechslera prolata (teleomorph: sorokinianum = H. sativum), Epicoccum nigrum, (anamorph: *Scolecosporiella* sp.), Paraphaeosphaeria michotii, *Phoma* sp., *Septoria zeae*, S. zeicola, S. zeina |
| Rust fungi | *Puccinia veronicae-longifoliae* |
| Musk rose rust | Phragmidium rosae-moschatae |
| Multiflora rose rust | Phragmidium rosae-multiflorae |
| Northern corn leaf blight | *Exaerohilum turcicum = Helminthosporium turcicum, Setosphaeria turcica* |
| Northern corn leaf spot | Cochliobolus carbonum |
| Oat crown rust | *Puccinia coronate* |
| Oat stem Rust | *Puccinia graminis* |
| Peanut rust | *Puccinia arachidis* |
| *Penicillium* ear rot (blue eye, blue mold) | *Penicillium* spp., *P. chrysogenum, P. expansum, P. oxalicum* |
| Bay willow-larch rust | Melampsora larici-pentandrae |
| Phaeocytostroma stalk rot and root rot | Phaeocytostroma ambiguum, *Phaeocytosporella zeae* |
| Phaeosphaeria leaf spot | *Phaeosphaeria maydis, Sphaerulina maydis* |
| Philippine downy mildew | *Peronosclerospora philippinensis = Sclerospora philippinensis* |
| Physalospora ear rot | *Botryosphaeria Botryosphaeria festucae = Physalospora zeicola*, (anamorph: Diplodia frumenti) |
| Potato common rust | *Puccinia pittierianap* |
| Potato deforming rust | Aecidium cantensis |
| Cereals and grasses Powdery mildew | *Erysiphe graminis* |
| Rose Powdery mildew | Sphaerotheca pannosa |
| Wheat Powdery mildew | *Blumeria graminis* f. sp. *tritici*, |
| Barley Powdery mildew | *Blumeria graminis* f. sp. *hordei* |
| Grape Powdery mildew | Microsphaera diffusa |
| Legume Powdery mildew | Erysiphe necator (or Uncinula necator) |
| Grape Powdery mildew | Leveillula taurica, or Oidiopsis taurica |
| Onion Powdery mildew | Podosphaera leucotricha |
| Apple Powdery mildew | Podosphaera xanthii, Erysiphe cichoracearum, Podosphaera fusca, Leveillula taurica |
| Cucurbits Powdery mildew | Microsphaera syringae |
| Lilacs Powdery mildew | Podosphaera aphanis, Geum rivale |
| Strawberry Powdery mildew | Erysiphe berberidis |
| Hawthorn Powdery mildew | Podosphaera oxyacanthae |

TABLE 6-continued

Fungal pests

| Disease | Causative Agent |
|---|---|
| Gooseberry Powdery mildew | Sphaerotheca mors-uvae |
| Purple leaf sheath | Hemiparasitic bacteria and fungi |
| *Pyrenochaeta* stalk rot and root rot | *Phoma terrestris, Pyrenochaeta terrestris* |
| *Pythium* root rot | *Pythium* spp., *P. arrhenomanes, P. graminicola* |
| *Pythium* stalk rot | *Pythium aphanidermatum* = P. butleri L. |
| Red kernel disease (ear mold, leaf and seed rot) | Epicoccum nigrum |
| *Rhizoctonia* ear rot | *Rhizoctonia zeae* (teleomorph: Waitea circinata) |
| *Rhizoctonia* root rot and stalk rot | *Rhizoctonia solani, Rhizoctonia zeae* |
| Root rots, minor | Alternaria alternata, *Cercospora sorghi*, Dictochaeta fertilis, Fusarium acuminatum (teleomorph: *Gibberella acuminate*), F. equiseti (teleomorph: G. intricans), F. oxysporum, F. pallidoroseum, F. poae, F. roseum, F. cyanogena, (anamorph: F. sulphureum), Microdochium bolleyi, *Mucor* sp., Periconia circinata, Phytophthora cactorum, P. drechsleri, *P. nicotianae* var. *parasitica*, Rhizopus arrhizus |
| Rostratum leaf spot (leaf disease, ear and, stalk rot) | Setosphaeria rostrata, Helminthosporium (anamorph: *Exserohilum rostratum* = *Helminthosporium rostratum*) |
| rugosae | Phragmidium rosae |
| Rust, common corn | *Puccinia sorghi* |
| Rust, southern corn | *Puccinia polysora* |
| Rust, tropical corn | Physopella pallescens, *P. zeae* = *Angiospora zeae* |
| sativae | Balansia oryzae |
| Sclerotium ear rot (southern blight) | Sclerotium rolfsii (teleomorph: Athelia rolfsii) |
| Seed rot-seedling blight | Bipolaris sorokiniana, B. zeicola = *Helminthosporium carbonum*, *Diplodia maydis, Exserohilum pedicellatum, Exserohilum turcicum* = *Helminthosporium turcicum*, Fusarium avenaceum, F. culmorum, F. moniliforme, *Gibberella zeae* (anamorph: F. graminearum), Macrophomina phaseolina, *Penicillium* spp., *Phomopsis* sp., *Pythium* spp., *Rhizoctonia solani, R. zeae*, Sclerotium rolfsii, *Spicaria* sp. |
| *Selenophoma* leaf spot | *Selenophoma* sp. |
| Sheath rot | *Gaeumannomyces graminis* |
| Shuck rot | Myrothecium gramineum |
| sieboldii | Hamaspora rubi |
| Silage mold | Monascus purpureus, M. rubber |
| Smut, common | *Ustilago zeae* = *U. maydis* |
| Smut, false | Ustilaginoidea virens |
| Smut, head | Sphacelotheca reiliana = Sporisorium holci-sorghi |
| Sorghum downy mildew | *Peronosclerospora sorghi* = *Sclerospora sorghi* |
| Southern corn leaf blight and stalk rot | Cochliobolus heterostrophus (anamorph: *Bipolaris maydis* - *Helminthosporium maydis*) |
| Southern leaf spot | *Stenocarpella macrospora* = *Diplodia macrospora* |
| Soybean rust | Phakopsora pachyrhizi |
| Spontaneum downy mildew | *Peronosclerospora spontanea* = *Sclerospora spontanea* |
| Stalk rots, minor | *Cercospora sorghi*, Fusarium episphaeria, F. merismoides, F. oxysportum, F. poae, F. roseum, *F. solani* (teleomorph: Nectria haematococca), F. tricinctum, Mariannaea elegans, *Mucor* sp., *Rhopographus zeae, Spicaria* sp. |
| Stem rust | *Puccinia graminis* = *P. graminis* f. sp. *secalis* |
| Storage rots | *Aspergillus* spp., *Penicillium* spp. and other fungi |
| Sugarcane common rust | *Puccinia melanocephala* = P. eriantha |
| Sugarcane downy mildew | *Peronosclerospora sacchari* = *Sclerospora sacchari* |
| Tar spot | *Phyllachora maydis* |
| thunbergii | Phragmidium rubi |
| Trichoderma ear rot and root rot | Trichoderma viride = T. lignorum (teleomorph: Hypocrea sp.) |
| Wheat leaf (brown) rust | *Puccinia triticina* = *P. Recondita* f. Sp. *tritici* = *P. tritici-duri* |
| Wheat stem (black) rust | *Puccinia graminis* = *P. graminis* f. sp. *tritici* |
| Wheat stripe (yellow) rust | *Puccinia striiformis* (anamorph: P. uredoglumarum) |
| White ear rot, root and stalk rot | *Stenocarpella maydis* = *Diplodia zeae* |
| Yellow leaf blight | Ascochyta ischaemi, *Phyllosticta maydis* (teleomorph: *Mycosphaerella zeae-maydis*) |
| Zonate leaf spot | *Gloeocercospora sorghi* | ii. Bacteria

The PMP compositions and related methods can be useful for decreasing the fitness of a bacterium, e.g., to prevent or treat a bacterial infection in a plant. Included are methods for delivering a PMP composition to a bacterium by contacting the bacteria with the PMP composition. Additionally or alternatively, the methods include delivering the biopesticide to a plant at risk of or having a bacterial infection, by contacting the plant with the PMP composition.

The PMP compositions and related methods are suitable for delivery to bacteria, or a plant infected therewith, including any bacteria described further below. For example, the bacteria may be one belonging to Actinobacteria or Proteobacteria, such as bacteria in the families of the Burkholderiaceae, Xanthomonadaceae, Pseudomonadaceae, Enterobacteriaceae, Microbacteriaceae, and Rhizobiaceae.

In some instances, the bacteria is an *Acidovorax avenae* subsp., including e.g., *Acidovorax avenae* subsp. *avenae* (=*Pseudomonas avenae* subsp. *avenae*), *Acidovorax avenae* subsp. *cattleyae* (=*Pseudomonas cattleyae*), or *Acidovorax avenae* subsp. *citrulli* (=*Pseudomonas pseudoalcaligenes* subsp. *citrulli*, *Pseudomonas avenae* subsp. *citrulli*)).

In some instances, the bacteria is a *Burkholderia* spp., including e.g., *Burkholderia andropogonis* (=*Pseudomonas andropogonis*, *Pseudomonas woodsii*), *Burkholderia caryophylli* (=*Pseudomonas caryophylli*), *Burkholderia cepacia* (=*Pseudomonas cepacia*), *Burkholderia gladioli* (=*Pseudomonas gladioli*), *Burkholderia gladioli* pv. *agaricicola* (=Pseudomnas *gladioli* pv. *agaricicola*), *Burkholderia gladioli* pv. *alliicola* (i.e., *Pseudomonas gladioli* pv. *alliicola*), *Burkholderia gladioli* pv. *gladioli* (i.e., *Pseudomonas gladioli*, *Pseudomonas gladioli* pv. *gladioli*), *Burkholderia glumae* (i.e., *Pseudomonas glumae*), *Burkholderia plantarii* (i.e., *Pseudomonas plantarii*), *Burkholderia solanacearum* (i.e., *Ralstonia solanacearum*), or *Ralstonia* spp.

In some instances, the bacteria is a *Liberibacter* spp., including *Candidatus Liberibacter* spec., including e.g., *Candidatus Liberibacter asiaticus*, *Liberibacter africanus* (Laf), *Liberibacter americanus* (Lam), *Liberibacter asiaticus* (Las), *Liberibacter europaeus* (Leu), *Liberibacter psyllaurous*, or *Liberibacter solanacearum* (Lso).

In some instances, the bacteria is a *Corynebacterium* spp. including e.g., *Corynebacterium fascians*, *Corynebacterium flaccumfaciens* pv. *flaccumfaciens*, *Corynebacterium michiganensis*, *Corynebacterium michiganense* pv. *tritici*, *Corynebacterium michiganense* pv. *nebraskense*, or *Corynebacterium sepedonicum*.

In some instances, the bacteria is a *Erwinia* spp. including e.g., *Erwinia amylovora*, *Erwinia ananas*, *Erwinia carotovora* (i.e., *Pectobacterium carotovorum*), *Erwinia carotovora* subsp. *atroseptica*, *Erwinia carotovora* subsp. *carotovora*, *Erwinia chrysanthemi*, *Erwinia chrysanthemi* pv. *zeae*, *Erwinia dissolvens*, *Erwinia herbicola*, *Erwinia rhapontic*, *Erwinia stewartiii*, *Erwinia tracheiphila*, or *Erwinia uredovora*.

In some instances, the bacteria is a *Pseudomonas syringae* subsp., including e.g., *Pseudomonas syringae* pv. *actinidiae* (Psa), *Pseudomonas syringae* pv. *atrofaciens*, *Pseudomonas syringae* pv. *coronafaciens*, *Pseudomonas syringae* pv. *glycinea*, *Pseudomonas syringae* pv. *lachrymans*, *Pseudomonas syringae* pv. *maculicola Pseudomonas syringae* pv. *papulans*, *Pseudomonas syringae* pv. *striafaciens*, *Pseudomonas syringae* pv. *syringae*, *Pseudomonas syringae* pv. *tomato*, or *Pseudomonas syringae* pv. *tabaci*.

In some instances, the bacteria is a *Streptomyces* spp., including e.g., *Streptomyces acidiscabies*, *Streptomyces albidoflavus*, *Streptomyces candidus* (i.e., *Actinomyces candidus*), *Streptomyces caviscabies*, *Streptomyces collinus*, *Streptomyces europaeiscabiei*, *Streptomyces intermedius*, *Streptomyces ipomoeae*, *Streptomyces luridiscabiei*, *Streptomyces niveiscabiei*, *Streptomyces puniciscabiei*, *Streptomyces retuculiscabiei*, *Streptomyces scabiei*, *Streptomyces scabies*, *Streptomyces setonii*, *Streptomyces steliiscabiei*, *Streptomyces turgidiscabies*, or *Streptomyces wedmorensis*.

In some instances, the bacteria is a *Xanthomonas axonopodis* subsp., including e.g., *Xanthomonas axonopodis* pv. *alfalfae* (=*Xanthomonas alfalfae*), *Xanthomonas axonopodis* pv. *aurantifolii* (=*Xanthomonas fuscans* subsp. *aurantifolii*), *Xanthomonas axonopodis* pv. *allii* (=*Xanthomonas campestris* pv. *allii*), *Xanthomonas axonopodis* pv. *axonopodis*, *Xanthomonas axonopodis* pv. *bauhiniae* (=*Xanthomonas campestris* pv. *bauhiniae*), *Xanthomonas axonopodis* pv. *begoniae* (=*Xanthomonas campestris* pv. *begoniae*), *Xanthomonas axonopodis* pv. *betlicola* (=*Xanthomonas campestris* pv. *betlicola*), *Xanthomonas axonopodis* pv. *biophyti* (=*Xanthomonas campestris* pv. *biophyti*), *Xanthomonas axonopodis* pv. *cajani* (=*Xanthomonas campestris* pv. *cajani*), *Xanthomonas axonopodis* pv. *cassavae* (=*Xanthomonas cassavae*, *Xanthomonas campestris* pv. *cassavae*), *Xanthomonas axonopodis* pv. *cassiae* (=*Xanthomonas campestris* pv. *cassiae*), *Xanthomonas axonopodis* pv. *citri* (=*Xanthomonas citri*), *Xanthomonas axonopodis* pv. *citrumelo* (=*Xanthomonas alfalfae* subsp. *citrumelonis*), *Xanthomonas axonopodis* pv. *clitoriae* (=*Xanthomonas campestris* pv. *clitoriae*), *Xanthomonas axonopodis* pv. *coracanae* (=*Xanthomonas campestris* pv. *coracanae*), *Xanthomonas axonopodis* pv. *cyamopsidis* (=*Xanthomonas campestris* pv. *cyamopsidis*), *Xanthomonas axonopodis* pv. *desmodii* (=*Xanthomonas campestris* pv. *desmodii*), *Xanthomonas axonopodis* pv. *desmodiigangetici* (=*Xanthomonas campestris* pv. *desmodiigangetici*), *Xanthomonas axonopodis* pv. *desmodiilaxiflori* (=*Xanthomonas campestris* pv. *desmodiilaxiflori*), *Xanthomonas axonopodis* pv. *desmodiirotundifolii* (=*Xanthomonas campestris* pv. *desmodiirotundifolii*), *Xanthomonas axonopodis* pv. *dieffenbachiae* (=*Xanthomonas campestris* pv. *dieffenbachiae*), *Xanthomonas axonopodis* pv. *erythrinae* (=*Xanthomonas campestris* pv. *erythrinae*), *Xanthomonas axonopodis* pv. *fascicularis* (=*Xanthomonas campestris* pv. *fasciculari*), *Xanthomonas axonopodis* pv. *glycines* (=*Xanthomonas campestris* pv. *glycines*), *Xanthomonas axonopodis* pv. *khayae* (=*Xanthomonas campestris* pv. *khayae*), *Xanthomonas axonopodis* pv. *lespedezae* (=*Xanthomonas campestris* pv. *lespedezae*), *Xanthomonas axonopodis* pv. *maculifoliigardeniae* (=*Xanthomonas campestris* pv. *maculifoliigardeniae*), *Xanthomonas axonopodis* pv. *malvacearum* (=*Xanthomonas citri* subsp. *malvacearum*), *Xanthomonas axonopodis* pv. *manihotis* (=*Xanthomonas campestris* pv. *manihotis*), *Xanthomonas axonopodis* pv. *martyniicola* (=*Xanthomonas campestris* pv. *martyniicola*), *Xanthomonas axonopodis* pv. *melhusii* (=*Xanthomonas campestris* pv. *melhusii*), *Xanthomonas axonopodis* pv. *nakataecorchori* (=*Xanthomonas campestris* pv. *nakataecorchori*), *Xanthomonas axonopodis* pv. *passiflorae* (=*Xanthomonas campestris* pv. *passiflorae*), *Xanthomonas axonopodis* pv. *patelii* (=*Xanthomonas campestris* pv. *patelii*), *Xanthomonas axonopodis* pv. *pedalii* (=*Xanthomonas campestris* pv. pedalii), *Xanthomonas axonopodis* pv. *phaseoli* (=*Xanthomonas campestris* pv. *phaseoli*, *Xanthomonas phaseoli*), *Xanthomonas axonopodis* pv. *phaseoli* var. *fuscans* (=*Xanthomonas fuscans*), *Xanthomonas axonopodis* pv. *phyllanthi* (=*Xanthomonas campestris* pv. *phyllanthi*), *Xanthomonas axonopodis* pv. *physalidicola* (=*Xanthomonas campestris* pv. *physalidicola*), *Xanthomonas axonopodis* pv. *poinsettiicola* (=*Xanthomonas campestris* pv. *poinsettiicola*), *Xanthomonas axonopodis* pv. *punicae* (=*Xanthomonas campestris* pv. *punicae*), *Xanthomonas axonopodis* pv. *rhynchosiae* (=*Xanthomonas campestris* pv. *rhynchosiae*), *Xanthomonas axonopodis* pv. *ricini* (=*Xanthomonas campestris* pv. *ricini*), *Xanthomonas axonopodis* pv. *sesbaniae* (=*Xanthomonas campestris* pv. *sesbaniae*), *Xanthomonas axonopodis* pv. *tamarindi* (=*Xanthomonas campestris* pv. *tamarindi*), *Xanthomonas axonopodis* pv. *vasculorum* (=*Xanthomonas campestris* pv. *vasculorum*), *Xanthomonas axonopodis* pv. *vesicatoria* (=*Xanthomonas campestris* pv.-

*vesicatoria, Xanthomonas vesicatoria*), *Xanthomonas axonopodis* pv. vignaeradiatae (=*Xanthomonas campestris* pv. vignaeradiatae), *Xanthomonas axonopodis* pv. *vignicola* (=*Xanthomonas campestris* pv. *vignicola*), or *Xanthomonas axonopodis* pv. vitians (=*Xanthomonas campestris* pv. vitians).

In some instances, the bacteria is a Xylella fastidiosa from the family of Xanthomonadaceae.

Table 7 shows further examples of bacteria, and diseases associated therewith, that can be treated or prevented using the PMP composition and related methods described herein.

TABLE 7

Bacterial pests

| Disease | Causative Agent |
|---|---|
| Bacterial leaf blight and stalk rot | *Pseudomonas avenae* subsp. *avenae* |
| Bacterial leaf spot | Xanthomonas campestris pv. holcicola |
| Bacterial stalk rot | Enterobacter dissolvens = Erwinia dissolvens |
| Bacterial stalk and top rot | *Erwinia carotovora* subsp. *carotovora*, Erwinia chrysanthemi pv. Zeae |
| Bacterial stripe | Pseudomonas andropogonis |
| Chocolate spot | Pseudomonas syringae pv. Coronafaciens |
| Goss's bacterial wilt blight (leaf freckles and wilt) | *Clavibacter michiganensis* subsp. *nebraskensis* = Cornebacterium michiganense pv. Nebraskense |
| Holcus spot | Pseudomonas syringae pv. Syringae |
| Purple leaf sheath | Hemiparasitic bacteria |
| Seed rot-seedling blight | Bacillus subtilis |
| Stewart's disease (bacterial wilt) | Pantoea stewartii = Erwinia stewartii |
| Corn stunt (Mesa Central or Rio Grande stunt) | Achapparramiento, stunt, Spiroplasma kunkelii |
| Soft rot | Dickeya dianthicola |
| Soft rot | Dickeya solani |
| Fire blight | Erwinia amylovora |
| Soft rot | P. atrosepticum |
| Soft rot | *Pectobacterium carotovorum* ssp. *carotovorum* |
| Soft rot | Pectobacterium wasabiae |
| Bacterial blight | Pseudomonas syringae pv. Porri and pv. Tomato |
| Brown blotch Disease | Pseudomonas tolaasii |
| Bacterial wilt | Ralstonia solanacearum |
| Bacteria wilt | Ralstonia solanacearum |
| Common scab | Streptomyces scabies |
| Common scab | Streptomyces scabies |
| Xanthomonasleaf blight of onion | Xanthomonas axonopodis pv. allii |
| Asiatic citrus canker | Xanthomonas axonopodis pv. citri |
| Citrus bacterial spot | Xanthomonas axonopodis pv. citrumelo |
| Bacterial spot | Xanthomonas campestris pv. vesicatoria |
| Pierce's Disease | Xylella fastidiosa |

In some instances, the bacteria is *Xanthomonas campestris* pv. *musacearum, Xanthomonas campestris* pv. *pruni* (=*Xanthomonas arboricola* pv. *pruni*), or *Xanthomonas fragariae*.

In some instances, the bacteria is a *Xanthomonas translucens* supsp. (=*Xanthomonas campestris* pv. *hordei*) including e.g., *Xanthomonas translucens* pv. *arrhenatheri* (=*Xanthomonas campestris* pv. *arrhenatheri*), *Xanthomonas translucens* pv. *cerealis* (=*Xanthomonas campestris* pv. *cerealis*), *Xanthomonas translucens* pv. *graminis* (=*Xanthomonas campestris* pv. *graminis*), *Xanthomonas translucens* pv. *phlei* (=*Xanthomonas campestris* pv. *phlei*), *Xanthomonas translucens* pv. phleipratensis (=*Xanthomonas campestris* pv. phleipratensis), *Xanthomonas translucens* pv. *poae* (=*Xanthomonas campestris* pv. *poae*), *Xanthomonas translucens* pv. *secalis* (=*Xanthomonas campestris* pv. *secalis*), *Xanthomonas translucens* pv. *translucens* (=*Xanthomonas campestris* pv. *translucens*), or *Xanthomonas translucens* pv. *undulosa* (=*Xanthomonas campestris* pv. *undulosa*).

In some instances, the bacteria is a *Xanthomonas oryzae* supsp., *Xanthomonas oryzae* pv. *oryzae* (=*Xanthomonas campestris* pv. *oryzae*), or *Xanthomonas oryzae* pv. *oryzicola* (=*Xanthomonas campestris* pv. *oryzicola*).

iii. Insects

The PMP compositions and related methods can be useful for decreasing the fitness of an insect, e.g., to prevent or treat an insect infestation in a plant. The term "insect" includes any organism belonging to the phylum Arthropoda and to the class Insecta or the class Arachnida, in any stage of development, i.e., immature and adult insects. Included are methods for delivering a PMP composition to an insect by contacting the insect with the PMP composition. Additionally or alternatively, the methods include delivering the biopesticide to a plant at risk of or having an insect infestation, by contacting the plant with the PMP composition.

The PMP compositions and related methods are suitable for preventing or treating infestation by an insect, or a plant infested therewith, including insects belonging to the following orders: Acari, Araneae, Anoplura, Coleoptera, Collembola, Dermaptera, Dictyoptera, Diplura, Diptera (e.g., spotted-wing *Drosophila*), Embioptera, Ephemeroptera, Grylloblatodea, Hemiptera (e.g., aphids, Greenhous whitefly), Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, or Zoraptera.

In some instances, the insect is from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., or *Vasates lycopersici*.

In some instances, the insect is from the class Chilopoda, for example, *Geophilus* spp. or *Scutigera* spp.

In some instances, the insect is from the order Collembola, for example, *Onychiurus armatus*.

In some instances, the insect is from the class Diplopoda, for example, *Blaniulus guttulatus*; from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., or *Supella longipalpa*.

In some instances, the insect is from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp. (e.g., corn rootworm), *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., or *Zabrus* spp.

In some instances, the insect is from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia* anthropophage, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp. (e.g., *Musca domestica*), *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., or *Tipula* spp.

In some instances, the insect is from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, Miridae, *Monalonion atratum*, *Nezara* spp., *Oebalus* spp., Pentomidae, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., or *Triatoma* spp.

In some instances, the insect is from the order Homiptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp. (e.g., *Apis gossypii*), *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, Cercopidae, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Homalodisca vitripennis*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., Pentamomidae spp. (e.g., *Halyomorpha halys*), *Peregrinus maidis*, *Phenacoccus* spp., *Phloeomyzus passerinii*, *Phorodon humuli*, *Phylloxera* spp., *Pinnaspis aspidistrae*, *Planococcus* spp.,

*Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae,* Tenalaphara *malayensis,* Tetragonocephela spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.; from the order Hymenoptera, for example, *Acromyrmex* spp., *Athalia* spp., *Atta* spp., Diprion spp., *Hoplocampa* spp., *Lasius* spp., *Monomorium pharaonis,* Sirex spp., *Solenopsis invicta, Tapinoma* spp., Urocerus spp., *Vespa* spp., or Xeris spp.

In some instances, the insect is from the order Isopoda, for example, *Armadillidium vulgare, Oniscus asellus,* or *Porcellio scaber.*

In some instances, the insect is from the order Isoptera, for example, *Coptotermes* spp., *Cornitermes cumulans, Cryptotermes* spp., *Incisitermes* spp., *Microtermes obesi, Odontotermes* spp., or *Reticulitermes* spp.

In some instances, the insect is from the order Lepidoptera, for example, *Achroia grisella, Acronicta major, Adoxophyes* spp., *Aedia leucomelas, Agrotis* spp., Alabama spp., *Amyelois transitella, Anarsia* spp., *Anticarsia* spp., *Argyroploce* spp., Barathra *brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis,* Cheimatobia *brumata, Chilo* spp., *Choristoneura* spp., *Clysia ambiguella,* Cnaphalocerus spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea* saccharalis, *Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., Hedylepta spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., Loxagrotis *albicosta, Lymantria* spp., *Lyonetia* spp., *Malacosoma neustria, Maruca* testulalis, Mamstra *brassicae, Melanitis leda, Mocis* spp., *Monopis obviella, Mythimna separata, Nemapogon* cloacellus, *Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., Prodenia spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., Tryporyza *incertulas, Tuta absoluta,* or *Virachola* spp.

In some instances, the insect is from the order Orthoptera or Saltatoria, for example, *Acheta domesticus, Dichroplus* spp., *Gryllotalpa* spp., *Hieroglyphus* spp., *Locusta* spp., *Melanoplus* spp., or *Schistocerca gregaria.*

In some instances, the insect is from the order Phthiraptera, for example, *Damalinia* spp., *Haematopinus* spp., *Linognathus* spp., *Pediculus* spp., Ptirus *pubis, Trichodectes* spp.

In some instances, the insect is from the order Psocoptera for example Lepinatus spp., or *Liposcelis* spp.

In some instances, the insect is from the order Siphonaptera, for example, *Ceratophyllus* spp., *Ctenocephalides* spp., *Pulex irritans, Tunga penetrans,* or *Xenopsylla* cheopsis.

In some instances, the insect is from the order Thysanoptera, for example, *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi,* or *Thrips* spp.

In some instances, the insect is from the order Zygentoma (=Thysanura), for example, Ctenolepisma spp., *Lepisma saccharina, Lepismodes inquilinus,* or *Thermobia domestica.*

In some instances, the insect is from the class Symphyla, for example, *Scutigerella* spp.

In some instances, the insect is a mite, including but not limited to, Tarsonemid mites, such as *Phytonemus pallidus, Polyphagotarsonemus latus,* Tarsonemus *bilobatus,* or the like; Eupodid mites, such as Penthaleus *erythrocephalus,* Penthaleus major, or the like; Spider mites, such as *Oligonychus shinkajii, Panonychus citri, Panonychus mori, Panonychus ulmi, Tetranychus kanzawai, Tetranychus urticae,* or the like; Eriophyid mites, such as Acaphylla theavagrans, Aceria *tulipae, Aculops lycopersici, Aculops pelekassi, Aculus schlechtendali, Eriophyes chibaensis, Phyllocoptruta oleivora,* or the like; Acarid mites, such as Rhizoglyphus *robini,* Tyrophagus putrescentiae, Tyrophagus *similis,* or the like; Bee brood mites, such as *Varroa jacobsoni, Varroa destructor* or the like; Ixodides, such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., or the like; Cheyletidae, such as *Cheyletiella yasguri, Cheyletiella blakei,* or the like; Demodicidae, such as *Demodex canis, Demodex cati,* or the like; Psoroptidae, such as *Psoroptes ovis,* or the like; Scarcoptidae, such as *Sarcoptes scabiei,* Notoedres *cati,* Knemidocoptes spp., or the like.

Table 8 shows further examples of insects that cause infestations that can be treated or prevented using the PMP compositions and related methods described herein.

TABLE 8

| Insect pests | |
|---|---|
| Common Name | Latin name |
| European corn borer | Ostrinia nubilalis |
| Corn earworm | Helicoverpa zea |
| Beet armyworm | Spodoptera exigua |
| Fall armyworm | Spodoptera frugiperda |
| Southwestern corn borer | Diatraea grandiosella |
| Lesser cornstalk borer | Elasmopalpus lignosellus |
| Stalk borer | Papaipema nebris |
| Common armyworm | Pseudaletia unipuncta |
| Black cutworm | Agrotis ipsilon |
| Western bean cutworm | Striacosta albicosta |
| Yellowstriped armyworm | Spodoptera ornithogalli |
| Western yellowstriped armyworm | Spodoptera praefica |

TABLE 8-continued

Insect pests

| Common Name | Latin name |
|---|---|
| Southern armyworm | Spodoptera eridania |
| Southern armyworm | Spodoptera eridania |
| Variegated cutworm | Peridroma saucia |
| Stalk borer | Papaipema nebris |
| Cabbage looper | Trichoplusia ni |
| Tomato pinworm | Keiferia lycopersicella |
| Tobacco hornworm | Manduca sexta |
| Tomato hornworm | Manduca quinquemaculata |
| Imported cabbageworm | Artogeia rapae |
| Cabbage butterfly | Pieris brassicae |
| Cabbage looper | Trichoplusia ni |
| Diamondback moth | Plutella xylostella |
| Beet armyworm | Spodoptera exigua |
| Common cutworm | Agrotis segetum |
| Potato tuberworm | Phthorimaea operculella |
| Diamondback moth | Plutella xylostella |
| Sugarcane borer | Diatraea saccharalis |
| Glassy cutworm | Crymodes devastator |
| Dingy cutworm | Feltia ducens |
| Claybacked cutworm | Agrotis gladiaria |
| Green cloverworm | Plathypena scabra |
| Soybean looper | Pseudoplusia includes |
| Velvetbean caterpillar | Anticarsia gemmatalis |
| Northern corn rootworm | Coleoptera Diabrotica barberi |
| Southern corn rootworm | Diabrotica undecimpunctata |
| Western corn rootworm | Diabrotica virgifera |
| Maize weevil | Sitophilus zeamais |
| Colorado potato beetle | Leptinotarsa decemlineata |
| Tobacco flea beetle | Epitrix hirtipennis |
| Crucifer flea beetle | Phyllotreta Cruciferae |
| Western black flea beetle | Phyllotreta pusilia |
| Pepper weevil | Anthonomus eugenii |
| Colorado potato beetle | Leptinotarsa decemlineata |
| Potato flea beetle | Epitrix cucumeris |
| Wireworms Melanpotus spp. | Hemicrepidus memnonius |
| Wireworms | Ceutorhychus assimilis |
| Cabbage seedpod weevil | Phyllotreta Cruciferae |
| Crucifer flea beetle | Melanolus spp. |
| Wireworm | Aeolus mellillus |
| Wheat wireworm | Aeolus mancus |
| Sand wireworm | Horistonotus uhlerii |
| Maize billbug | Sphenophorus maidis |
| Timothy bilibug | Sphenophorus zeae |
| Bluegrass billbug | Sphenophorus parvulus |
| Southern corn billbug | Sphenophorus callosus |
| White grubs | Phyllophaga spp. |
| Corn flea beetle | Chaetocnema pulicaria |
| Japanese beetle | Popillia japonica |
| Mexican bean beetle | Epilachna varivestis |
| Bean leaf beetle | Cerotoma trifurcate |
| Blister beetles | Epicauta pestifera Epicauta lemniscata |
| Corn leaf aphid | Homoptera Rhopalosiphum maidis |
| Corn root aphid | Anuraphis maidiradicis |
| Green peach aphid | Myzus persicae |
| Potato aphid | Macrosiphum euphorbiae |
| Greenhouse whitefly | Trileurodes vaporariorum |
| Sweetpotato whitefly | Bemisia tabaci |
| Silverleaf whitefly | Bemisia argentifolii |
| Cabbage aphid | Brevicoryne brassicae |
| Green peach aphid | Myzus persicae |
| Potato leafhopper | Empoasca fabae |
| Potato psyllid | Paratrioza cockerelli |
| Silverleaf whitefly | Bemisia argentifolii |
| Sweetpotato whitefly | Bemisia tabaci |
| Carrot aphid | Cavariella aegopodii |
| Cabbage aphid | Brevicoryne brassicae |
| West Indian canefly | Saccharosydne saccharivora |
| Yellow sugarcane aphid | Sipha flava |
| Threecornered alfalfa hopper | Spissistilus festinus |
| Lygus Hesperus | Hemiptera Lygus lineolaris |
| Lygus bug | Lygus rugulipennis |
| Green stink bug | Acrosternum hilare |
| Brown stick bug | Euschistus servus |
| Chinch bug | Blissus leucopterus leucopterus |
| Leafminer | Diptera Liriomyza trifolii |
| Vegetable leafminer | Liriomyza sativae |
| Tomato leafminer | Scrobipalpula absoluta |
| Seedcorn maggot | Delia platura |
| Cabbage maggot | Delia brassicae |
| Cabbage root fly | Delia radicum |
| Carrot rust fly | Psilia rosae |
| Sugarbeet root maggot | Tetanops myopaeformis |
| Differential grasshopper | Orthoptera Melanoplus differentialis |
| Redlegged grasshopper | Melanoplus femurrubrum |
| Twostriped grasshopper | Melanoplus bivittatus | iv. Mollusks

The PMP compositions and related methods can be useful for decreasing the fitness of a mollusk, e.g., to prevent or treat a mollusk infestation in a plant. The term "mollusk" includes any organism belonging to the phylum Mollusca. Included are methods for delivering a PMP composition to a mollusk by contacting the mollusk with the PMP composition. Additionally or alternatively, the methods include delivering the biopesticide to a plant at risk of or having a mollusk infestation, by contacting the plant with the PMP composition.

The PMP compositions and related methods are suitable for preventing or treating infestation by terrestrial Gastropods (e.g., slugs and snails) in agriculture and horticulture. They include all terrestrial slugs and snails which mostly occur as polyphagous pests on agricultural and horticultural crops. For example, the mollusk may belong to the family Achatinidae, Agriolimacidae, Ampullariidae, Arionidae, Bradybaenidae, Helicidae, Hydromiidae, Lymnaeidae, Milacidae, Urocyclidae, or Veronicellidae.

For example, in some instances, the mollusk is *Achatina* spp., *Archachatina* spp. (e.g., *Archachatina marginata*), *Agriolimax* spp., *Arion* spp. (e.g., *A. ater, A. circumscriptus, A. distinctus, A. fasciatus, A. hortensis, A. intermedius, A. rufus, A. subfuscus, A. silvaticus,* A. *lusitanicus*), Arliomax spp. (e.g., Ariolimax *columbianus*), *Biomphalaria* spp., *Bradybaena* spp. (e.g., B. *fruticum*), *Bulinus* spp., *Cantareus* spp. (e.g., C. asperses), *Cepaea* spp. (e.g., *C. hortensis, C. nemoralis, C. hortensis*), *Cernuella* spp., *Cochlicella* spp., *Cochlodina* spp. (e.g., *C. laminata*), *Deroceras* spp. (e.g., *D. agrestis*, D. *empiricorum, D. laeve*, D. panornimatum, *D. reticulatum*), *Discus* spp. (e.g., *D. rotundatus*), *Euomphalia* spp., *Galba* spp. (e.g., G. *trunculata*), *Helicella* spp. (e.g., *H. itala, H. obvia*), *Helicigona* spp. (e.g., H. *arbustorum*), *Helicodiscus* spp., *Helix* spp. (e.g., *H. aperta, H. aspersa, H. pomatia*), *Limax* spp. (e.g., *L. cinereoniger,* L. *flavus, L. marginatus, L. maximus, L. tenellus*), *Limicolaria* spp. (e.g., *Limicolaria* aurora), *Lymnaea* spp. (e.g., *L. stagnalis*), Mesodon spp. (e.g., Meson thyroidus), *Monadenia* spp. (e.g., *Monadenia fidelis*), *Milax* spp. (e.g., *M. gagates, M. marginatus, M. sowerbyi*, M. *budapestensis*), *Oncomelania* spp., Neohelix spp. (e.g., Neohelix *albolabris*), *Opeas* spp., *Otala* spp. (e.g., *Otala lacteal*), *Oxyloma* spp. (e.g., *O. pfeifferi*), *Pomacea* spp. (e.g., *P. canaliculata*), *Succinea* spp., *Tandonia* spp. (e.g., *T. budapestensis, T. sowerbyi*), *Theba* spp., *Vallonia* spp., or *Zonitoides* spp. (e.g., *Z. nitidus*).

v. Nematodes

The PMP compositions and related methods can be useful for decreasing the fitness of a nematode, e.g., to prevent or treat a nematode infestation in a plant. The term "nematode" includes any organism belonging to the phylum Nematoda. Included are methods for delivering a PMP composition to a nematode by contacting the nematode with the PMP composition. Additionally or alternatively, the methods include delivering the biopesticide to a plant at risk of or having a nematode infestation, by contacting the plant with the PMP composition.

The PMP compositions and related methods are suitable for preventing or treating infestation by nematodes that cause damage plants including, for example, *Meloidogyne* spp. (root-knot), *Heterodera* spp., *Globodera* spp., *Pratylenchus* spp., *Helicotylenchus* spp., *Radopholus similis*, *Ditylenchus dipsaci*, *Rotylenchulus reniformis*, *Xiphinema* spp., *Aphelenchoides* spp. and *Belonolaimus longicaudatus*. In some instances, the nematode is a plant parasitic nematode or a nematode living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonema* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cystforming nematodes of the genera *Heterodera* or *Globodera*, and/or root knot nematodes of the genus *Meloidogyne*. Harmful species of these genera are for example *Meloidogyne incognita*, *Heterodera glycines* (soybean cyst nematode), *Globodera pallida* and *Globodera rostochiensis* (potato cyst nematode), which species are effectively controlled with the PMP compositions described herein. However, the use of the PMP compositions described herein is in no way restricted to these genera or species, but also extends in the same manner to other nematodes.

Other examples of nematodes that can be targeted by the methods and compositions described herein include but are not limited to e.g. Aglenchus *agricola*, Anguina *tritici*, *Aphelenchoides arachidis*, *Aphelenchoides fragaria* and the stem and leaf endoparasites *Aphelenchoides* spp. in general, *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus*, *Bursaphelenchus mucronatus*, and *Bursaphelenchus* spp. in general, Cacopaurus *pestis*, Criconemella *curvata*, Criconemella *onoensis*, Criconemella *ornata*, Criconemella *rusium*, Criconemella *xenoplax* (=Mesocriconema *xenoplax*) and Criconemella spp. in general, Criconemoides *femiae*, Criconemoides *onoense*, Criconemoides *ornatum* and Criconemoides spp. in general, *Ditylenchus destructor*, *Ditylenchus dipsaci*, *Ditylenchus myceliophagus* and the stem and leaf endoparasites *Ditylenchus* spp. in general, Dolichodorus *heterocephalus*, *Globodera pallida* (=*Heterodera pallida*), *Globodera rostochiensis* (potato cyst nematode), *Globodera solanacearum*, *Globodera tabacum*, *Globodera virginia* and the sedentary, cyst forming parasites *Globodera* spp. in general, *Helicotylenchus* digonicus, *Helicotylenchus dihystera*, *Helicotylenchus erythrine*, *Helicotylenchus multicinctus*, *Helicotylenchus nannus*, *Helicotylenchus pseudorobustus* and *Helicotylenchus* spp. in general, Hemicriconemoides, Hemicycliophora *arenaria*, Hemicycliophora *nudata*, Hemicycliophora *parvana*, Heterodera *avenae*, Heterodera *cruciferae*, Heterodera *glycines* (soybean cyst nematode), Heterodera *oryzae*, Heterodera *schachtii*, Heterodera *zeae* and the sedentary, cyst forming parasites *Heterodera* spp. in general, Hirschmaniella *gracilis*, Hirschmaniella *oryzae* Hirschmaniella *spinicaudata* and the stem and leaf endoparasites Hirshmaniella spp. in general, Hoplolaimus *aegyptii*, Hoplolaimus *califomicus*, Hoplolaimus *columbus*, Hoplolaimus *galeatus*, Hoplolaimus *indicus*, Hoplolaimus magnistylus, Hoplolaimus *pararobustus*, *Longidorus africanus*, *Longidorus breviannulatus*, *Longidorus elongatus*, *Longidorus laevicapitatus*, *Longidorus vineacola* and the ectoparasites *Longidorus* spp. in general, *Meloidogyne* acronea, *Meloidogyne africana*, *Meloidogyne arenaria*, *Meloidogyne arenaria* thamesi, *Meloidogyne* artiella, *Meloidogyne* chitwoodi, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor*, *Meloidogyne naasi*, *Meloidogyne paranaensis*, *Meloidogyne* thamesi and the sedentary parasites *Meloidogyne* spp. in general, Meloinema spp., Nacobbus *aberrans*, Neotylenchus vigissi, Paraphelenchus pseudoparietinus, Paratrichodorus *allius*, Paratrichodorus *lobatus*, Paratrichodorus *minor*, Paratrichodorus *nanus*, Paratrichodorus *porosus*, Paratrichodorus *teres* and Paratrichodorus spp. in general, Paratylenchus *hamatus*, Paratylenchus *minutus*, Paratylenchus *projectus* and Paratylenchus spp. in general, *Pratylenchus agilis*, *Pratylenchus alleni*, *Pratylenchus andinus*, *Pratylenchus brachyurus*, *Pratylenchus cerealis*, *Pratylenchus coffeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus neglectus*, *Pratylenchus penetrans*, *Pratylenchus pratensis*, *Pratylenchus scribneri*, *Pratylenchus teres*, *Pratylenchus thornei*, *Pratylenchus vulnus*, *Pratylenchus zeae* and the migratory endoparasites *Pratylenchus* spp. in general, Pseudohalenchus *minutus*, Psilenchus *magnidens*, Psilenchus *tumidus*, Punctodera chalcoensis, Quinisulcius *acutus*, Radopholus *citrophilus*, *Radopholus similis*, the migratory endoparasites *Radopholus* spp. in general, *Rotylenchulus borealis*, *Rotylenchulus parvus*, *Rotylenchulus reniformis* and *Rotylenchulus* spp. in general, Rotylenchus *laurentinus*, Rotylenchus *macrodoratus*, Rotylenchus *robustus*, Rotylenchus *uniformis* and Rotylenchus spp. in general, Scutellonema *brachyurum*, Scutellonema bradys, Scutellonema clathricaudatum and the migratory endoparasites Scutellonema spp. in general, *Subanguina* radiciola, Tetylenchus *nicotianae*, *Trichodorus cylindricus*, *Trichodorus minor*, *Trichodorus primitivus*, *Trichodorus proximus*, *Trichodorus similis*, *Trichodorus sparsus* and the ectoparasites *Trichodorus* spp. in general, *Tylenchorhynchus agri*, *Tylenchorhynchus brassicae*, *Tylenchorhynchus clarus*, *Tylenchorhynchus claytoni*, *Tylenchorhynchus digitatus*, *Tylenchorhynchus ebriensis*, *Tylenchorhynchus maximus*, *Tylenchorhynchus nudus*, *Tylenchorhynchus vulgaris* and *Tylenchorhynchus* spp. in general, *Tylenchulus semipenetrans* and the semiparasites *Tylenchulus* spp. in general, *Xiphinema americanum*, *Xiphinema brevicolle*, *Xiphinema dimorphicaudatum*, *Xiphinema index* and the ectoparasites *Xiphinema* spp. in general.

Other examples of nematode pests include species belonging to the family Criconematidae, Belonolaimidae, Hoploaimidae, Heteroderidae, Longidoridae, Pratylenchidae, Trichodoridae, or Anguinidae.

Table 9 shows further examples of nematodes, and diseases associated therewith, that can be treated or prevented using the PMP compositionsand related methods described herein.

TABLE 9

Nematode Pests

| Disease | Causative Agent |
| --- | --- |
| Awl | *Dolichoderus* spp., *D. heterocephalus* |
| Bulb and stem (Europe) | Ditylenchus dipsaci |
| Burrowing | Radopholus similes R. similis |
| Cyst | Heterodera avenae, H. zeae, H. schachti; Globodera rostochiensis, G. pallida, and G. tabacum; Heterodera trifolii, H. medicaginis, H. ciceri, H. mediterranea, H. cyperi, H. salixophila, H. zeae, H. goettingiana, H. riparia, H. humuli, H. latipons, H. sorghi, H. fici, H. litoralis, and H. turcomanica; Punctodera chalcoensis |
| Dagger | *Xiphinema* spp., *X. americanum, X. Mediterraneum* |
| False root-knot | Nacobbus dorsalis |
| Lance | *Hoplolaimus* spp., *H. galeatus* |
| Lance, Columbia | Hoplolaimus Columbus |
| Lesion | *Pratylenchus* spp., *P. brachyurus, P. coffeae P. crenatus, P. hexincisus, P. neglectus, P. penetrans, P. scribneri, P. magnica, P. neglectus, P. thornei, P. vulnus, P. zeae* |
| Needle | *Longidorus* spp., *L. breviannulatus* |
| Others | *Hirschmanniella* species, Pratylenchoid magnicauda |
| Ring | *Criconemella* spp., *C. ornata* |
| Root-knot | *Meloidogyne* spp., *M. arenaria, M. chitwoodi, M. artiellia, M. fallax, M. hapla, M. javanica, M. incognita, M. microtyla, M. partityla, M. panyuensis, M, paranaensis* |
| Spiral | *Helicotylenchus* spp. |
| Sting | *Belonolaimus* spp., *B. longicaudatus* |
| Stubby-root | *Paratrichodorus* spp., *P. christiei, P. minor*, Quinisulcius acutus, *Trichodorus* spp. |
| Stunt | Tylenchorhynchus dubius | vi. Viruses

The PMP compositions and related methods can be useful for decreasing the fitness of a virus, e.g., to prevent or treat a viral infection in a plant. Included are methods for delivering a PMP composition to a virus by contacting the virus with the PMP composition. Additionally or alternatively, the methods include delivering the PMP composition to a plant at risk of or having a viral infection, by contacting the plant with the PMP composition.

The PMP compositions and related methods are suitable for delivery to a virus that causes viral diseases in plants, including the viruses and diseases listed in Table 10.

TABLE 10

Viral Plant Pathogens

| Disease | Causative Agent |
| --- | --- |
| Alfamoviruses: Bromoviridae | Alfalfa mosaic alfamovirus |
| Alphacryptoviruses: Partitiviridae | Alfalfa 1 alphacryptovirus, Beet 1 alphacryptovirus, Beet 2 alphacryptovirus, Beet 3 alphacryptovirus, Carnation 1 alphacryptovirus, Carrot temperate 1 alphacryptovirus, Carrot temperate 3 alphacryptovirus, Carrot temperate 4 alphacryptovirus, Cocksfoot alphacryptovirus, Hop trefoil 1 alphacryptovirus, Hop trefoil 3 alphacryptovirus, Radish yellow edge alphacryptovirus, Ryegrass alphacryptovirus, Spinach temperate alphacryptovirus, Vicia alphacryptovirus, White clover 1 alphacryptovirus, White clover 3 alphacryptovirus |
| Badnaviruses | Banana streak badnavirus, Cacao swollen shoot badnavirus, Canna yellow mottle badnavirus, Commelina yellow mottle badnavirus, Dioscorea bacilliform badnavirus, Kalanchoe top-spotting badnavirus, Rice tungro bacilliform badnavirus, Schefflera ringspot badnavirus, Sugarcane bacilliform badnavirus |
| Betacryptoviruses: Partitiviridae | Carrot temperate 2 betacryptovirus, Hop trefoil 2 betacryptovirus, Red clover 2 betacryptovirus, White clover 2 betacryptovirus |
| Bigeminiviruses: Geminiviridae | Abutilon mosaic bigeminivirus, Ageratum yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomate bigeminivirus, Cotton leaf crumple bigeminivirus, Cotton leaf curl bigeminivirus, Croton yellow vein mosaic bigeminivirus, Dolichos yellow mosaic bigeminivirus, Euphorbia mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigeminivirus, Rhynchosia mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus, Watermelon curly mottle Bigeminivirus |

TABLE 10-continued

Viral Plant Pathogens

| Disease | Causative Agent |
|---|---|
| Bromoviruses: Bromoviridae | Broad bean mottle bromovirus, Brome mosaic bromovirus, Cassia yellow blotch bromovirus, Cowpea chlorotic mottle bromovirus, Melandrium yellow fleck bromovirus, Spring beauty latent Bromovirus |
| Bymoviruses: Potyviridae | Barley mild mosaic bymovirus, Barley yellow mosaic bymovirus, Oat mosaic bymovirus, Rice necrosis mosaic bymovirus, Wheat spindle streak mosaic bymovirus, Wheat yellow mosaic bymovirus |
| Capilloviruses | Apple stem grooving capillovirus, Cherry A capillovirus, Citrus tatter leaf capillovirus, Lilac chlorotic leafspot capillovirus |
| Carlaviruses | Blueberry scorch carlavirus, Cactus 2 carlavirus, Caper latent carlavirus, Carnation latent carlavirus, Chrysanthemum B carlavirus, Dandelion latent carlavirus, Elderberry carlavirus, Fig S carlavirus, Helenium S carlavirus, Honeysuckle latent carlavirus, Hop American latent carlavirus, Hop latent carlavirus, Hop mosaic carlavirus, Kalanchoe latent carlavirus, Lilac mottle carlavirus, Lily symptomless carlavirus, Mulberry latent carlavirus, Muskmelon vein necrosis carlavirus, Nerine latent carlavirus, Passiflora latent carlavirus, Pea streak carlavirus, Poplar mosaic carlavirus, Potato M carlavirus, Potato S carlavirus, Red clover vein mosaic carlavirus, Shallot latent carlavirus, Strawberry pseudo mild yellow edge Carlavirus |
| Carmoviruses: Tombusviridae | Bean mild mosaic carmovirus, Cardamine chlorotic fleck carmovirus, Carnation mottle carmovirus, Cucumber leaf spot carmovirus, Cucumber soil-borne carmovirus, Galinsoga mosaic carmovirus, Hibiscus chlorotic ringspot carmovirus, Melon necrotic spot carmovirus, Pelargonium flower break carmovirus, Turnip crinkle carmovirus |
| Caulimoviruses | Blueberry red ringspot caulimovirus, Carnation etched ring caulimovirus, Cauliflower mosaic caulimovirus, Dahlia mosaic caulimovirus, Figwort mosaic caulimovirus, Horseradish latent caulimovirus, Mirabilis mosaic caulimovirus, Peanut chlorotic streak caulimovirus, Soybean chlorotic mottle caulimovirus, Sweet potato caulimovirus, Thistle mottle caulimovirus |
| Closteroviruses | Beet yellow stunt closterovirus, Beet yellows closterovirus, Broad bean severe chlorosis closterovirus, Burdock yellows closterovirus, Carnation necrotic fleck closterovirus, Citrus tristeza closterovirus, Clover yellows closterovirus, Grapevine stem pitting associated closterovirus, Wheat yellow leaf closterovirus |
| Comoviruses: Comoviridae | Bean pod mottle comovirus, Bean rugose mosaic comovirus, Broad bean stain comovirus, Broad bean true mosaic comovirus, Cowpea mosaic comovirus, Cowpea severe mosaic comovirus, Glycine mosaic comovirus, Pea mild mosaic comovirus, Potato Andean mottle comovirus, Quail pea mosaic comovirus, Radish mosaic comovirus, Red clover mottle comovirus, Squash mosaic comovirus, Ullucus C comovirus |
| Cucumoviruses: Bromoviridae | Cucumber mosaic cucuamovirus, Peanut stunt cucumovirus, Tomato aspermy cucumovirus |
| Cytorhabdoviruses: Rhabdoviridae | Barley yellow striate mosaic cytorhabdovirus, Broad bean yellow vein cytorhabdovirus, Broccoli necrotic yellows cytorhabdovirus, Cereal northern mosaic cytorhabdovirus, Festuca leaf streak cytorhabdovirus, Lettuce necrotic yellows cytorhabdovirus, Sonchus cytorhabdovirus, Strawberry crinkle cytorhabdovirus |
| Dianthoviruses | Carnation ringspot dianthovirus, Red clover necrotic mosaic dianthovirus, Sweet clover necrotic mosaic dianthovirus |
| Enamoviruses | Pea enation mosaic enamovirus |
| Fijiviruses: Reoviridae | Maize rough dwarf fijivirus, Oat sterile dwarf fijivirus, Pangola stunt fijivirus, Rice black-streaked dwarf fijivirus, Sugarcane Fiji disease fijivirus |
| Furoviruses | Beet necrotic yellow vein furovirus, Beet soil-borne furovirus, Broad bean necrosis furovirus, Oat golden stripe furovirus, Peanut clump furovirus, Potato mop-top furovirus, Sorghum chlorotic spot furovirus, Wheat soil-borne mosaic furovirus |
| Hordeiviruses | Anthoxanthum latent blanching hordeivirus, Barley stripe mosaic hordeivirus, Lychnis ringspot hordeivirus, Poa semilatent Hordeivirus |
| Hybrigeminiviruses: Geminiviridae | Beet curly top hybrigeminivirus, Tomato pseudo curly top Hybrigeminivirus |
| Idaeoviruses | Raspberry bushy dwarf idaeovirus |
| Ilarviruses: Bromoviridae | Apple mosaic ilarvirus, Asparagus 2 ilarvirus, Blueberry necrotic shock ilarvirus, Citrus leaf rugose ilarvirus, Citrus variegation ilarvirus, Elm mottle ilarvirus, Humulus japonicus ilarvirus, Hydrangea mosaic ilarvirus, Lilac ring mottle ilarvirus, Parietaria mottle ilarvirus, Plum American line pattern ilarvirus, Prune dwarf ilarvirus, Prunus necrotic ringspot ilarvirus, Spinach latent ilarvirus, Tobacco streak ilarvirus, Tulare apple mosaic ilarvirus |

TABLE 10-continued

Viral Plant Pathogens

| Disease | Causative Agent |
|---|---|
| Ipomoviruses: Potyviridae | Sweet potato mild mottle ipomovirus, Sweet potato yellow dwarf Ipomovirus |
| Luteoviruses | Barley yellow dwarf luteovirus, Bean leaf roll luteovirus, Beet mild yellowing luteovirus, Beet western yellows luteovirus, Carrot red leaf luteovirus, Groundnut rosette assistor luteovirus, Potato leafroll luteovirus, Solanum yellows luteovirus, Soybean dwarf luteovirus, Soybean Indonesian dwarf luteovirus, Strawberry mild yellow edge luteovirus, Subterranean clover red leaf luteovirus, Tobacco necrotic dwarf luteovirus |
| Machlomoviruses | Maize chlorotic mottle machlomovirus |
| Macluraviruses | Madura mosaic macluravirus, Narcissus latent macluravirus |
| Marafiviruses | Bermuda grass etched-line marafivirus, Maize rayado fino marafivirus, Oat blue dwarf marafivirus |
| Monogeminiviruses: Geminiviridae | Chloris striate mosaic monogeminivirus, Digitaria striate mosaic monogeminivirus, Digitaria streak monogeminivirus, Maize streak monogeminivirus, Miscanthus streak monogeminivirus, Panicum streak monogeminivirus, Paspalum striate mosaic monogeminivirus, Sugarcane streak monogeminivirus, Tobacco yellow dwarf monogeminivirus, Wheat dwarf monogeminivirus |
| Nanaviruses | Banana bunchy top nanavirus, Coconut foliar decay nanavirus, Faba bean necrotic yellows nanavirus, Milk vetch dwarf nanavirus, Subterranean clover stunt nanavirus |
| Necroviruses | Tobacco necrosis necrovirus, Carnation yellow stripe necrovirus, Lisianthus necrosis necrovirus |
| Nepoviruses: Comoviridae | Arabis mosaic nepovirus, Arracacha A nepovirus, Artichoke Italian latent nepovirus, Artichoke yellow ringspot nepovirus, Blueberry leaf mottle nepovirus, Cacao necrosis nepovirus, Cassava green mottle nepovirus, Cherry leaf roll nepovirus, Cherry rasp leaf nepovirus, Chicory yellow mottle nepovirus, Crimson clover latent nepovirus, Cycas necrotic stunt nepovirus, Grapevine Bulgarian latent nepovirus, Grapevine chrome mosaic nepovirus, Grapevine fanleaf nepovirus, Hibiscus latent ringspot nepovirus, Lucerne Australian latent nepovirus, Mulberry ringspot nepovirus, Myrobalan latent ringspot nepovirus, Olive latent ringspot nepovirus, Peach rosette mosaic nepovirus, Potato black ringspot nepovirus, Potato U nepovirus, Raspberry ringspot nepovirus, Tobacco ringspot nepovirus, Tomato black ring nepovirus, Tomato ringspot nepovirus |
| Nucleorhabdoviruses: Rhabdoviridae | Carrot latent nucleorhabdovirus, Coriander feathery red vein nucleorhabdovirus, Cow parsnip mosaic nucleorhabdovirus, Cynodon chlorotic streak nucleorhabdovirus, Datura yellow vein nucleorhabdovirus, Eggplant mottled dwarf nucleorhabdovirus, Maize mosaic nucleorhabdovirus, Pittosporum vein yellowing nucleorhabdovirus, Potato yellow dwarf nucleorhabdovirus, Sonchus yellow net nucleorhabdovirus, Sowthistle yellow vein nucleorhabdovirus, Tomato vein clearing nucleorhabdovirus, Wheat American striate mosaic nucleorhabdovirus |
| Oryzaviruses: Reoviridae | Echinochloa ragged stunt oryzavirus, Rice ragged stunt oryzavirus |
| Ourmiaviruses | Cassava Ivorian bacilliform ourmiavirus, Epirus cherry ourmiavirus, Melon Ourmia ourmiavirus, Pelargonium zonate spot Ourmiavirus |
| Phytoreoviruses: Reoviridae | Clover wound tumor phytoreovirus, Rice dwarf phytoreovirus, Rice gall dwarf phytoreovirus, Rice bunchy stunt phytoreovirus, Sweet potato phytoreovirus |
| Potexviruses | Asparagus 3 potexvirus, Cactus x potexvirus, Cassava x potexvirus, Chicory x potexvirus, Clover yellow mosaic potexvirus, Commelina x potexvirus, Cymbidium mosaic potexvirus, Daphne x potexvirus, Foxtail mosaic potexvirus, Hydrangea ringspot potexvirus, Lily x potexvirus, Narcissus mosaic potexvirus, Nerine x potexvirus, Papaya mosaic potexvirus, Pepino mosaic potexvirus, Plantago asiatica mosaic potexvirus, Plantain x potexvirus, Potato aucuba mosaic potexvirus, Potato x potexvirus, Tulip x potexvirus, Viola mottle potexvirus, White clover mosaic potexvirus |
| Potyviruses: Potyviridae | Alstroemeria mosaic potyvirus, Amaranthus leaf mottle potyvirus, Araujia mosaic potyvirus, Arracacha Y potyvirus, Artichoke latent potyvirus, Asparagus 1 potyvirus, Banana bract mosaic potyvirus, Bean common mosaic necrosis potyvirus, Bean common mosaic potyvirus, Bean yellow mosaic potyvirus, Beet mosaic potyvirus, Bidens mosaic potyvirus, Bidens mottle potyvirus, Cardamom mosaic potyvirus, Carnation vein mottle potyvirus, Carrot thin leaf potyyirus, Cassava brown streak potyvirus, Cassia yellow spot potyvirus, Celery mosaic potyvirus, Chickpea bushy dwarf potyvirus, Chickpea distortion mosaic potyvirus, Clover yellow vein potyvirus, Commelina diffusa potyvirus, Commelina mosaic |

TABLE 10-continued

Viral Plant Pathogens

| Disease | Causative Agent |
|---|---|
| | potyvirus, Cowpea green vein-banding potyvirus, Cowpea Moroccan aphid-borne mosaic potyvirus, Cowpea rugose mosaic potyvirus, Crinum mosaic potyvirus, Daphne Y potyvirus, Dasheen mosaic potyvirus, Datura Colombian potyvirus, Datura distortion mosaic potyvirus, Datura necrosis potyvirus, Datura shoestring potyvirus, Dendrobium mosaic potyvirus, Desmodium mosaic potyvirus, Dioscorea alata potyvirus, Dioscorea green banding mosaic potyvirus, Eggplant green mosaic potyvirus, Euphorbia ringspot potyvirus, Freesia mosaic potyvirus, Groundnut eyespot potyvirus, Guar symptomless potyvirus, Guinea grass mosaic potyvirus, Helenium Y potyvirus, Henbane mosaic potyvirus, Hippeastrum mosaic potyvirus, Hyacinth mosaic potyvirus, Iris fulva mosaic potyvirus, Iris mild mosaic potyvirus, Iris severe mosaic potyvirus, Johnsongrass mosaic potyvirus, Kennedya Y potyvirus, Leek yellow stripe potyvirus, Lettuce mosaic potyvirus, Lily mottle potyvirus, Maize dwarf mosaic potyvirus, Malva vein clearing potyvirus, Marigold mottle potyvirus, Narcissus yellow stripe potyvirus, Nerine potyvirus, Onion yellow dwarf potyvirus, Ornithogalum mosaic potyvirus, Papaya ringspot potyvirus, Parsnip mosaic potyvirus, Passiflora ringspot potyvirus, Passiflora South African potyvirus, Passionfruit woodiness potyvirus, Patchouli mosaic potyvirus, Pea mosaic potyvirus, Pea seed-borne mosaic potyvirus, Peanut green mosaic potyvirus, Peanut mottle potyvirus, Pepper Indian mottle potyvirus, Pepper mottle potyvirus, Pepper severe mosaic potyvirus, Pepper veinal mottle potyvirus, Plum pox potyvirus, Pokeweed mosaic potyvirus, Potato A potyvirus, Potato V potyvirus, Potato Y potyvirus, Primula mosaic potyvirus, Ranunculus mottle potyvirus, Sorghum mosaic potyvirus, Soybean mosaic potyvirus, Statice Y potyvirus, Sugarcane mosaic potyvirus, Sweet potato feathery mottle potyvirus, Sweet potato G potyvirus, Swordbean distortion mosaic potyvirus, Tamarillo mosaic potyvirus, Telfairia mosaic potyvirus, Tobacco etch potyvirus, Tobacco vein-banding mosaic potyvirus, Tobacco vein mottling potyvirus, Tobacco wilt potyvirus, Tomato Peru potyvirus, Tradescantia-Zebrina potyvirus, Tropaeolum 1 potyvirus, Tropaeolum 2 potyvirus, Tuberose potyvirus, Tulip band-breaking potyvirus, Tulip breaking potyvirus, Tulip chlorotic blotch potyvirus, Turnip mosaic potyvirus, Ullucus mosaic potyvirus, Vallota mosaic potyvirus, Vanilla mosaic potyvirus, Vanilla necrosis potyvirus, Voandzeia distortion mosaic potyvirus, Watermelon mosaic 1 potyvirus, Watermelon mosaic 2 potyvirus, Wild potato mosaic potyvirus, Wisteria vein mosaic potyvirus, Yam mosaic potyvirus, Zucchini yellow fleck potyvirus, Zucchini yellow mosaic potyvirus |
| Rymoviruses: Potyviridae Agropyron mosaic rymovirus | Hordeum mosaic rymovirus, Oat necrotic mottle rymovirus, Ryegrass mosaic rymovirus, Wheat streak mosaic Rymovirus |
| Satellite RNAs | Arabis mosaic satellite RNA, Chicory yellow mottle satellite RNA, Cucumber mosaic satellite RNA, Grapevine fanleaf satellite RNA, Strawberry latent ringspot satellite RNA, Tobacco ringspot satellite RNA, Tomato black ring satellite RNA, Velvet tobacco mottle satellite RNA |
| Satelliviruses | Maize white line mosaic satellivirus, Panicum mosaic satellivirus, Tobacco mosaic satellivirus, Tobacco necrosis satellivirus |
| Sequiviruses: Sequiviridae | Dandelion yellow mosaic sequivirus, Parsnip yellow fleck Sequivirus |
| Sobemoviruses | Bean southern mosaic sobemovirus, Blueberry shoestring sobemovirus, Cocksfoot mottle sobemovirus, Lucerne transient streak sobemovirus, Rice yellow mottle sobemovirus, Rottboellia yellow mottle sobemovirus, Solanum nodiflorum mottle sobemovirus, Sowbane mosaic sobemovirus, Subterranean clover mottle sobemovirus, Turnip rosette sobemovirus, Velvet tobacco mottle, sobemovirus |
| Tenuiviruses | Maize stripe tenuivirus, Rice grassy stunt tenuivirus, Rice hoja blanca tenuivirus, Rice stripe tenuivirus |
| Tobamoviruses | Cucumber green mottle mosaic tobamovirus, Frangipani mosaic tobamovirus, Kyuri green mottle mosaic tobamovirus, Odontoglossum ringspot tobamovirus, Paprika mild mottle tobamovirus, Pepper mild mottle tobamovirus, Ribgrass mosaic tobamovirus, Opuntia Sammons' tobamovirus, Sunn-hemp mosaic tobamovirus, Tobacco mild green mosaic tobamovirus, Tobacco mosaic tobamovirus, Tomato mosaic tobamovirus, Ullucus mild mottle tobamovirus |

TABLE 10-continued

Viral Plant Pathogens

| Disease | Causative Agent |
| --- | --- |
| Tobraviruses | Pea early browning tobravirus, Pepper ringspot tobravirus, Tobacco rattle tobravirus |
| Tombusviruses: Tombusviridae | Artichoke mottled crinkle tombusvirus, Carnation Italian ringspot tombusvirus, Cucumber necrosis tombusvirus, Cymbidium ringspot tombusvirus, Eggplant mottled crinkle tombusvirus, Grapevine Algerian latent tombusvirus, Lato River tombusvirus, Neckar River tombusvirus, Pelargonium leaf curl tombusvirus, Pepper Moroccan tombusvirus, Petunia asteroid mosaic tombusvirus, Tomato bushy stunt tombusvirus |
| Tospoviruses: Bunyaviridae | Impatiens necrotic spot tospovirus, Peanut yellow spot tospovirus, Tomato spotted wilt tospovirus |
| Trichoviruses | Apple chlorotic leaf spot trichovirus, Heracleum latent trichovirus, Potato T trichovirus |
| Tymoviruses | Abelia latent tymovirus, Belladonna mottle tymovirus, Cacao yellow mosaic tymovirus, Clitoria yellow vein tymovirus, Desmodium yellow mottle tymovirus, Dulcamara mottle tymovirus, Eggplant mosaic tymovirus, Erysimum latent tymovirus, Kennedya yellow mosaic tymovirus, Melon rugose mosaic tymovirus, Okra mosaic tymovirus, Ononis yellow mosaic tymovirus, Passionfruit yellow mosaic tymovirus, Physalis mosaic tymovirus, Plantago mottle tymovirus, Potato Andean latent tymovirus, Scrophularia mottle tymovirus, Turnip yellow mosaic, tymovirus, Voandzeia necrotic mosaic tymovirus, Wild cucumber mosaic tymovirus |
| Umbraviruses | Bean yellow vein banding umbravirus, Carrot mottle mimic umbravirus, Carrot mottle umbravirus, Carrot mottle mimic umbravirus, Groundnut rosette umbravirus, Lettuce speckles mottle umbravirus, Tobacco mottle umbravirus |
| Varicosaviruses | Freesia leaf necrosis varicosavirus, Lettuce big-vein varicosavirus, Tobacco stunt varicosavirus |
| Waikaviruses: Sequiviridae | Anthriscus yellows waikavirus, Maize chlorotic dwarf waikavirus, Rice tungro spherical waikavirus |
| Putative Ungrouped Viruses | Alsike clover vein mosaic virus, Alstroemeria streak potyvirus, Amaranthus mosaic potyvirus, Amazon lily mosaic potyvirus, Anthoxanthum mosaic potyvirus, Apple stem pitting virus, Aquilegia potyvirus, *Asclepias* rhabdovirus, Atropa belladonna rhabdovirus, Barley mosaic virus, Barley yellow streak mosaic virus, Beet distortion mosaic virus, Beet leaf curl rhabdovirus, Beet western yellows ST9-associated RNA virus, Black raspberry necrosis virus, Bramble yellow mosaic potyvirus, Brinjal mild mosaic potyvirus, Broad bean B virus, Broad bean V potyvirus, Broad bean yellow ringspot virus, Bryonia mottle potyvirus, Burdock mosaic virus, Burdock mottle virus, Callistephus chinensis chlorosis rhabdovirus, Canary reed mosaic potyvirus, Canavalia maritima mosaic potyvirus, Carnation rhabdovirus, Carrot mosaic potyvirus, Cassava symptomless rhabdovirus, Cassia mosaic virus, Cassia ringspot virus, Celery yellow mosaic potyvirus, Celery yellow net virus, Cereal flame chlorosis virus, Chickpea filiform potyvirus, Chilli veinal mottle potyvirus, Chrysanthemum spot potyvirus, Chrysanthemum vein chlorosis rhabdovirus, Citrus leprosis rhabdovirus, Citrus ringspot virus, Clover mild mosaic virus, Cocksfoot streak potyvirus, Colocasia bobone disease rhabdovirus, Cucumber toad-skin rhabdovirus, Cucumber vein yellowing virus, *Cypripedium calceolus* potyvirus, Datura innoxia Hungarian mosaic potyvirus, Dioscorea trifida potyvirus, Dock mottling mosaic potyvirus, Dodonaea yellows-associated virus, Eggplant severe mottle potyvirus, Euonymus fasciation rhabdovirus, Euonymus rhabdovirus, Fern potyvirus, Fig potyvirus, Gerbera symptomless rhabdovirus, Grapevine fleck virus, Grapevine stunt virus, Guar top necrosis virus, Habenaria mosaic potyvirus, Holcus lanatus yellowing rhabdovirus, Holcus streak potyvirus, Iris germanica leaf stripe rhabdovirus, Iris Japanese necrotic ring virus, Isachne mosaic potyvirus, Kalanchoe isometric virus, Kenaf vein-clearing rhabdovirus, Launaea mosaic potyvirus, Lupin yellow vein rhabdovirus, Maize eyespot virus, Maize line virus, Maize mottle/chlorotic stunt virus, Maize white line mosaic virus, Malvastrum mottle virus, Melilotus mosaic potyvirus, Melon vein-banding mosaic potyvirus, Melothria mottle potyvirus, Mimosa mosaic virus, Mung bean mottle potyvirus, Narcissus degeneration potyvirus, Narcissus late season yellows potyvirus, Nerine Y potyvirus, Nothoscordum mosaic potyvirus, Oak ringspot virus, Orchid fleck rhabdovirus, Palm mosaic potyvirus, Parsley green mottle potyvirus, Parsley rhabdovirus, Parsnip leafcurl virus, Passionfruit Sri Lankan mottle potyvirus, Passionfruit vein-clearing rhabdovirus, Patchouli mottle rhabdovirus, Pea stem necrosis virus, Peanut top paralysis potyvirus, Peanut veinal chlorosis rhabdovirus, Pecteilis mosaic potyvirus, Pepper mild mosaic potyvirus, Perilla |

TABLE 10-continued

Viral Plant Pathogens

| Disease | Causative Agent |
|---|---|
| | mottle potyvirus, Pigeonpea proliferation rhabdovirus, Pigeonpea sterility mosaic virus, Plantain 7 potyvirus, Plantain mottle rhabdovirus, Pleioblastus chino potyvirus, Poplar decline potyvirus, Primula mottle potyvirus, Purple granadilla mosaic virus, Ranunculus repens symptomless rhabdovirus, Rice yellow stunt virus, Saintpaulia leaf necrosis rhabdovirus, Sambucus vein clearing rhabdovirus, Sarracenia purpurea rhabdovirus, Shamrock chlorotic ringspot potyvirus, Soybean mild mosaic virus, Soybean rhabdovirus, Soybean spherical virus, Soybean yellow vein virus, Soybean Z potyvirus, Strawberry latent C rhabdovirus, Strawberry mottle virus, Strawberry pallidosis virus, Sunflower mosaic potyvirus, Sweet potato latent potyvirus, Teasel mosaic potyvirus, Thimbleberry ringspot virus, Tomato mild mottle potyvirus, Trichosanthes mottle potyvirus, Tulip halo necrosis virus, Tulip mosaic virus, Turnip vein-clearing virus, Urd bean leaf crinkle virus, Vigna sinensis mosaic rhabdovirus, Watercress yellow spot virus, Watermelon Moroccan mosaic potyvirus, Wheat chlorotic spot rhabdovirus, White bryony potyvirus, Wineberry latent virus, Zinnia mild mottle potyvirus, Zoysia mosaic potyvirus |

C. Delivery to a Plant Symbiont

Provided herein are methods of delivering to a plant symbiont a PMP composition disclosed herein. Included are methods for delivering a PMP composition to a symbiont (e.g., a bacterial endosymbiont, a fungal endosymbiont, or an insect) by contacting the symbiont with a PMP composition. The methods can be useful for increasing the fitness of plant symbiont, e.g., a symbiont that is beneficial to the fitness of a plant. In some instances, plant symbiont may be treated with unloaded PMPs. In other instances, the PMPs include a heterologous functional agent, e.g., fertilizing agents.

As such, the methods can be used to increase the fitness of a plant symbiont. In one aspect, provided herein is a method of increasing the fitness of a symbiont, the method including delivering to the symbiont the PMP composition described herein (e.g., in an effective amount and for an effective duration) to increase the fitness of the symbiont relative to an untreated symbiont (e.g., a symbiont that has not been delivered the PMP composition).

In one aspect, provided herein is a method of increasing the fitness of a fungus (e.g., a fungal endosymbiont of a plant), wherein the method includes delivering to the endosymbiont a PMP composition including a plurality of PMPs (e.g., a PMP composition described herein). For example, the plant symbiont may be an endosymbiotic fungus, such as a fungus of the genus Aspergillaceae, Ceratobasidiaceae, Coniochaetaceae, Cordycipitaceae, Corticiaceae, Cystofilobasidiaceae, Davidiellaceae, Debaryomycetaceae, Dothioraceae, Erysiphaceae, Filobasidiaceae, Glomerellaceae, Hydnaceae, Hypocreaceae, Leptosphaeriaceae, Montagnulaceae, Mortierellaceae, Mycosphaerellaceae, Nectriaceae, Orbiliaceae, Phaeosphaeriaceae, Pleosporaceae, Pseudeurotiaceae, Rhizopodaceae, Sclerotiniaceae, Stereaceae, or Trichocomacea.

In another aspect, provided herein is a method of increasing the fitness of a bacterium (e.g., a bacterial endosymbiont of a plant), wherein the method includes delivering to the bacteria a PMP composition including a plurality of PMPs (e.g., a PMP composition described herein). For example, the plant symbiont may be an endosymbiotic bacteria, such as a bacterium of the genus Acetobacteraceae, Acidobacteriaceae, Acidothermaceae, Aerococcaceae, Alcaligenaceae, Alicyclobacillaceae, Alteromonadaceae, Anaerolineaceae, Aurantimonadaceae, Bacillaceae, Bacteriovoracaceae, Bdellovibrionaceae, Bradyrhizobiaceae, Brevibacteriaceae, Brucellaceae, Burkholderiaceae, Carboxydocellaceae, Caulobacteraceae, Cellulomonadaceae, Chitinophagaceae, Chromatiaceae, Chthoniobacteraceae, Chthonomonadaceae, Clostridiaceae, Comamonadaceae, Corynebacteriaceae, Coxiellaceae, Cryomorphaceae, Cyclobacteriaceae, Cytophagaceae, Deinococcaceae, Dermabacteraceae, Dermacoccaceae, Enterobacteriaceae, Enterococcaceae, Erythrobacteraceae, Fibrobacteraceae, Flammeovirgaceae, Flavobacteriaceae, Frankiaceae, Fusobacteriaceae, Gaiellaceae, Gemmatimonadaceae, Geodermatophilaceae, Gly corny cetaceae, Haliangiaceae, Halomonadaceae, Holosporaceae, Hyphomicrobiaceae, Iamiaceae, Intrasporangiaceae, Kineosporiaceae, Koribacteraceae, Lachnospiraceae, *Lactobacillus*, Legionellaceae, Leptospiraceae, Leuconostocaceae, Methylobacteriaceae, Methylocystaceae, Methylophilaceae, Microbacteriaceae, Micrococcaceae, Micromonosporaceae, Moraxellaceae, Mycobacteriaceae, Mycoplasmataceae, Myxococcaceae, Nakamurellaceae, Neisseriaceae, Nitrosomonadaceae, Nocardiaceae, Nocardioidaceae, Oceanospirillaceae, Opitutaceae, Oxalobacteraceae, Paenibacillaceae, Parachlamydiaceae, Pasteurellaceae, Patulibacteraceae, Peptostreptococcaceae, Phyllobacteriaceae, Piscirickettsiaceae, Planctomycetaceae, Planococcaceae, Polyangiaceae, Porphyromonadaceae, Prevotellaceae, Promicromonosporaceae, Pseudomonadaceae, Pseudonocardiaceae, Rhizobiaceae, Rhodobacteraceae, Rhodospirillaceae, Roseiflexaceae, Rubrobacteriaceae, Sandaracinaceae, Sanguibacteraceae, Saprospiraceae, Segniliparaceae, Shewanellaceae, Sinobacteraceae, Solibacteraceae, Solimonadaceae, Solirubrobacteraceae, Sphingobacteriaceae, Sphingomonadaceae, Spiroplasmataceae, Sporichthyaceae, Sporolactobacillus, Staphylococcaceae, Streptococcaceae, Streptomycetaceae, Syntrophobacteraceae, Veillonellaceae, Verrucomicrobiaceae, Weeksellaceae, Xanthobacteraceae, or Xanthomonadaceae.

In yet another aspect, provided herein is a method of increasing the fitness of an insect (e.g., an insect symbiont of a plant), wherein the method includes delivering to the insect a PMP composition including a plurality of PMPs (e.g., a PMP composition described herein). In some instances, the insect is a plant pollinator. For example, the insect may be of the genus Hymenoptera or Diptera. In some instances, the insect of the genus Hymenoptera is a bee. In other instances, the insect of the genus Diptera is a fly.

In some instances, the increase in symbiont fitness may manifest as an improvement in the physiology of the symbiont (e.g., improved health or survival) as a consequence of administration of the PMP composition. In some instances, the fitness of an organism may be measured by one or more parameters, including, but not limited to, reproductive rate, lifespan, mobility, fecundity, body weight, metabolic rate or activity, or survival in comparison to a symbiont to which the PMP composition has not been delivered. For example, the methods or compositions provided herein may be effective to improve the overall health of the symbiont or to improve the overall survival of the symbiont in comparison to a symbiont organism to which the PMP composition has not been administered. In some instances, the improved survival of the symbiont is about 2%, 5%, 10%, 20%, 30%, 40%, 50%, 60%, 70%, 80%, 90%, 100%, or greater than 100% greater relative to a reference level (e.g., a level found in a symbiont that does not receive a PMP composition). In some instances, the methods and compositions are effective to increase symbiont reproduction (e.g., reproductive rate) in comparison to a symbiont organism to which the PMP composition has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as an increase in the frequency or efficacy of a desired activity carried out by the symbiont (e.g., pollination, predation on pests, seed spreading, or breakdown of waste or organic material) in comparison to a symbiont organism to which the PMP composition has not been administered. In some instances, the methods or compositions provided herein may be effective to increase the frequency or efficacy of a desired activity carried out by the symbiont (e.g., pollination, predation on pests, seed spreading, or breakdown of waste or organic material) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as an increase in the production of one or more nutrients in the symbiont (e.g., vitamins, carbohydrates, amino acids, or polypeptides) in comparison to a symbiont organism to which the PMP composition has not been administered. In some instances, the methods or compositions provided herein may be effective to increase the production of nutrients in the symbiont (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition). In some instances, the methods or compositions provided herein may increase nutrients in an associated plant by increasing the production or metabolism of nutrients by one or more microorganisms (e.g., endosymbiont) in the symbiont.

In some instances, the increase in symbiont fitness may manifest as a decrease in the symbiont's sensitivity to a pesticidal agent and/or an increase in the symbiont's resistance to a pesticidal agent in comparison to a symbiont organism to which the PMP composition has not been administered. In some instances, the methods or compositions provided herein may be effective to decrease the symbiont's sensitivity to a pesticidal agent by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as a decrease in the symbiont's sensitivity to an allelochemical agent and/or an increase in the symbiont's resistance to an allelochemical agent in comparison to a symbiont organism to which the PMP composition has not been administered. In some instances, the methods or compositions provided herein may be effective to increase the symbiont's resistance to an allelochemical agent by about 2%, 5%, 10%, 20%, 30%, 40%, 50%, 60%, 70%, 80%, 90%, 100%, or greater than 100% relative to a reference level (e.g., a level found in a symbiont that does not receive a PMP composition). In some instances, the allelochemical agent is caffeine, soyacystatin N, monoterpenes, diterpene acids, or phenolic compounds. In some instances, the methods or compositions provided herein may decrease the symbiont's sensitivity to an allelochemical agent by increasing the symbiont's ability to metabolize or degrade the allelochemical agent into usable substrates.

In some instances, the methods or compositions provided herein may be effective to increase the symbiont's resistance to parasites or pathogens (e.g., fungal, bacterial, or viral pathogens; or parasitic mites (e.g., *Varroa destructor* mite in honeybees)) in comparison to a symbiont organism to which the PMP composition has not been administered. In some instances, the methods or compositions provided herein may be effective to increase the symbiont's resistance to a pathogen or parasite (e.g., fungal, bacterial, or viral pathogens; or parasitic mites (e.g., *Varroa destructor* mite in honeybees)) by about 2%, 5%, 10%, 20%, 30%, 40%, 50%, 60%, 70%, 80%, 90%, 100%, or greater than 100% relative to a reference level (e.g., a level found in a symbiont that does not receive a PMP composition).

In some instances, the increase in symbiont fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to a symbiont organism to which the PMP composition has not been administered. In some instances, the methods or compositions provided herein may be effective to increase symbiont fitness in any plurality of ways described herein. Further, the PMP composition may increase symbiont fitness in any number of symbiont classes, orders, families, genera, or species (e.g., 1 symbiont species, 2, 3, 4, 5, 6, 7, 8, 9, 10, 15, 20, 30, 40, 50, 60, 70, 80, 90, 100, 150, 200, 200, 250, 500, or more symbiont species). In some instances, the PMP composition acts on a single symbiont class, order, family, genus, or species.

Symbiont fitness may be evaluated using any standard methods in the art. In some instances, symbiont fitness may be evaluated by assessing an individual symbiont. Alternatively, symbiont fitness may be evaluated by assessing a symbiont population. For example, an increase in symbiont fitness may manifest as an increase in successful competition against other insects, thereby leading to an increase in the size of the symbiont population.

Examples of plant symbionts that can be treated with the present compositions or related methods are further described herein.

i. Fungi

The PMP compositions and related methods can be useful for increasing the fitness of a fungus, e.g., a fungus that is an endosymbiont of a plant (e.g., mycorrhizal fungus).

In some instances, the fungus is of the family Aspergillaceae, Ceratobasidiaceae, Coniochaetaceae, Cordycipitaceae, Corticiaceae, Cystofilobasidiaceae, Davidiellaceae, Debaryomycetaceae, Dothioraceae, Erysiphaceae, Filobasidiaceae, Glomerellaceae, Hydnaceae, Hypocreaceae, Leptosphaeriaceae, Montagnulaceae, Mortierellaceae, Mycosphaerellaceae, Nectriaceae, Orbiliaceae, Phaeosphaeriaceae, Pleosporaceae, Pseudeurotiaceae, Rhizopodaceae, Sclerotiniaceae, Stereaceae, or Trichocomacea.

In some instances, the fungus is a fungus having a mychorrhizal (e.g., ectomycorrhizal or endomycorrhizal) association with the roots of a plant, including fungi belonging to Glomeromycota, Basidiomycota, Ascomycota, or Zygomycota.

ii. Bacteria

The PMP compositions and related methods can be useful for increasing the fitness of a bacterium, e.g., a bacterium that is an endosymbiont of a plant (e.g., nitrogen-fixing bacteria).

For example, the bacterium may be of the genus *Acidovorax, Agrobacterium, Bacillus, Burkholderia, Chryseobacterium, Curtobacterium, Enterobacter, Escherichia, Methylobacterium, Paenibacillus, Pantoea, Pseudomonas, Ralstonia, Rhizobium, Saccharibacillus, Sphingomonas,* or *Stenotrophomonas*.

In some instances, the bacteria is of the family: Acetobacteraceae, Acidobacteriaceae, Acidothermaceae, Aerococcaceae, Alcaligenaceae, Alicyclobacillaceae, Alteromonadaceae, Anaerolineaceae, Aurantimonadaceae, Bacillaceae, Bacteriovoracaceae, Bdellovibrionaceae, Bradyrhizobiaceae, Brevibacteriaceae, Brucellaceae, Burkholderiaceae, Carboxydocellaceae, Caulobacteraceae, Cellulomonadaceae, Chitinophagaceae, Chromatiaceae, Chthoniobacteraceae, Chthonomonadaceae, Clostridiaceae, Comamonadaceae, Corynebacteriaceae, Coxiellaceae, Cryomorphaceae, Cyclobacteriaceae, Cytophagaceae, Deinococcaceae, Dermabacteraceae, Dermacoccaceae, Enterobacteriaceae, Enterococcaceae, Erythrobacteraceae, Fibrobacteraceae, Flammeovirgaceae, Flavobacteriaceae, Frankiaceae, Fusobacteriaceae, Gaiellaceae, Gemmatimonadaceae, Geodermatophilaceae, Gly corny cetaceae, Haliangiaceae, Halomonadaceae, Holosporaceae, Hyphomicrobiaceae, lamiaceae, Intrasporangiaceae, Kineosporiaceae, Koribacteraceae, Lachnospiraceae, *Lactobacillus,* Legionellaceae, Leptospiraceae, Leuconostocaceae, Methylobacteriaceae, Methylocystaceae, Methylophilaceae, Microbacteriaceae, Micrococcaceae, Micromonosporaceae, Moraxellaceae, Mycobacteriaceae, Mycoplasmataceae, Myxococcaceae, Nakamurellaceae, Neisseriaceae, Nitrosomonadaceae, Nocardiaceae, Nocardioidaceae, Oceanospirillaceae, Opitutaceae, Oxalobacteraceae, Paenibacillaceae, Parachlamydiaceae, Pasteurellaceae, Patulibacteraceae, Peptostreptococcaceae, Phyllobacteriaceae, Piscirickettsiaceae, Planctomycetaceae, Planococcaceae, Polyangiaceae, Porphyromonadaceae, Prevotellaceae, Promicromonosporaceae, Pseudomonadaceae, Pseudonocardiaceae, Rhizobiaceae, Rhodobacteraceae, Rhodospirillaceae, Roseiflexaceae, Rubrobacteriaceae, Sandaracinaceae, Sanguibacteraceae, Saprospiraceae, Segniliparaceae, Shewanellaceae, Sinobacteraceae, Solibacteraceae, Solimonadaceae, Solirubrobacteraceae, Sphingobacteriaceae, Sphingomonadaceae, Spiroplasmataceae, Sporichthyaceae, Sporolactobacillus, Staphylococcaceae, Streptococcaceae, Streptomycetaceae, Syntrophobacteraceae, Veillonellaceae, Verrucomicrobiaceae, Weeksellaceae, Xanthobacteraceae, or Xanthomonadaceae.

In some instances, the endosymbiotic bacterium is of a family selected from the group consisting of: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, and Xanthomonadaceae.

In some instances, the endosymbiotic bacterium is of a genus selected from the group consisting of: *Acidovorax, Agrobacterium, Bacillus, Burkholderia, Chryseobacterium, Curtobacterium, Enterobacter, Escherichia, Methylobacterium, Paenibacillus, Pantoea, Pseudomonas, Ralstonia, Saccharibacillus, Sphingomonas,* and *Stenotrophomonas.* iii. Insects

The PMP compositions and related methods can be useful for increasing the fitness of an insect, e.g., an insect that is beneficial to plant. The term insect includes any organism belonging to the phylum Arthropoda and to the class Insecta or the class Arachnida, in any stage of development, i.e., immature and adult insects. For example, the host may include insects that are used in agricultural applications, including insects that aid in the pollination of crops, spreading seeds, or pest control.

In some instances, the host aids in pollination of a plant (e.g., bees, beetles, wasps, flies, butterflies, or moths). In some instances, the host aiding in pollination of a plant is a bee. In some instances, the bee is in the family Andrenidae, Apidae, Colletidae, Halictidae, or Megachilidae. In some examples, the host aiding in pollination of a plant is beetle. In particular instances, the PMP composition may be used to increase the fitness of a honeybee.

In some instances, the host aiding in pollination of a plant is a beetle, e.g., a species in the family Buprestidae, Cantharidae, Cerambycidae, Chrysomelidae, Cleridae, Coccinellidae, Elateridae, Melandryidae, Meloidae, Melyridae, Mordellidae, Nitidulidae, Oedemeridae, Scarabaeidae, or Staphyllinidae.

In some instances, the host aiding in pollination of a plant is a butterfly or moth (e.g., Lepidoptera). In some instances, the butterfly or moth is a species in the family Geometridae, Hesperiidae, Lycaenidae, Noctuidae, Nymphalidae, Papilionidae, Pieridae, or Sphingidae.

In some instances, the host aiding in pollination of a plant is a fly (e.g., Diptera). In some instances, the fly is in the family Anthomyiidae, Bibionidae, Bombyliidae, Calliphoridae, Cecidomiidae, Certopogonidae, Chrionomidae, Conopidae, Culicidae, Dolichopodidae, Empididae, Ephydridae, Lonchopteridae, Muscidae, Mycetophilidae, Phoridae, Simuliidae, Stratiomyidae, or Syrphidae.

In some instances, the host aiding in pollination is an ant (e.g., Formicidae), sawfly (e.g., Tenthredinidae), or wasp (e.g., Sphecidae or Vespidae).

D. Delivery to an Animal Pathogen

Provided herein are methods of delivering a PMP composition (e.g., manufactured in accordance with the methods or bioreactors herein) to an animal (e.g., human) pathogen, such as one disclosed herein, by contacting the pathogen with a PMP composition. As used herein the term "pathogen" refers to an organism, such as a microorganism or an invertebrate, which causes disease or disease symptoms in an animal by, e.g., (i) directly infecting the animal, (ii) by producing agents that causes disease or disease symptoms in an animal (e.g., bacteria that produce pathogenic toxins and the like), and/or (iii) that elicit an immune (e.g., inflammatory response) in animals (e.g., biting insects, e.g., bedbugs). As used herein, pathogens include, but are not limited to bacteria, protozoa, parasites, fungi, nematodes, insects, viroids and viruses, or any combination thereof, wherein each pathogen is capable, either by itself or in concert with another pathogen, of eliciting disease or symptoms in animals, such as humans.

In some instances, animal (e.g., human) pathogen may be treated with unloaded PMPs. In other instances, the PMPs include a heterologous functional agent, e.g., a heterologous therapeutic agent (e.g., antibacterial agent, antifungal agent, insecticide, nematicide, antiparasitic agent, antiviral agent, or a repellent). The methods can be useful for decreasing the fitness of an animal pathogen, e.g., to prevent or treat a pathogen infection or control the spread of a pathogen as a consequence of delivery of the PMP composition.

Examples of pathogens that can be targeted in accordance with the methods described herein include bacteria (e.g., *Streptococcus* spp., Pneumococcus spp., *Pseudomonas* spp., *Shigella* spp, *Salmonella* spp., *Campylobacter* spp., or an *Escherichia* spp), fungi (*Saccharomyces* spp. or a *Candida* spp), parasitic insects (e.g., *Cimex* spp), parasitic nematodes (e.g., Heligmosomoides spp), or parasitic protozoa (e.g., Trichomoniasis spp).

For example, provided herein is a method of decreasing the fitness of a pathogen, the method including delivering to the pathogen a PMP composition described herein, wherein the method decreases the fitness of the pathogen relative to an untreated pathogen. In some embodiments, the method includes delivering the composition to at least one habitat where the pathogen grows, lives, reproduces, feeds, or infests. In some instances of the methods described herein, the composition is delivered as a pathogen comestible composition for ingestion by the pathogen. In some instances of the methods described herein, the composition is delivered (e.g., to a pathogen) as a liquid, a solid, an aerosol, a paste, a gel, or a gas.

Also provided herein is a method of decreasing the fitness of a parasitic insect, wherein the method includes delivering to the parasitic insect a PMP composition including a plurality of PMPs. In some instances, the method includes delivering to the parasitic insect a PMP composition including a plurality of PMPs, wherein the plurality of PMPs includes an insecticidal agent. For example, the parasitic insect may be a bedbug. Other non-limiting examples of parasitic insects are provided herein. In some instances, the method decreases the fitness of the parasitic insect relative to an untreated parasitic insect Additionally provided herein is a method of decreasing the fitness of a parasitic nematode, wherein the method includes delivering to the parasitic nematode a PMP composition including a plurality of PMPs. In some instances, the method includes delivering to the parasitic nematode a PMP composition including a plurality of PMPs, wherein the plurality of PMPs includes a nematicidal agent. For example, the parasitic nematode is Heligmosomoides polygyrus. Other non-limiting examples of parasitic nematodes are provided herein. In some instances, the method decreases the fitness of the parasitic nematode relative to an untreated parasitic nematode.

Further provided herein is a method of decreasing the fitness of a parasitic protozoan, wherein the method includes delivering to the parasitic protozoan a PMP composition including a plurality of PMPs. In some instances, the method includes delivering to the parasitic protozoan a PMP composition including a plurality of PMPs, wherein the plurality of PMPs includes an antiparasitic agent. For example, the parasitic protozoan may be *T. vaginalis*. Other non-limiting examples of parasitic protozoans are provided herein. In some instances, the method decreases the fitness of the parasitic protozoan relative to an untreated parasitic protozoan.

A decrease in the fitness of the pathogen as a consequence of delivery of a PMP composition can manifest in a number of ways. In some instances, the decrease in fitness of the pathogen may manifest as a deterioration or decline in the physiology of the pathogen (e.g., reduced health or survival) as a consequence of delivery of the PMP composition. In some instances, the fitness of an organism may be measured by one or more parameters, including, but not limited to, reproductive rate, fertility, lifespan, viability, mobility, fecundity, pathogen development, body weight, metabolic rate or activity, or survival in comparison to a pathogen to which the PMP composition has not been administered. For example, the methods or compositions provided herein may be effective to decrease the overall health of the pathogen or to decrease the overall survival of the pathogen. In some instances, the decreased survival of the pathogen is about 2%, 5%, 10%, 20%, 30%, 40%, 50%, 60%, 70%, 80%, 90%, 100%, or greater than 100% greater relative to a reference level (e.g., a level found in a pathogen that does not receive a PMP composition. In some instances, the methods and compositions are effective to decrease pathogen reproduction (e.g., reproductive rate, fertility) in comparison to a pathogen to which the PMP composition has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a pathogen that does not receive a PMP composition).

In some instances, the decrease in pest fitness may manifest as an increase in the pathogen's sensitivity to an antipathogen agent and/or a decrease in the pathogen's resistance to an antipathogen agent in comparison to a pathogen to which the PMP composition has not been delivered. In some instances, the methods or compositions provided herein may be effective to increase the pathogen's sensitivity to a pesticidal agent by about 2%, 5%, 10%, 20%, 30%, 40%, 50%, 60%, 70%, 80%, 90%, 100%, or greater than 100% relative to a reference level (e.g., a level found in a pest that does not receive a PMP composition).

In some instances, the decrease in pathogen fitness may manifest as other fitness disadvantages, such as a decreased tolerance to certain environmental factors (e.g., a high or low temperature tolerance), a decreased ability to survive in certain habitats, or a decreased ability to sustain a certain diet in comparison to a pathogen to which the PMP composition has not been delivered. In some instances, the methods or compositions provided herein may be effective to decrease pathogen fitness in any plurality of ways described herein. Further, the PMP composition may decrease pathogen fitness in any number of pathogen classes, orders, families, genera, or species (e.g., 1 pathogen species, 2, 3, 4, 5, 6, 7, 8, 9, 10, 15, 20, 30, 40, 50, 60, 70, 80, 90, 100, 150, 200, 200, 250, 500, or more pathogen species). In some instances, the PMP composition acts on a single pest class, order, family, genus, or species.

Pathogen fitness may be evaluated using any standard methods in the art. In some instances, pest fitness may be evaluated by assessing an individual pathogen. Alternatively, pest fitness may be evaluated by assessing a pathogen population. For example, a decrease in pathogen fitness may manifest as a decrease in successful competition against other pathogens, thereby leading to a decrease in the size of the pathogen population.

The PMP compositions and related methods described herein are useful to decrease the fitness of an animal pathogen and thereby treat or prevent infections in animals. Examples of animal pathogens, or vectors thereof, that can be treated with the present compositions or related methods are further described herein.

i. Fungi

The PMP compositions and related methods can be useful for decreasing the fitness of a fungus, e.g., to prevent or treat a fungal infection in an animal. Included are methods for delivering a PMP composition to a fungus by contacting the fungus with the PMP composition. Additionally or alternatively, the methods include preventing or treating a fungal infection (e.g., caused by a fungus described herein) in an animal at risk of or in need thereof, by administering to the animal a PMP composition.

The PMP compositions and related methods are suitable for treatment or preventing of fungal infections in animals, including infections caused by fungi belonging to Ascomycota (*Fusarium oxysporum, Pneumocystis jirovecii, Aspergillus* spp., *Coccidioides immitis/posadasii, Candida albicans*), Basidiomycota (*Filobasidiella neoformans, Trichosporon*), Microsporidia (*Encephalitozoon cuniculi, Enterocytozoon bieneusi*), Mucoromycotina (*Mucor circinelloides, Rhizopus oryzae, Lichtheimia corymbifera*).

In some instances, the fungal infection is one caused by a belonging to the phylum Ascomycota, Basidiomycota, Chytridiomycota, Microsporidia, or Zygomycota. The fungal infection or overgrowth can include one or more fungal species, e.g., *Candida albicans, C. tropicalis, C. parapsilosis, C. glabrata, C. auris, C. krusei, Saccharomyces cerevisiae, Malassezia globose, M. restricta*, or *Debaryomyces hansenii, Gibberella moniliformis, Alternaria brassicicola, Cryptococcus neoformans, Pneumocystis carinii, P. jirovecii, P. murina, P. oryctolagi, P. wakefieldiae*, and *Aspergillus clavatus*. The fungal species may be considered a pathogen or an opportunistic pathogen.

In some instances, the fungal infection is caused by a fungus in the genus *Candida* (i.e., a *Candida* infection). For example, a *Candida* infection can be caused by a fungus in the genus *Candida* that is selected from the group consisting of *C. albicans, C. glabrata, C. dubliniensis, C. krusei, C. auris, C. parapsilosis, C. tropicalis, C. orthopsilosis, C. guilliermondii, C. rugose*, and *C. lusitaniae*. *Candida* infections that can be treated by the methods disclosed herein include, but are not limited to candidemia, oropharyngeal candidiasis, esophageal candidiasis, mucosal candidiasis, genital candidiasis, vulvovaginal candidiasis, rectal candidiasis, hepatic candidiasis, renal candidiasis, pulmonary candidiasis, splenic candidiasis, otomycosis, osteomyelitis, septic arthritis, cardiovascular candidiasis (e.g., endocarditis), and invasive candidiasis.

ii. Bacteria

The PMP compositions and related methods can be useful for decreasing the fitness of a bacterium, e.g., to prevent or treat a bacterial infection in an animal. Included are methods for administering a PMP composition to a bacterium by contacting the bacteria with the PMP composition. Additionally or alternatively, the methods include preventing or treating a bacterial infection (e.g., caused by a bacterium described herein) in an animal at risk of or in need thereof, by administering to the animal a PMP composition.

The PMP compositions and related methods are suitable for preventing or treating a bacterial infection in animals caused by any bacteria described further below. For example, the bacteria may be one belonging to Bacillales (*B. anthracis, B. cereus, S. aureus, L. monocytogenes*), Lactobacillus (*S. pneumoniae, S. pyogenes*), Clostridiales (*C. botulinum, C. difficile, C. perfringens, C. tetani*), Spirochaetales (*Borrelia burgdorferi, Treponema pallidum*), Chlamydiales (*Chlamydia trachomatis, Chlamydophila psittaci*), Actinomycetales (*C. diphtheriae, Mycobacterium tuberculosis, M. avium*), Rickettsiales (*R. prowazekii, R. rickettsii, R. typhi, A. phagocytophilum, E. chaffeensis*), Rhizobiales (*Brucella melitensis*), Burkholderiales (*Bordetella pertussis, Burkholderia mallei, B. pseudomallei*), Neisseriales (*Neisseria gonorrhoeae, N. meningitidis*), Campylobacterales (*Campylobacter jejuni, Helicobacter pylori*), Legionellales (*Legionella pneumophila*), Pseudomonadales (*A. baumannii, Moraxella catarrhalis, P. aeruginosa*), Aeromonadales (*Aeromonas* sp.), Vibrionales (*Vibrio cholerae, V. parahaemolyticus*), Thiotrichales, Pasteurellales (*Haemophilus influenzae*), Enterobacteriales (*Klebsiella pneumoniae, Proteus mirabilis, Yersinia pestis, Y. enterocolitica, Shigella flexneri, Salmonella enterica, E. coli*).

iii. Parasitic Insects

The PMP compositions and related methods can be useful for decreasing the fitness of a parasitic insect, e.g., to prevent or treat a parasitic insect infection in an animal. The term "insect" includes any organism belonging to the phylum Arthropoda and to the class Insecta or the class Arachnida, in any stage of development, i.e., immature and adult insects. Included are methods for delivering a PMP composition to an insect by contacting the insect with the PMP composition. Additionally or alternatively, the methods include preventing or treating a parasitic insect infection (e.g., caused by a parasitic insect described herein) in an animal at risk of or in need thereof, by administering to the animal a PMP composition.

The PMP compositions and related methods are suitable for preventing or treating infection in animals by a parasitic insect, including infections by insects belonging to Phthiraptera: Anoplura (Sucking lice), Ischnocera (Chewing lice), Amblycera (Chewing lice). Siphonaptera: Pulicidae (Cat fleas), Ceratophyllidae (Chicken-fleas). Diptera: Culicidae (Mosquitoes), Ceratopogonidae (Midges), Psychodidae (Sandflies), Simuliidae (Blackflies), Tabanidae (Horse-flies), Muscidae (House-flies, etc.), Calliphoridae (Blow-flies), Glossinidae (Tsetse-flies), Oestridae (Bot-flies), Hippoboscidae (Louse-flies). Hemiptera: Reduviidae (Assassin-bugs), Cimicidae (Bed-bugs). Arachnida: Sarcoptidae (Sarcoptic mites), Psoroptidae (Psoroptic mites), Cytoditidae (Air-sac mites), Laminosioptes (Cyst-mites), Analgidae (Feather-mites), Acaridae (Grain-mites), Demodicidae (Hair-follicle mites), Cheyletiellidae (Fur-mites), Trombiculidae (Trombiculids), Dermanyssidae (Bird mites), Macronyssidae (Bird mites), Argasidae (Soft-ticks), Ixodidae (Hard-ticks).

iv. Protozoa

The PMP compositions and related methods can be useful for decreasing the fitness of a parasitic protozoa, e.g., to prevent or treat a parasitic protozoa infection in an animal. The term "protozoa" includes any organism belonging to the phylum Protozoa. Included are methods for delivering a PMP composition to a parasitic protozoa by contacting the parasitic protozoa with the PMP composition. Additionally or alternatively, the methods include preventing or treating a protozoal infection (e.g., caused by a protozoan described herein) in an animal at risk of or in need thereof, by administering to the animal a PMP composition.

The PMP compositions and related methods are suitable for preventing or treating infection by parasitic protozoa in animals, including protozoa belonging to Euglenozoa (*Trypanosoma cruzi, Trypanosoma brucei, Leishmania* spp.), Heterolobosea (*Naegleria fowleri*), Diplomonadida (*Giardia intestinalis*), Amoebozoa (*Acanthamoeba castellanii, Balamuthia mandrillaris, Entamoeba histolytica*), Blastocystis (*Blastocystis hominis*), Apicomplexa (*Babesia microti, Cryptosporidium parvum, Cyclospora cayetanensis, Plasmodium* spp., *Toxoplasma gondii*).

v. Nematodes

The PMP compositions and related methods can be useful for decreasing the fitness of a parasitic nematode, e.g., to prevent or treat a parasitic nematode infection in an animal. Included are methods for delivering a PMP composition to a parasitic nematode by contacting the parasitic nematode with the PMP composition. Additionally or alternatively, the methods include preventing or treating a parasitic nematode infection (e.g., caused by a parasitic nematode described herein) in an animal at risk of or in need thereof, by administering to the animal a PMP composition.

The PMP compositions and related methods are suitable for preventing or treating infection by parasitic nematodes in animals, including nematodes belonging to Nematoda (roundworms): *Angiostrongylus cantonensis* (rat lungworm), *Ascaris lumbricoides* (human roundworm), *Baylisascaris procyonis* (raccoon roundworm), *Trichuris trichiura* (human whipworm), *Trichinella spiralis, Strongyloides stercoralis, Wuchereria bancrofti, Brugia malayi, Ancylostoma duodenale* and *Necator americanus* (human hookworms), Cestoda (tapeworms): *Echinococcus granulosus, Echinococcus multilocularis, Taenia solium* (pork tapeworm).

vi. Viruses

The PMP compositions and related methods can be useful for decreasing the fitness of a virus, e.g., to prevent or treat a viral infection in an animal. Included are methods for delivering a PMP composition to a virus by contacting the virus with the PMP composition. Additionally or alternatively, the methods include preventing or treating a viral infection (e.g., caused by a virus described herein) in an animal at risk of or in need thereof, by administering to the animal a PMP composition.

The PMP compositions and related methods are suitable for preventing or treating a viral infection in animals, including infections by viruses belonging to DNA viruses: Parvoviridae, Papillomaviridae, Polyomaviridae, Poxviridae, Herpesviridae; Single-stranded negative strand RNA viruses: Arenaviridae, Paramyxoviridae (Rubulavirus, Respirovirus, Pneumovirus, Moribillivirus), Filoviridae (Marburgvirus, Ebolavirus), Bornaoviridae, Rhabdoviridae, Orthomyxoviridae, Bunyaviridae, Nairovirus, Hantaviruses, Orthobunyavirus, Phlebovirus. Single-stranded positive strand RNA viruses: Astroviridae, Coronaviridae, Caliciviridae, Togaviridae (Rubivirus, Alphavirus), Flaviviridae (Hepacivirus, Flavivirus), Picornaviridae (Hepatovirus, Rhinovirus, Enterovirus); or dsRNA and Retro-transcribed Viruses: Reoviridae (Rotavirus, Coltivirus, Seadornavirus), Retroviridae (Deltaretrovirus, Lentivirus), Hepadnaviridae (Orthohepadnavirus).

E. Delivery to a Pathogen Vector

Provided herein are methods of delivering a PMP composition (e.g., manufactured in accordance with the methods or bioreactors herein) to pathogen vector, such as one disclosed herein, by contacting the pathogen vector with a PMP composition. As used herein, the term "vector" refers to an insect that can carry or transmit an animal pathogen from a reservoir to an animal. Exemplary vectors include insects, such as those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites.

In some instances, the vector of the animal (e.g., human) pathogen may be treated with unloaded PMPs. In other instances, the PMPs include a heterologous functional agent, e.g., a heterologous therapeutic agent (e.g., antibacterial agent, antifungal agent, insecticide, nematicide, antiparasitic agent, antiviral agent, or a repellent). The methods can be useful for decreasing the fitness of a pathogen vector, e.g., to control the spread of a pathogen as a consequence of delivery of the PMP composition. Examples of pathogen vectors that can be targeted in accordance with the present methods include insects, such as those described herein.

For example, provided herein is a method of decreasing the fitness of an animal pathogen vector, the method including delivering to the vector an effective amount of the PMP compositions described herein, wherein the method decreases the fitness of the vector relative to an untreated vector. In some instances, the method includes delivering the composition to at least one habitat where the vector grows, lives, reproduces, feeds, or infests. In some instances, the composition is delivered as a comestible composition for ingestion by the vector. In some instances, the vector is an insect. In some instances, the insect is a mosquito, a tick, a mite, or a louse. In some instances, the composition is delivered (e.g., to the pathogen vector) as a liquid, a solid, an aerosol, a paste, a gel, or a gas.

For example, provided herein is a method of decreasing the fitness of an insect vector of an animal pathogen, wherein the method includes delivering to the vector a PMP composition including a plurality of PMPs. In some instances, the method includes delivering to the vector a PMP composition including a plurality of PMPs, wherein the plurality of PMPs includes an insecticidal agent. For example, the insect vector may be a mosquito, tick, mite, or louse. Other non-limiting examples of pathogen vectors are provided herein. In some instances, the method decreases the fitness of the vector relative to an untreated vector.

In some instances, the decrease in vector fitness may manifest as a deterioration or decline in the physiology of the vector (e.g., reduced health or survival) as a consequence of administration of a composition. In some instances, the fitness of an organism may be measured by one or more parameters, including, but not limited to, reproductive rate, lifespan, mobility, fecundity, body weight, metabolic rate or activity, or survival in comparison to a vector organism to which the composition has not been delivered. For example, the methods or compositions provided herein may be effective to decrease the overall health of the vector or to decrease the overall survival of the vector. In some instances, the decreased survival of the vector is about 2%, 5%, 10%, 20%, 30%, 40%, 50%, 60%, 70%, 80%, 90%, 100%, or greater than 100% greater relative to a reference level (e.g., a level found in a vector that does not receive a composition). In some instances, the methods and compositions are effective to decrease vector reproduction (e.g., reproductive rate) in comparison to a vector organism to which the composition has not been delivered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a vector that is not delivered the composition).

In some instances, the decrease in vector fitness may manifest as an increase in the vector's sensitivity to a pesticidal agent and/or a decrease in the vector's resistance to a pesticidal agent in comparison to a vector organism to which the composition has not been delivered. In some instances, the methods or compositions provided herein may be effective to increase the vector's sensitivity to a pesticidal agent by about 2%, 5%, 10%, 20%, 30%, 40%, 50%, 60%, 70%, 80%, 90%, 100%, or greater than 100% relative to a reference level (e.g., a level found in a vector that does not receive a composition). The pesticidal agent may be any pesticidal agent known in the art, including insecticidal agents. In some instances, the methods or compositions provided herein may increase the vector's sensitivity to a pesticidal agent by decreasing the vector's ability to metabolize or degrade the pesticidal agent into usable substrates in comparison to a vector to which the composition has not been delivered.

In some instances, the decrease in vector fitness may manifest as other fitness disadvantages, such as decreased tolerance to certain environmental factors (e.g., a high or low temperature tolerance), decreased ability to survive in certain habitats, or a decreased ability to sustain a certain diet in comparison to a vector organism to which the composition has not been delivered. In some instances, the methods or compositions provided herein may be effective to decrease vector fitness in any plurality of ways described herein. Further, the composition may decrease vector fitness in any number of vector classes, orders, families, genera, or species (e.g., 1 vector species, 2, 3, 4, 5, 6, 7, 8, 9, 10, 15, 20, 30, 40, 50, 60, 70, 80, 90, 100, 150, 200, 200, 250, 500, or more vector species). In some instances, the composition acts on a single vector class, order, family, genus, or species.

Vector fitness may be evaluated using any standard methods in the art. In some instances, vector fitness may be evaluated by assessing an individual vector. Alternatively, vector fitness may be evaluated by assessing a vector population. For example, a decrease in vector fitness may manifest as a decrease in successful competition against other vectors, thereby leading to a decrease in the size of the vector population.

By decreasing the fitness of vectors that carry animal pathogens, the compositions provided herein are effective to reduce the spread of vector-borne diseases. The composition may be delivered to the insects using any of the formulations and delivery methods described herein, in an amount and for a duration effective to reduce transmission of the disease, e.g., reduce vertical or horizontal transmission between vectors and/or reduce transmission to animals. For example, the composition described herein may reduce vertical or horizontal transmission of a vector-borne pathogen by about 2%, 5%, 10%, 20%, 30%, 40%, 50%, 60%, 70%, 80%, 90%, 100%, or more in comparison to a vector organism to which the composition has not been delivered. As another example, the composition described herein may reduce vectorial competence of an insect vector by about 2%, 5%, 10%, 20%, 30%, 40%, 50%, 60%, 70%, 80%, 90%, 100%, or more in comparison to a vector organism to which the composition has not been delivered.

Non-limiting examples of diseases that may be controlled by the compositions and methods provided herein include diseases caused by Togaviridae viruses (e.g., Chikungunya, Ross River fever, Mayaro, Onyon-nyong fever, Sindbis fever, Eastern equine enchephalomyeltis, Wesetern equine encephalomyelitis, Venezualan equine encephalomyelitis, or Barmah forest); diseases caused by Flavivirdae viruses (e.g., Dengue fever, Yellow fever, Kyasanur Forest disease, Omsk haemorrhagic fever, Japaenese encephalitis, Murray Valley encephalitis, Rocio, St. Louis encephalitis, West Nile encephalitis, or Tick-borne encephalitis); diseases caused by Bunyaviridae viruses (e.g., Sandly fever, Rift Valley fever, La Crosse encephalitis, California encephalitis, Crimean-Congo haemorrhagic fever, or Oropouche fever); disease caused by Rhabdoviridae viruses (e.g., Vesicular stomatitis); disease caused by Orbiviridae (e.g., Bluetongue); diseases caused by bacteria (e.g., Plague, Tularaemia, Q fever, Rocky Mountain spotted fever, Murine typhus, Boutonneuse fever, Queensland tick typhus, Siberian tick typhus, Scrub typhus, Relapsing fever, or Lyme disease); or diseases caused by protozoa (e.g., Malaria, African trypanosomiasis, Nagana, Chagas disease, Leishmaniasis, Piroplasmosis, Bancroftian filariasis, or Brugian filariasis).

i. Pathogen Vectors

The methods and compositions provided herein may be useful for decreasing the fitness of a vector for an animal pathogen. In some instances, the vector may be an insect. For example, the insect vector may include, but is not limited to those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites; order, class or family of Acarina (ticks and mites) e.g. representatives of the families Argasidae, Dermanyssidae, Ixodidae, Psoroptidae or Sarcoptidae and representatives of the species *Amblyomma* spp., Anocenton spp., *Argas* spp., *Boophilus* spp., *Cheyletiella* spp., Chorioptes spp., *Demodex* spp., *Dermacentor* spp., Denmanyssus spp., Haemophysalis spp., *Hyalomma* spp., *Ixodes* spp., Lynxacarus spp., Mesostigmata spp., Notoednes spp., Ornithodoros spp., *Ornithonyssus* spp., *Otobius* spp., otodectes spp., Pneumonyssus spp., *Psoroptes* spp., *Rhipicephalus* spp., Sancoptes spp., or Trombicula spp.; Anoplura (sucking and biting lice) e.g. representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g. representatives of the species *Aedes* spp., *Anopheles* spp., *Calliphora* spp., *Chrysomyia* spp., *Chrysops* spp., *Cochliomyia* spp., Cw/ex spp., *Culicoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., Acari (sarcoptic mange) e.g., Sarcoptidae spp., *Sarcophaga* spp., *Simulium* spp., *Stomoxys* spp., *Tabanus* spp., Tannia spp. or Zzpu/alpha spp.; Mallophaga (biting lice) e.g. representatives of the species *Damalina* spp., *Felicola* spp., *Heterodoxus* spp. or *Trichodectes* spp.; or *Siphonaptera* (wingless insects) e.g. representatives of the species *Ceratophyllus* spp., *Xenopsylla* spp; Cimicidae (true bugs) e.g. representatives of the species *Cimex* spp., Tritominae spp., Rhodinius spp., or *Triatoma* spp. In some instances, the insect is a blood-sucking insect from the order Diptera (e.g., suborder Nematocera, e.g., family Colicidae). In some instances, the insect is from the subfamilies Culicinae, Corethrinae, Ceratopogonidae, or Simuliidae. In some instances, the insect is of a *Culex* spp., *Theobaldia* spp., *Aedes* spp., *Anopheles* spp., *Aedes* spp., Forciponiyia spp., *Culicoides* spp., or *Helea* spp.

In certain instances, the insect is a mosquito. In certain instances, the insect is a tick. In certain instances, the insect is a mite. In certain instances, the insect is a biting louse.

F. Application Methods A plant described herein can be exposed to a PMP composition described herein in any suitable manner that permits delivering or administering the composition to the plant. The PMP composition may be delivered either alone or in combination with other active (e.g., fertilizing agents) or inactive substances and may be applied by, for example, spraying, injection (e.g., microinjection), through plants, pouring, dipping, in the form of concentrated liquids, gels, solutions, suspensions, sprays, powders, pellets, briquettes, bricks and the like, formulated to deliver an effective concentration of the PMP composition. Amounts and locations for application of the compositions described herein are generally determined by the habitat of the plant, the lifecycle stage at which the plant can be targeted by the PMP composition, the site where the application is to be made, and the physical and functional characteristics of the PMP composition.

In some instances, the composition is sprayed directly onto a plant e.g., crops, by e.g., backpack spraying, aerial spraying, crop spraying/dusting etc. In instances where the PMP composition is delivered to a plant, the plant receiving the PMP composition may be at any stage of plant growth. For example, formulated PMP compositions can be applied as a seed-coating or root treatment in early stages of plant growth or as a total plant treatment at later stages of the crop cycle. In some instances, the PMP composition may be applied as a topical agent to a plant.

Further, the PMP composition may be applied (e.g., in the soil in which a plant grows, or in the water that is used to water the plant) as a systemic agent that is absorbed and distributed through the tissues of a plant. In some instances, plants or food organisms may be genetically transformed to express the PMP composition.

Delayed or continuous release can also be accomplished by coating the PMP composition or a composition with the PMP composition(s) with a dissolvable or bioerodable coating layer, such as gelatin, which coating dissolves or erodes in the environment of use, to then make the PMP composition available, or by dispersing the agent in a dissolvable or erodable matrix. Such continuous release and/or dispensing devices may be advantageously employed to consistently maintain an effective concentration of one or more of the PMP compositions described herein.

In some instances, the PMP composition is delivered to a part of the plant, e.g., a leaf, seed, pollen, root, fruit, shoot, or flower, or a tissue, cell, or protoplast thereof. In some instances, the PMP composition is delivered to a cell of the plant. In some instances, the PMP composition is delivered to a protoplast of the plant. In some instances, the PMP composition is delivered to a tissue of the plant. For example, the composition may be delivered to meristematic tissue of the plant (e.g., apical meristem, lateral meristem, or intercalary meristem). In some instances, the composition is delivered to permanent tissue of the plant (e.g., simple tissues (e.g., parenchyma, collenchyma, or sclerenchyma) or complex permanent tissue (e.g., xylem or phloem)). In some instances, the composition is delivered to a plant embryo.

In some instances, the PMP composition may be recommended for field application as an amount of PMPs per hectare (g/ha or kg/ha) or the amount of active ingredient (e.g., PMP with or without a heterologous functional agent) or acid equivalent per hectare (kg a.i./ha or g a.i./ha). In some instances, a lower amount of heterologous functional agent in the present compositions may be required to be applied to soil, plant media, seeds plant tissue, or plants to achieve the same results as where the heterologous functional agent is applied in a composition lacking PMPs. For example, the amount of heterologous functional agent may be applied at levels about 2, 3, 4, 5, 6, 7, 8, 9, 10, 15, 20, 30, 50, or 100-fold (or any range between about 2 and about 100-fold, for example about 2- to 10-fold; about 5- to 15-fold, about 10- to 20-fold; about 10- to 50-fold) less than the same heterologous functional agent applied in a non-PMP composition, e.g., direct application of the same heterologous functional agent without PMPs. PMP compositions of the invention can be applied at a variety of amounts per hectare, for example at about 0.0001, 0.001, 0.005, 0.01, 0.1, 1, 2, 10, 100, 1,000, 2,000, 5,000 (or any range between about 0.0001 and 5,000) kg/ha. For example, about 0.0001 to about 0.01, about 0.01 to about 10, about 10 to about 1,000, about 1,000 to about 5,000 kg/ha.

G. Therapeutic Methods

The PMP compositions described herein are useful in a variety of therapeutic methods. For example, the methods and composition may be used for the prevention or treatment of pathogen infections in animals (e.g., humans). As used herein, the term "treatment" refers to administering a pharmaceutical composition to an animal for prophylactic and/or therapeutic purposes. To "prevent an infection" refers to prophylactic treatment of an animal who is not yet ill, but who is susceptible to, or otherwise at risk of, a particular disease. To "treat an infection" refers to administering treatment to an animal already suffering from a disease to improve or stabilize the animal's condition. The present methods involve delivering the PMP compositions described herein to an animal, such as a human.

For example, provided herein is a method of treating an animal having a fungal infection, wherein the method includes administering to the animal an effective amount of a PMP composition including a plurality of PMPs. In some instances, the method includes administering to the animal an effective amount of a PMP composition including a plurality of PMPs, wherein the plurality of PMPs includes an antifungal agent. In some instances, the antifungal agent is a nucleic acid that inhibits expression of a gene in a fungus that causes the fungal infection (e.g., Enhanced Filamentous Growth Protein (EFG1)). In some instances, the fungal infection is caused by *Candida albicans*. In some instances, composition includes a PMP produced from an *Arabidopsis* apoplast EV. In some instances, the method decreases or substantially eliminates the fungal infection.

In another aspect, provided herein is a method of treating an animal having a bacterial infection, wherein the method includes administering to the animal an effective amount of a PMP composition including a plurality of PMPs. In some instances, the method includes administering to the animal an effective amount of a PMP composition including a plurality of PMPs, and wherein the plurality of PMPs includes an antibacterial agent (e.g., Amphotericin B). In some instances, the bacterium is a *Streptococcus* spp., Pneumococcus spp., *Pseudomonas* spp., *Shigella* spp, *Salmonella* spp., *Campylobacter* spp., or an *Escherichia* spp. In some instances, the composition includes a PMP produced from an *Arabidopsis* apoplast EV. In some instances, the method decreases or substantially eliminates the bacterial infection. In some instances, the animal is a human, a veterinary animal, or a livestock animal.

The present methods are useful to treat an infection (e.g., as caused by an animal pathogen) in an animal, which refers to administering treatment to an animal already suffering from a disease to improve or stabilize the animal's condition. This may involve reducing colonization of a pathogen in, on, or around an animal by one or more pathogens (e.g., by about 1%, 2%, 5%, 10%, 20%, 30%, 40%, 50%, 60%, 70%, 80%, 90%, or 100%) relative to a starting amount and/or allow benefit to the individual (e.g., reducing colonization in an amount sufficient to resolve symptoms). In such instances, a treated infection may manifest as a decrease in symptoms (e.g., by about 1%, 2%, 5%, 10%, 20%, 30%, 40%, 50%, 60%, 70%, 80%, 90%, or 100%). In some instances, a treated infection is effective to increase the likelihood of survival of an individual (e.g., an increase in likelihood of survival by about 1%, 2%, 5%, 10%, 20%, 30%, 40%, 50%, 60%, 70%, 80%, 90%, or 100%) or increase the overall survival of a population (e.g., an increase in likelihood of survival by about 1%, 2%, 5%, 10%, 20%, 30%, 40%, 50%, 60%, 70%, 80%, 90%, or 100%). For example, the compositions and methods may be effective to "substantially eliminate" an infection, which refers to a decrease in the infection in an amount sufficient to sustainably resolve symptoms (e.g., for at least 1, 2, 3, 4, 5, 6, 7, 8, 9, 10, 11, or 12 months) in the animal.

The present methods are useful to prevent an infection (e.g., as caused by an animal pathogen), which refers to preventing an increase in colonization in, on, or around an animal by one or more pathogens (e.g., by about 1%, 2%, 5%, 10%, 20%, 30%, 40%, 50%, 60%, 70%, 80%, 90%, 100%, or more than 100% relative to an untreated animal) in an amount sufficient to maintain an initial pathogen population (e.g., approximately the amount found in a healthy individual), prevent the onset of an infection, and/or prevent symptoms or conditions associated with infection. For example, individuals may receive prophylaxis treatment to prevent a fungal infection while being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit), in immunocompromised individuals (e.g., individuals with cancer, with HIV/AIDS, or taking immunosuppressive agents), or in individuals undergoing long term antibiotic therapy.

The PMP composition can be formulated for administration or administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some instances, PMP composition is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of an infection described herein (when used alone or in combination with one or more other additional therapeutic agents) will depend on the type of disease to be treated, the severity and course of the disease, whether the is administered for preventive or therapeutic purposes, previous therapy, the patient's clinical history and response to the PMP composition. The PMP composition can be, e.g., administered to the patient at one time or over a series of treatments. For repeated administrations over several days or longer, depending on the condition, the treatment would generally be sustained until a desired suppression of disease symptoms occurs or the infection is no longer detectable. Such doses may be administered intermittently, e.g., every week or every two weeks (e.g., such that the patient receives, for example, from about two to about twenty, doses of the PMP composition. An initial higher loading dose, followed by one or more lower doses may be administered. However, other dosage regimens may be useful. The progress of this therapy is easily monitored by conventional techniques and assays.

In some instances, the amount of the PMP composition administered to individual (e.g., human) may be in the range of about 0.01 mg/kg to about 5 g/kg (e.g., about 0.01 mg/kg-0.1 mg/kg, about 0.1 mg/kg-1 mg/kg, about 1 mg/kg-10 mg/kg, about 10 mg/kg-100 mg/kg, about 100 mg/kg-1 g/kg, or about 1 g/kg-5 g/kg), of the individual's body weight. In some instances, the amount of the PMP composition administered to individual (e.g., human) is at least 0.01 mg/kg (e.g., at least 0.01 mg/kg, at least 0.1 mg/kg, at least 1 mg/kg, at least 10 mg/kg, at least 100 mg/kg, at least 1 g/kg, or at least 5 g/kg), of the individual's body weight. The dose may be administered as a single dose or as multiple doses (e.g., 2, 3, 4, 5, 6, 7, or more than 7 doses). In some instances, the PMP composition administered to the animal may be administered alone or in combination with an additional therapeutic agent. The dose of the antibody administered in a combination treatment may be reduced as compared to a single treatment. The progress of this therapy is easily monitored by conventional techniques.

V. Kits

The present invention also provides a kit including a container having a PMP composition described herein. The kit may further include instructional material for applying or delivering the PMP composition to a plant in accordance with a method of the present invention. The skilled artisan will appreciate that the instructions for applying the PMP composition in the methods of the present invention can be any form of instruction. Such instructions include, but are not limited to, written instruction material (such as, a label, a booklet, a pamphlet), oral instructional material (such as on an audio cassette or CD) or video instructions (such as on a video tape or DVD).

EXAMPLES

The following are examples of the methods of the invention. It is understood that various other embodiments may be practiced, given the general description provided above.

| Table of Contents (Examples): |  |
| --- | --- |
| Example 1. | Crude isolation of Plant Messenger Packs from plant cell culture medium. |
| Example 2. | Production of purified Plant Messenger Packs (PMPs). |
| Example 3. | Plant Messenger Pack characterization. |
| Example 4. | Characterization of Plant Messenger Pack stability. |
| Example 5. | Enhanced production of PMPs from plant cell culture using abiotic stimulants. |
| Example 6. | Enhanced production of PMPs from plant cell culture using biotic stimulants. |
| Example 7. | Enhanced production of PMPs from plant cell culture using chemical stimulants. |
| Example 8. | Enhanced release of PMPs by overexpressing exocyst complex members in plants. |
| Example 9. | Scaled Isolation of PMPs from plant cell culture using a bioreactor. |
| Example 10. | PMP production from plant cell culture medium. |
| Example 11. | Uptake of PMPs in plants. |
| Example 12. | PMP production from crucifer plant liquid culture. |
| Example 13. | PMP production from crucifer plant root culture. |
| Example 14. | Enhanced production of PMPs from plant cell culture using abiotic, biotic, and chemical stimulants. |
| Example 15. | Large-scale PMP production from plant cell culture medium using a bioreactor |
| Example 16. | Isolation of PMPs from roots of tomato grown in hydroponic culture and enhancement of PMP production using chemical stimuli |

Example 1: Crude Isolation of Plant Messenger Packs from Plant Cell Culture Medium This example describes the crude isolation of Plant Messenger Packs (PMPs) from various plant cell culture media.
Experimental design:
a) PMP Isolation from Tobacco BY-2 Cell Culture Medium Tobacco BY-2 (*Nicotiana tabacum* L cv. Bright Yellow 2; #PC-1181) cell culture is obtained from the German Collection of Microorganisms and Cell Cultures (Leibniz Institute DSMZ Braunschweig, Germany). Cells are cultured in the dark at 26° C., on a shaker at 130 rpm in MS (Murashige and Skoog, 1962) BY-2 culture medium (pH 5.8) comprising MS salts supplemented with 30 g/L sucrose, 2.0 mg/L potassium dihydrogen phosphate, 0.1 g/L myo-inositol, 0.2 mg/L 2,4-dichlorophenoxyacetic acid, and 1 mg/L thiamine HCl. The BY-2 cells are subcultured weekly by transferring 5% (v/v) of a 7-day-old cell culture into 100 mL fresh liquid culture medium. After 72-96 hours, BY-2 culture medium is collected and centrifuged at 300 g at 4° C. for 10 minutes to remove cells. The supernatant containing PMPs is collected and cleared of debris by filtration on a 0.85 μm filter. PMPs are purified as described in Example 2.
b) PMP Isolation from Soybean Cell Culture Medium Soybean (*Glycine max* (L.) Merr. cv. Mandarin; #PC-1026) cell culture is obtained from the German Collection of Microorganisms and Cell Cultures (Leibniz Institute DSMZ, Germany). Cells are cultured in the dark at 23° C., on a shaker at 100 rpm in B5 Medium (pH 5.5), comprised of 1×B5 Gamborg salts with vitamins (Sigma Aldrich G5893), 20 g/L sucrose (Sigma Aldrich), and 2 mg/L 2,4-dichlorophenoxyacetic acid. All reagents are purchased from Sigma Aldrich. *Glycine max* cells are subcultured weekly by transferring 20% (v/v) of a 7-day-old cell culture into 100 mL fresh liquid cuture medium. After 72-96 hours, *Glycine max* culture medium is collected and centrifuged at 300 g at 4° C. for 10 minutes to remove cells. The supernatant containing PMPs is collected and cleared of debris by filtration on a 0.85 μm filter. PMPs are purified as described in Example 2.
c) PMP Isolation from Corn Cell Culture Medium A corn Black Mexican Sweet cell line (BMS; *Zea mays*; CCL84842) is obtained from the *Arabidopsis* Biological Resource Center (ABRC, USA). Cells are cultured in the dark at 23° C., on a shaker at 100 rpm in MS Medium (pH 5.8), comprised of 4.3 g/L MS Salt (Sigma Aldrich M5524), 30 g/L sucrose and 2 mg/mL 2,4-dichlorophenoxyacetic acid. All reagents are purchased from Sigma Aldrich. The BMS cells are subcultured weekly by transferring 20% (v/v) of a 7-day-old cell culture into 100 ml fresh liquid culture medium. After 72-96 hours, BMS culture medium is collected and centrifuged at 300 g at 4° C. for 10 minutes to remove cells. The supernatant containing PMPs is collected and cleared of debris by filtration on a 0.85 μm filter. PMPs are purified as described in Example 2.
d) PMP Isolation from Wheat Cell Culture Medium Wheat (*Triticum aestivum*; #PC-998) cell culture is obtained from the German Collection of Microorganisms and Cell Cultures (Leibniz Institute DSMZ, Germany). Cells are cultured in the dark at 23° C., on a shaker at 100 rpm in B5 Medium (pH 5.5), comprised of 1×B5 Gamborg salts with vitamins (Sigma Aldrich G5893), 20 g/L sucrose (Sigma Aldrich), and 2 mg/L 2,4-dichlorophenoxyacetic acid. All reagents are purchased from Sigma Aldrich. Wheat cells are subcultured by transferring 20% (v/v) of a 14-day-old cell culture into 100 mL fresh liquid culture medium. After 72-96 hours, wheat cultured medium is collected and centrifuged at 300 g at 4° C. for 10 minutes to remove cells. The supernatant containing PMPs is collected and cleared of debris by filtration on a 0.85 μm filter. PMPs are purified as described in Example 2.
e) PMP Isolation from Pomelo Cell Culture Medium Pomelo (*Citrus decumana* (L.) L. cv. White Marsh; #PC-44) cell culture is obtained from the German Collection of Microorganisms and Cell Cultures (Leibniz Institute DSMZ Braunschweig, Germany). Cells are cultured in the dark at 23° C., on a shaker at 100 rpm in LS Medium (pH 6), comprised of 1650 mg/L $NH_4NO_3$, 199 mg/L $KNO_3$, 180 mg/L $MgSO_4$, 170 mg/L $KH_2PO_4$, 332.02 mg/L $CaCl_2$), 36.7 mg/L FeNaEDTA, 6.2 mg/L $H_3BO_3$, 16.9 mg/mL $MnSO_4 \times H_2O$, 8.6 mg/L $ZnSO_4 \times 4H_2O$, 0.83 mg/L KJ, 0.25 mg/L $Na_2MoO_4 \times 2H_2O$, 0.025 mg/mL $CuSO_4 \times 5H_2O$, 0.025 mg/L $CoCl_2 \times 6 H_2O$, 0.4 mg/L Thiamine hydrochloride, 100 mg/L myo-Inositol, 0.22 mg/L 2,4-Dichlorophenoxyacetic acid, 0.186 mg/L 1-Naphtylacetic acid, and 30 g/L sucrose. All reagents are purchased from Sigma Aldrich. Pomelo cells are subcultured by transferring 20% (v/v) of a 14-day-old cell culture into 100 mL fresh liquid medium. After 72-96 hours, pomelo culture medium is collected and centrifuged at 300 g at 4° C. for 10 minutes to remove cells. The supernatant containing PMPs is collected and cleared of debris by filtration on a 0.85 μm filter. PMPs are purified as described in Example 2.

f) EV Isolation from Grape Cell Culture Medium

Grape (*Vitis vinifera*; #PC-1137) cell culture is obtained from the German Collection of Microorganisms and Cell Cultures (Leibniz Institute DSMZ Braunschweig, Germany). Cells are cultured in the dark at 23° C., on a shaker at 100 rpm in B5 Medium (pH 5.5), comprised of 1×B5 Gamborg salts with vitamins (Sigma Aldrich G5893), 20 g/L sucrose (Sigma Aldrich), and 2 mg/L 2,4-dichlorophenoxyacetic acid. All reagents are purchased from Sigma Aldrich. Grape cells are subcultured by transferring 20% (v/v) of a 14-day-old cell culture into 100 mL fresh liquid culture medium. After 72-96 hours, grape culture medium is collected and centrifuged at 300 g at 4° C. for 10 minutes to remove cells. The supernatant containing PMPs is collected and cleared of debris by filtration on a 0.85 µm filter. PMPs are purified as described in Example 2.

Example 2: Production of Purified Plant Messenger Packs (PMPs)

This example describes the production of purified PMPs from crude PMP fractions as described in Example 1, using ultrafiltration combined with size-exclusion chromatography, a density gradient (iodixanol or sucrose), and the removal of aggregates by precipitation or size-exclusion chromatography.

Experimental Design:

a) Purification of BY-2 PMPs Using Ultrafiltration Combined with Size-Exclusion Chromatography The crude BY-2 PMP fraction from Example 1a is concentrated using 100-kDA molecular weight cut-off (MWCO) Amicon spin filter (Merck Millipore). Subsequently, the concentrated crude PMP solution is loaded onto a PURE-EV size exclusion chromatography column (HansaBioMed Life Sciences Ltd) and isolated according to the manufacturer's instructions. The purified PMP-containing fractions are pooled after elution. Optionally, PMPs can be further concentrated using a 100-kDa MWCO Amicon spin filter, or by Tangential Flow Filtration (TFF). The purified PMPs are analyzed as described in Example 3.

b) Purification of BMS PMPs Using an Iodixanol Gradient

Crude BMS PMPs are isolated as described in Example 1, and PMPs are produced by using an iodixanol gradient as described in Rutter and Innes, Plant Physiology 2016. To prepare discontinuous iodixanol gradients (OptiPrep; Sigma-Aldrich), solutions of 40% (v/v), 20% (v/v), 10% (v/v), and 5% (v/v) iodixanol are created by diluting an aqueous 60% OptiPrep stock solution in vesicle isolation buffer (VIB; 20 mM MES, and 0.1 M NaCl, pH6). The gradient is formed by layering 3 mL of 40% solution, 3 mL of 20% solution, 3 mL of 10% solution, and 2 mL of 5% solution. The crude PMP solution from Example 1a is centrifuged at 40,000 g for 60 min at 4° C. The pellet is resuspended in 0.5 mL of VIB and layered on top of the gradient. Centrifugation is performed at 100,000 g for 17 h at 4° C. The first 4.5 mL at the top of the gradient is discarded, and subsequently 3 volumes of 0.7 mL that contain the apoplast PMPs are collected, brought up to 3.5 mL with VIB, and centrifuged at 100,000 g for 60 min at 4° C. The pellets are washed with 3.5 mL of VIB and repelleted using the same centrifugation conditions. The purified PMP pellets are combined for subsequent analysis, as described in Example 3.

c) Purification of Wheat Cell Culture PMPs Using a Sucrose Gradient

Crude wheat cell culture PMPs are isolated as described in Example 1, centrifuged at 150,000 g for 90 min, and the PMP-containing pellet is resuspended in 1 mL PBS as described in Mu et al., Molecular Nutrition & Food Research 2014. The resuspended pellet is transferred to a sucrose step gradient (8%/15%/30%/45%/60%) and centrifuged at 150,000 g for 120 min to produce purified PMPs. Purified wheat cell culture PMPs are harvested from the 30%/45% interface, and subsequently analyzed, as described in Example 3.

d) Removal of Aggregates from Isolated BY-2 PMPs

In order to remove protein aggregates from crude BY-2 PMPs as described in Example 1 or purified PMPs from Examples 2a-2c, an additional purification step can be included. The crude or purified PMP solution is taken through a range of pHs to precipitate protein aggregates in the solution. The pH is adjusted to 3, 5, 7, 9, and 11 with the addition of sodium hydroxide or hydrochloric acid. pH is measured using a calibrated pH probe. Once the solution is at the specified pH, it is filtered to remove particulates. Alternatively, the PMP solution can be flocculated using the addition of charged polymers, such as Polymin-P or Praestol 2640. Briefly, 2-5 g per L of Polymin-P or Praestol 2640 is added to the solution and mixed with an impeller. The solution is then filtered to remove particulates. Alternatively, aggregates are solubilized by increasing salt concentration. NaCl is added to the PMP solution until it is at 1 mol/L. The solution is then filtered to produce the PMPs. Alternatively, aggregates are solubilized by increasing the temperature. The PMP solution is heated under mixing until it has reached a uniform temperature of 50° C. for 5 minutes. The PMP mixture is then filtered to isolate the PMPs. Alternatively, soluble contaminants from PMP solutions are separated by using a size-exclusion chromatography column according to standard procedures, wherein PMPs elute in the first fractions, whereas proteins and ribonucleoproteins and some lipoproteins are eluted later. The efficiency of protein aggregate removal is determined by measuring and comparing the protein concentration before and after removal of protein aggregates via bicinchoninic acid assay (BCA)/Bradford protein quantification. The purified PMPs are analyzed as described in Example 3.

Example 3: Plant Messenger Pack Characterization

This example describes the characterization of PMPs purified as described in Example 2.

Experimental Design:

a) Determining PMP Concentration

PMP particle concentration is determined by high sensitivity flow cytometry using a NanoFCM, or Nanoparticle Tracking Analysis (NTA) using a Malvern NanoSight, or by Tunable Resistive Pulse Sensing (TRPS) using an iZon qNano, following the manufacturer's instructions. The protein concentration of purified PMPs is determined by using the DC Protein assay (Bio-Rad). The lipid concentration of purified PMPs is determined using a fluorescent lipophilic dye, such as DiOC6 (ICN Biomedicals) as described by *Rutter and Innes, Plant Physiology* 2017. Briefly, purified PMP pellets from Example 2 are resuspended in 100 mL of 10 mM DiOC6 (ICN Biomedicals) diluted with MES buffer (20 mM MES, pH 6) plus 1% plant protease inhibitor cocktail (Sigma-Aldrich) and 2 mM 2,29-dipyridyl disulfide. The resuspended PMPs are incubated at 37° C. for 10 min, washed with 3 mL of MES buffer, repelleted (40,000 g, 60 min, at 4° C.), and resuspended in fresh MES buffer. DiOC6 fluorescence intensity is measured at 485 nm excitation and 535 nm emission.

b) Biophysical and Molecular Characterization of PMPs

PMPs are characterized by electron and cryo-electron microscopy on a JEOL 1010 transmission electron microscope, following the protocol from Wu et al., Analyst, 2015. The PMP size is determined by high sensitivity flow cytometry (NanoFCM), Malvern NanoSight or iZon qNano, and zeta potential of the PMPs is measured using a Malvern Zetasizer or iZon qNano, following the manufacturer's instructions. Lipids are isolated from PMPs using chloroform extraction and characterized with LC-MS/MS as demonstrated in Xiao et al. Plant Cell, 2010. Glycosyl inositol phosphorylceramides (GIPCs) are extracted and purified as described by Cacas et al Plant Physiology 2016, and analyzed by LC-MS/MS as described above. Total RNA, DNA, and protein are characterized using Quant-It kits from Thermo Fisher according to instructions. Proteins on the PMPs are characterized by LC-MS/MS following the protocol in Rutter and Innes, Plant Physiology, 2016. RNA and DNA are extracted using Trizol, prepared into libraries with the TruSeq Total RNA with Ribo-Zero Plant kit and the Nextera Mate Pair Library Prep Kit from Illumina, and sequenced on an Illumina MiSeq following manufacturer's instructions.

Example 4: Characterization of Plant Messenger Pack Stability

This example describes measuring the stability of PMPs under a wide variety of storage and physiological conditions.

Experimental Design:

PMPs produced as described in Examples 1 and 2 are subjected to various conditions. PMPs are suspended in water, 5% sucrose, or PBS and left for 1, 7, 30, and 180 days at −20° C., 4° C., 20° C., and 37° C. PMPs are also suspended in water and dried using a rotary evaporator system and left for 1, 7, and 30, and 180 days at 4° C., 20° C., and 37° C. PMPs are also suspended in water or 5% sucrose solution, flash-frozen in liquid nitrogen and lyophilized. After 1, 7, 30, and 180 days, dried and lyophilized PMPs are then resuspended in water. The previous three experiments with conditions at temperatures above 0° C. are also exposed to an artificial sunlight simulator in order to determine content stability in simulated outdoor UV conditions. PMPs are also subjected to temperatures of 37° C., 40° C., 45° C., 50° C., and 55° C. for 1, 6, and 24 hours in buffered solutions with a pH of 1, 3, 5, 7, and 9 with or without the addition of 1 unit of trypsin or in other simulated gastric fluids.

After each of these treatments, PMPs are bought back to 20° C., neutralized to pH 7.4, and characterized using some or all of the methods described in Example 3.

Example 5: Enhanced Production of PMPs from Plant Cell Culture Using Abiotic Stimulants This example describes the enhanced production of PMPs from plant cell cultures that are elicited by abiotic stimuli. The BY-2 cell line is used as model plant cell line, and temperature, pH, light and salinity are used as model abiotic stimulants.

a) BY2 Growth Conditions and Preparation of the Inoculums

As described in Example 1, BY-2 cells are cultured in the dark at 26° C., on an Innova 44R orbital shaker at 130 rpm in MS (Murashige and Skoog, 1962) medium (pH 5.8). The BY-2 cells are routinely subcultured weekly by transferring 5% (v/v) of a 7-day-old cell culture into 100 mL fresh liquid culture medium into a 250 mL sterile shake flask.

The preculture used for inoculation of elicitation experiments should be in the exponential growth phase. To determine the percentage packed cell volume (PCV) or fresh weight (FW) of exponentially growing cells, a growth curve is recorded from shake-flask cultures based on samples each consisting of at least three biological replicates. Three shake flasks are inoculated with 5-10% (v/v) of a routine BY-2 culture. 10 mL samples are taken at 0, 72, 96, 120, 148, 172, and 196 hours. The % PCV is measured by transferring a 10 mL sample of the cell culture to a graduated tube and centrifuging for 5 min at 4000× g at room temperature. The % PCV is the ratio of the volume of the cell pellet to the volume of the cells+medium×100%. The fresh weight (FW) is determined by vacuum filtering 10 mL of the medium through filter paper (pore size 4-12 µm) and weighing the cells retained on the filter paper. Then, cells are dried at 60° C. until the weight stays constant (at least 24 h) to determine the dry weight (DW). The % PCV, FW, and DW are plotted against the cultivation time to obtain the growth curve. To determine the optimal harvest time for the preculture, i.e., the mid-exponential phase, either an exponential function is plotted to the data and the derivative of that fit is used to plot the growth rate, or the optimal harvest time for the preculture is visually determined.

For experiments, the fresh weight is determined from a 7-day-old pre-culture in the exponential growth phase, and fresh cultures are seeded with a final concentration 3% FW (3 g cells/100 mL) in a final volume of 100 mL BY2 medium into 250 mL disposable shaker flasks.

b) Increased PMP Production by Tobacco BY-2 Cells by Temperature Elicitation

To determine the effect of temperature on PMP production by BY-2 cells, 100 mL BY-2 cultures are prepared as described in Example 5a and are grown at different temperatures: 20° C., 26° C. (normal control temperature), and 30° C., with three flasks per temperature per time point. After 24, 48, 72 and 96 hours, the FW and DW are determined by analyzing 10 mL cell culture as described in Example 5a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and temperature conditions. Temperature changes stimulate the production of PMPs.

c) Increased PMP Production by Tobacco BY-2 Cells by pH Elicitation

To determine the effect of pH on the PMP production by BY-2 cells, 100 mL BY-2 cultures are prepared as described in Example 5a in MS-medium with pH 4.5, pH 5, pH 5.8 (control pH), pH 6, and pH 6.5 and grown at 26° C. in the dark, with three flasks per condition per time point. After 24, 48, 72 and 96 hours, the FW and DW are determined by analyzing 10 mL cell culture as described in Example 5a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and pH conditions. pH changes stimulate the production of PMPs.

d) Increased PMP Production by Tobacco BY-2 Cells by Light Elicitation

To determine the effect of light on the PMP production by BY-2 cells, 100 mL BY-2 cultures are prepared as described in Example 5a and grown at 26° C., either in the dark (control) or short-day (8 h light) and long-day conditions (16 h light), under flux density of 120 µmol m$^{-2}$ s$^{-1}$ or 60 µmol m$^{-2}$ s$^{-1}$, with three flasks per condition per time point. After 24, 48, 72 and 96 hours, the FW and DW are determined by analyzing 10 mL cell culture as described in Example 5a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and light conditions. Light exposure stimulates the production of PMPs.

e) Increased PMP Production by Tobacco BY-2 Cells by Salt Elicitation

To determine the effect of salinity on the PMP production by BY-2 cells, 100 mL BY-2 cultures are prepared as described in Example 5a in MS-medium supplemented with NaCl to a final concentration of 0 (control), 0.5 g/L NaCl, 1 g/L NaCl, 2.5 g/L NaCl and 5 g/L NaCl, and grown at 26° C. in the dark, with three flasks per condition per time point. After 24, 48, 72 and 96 hours, the FW and DW are determined by analyzing 10 mL cell culture as described in Example 5a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and salinity conditions. Salinity changes stimulate the production of PMPs.

Example 6: Enhanced Production of PMPs from Plant Cell Culture Using Biotic Stimulants This example describes the enhanced production of PMPs from plant cell cultures that are elicited by biotic stimuli. The BY-2 cell line is used as model plant cell line, and chitosan (fungal), flg22 (bacterial), and ELF18 (bacterial) stimulants are used as model biotic stimulants.

a) BY-2 Growth Conditions and Preparation of the Inoculums

As described in Example 1, BY-2 cells are cultured in the dark at 26° C., on an Innova 44R orbital shaker at 130 rpm in MS (Murashige and Skoog, 1962) medium (pH 5.8). The BY-2 cells are routinely subcultured weekly by transferring 5% (v/v) of a 7-day-old cell culture into 100 mL fresh liquid medium into a 250 mL sterile shake flask.

The preculture used for inoculation of elicitation experiments should be in the exponential growth phase. To determine the percentage packed cell volume (PCV) or fresh weight (FW) of exponentially growing cells, a growth curve is recorded from shake-flask cultures based on samples each consisting of at least three biological replicates. Three shake flasks are inoculated with 5-10% (v/v) of a routine BY-2 culture. 10 mL samples are taken at 0, 72, 96, 120, 148, 172, and 196 hours. The % PCV is measured by transferring a 10-mL sample of the cell culture to a graduated tube and centrifuging 5 min at 4000× g at room temperature. The % PCV is the ratio of the volume of the cell pellet to the volume of the cells+medium×100%. The Fresh weight (FW) is determined by vacuum filtering 10 mL of the medium through filter paper (pore size 4-12 µm) and weighing the cells retained on the filter paper. Then, cells are dried at 60° C. until the weight stays constant (at least 24 h) to determine the dry weight (DW). The % PCV, FW, and DW are plotted against the cultivation time to obtain the growth curve. To determine the optimal harvest time for the preculture, i.e., the mid-exponential phase, either an exponential function is plotted to the data and the derivative of that fit is used to plot the growth rate, or the optimal harvest time for the preculture is visually determined.

For experiments, the fresh weight is determined from a 7-day-old pre-culture in the exponential growth phase, and fresh cultures are seeded with a final concentration 3% FW (3 g cells/100 mL) in a final volume of 100 mL BY-2 culture medium into 250 mL disposable shaker flasks.

b) Increased PMP Production by Tobacco BY-2 Cells by Chitosan Elicitation

To determine the effect of chitosan on the PMP production by BY-2 cells, 100 mL BY-2 cultures are prepared as described in Example 6a in MS-medium supplemented with 0 (control), 25 mg/L chitosan (Sigma Aldrich), 50 mg/L chitosan, and 100 mg/L chitosan, and grown at 26° C. in the dark, with three flasks per condition per time point. After 24, 48, 72 and 96 hours, the FW and DW are determined by analyzing 10 mL cell culture as described in Example 6a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and chitosan conditions. Chitosan stimulates the production of PMPs.

c) Increased PMP Production by Tobacco BY-2 Cells by Flg22 Elicitation

To determine the effect of flg22 peptide (QRLSTGSRIN-SAKDDAAGLQIA) (SEQ ID NO: 7) on PMP production by BY-2 cells, 100 mL BY-2 cultures are prepared as described in Example 6a in MS medium supplemented with 0 (control), 5 µM flg22 (AnaSpec AS-62633), 10 µM flg22, and 20 UM flg22, and grown at 26° C. in the dark, with three flasks per condition per time point. After 24, 48, 72 and 96 hours, the FW and DW are determined by analyzing 10 mL cell culture as described in Example 6a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and flg22 conditions. Flg22 stimulates the production of PMPs.

d) Increased PMP Production by Tobacco BY-2 Cells by Elf18 Elicitation

To determine the effect of elf18 peptide (Ac-SKEKFER-TKPHVNVGTIG) (SEQ ID NO: 8) on PMP production by BY-2 cells, 100 mL BY-2 cultures are prepared as described in Example 5a in MS medium supplemented with 0 (control), 50 nM elf18 (EZBiolab), 100 nM elf18, and 500 nM elf18, 1M elf18, 2.5 µM elf18, and 5 µM elf18 and grown at 26° C. in the dark, with three flasks per condition per time point. After 24, 48, 72 and 96 hours, the FW and DW are determined by analyzing 10 mL cell culture as described in Example 5a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and temperature conditions. Elf18 stimulates the production of PMPs.

Example 7: Enhanced Production of PMPs from Plant Cell Culture Using Chemical Stimulants This example describes the enhanced production of PMPs from plant cell cultures that are elicited by chemical stimuli. The BY-2 cell line is used as model plant cell line, and salicylic acid, benzothiadiazole (BTH), 2,6-dichloroisonicotinic acid and methyl-jasmonate are used as model chemical elicitors.

a) BY-2 Growth Conditions and Preparation of the Inoculums

As described in Example 1, BY-2 cells are cultured in the dark at 26° C., on an Innova 44R orbital shaker at 130 rpm in MS (Murashige and Skoog, 1962) medium (pH 5.8). The BY-2 cells are routinely subcultured weekly by transferring 5% (v/v) of a 7-day-old cell culture into 100 mL fresh liquid medium into a 250 mL sterile shake flask.

The preculture used for inoculation of elicitation experiments should be in the exponential growth phase. To determine the percentage packed cell volume (PCV) or fresh weight (FW) of exponentially growing cells, a growth curve is recorded from shake-flask cultures based on samples each consisting of at least three biological replicates. Three shake flasks are inoculated with 5-10% (v/v) of a routine BY-2 culture. 10 mL samples are taken at 0, 72, 96, 120, 148, 172, and 196 hours. The % PCV is measured by transferring a 10-mL sample of the cell culture to a graduated tube and centrifuging 5 min at 4000× g at room temperature. The % PCV is the ratio of the volume of the cell pellet to the volume of the cells+medium×100%. The Fresh weight (FW) is determined by vacuum filtering 10 mL of the medium through filter paper (pore size 4-12 µm) and weighing the cells retained on the filter paper. Then, cells are dried at 60° C. until the weight stays constant (at least 24 h) to determine the dry weight (DW). The % PCV, FW, and DW are plotted against the cultivation time to obtain the growth curve. To determine the optimal harvest time for the preculture, i.e., the mid-exponential phase, either an exponential function is plotted to the data and the derivative of that fit is used to plot the growth rate, or the optimal harvest time for the preculture is visually determined.

For experiments, the fresh weight is determined from a 7-day-old pre-culture in the exponential growth phase, and fresh cultures are seeded with a final concentration 3% FW (3 g cells/100 mL) in a final volume of 100 mL BY2 medium into 250 mL disposable shaker flasks.

b) Increased PMP Production by Tobacco BY-2 Cells by Methyl-Jasmonate Elicitation To determine the effect of methyl-jasmonate on the PMP production by BY-2 cells, 100 mL BY-2 cultures are prepared as described in Example 7a in MS-medium supplemented with 0 (control), 50 µM methyl-jasmonate (Sigma Aldrich), 100 µM methyl-jasmonate, and 200 µM methyl-jasmonate, and grown at 26° C. in the dark, with three flasks per condition per time point. After 24, 48, 72 and 96 hours, the FW and DW are determined by analyzing 10 mL cell culture as described in Example 7a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and methyl jasmonate conditions. Methyl-jasmonate stimulates the production of PMPs.

c) Increased PMP Production by Tobacco BY-2 Cells by Salicylic Acid Elicitation

To determine the effect of salicylic acid on the PMP production by BY-2 cells, 100 mL BY-2 cultures are prepared as described in Example 7a in MS-medium supplemented with 0 (control), 500 µM salicylic acid (Sigma Aldrich), 1 mM salicylic acid, 2 mM salicylic acid, and 5 mM salicylic acid, and grown at 26° C. in the dark, with three flasks per condition per time point. After 24, 48, 72 and 96 hours, the FW and DW are determined by analyzing 10 mL cell culture as described in Example 7a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and salicylic acid conditions. Salicylic acid stimulates the production of PMPs.

d) Increased PMP Production by Tobacco BY-2 Cells by Benzothiadiazole Elicitation To determine the effect of Benzo-(1,2,3)-thiadiazole-7-carbothioic acid S-methyl ester (benzothiadiazole, BTH) on the PMP production by BY-2 cells, 100 mL BY-2 cultures are prepared as described in Example 7a in MS-medium supplemented with 0 (control), 500 µM benzothiadiazole (Sigma Aldrich), 300 µM benzothiadiazole, 100 µM benzothiadiazole, and 50 µM benzothiadiazole, and grown at 26° C. in the dark, with three flasks per condition per time point. After 24, 48, 72 and 96 hours, the FW and DW are determined by analyzing 10 mL cell culture as described in Example 7a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and BTH conditions. Benzothiadiazole stimulates the production of PMPs.

e) Increased PMP Production by Tobacco BY-2 Cells by 2,6-Dichloroisonicotinic Acid Elicitation To determine the effect of 2,6-dichloroisonicotinic acid on the PMP production by BY-2 cells, 100 mL BY-2 cultures are prepared as described in Example 7a in MS-medium supplemented with 0 (control), 500 µM 2,6-dichloroisonicotinic acid (Sigma Aldrich), 250 µM 2,6-dichloroisonicotinic acid, 100 µM 2,6-dichloroisonicotinic acid, and 50 µM 2,6-dichloroisonicotinic acid, and grown at 26° C. in the dark, with three flasks per condition per time point. After 24, 48, 72 and 96 hours, the FW and DW are determined by analyzing 10 mL cell culture as described in Example 7a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW BY-2 cells is determined and used to compare the different time points and 2,6-dichloroisonicotinic acid conditions. 2,6-dichloroisonicotinic acid stimulates the production of PMPs.

Example 8: Enhanced Release of PMPs by Overexpressing Exocyst Complex Members in Plants This example describes the enhanced release of PMPs from plant cells and plants by overexpression of exocyst complex members, like EXO70A1 and EXO84. In this example, EXO70A1 is a model exocyst complex member, BY-2 is a model cell line, and *Brassica napus* is used as model plant.

a) Generating an Exo70A1 Overexpression Construct for *Agrobacterium* Mediated Transfection Exo70A1 in *Brassica napus* (BnaCnng02750D-1, CDY10374) was previously identified by Samuel et al. (2009) *The Pant Cell* Vol. 21:2655-2671. The full BnExo70A1 coding sequence is synthesized by IDT, including a KOZAK sequence, Nco1 3' and 5' enzymatic sites with removal of the stop codon to generate BnExo70A1: mgfp5 fusion protein using the pCambia1302 Plant Expression Vector obtained from Marker Gene Technologies. In this vector, a double-enhancer version of the CaMV35S promoter drives the BnExo70A1: mgfp5 fusion protein, terminated by the CaMV35S polyA signal. To clone the construct, the BnExo70A1 synthesized sequence and pCambia1302 vector are digested with NcoI, isolated and BnExo70A1 is ligated into the vector. pCambia1302-BnExo70A1 is sequence verified and transformed into *E. coli* and GV3101:: pMP90 *Agrobacterium tumefaciens* according to the manufacturer's procedures.

>BnExo70A1 synthesized sequence
(SEQ ID NO: 9)
ACGAccatggaccATGGCCGTCGATAGCCGAATGGATCTGCTCAGCGAAA

GAGCTGTGCTGATGAGAGAGTCTCTCCAGAAGAGTCAAACCATCACCGAT

AATGTCGTCTCCATCCTCGGCTCCTTCGATAGCCGTCTCTCTGCTCTTGA

ATCCGCCATGCGTCCCACTCAGATTAGAACGCATGCGATAAGGAAAGCTC

ACGAGAATATCGATAAGACTCTCAAATCCGCTGAGGTTATTCTCTCTCAG

TTTGATCTCCTCCGTCAGGCAGAGACTAAAGTACTCAAGGGGCCACATGA

GGACCTGGAGAGTTATTTGGAGGCAATAGCTCAACTCAGAAAAGTTATTC

GTTATTTTAGCAGCAACAAAGGCTTTAAGAACAGTGATGGAGTCCTCAAC

CATGCAAATAGCTTGCTTGCCAAAGCTCAGTCGAAGCTGGAGGAGGAGTT

TAAACAGTTGCTAGCTTCTTACAGCAAAGCTGTGGAGCCTGATCGCCTTT

TTGATGGCCTTCCTAACTCACTGAGACCATCCGCTGACGGTGAGGGTAAT

GGAAAAGCCCACGGAGGACACCATAACGATGACTCAGAAACTGCTGCTTA

TACACTTCCAGTCCTCATTCCATCAAGGGTATTGCCACTTTTGCATGATT

TGGCTCAGCAAATGGTTCAGGCTGGTCACCAGCAACTGCTGCTACAAATT

TATAGAGAAACACGTACTTTTGTATTGGAAGAGAGCTTAAGAAAATTGGG

AGTTGAAAAACTTAGCAAAGAGGATGTTCAGAGGATGCAGTGGGAAGTTT

TGGAGGCCAAAATTGGAAATTGGATCCATTTCATGCGCATTGCTGTTAAA

TTGCTCTTTGCTGGAGAAAGGCAAGTATGTGACCAGATATTCCGAGGCTT

CGATTCTCTTAGTGATCAGTGTTTTGCAGAAGTTACAGTGAGCAGTGTCT

CAATGCTACTTAGCTTTGGGGATGCCATAGCTAGGAGCAAGAGATCTCCA

GAAAAGTTGTTTGTACTCTTAGACATGTATGAAATAATGCGGGAGCTTCA

TTCAGAGATTGAGACAATTTTCAAAGGTAAAGCATGCCTTGAAATTAGAA

ACTCTGCTACGGGGTTGACAAAGCGGCTGGCGCAGACTGCTCAGGAAACA

TTTGGTGACTTCGAAGAAGCTGTAGAAAAAGATGCTACAAAGACTGCTGT

TCTAGATGGGACTGTCCACCCACTAACAAGCTATGTTATCAATTATGTCA

AGTTCTTATTTGACTACCAAGCGACTTTGAAGCAACTTTTCTCGGAATTT

GGAAATGGAGATGACTCGAACTCTCAGCTTGCATCCGTAACAATGAGGAT

AATGCAGGCGCTTCAAAACAACCTGGAGGGAAAATCGAAACAGTACAAAG

ATCAAGCACTGACACACTTGTTCTTGATGAACAACATACATTACATGGTT

AGATCTGTGCGCAGGTCAGAAGCCAAGGATTTGTTAGGCGATGATTGGGT

TCAAAGGCACAGGCGTGTCGTTCAGCAACATGCAAACCTATACAAAAGGA

CTGCTTGGACAAAGATATTACAAACCTCGTCGGCGCAAGGGTTGACCTCA

TCCGGAGGAGGAAGTGTAGAGGGAGGAAACAGCAGCGGAGTTTCGAGAGG

GTTACTGAAAGAGAGGTTCAAGATGTTCAATATGCAATTTGATGAGTTGC

ATCAGAGACAATCACAATGGACAGTTCCGGACACAGAGCTAAGAGAGTCA

CTAAGACTTGCTGTTGCTGAAGTATTATTGCCTGCTTACAGATCATTCCT

CAAACGCTTTGGGCCTCTGGTTGAGAGTGGGAAGAATTCTCAGAGATACA

TAAAGTATACAGCTGAAGATCTTGAGAGATTGTTGGGTGAGTTGTTTGAA

GGAAAGTCTATGAACGAACCACGACGGccatggACGA b) BnExo70A1: Mgfp5 Overexpression in *B napus* Induces Enhanced PMP Release in the Apoplast The *Brassica napus* Westar cultivar is grown in growth chambers under long-day conditions consisting of a 16 hour light/8 hour dark photoperiod at 22C.

BnExo70A1: mgfp5 is transformed into *B. napus* plants using *Agrobacterium tumefaciens* carrying pCambia1302-BnExo70A1 as described Samuel et al. (2009) *The Plant Cell* Vol. 21:2655-2671, and selected with hygromycin B as described by Marker Gene Technologies. Transgenic lines are screened for Exo70A1 expression by RT-PCR using primers (BnExo70-FW 5'cgcccgggatggccgtcgatagccgaa 3' (SEQ ID NO: 10), BnExo70-REV 5' cgcgggccct-taccgtcgtggttcattcat 3' (SEQ ID NO: 11)) to detect the Exo70A1 mRNA, and actin (Actin-FW 5' ggctgatggtgaaga-tattca 3' (SEQ ID NO: 12), Actin-REV 5'caagcacaataccagtagtac3' (SEQ ID NO: 13)) is used as a positive control. For RT-PCR, total RNA is isolated from the stigmas from various transgenic and control plants and used to synthesize cDNA through oligo (dT)-mediated reverse transcription. GFP levels are determined by Western Blot. Robust transgenic lines are cultured for multiple generations to ensure stable integration of the transgene.

EVs are isolated from the apoplastic wash of 4-6-week old control and transgenic *Brassica napus*, as described by Rutter and Innes, *Plant Physiol* 2016. Briefly, whole leaves are harvested and vacuum infiltrated with vesicle isolation buffer (20 mM MES, 2 mM $CaCl_2$), and 0.1 M NaCl, pH6). Infiltrated plants are carefully blotted to remove excess fluid, placed inside 30-mL syringes, and centrifuged in 50 ml conical tubes at 700 g for 20 min at 2° C. to collect the apoplast extracellular fluid containing EVs. Next, the apoplast extracellular fluid is filtered through a 0.85 µm filter to remove large particles, and PMPs are produced as described in Example 2. The concentration of PMPs in the apoplastic fluid in BnExo70A1 is compared to the concentration of PMPs in the apoplastic fluid in non-transgenic plants according to methods described in Example 3. Exo70A1 overexpression in plant cell increases the release of PMPs.

c) BnExo70A1: Mgfp5 Overexpression in BY-2 Cells Induces Enhanced PMP Release in the Culture Medium Tobacco BY-2 (*Nicotiana tabacum* L cv. Bright Yellow 2; #PC-1181) cell culture is obtained from the German Collection of Microorganisms and Cell Cultures (Leibniz Institute DSMZ Braunschweig, Germany). Cells are cultured in the dark at 26° C., on a shaker at 130 rpm in MS (Murashige and Skoog, 1962) BY-2 cultivation medium (pH 5.8) comprised MS salts supplemented with 30 g/L sucrose, 2.0 mg/L potassium dihydrogen phosphate, 0.1 g/L myo-inositol, 0.2 mg/L 2,4-dichlorophenoxyacetic acid, and 1 mg/L thiamine HCl.

BnExo70A1: mgfp5 is transformed into BY-2 protoplast cells using *Agrobacterium tumefaciens* carrying pCambia1302-BnExo70A1 to generate stable transgenic lines, as described by Raven et al., 2015 Biotechnology and Bioengineering, Vol. 112, No. 2, and selected with hygromycin B as described by Marker Gene Technologies. After preselecting 50 independent callus clones with strong GFP fluorescence, clones are screened for Exo70A1 expression by RT-PCR as described in Example 8b. Cell suspension cultures are established from the five best-performing clones.

The control BY-2 cells and BY-2-BnExo70A1: mgfp5 cells are subcultured weekly by transferring 5% (v/v) of a 7-day-old cell culture into 100 mL fresh liquid medium. To determine the effect of Exo70A1 overexpression on PMP release by BY-2 cells, 100 mL BY-2 cultures are prepared as described in Example 7a and grown at 26° C. in the dark, with three flasks per condition per time point. After 24, 48, 72 and 96 hours, the FW and DW are determined by analyzing 10 mL cell culture as described in Example 7a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). PMPs are produced from the remaining cell culture by methods described in Example 1 and Example 2, and PMP concentration and size distribution are determined as described in Example 3. The relative concentration of produced PMPs per gram of FW and DW of BY-2 cells compared to the relative concentration of produced PMPs per gram of FW and DW BY-2-BnExo70A1: mgfp5 cells. Overexpression of Exo70A1 stimulates the production of PMPs.

Example 9: Scaled Isolation of PMPs from Plant Cell Culture Using a Bioreactor

This example describes the production of PMPs from plant cell culture scaled to large bioreactors, e.g., PMP production in a 100 mL, 200 mL, 5 L and 100 L bioreactor. The BY-2 cell line is used as model plant cell line.

a) BY2 Growth Conditions

As described in Example 1, BY-2 cells are cultured in the dark at 26° C., on an Innova 44R orbital shaker at 130 rpm in MS (Murashige and Skoog, 1962) medium (pH 5.8). The BY-2 cells are routinely subcultured weekly by transferring 5% (v/v) of a 7-day-old cell culture into 100 mL fresh liquid medium into a 250 mL sterile shake flask.

The preculture used for inoculation of elicitation experiments should be in the exponential growth phase. To determine the percentage packed cell volume (PCV) or fresh weight (FW) of exponentially growing cells, a growth curve is recorded from shake-flask cultures based on samples each consisting of at least three biological replicates. Three shake flasks are inoculated with 5-10% (v/v) of a routine BY-2 culture. 10 mL samples are taken at 0, 72, 96, 120, 148, 172, and 196 hours. The % PCV is measured by transferring a 10-mL sample of the cell culture to a graduated tube and centrifuging 5 min at 4000× g at room temperature. The % PCV is the ratio of the volume of the cell pellet to the volume of the cells+medium×100%. The Fresh weight (FW) is determined by vacuum filtering 10 mL of the medium through filter paper (pore size 4-12 µm) and weighing the cells retained on the filter paper. Then, cells are dried at 60° C. until the weight stays constant (at least 24 h) to determine the dry weight (DW). The % PCV, FW, and DW are plotted against the cultivation time to obtain the growth curve. To determine the optimal harvest time for the preculture, i.e., the mid-exponential phase, either an exponential function is plotted to the data and the derivative of that fit is used to plot the growth rate, or the optimal harvest time for the preculture is visually determined.

For bioreactor scaling the fresh weight is determined from a 7-day-old pre-culture in the exponential growth phase, and fresh cultures are seeded with a final concentration 3% FW (30 g cells/L) in a final volume of 100 mL BY-2 culture medium into 250 mL disposable shaker flasks.

b) Scalable PMP Production by Tobacco BY-2 Cells Using Bioreactors

In order to demonstrate that BY-2 cells can be scaled to grow in large bioreactors, while producing a similar concentration of PMPs, BY-2 cells are cultivated in different disposable bioreactor formats, modified from Raven et al., 2015 Biotechnology and Bioengineering, Vol. 112, No. 2. The PMP production in 100 mL and 500 mL flasks, and 5 L and 100 L bioreactors are compared by seeding fresh cultures with 3% FW (30 g BY-2 cells/L) in MS medium as described in Example 9a.

The cultivation volume of the 250 ml disposable shake flasks used with the BPM-60 system (Kuhner AG) is 100 mL, and the 500-mL glass shake flasks is filled with 200 mL. All shake flask cultures are incubated in the dark at 180 rpm and 26° C. in an Innova 44R incubator shakers (do 5 cm; Eppendorf). 5 L cultures of BY-2 cells are grown in 20-L Nalgene polycarbonate carboy vessels (Thermo Scientific), and the cultures are incubated at 26° C. and shaken at 180 rpm on a SR200-X shaker (do 7 cm; Kuhner AG). The SB200-X 200-L orbitally-shaken bioreactor system (Kuhner AG) is equipped with a 350-L disposable bag (Sartorius Stedim AG) filled with 100 L BY-2 suspension culture, head space aerated with air at a flow rate of 20 L/min and incubated at 26C and 80 rpm (do 5 cm).

The growth parameters, oxygen consumption and PMP production are monitored over a process time of seven days. At 0, 24, 48, 72, 96, 120, 144, 168 hours, the FW and DW are determined by analyzing 10 mL cell culture as described in Example 9a, and 1 mL of cell culture sample is used to determine the percentage of dead cells by adding 0.1 mL 0.4% (m/v) Trypan Blue solution to 0.9 mL cell culture and incubating for 5 min and recording (the proportion of dead cells should not exceed 5%). At 24, 48, 72, 96, 120, and 144 hrs 100 mL cell culture from all different vessel sizes is collected (5 L/100 L bioreactors are continuously sampled, for the smaller vessels additional flasks are seeded for different collection time points).

Next, the cell material from the harvested culture broth is removed by vacuum filtration over two layers of Miracloth (Merck-Millipore) and the remaining medium is filtered and crude PMPs are concentrated using Tangential flow filtration (TFF, HansaBiomed) followed by the production of PMPs using size exclusion chromatography (HansaBiomed), or other methods as described in Example 2. The PMP concentration and size distribution are determined as described in Example 3. The relative concentration of produced PMPs per gram of FW and DW BY-2 cells is determined, and used to compare the different culture vessels.

The BY-2 growth profiles and PMP production per gram of BY2 cell FW/DW is similar for all culture vessels, indicating that PMP production can be effectively scaled to bioreactors.

Example 10: PMP Production from Plant Cell Culture Medium

This example demonstrates that PMPs can be produced from plant cell culture. In this example, the *Zea mays* Black Mexican Sweet (BMS) cell line is a model plant cell line.

a) Production of *Zea mays* BMS Cell Line PMPs

The *Zea mays* Black Mexican sweet (BMS) cell line was purchased from the *Arabidopsis* Biological Resource Center (ABRC) and was grown in Murashige and Skoog basal medium pH 5.8, containing 4.3 g/L Murashige and Skoog Basal Salt Mixture (Sigma M5524), 2% sucrose (S0389, Millipore Sigma), 1× MS vitamin solution (M3900, Millipore Sigma), 2 mg/L 2,4-dichlorophenoxyacetic acid (D7299, Millipore Sigma) and 250 ug/L thiamine HCL (V-014, Millipore Sigma), at 24° C. with agitation (110 rpm), and was passaged 20% volume/volume every 7 days.

Figure 1A:
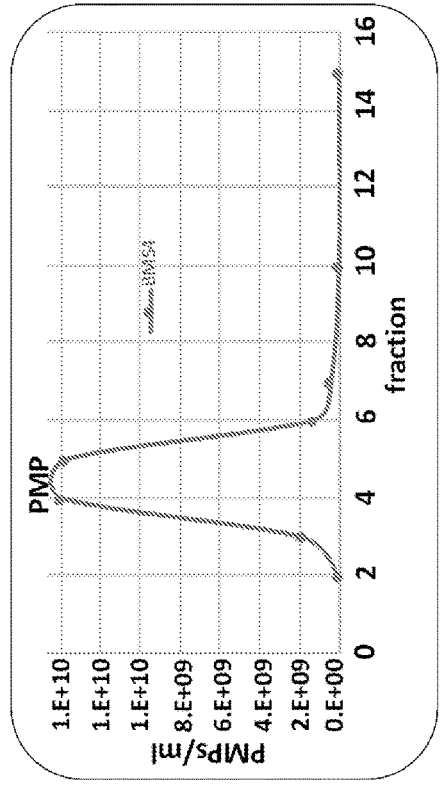
FIG. 1A is a graph showing particle concentration (particles/ml) in eluted BMS plant cell culture SEC fractions, as measured by nano-flow cytometry (NanoFCM). PMPs were eluted in SEC fractions 4-6.
Figure 1C:
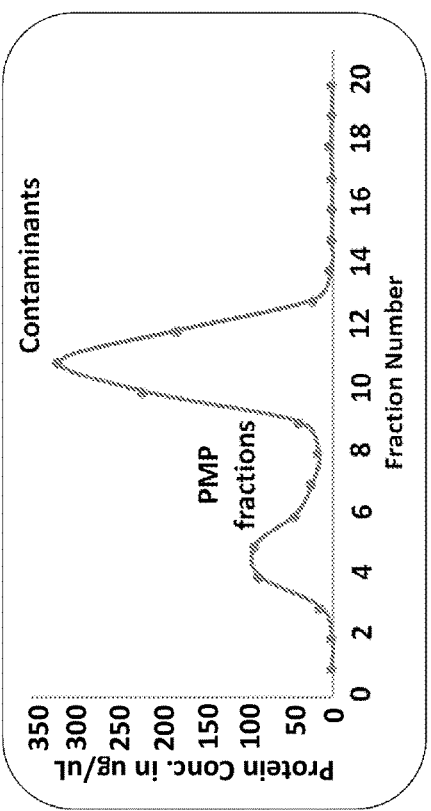
FIG. 1C is a graph showing protein concentration (μg/ml) in eluted BMS SEC fractions, as determined by BCA analysis. PMPs were eluted in fractions 4-6; fractions 9-13 contained contaminants.
Figure 1D:
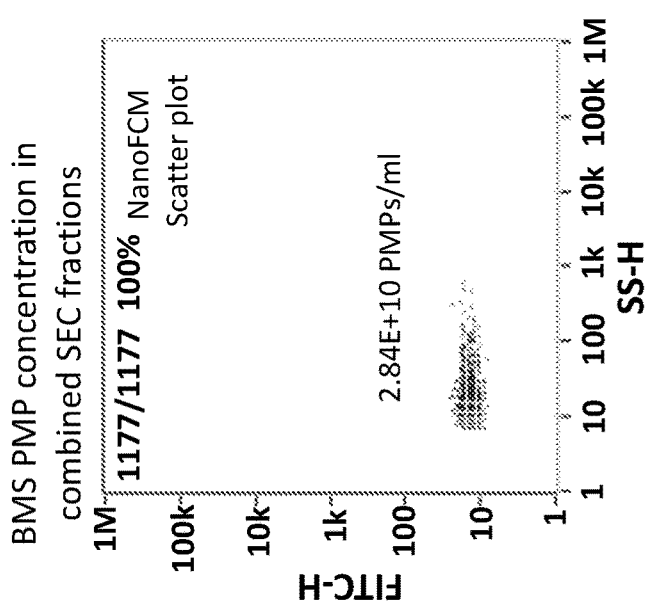
FIG. 1D is a scatter plot showing particles in the combined BMS PMP-containing SEC fractions as measured by nano-flow cytometry (NanoFCM). PMP concentration (particles/ml) was determined using a bead standard according to NanoFCM's instructions.
Figure 1E:
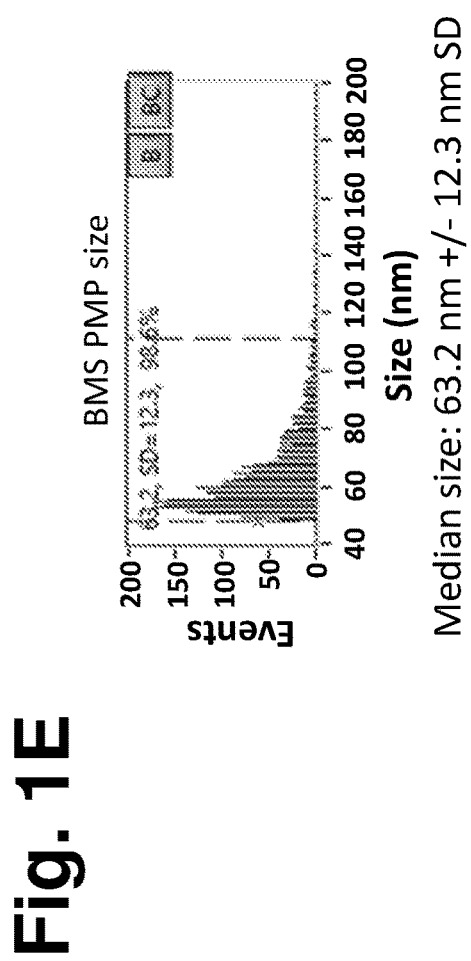
FIG. 1E is a graph showing the size distribution of BMS PMPs (nm) for the gated particles (background subtracted) of FIG. 1D. Median PMP size (nm) was determined using Exo bead standards according to NanoFCM's instructions.

Three days after passaging, 160 ml BMS cells was collected and spun down at 500× g for 5 min to remove cells, and 10,000×g for 40 min to remove large debris. Medium was passed through a 0.45 μm filter to remove large particles, and filtered medium was concentrated and washed (100 ml MES buffer, 20 mM MES, 100 mM NaCL, pH 6) by TFF (5 nm pore size) to 4 mL (40×). Next, size exclusion chromatography was used to elute the PMP-containing fractions, which were analyzed by NanoFCM for PMP concentration, by absorbance at 280 nm (SpectraMax®), and by a protein concentration assay (Pierce™ BCA assay, ThermoFisher) to verify the PMP-containing fractions and late fractions containing contaminants (FIGS. 1A-1C). SEC fractions 4-6 contained purified PMPs (fractions 9-13 contained contaminants), and were pooled together. The final PMP concentration ($2.84 \times 10^{10}$ PMPs/ml) and median PMP size (63.2 nm+/−12.3 nm SD) in the combined PMP containing fractions were determined by NanoFCM, using concentration and size standards provided by the manufacturer (FIGS. 1D-1E).

These data show that PMPs can be isolated, purified, and concentrated from plant liquid culture medium.

Example 11: Uptake of PMPs in Plants

This example demonstrates the ability of PMPs to be taken up and systemically transported in planta. In this example, *Arabidopsis thaliana* seedling PMPs are used as model PMPs, and *Arabidopsis* seedlings and alfalfa sprouts are used as model plants.

a) Production of *Arabidopsis thaliana* Seedling Culture Medium PMPs

Wild type *Arabidopsis thaliana* (At) Col-0 seeds were obtained from the ABRC, surface sterilized with 70% ethanol followed by incubation with 50% bleach/0.1% triton X-100 for 10 minutes and 4 sterile ddH$_2$O washes to remove the bleach solution. Seeds were stratified for 1d at 4° C. in the dark. Approximately 250 seeds were germinated per 100 cm$^2$ plate (pre-coated with 0.5% fetal calf serum in water), containing 20 mL 0.5× MS medium (2.15 g/L Murashige and Skoog salts, 1% sucrose, pH 5.8), sealed with 3M surgical tape and grown in an incubator with a photoperiod of 16 h light at 23° C./8 h dark at 21° C. Ten day-old seedling culture medium was collected from 70 culture plates, and the fresh weight (72.13 g) and dry weight (4.72 g) of the At seedlings was measured. A total of 900 ml culture medium was collected, and plates were washed with a 900 ml MES buffer (20 mM MES, 100 mM NaCL, pH 6). Medium was passed through a 0.45 μm filter to remove debris, and filtered medium was concentrated and washed (300 ml MES buffer) by TFF to 1000 ml (1.8×). Concentrated medium was dialyzed overnight at 4° C. in MES buffer, using 300 kDa dialysis membranes to remove contaminants. Subsequently, the dialyzed medium was further concentrated by TFF to a final concentration of 60 ml. Next, we used size exclusion chromatography to elute the PMP-containing fractions, which were analyzed by 280 nm absorbance (SpectraMax®) to verify the PMP-containing fractions and late fractions containing contaminants. SEC fractions 4-6 containing purified PMPs were pooled together, and concentrated further by pelleting PMPs for 1.5 hrs at 40,000× g and resuspending the pellet in Ultrapure water. The final PMP concentration ($1.50 \times 10^{11}$ PMPs/ml) and PMP size of 59.2 nm+/−5.5 nm (SD) were determined by NanoFCM, using concentration and size standards provided by the manufacturer.

b) Labeling of *Arabidopsis thaliana* Seedling PMPs with DyLight 800 NHS Ester

*Arabidopsis thaliana* seedling (Ats) PMPs were produced in Example 11 (a). PMPs were labeled with the DyLight 800

NHS Ester (Life Technologies, #46421) covalent membrane dye (DyL800). Briefly, Dyl800 was dissolved in DMSO to a final concentration of 10 mg/ml, 200 µl of PMPs were mixed with 5 µl dye, incubated for 1 h at room temperature on a shaker, and labeled PMPs were washed 2-3 times by ultracentrifugation at 100,000×g for 1 hr at 4° C. Pellets were resuspended with 1.5 ml UltraPure water. To control for the presence of potential dye aggregates, a dye-only control sample was prepared according to the same procedure, adding 200 µl of UltraPure water instead of PMPs. The final DyL800-labeled PMP pellet and DyL800 dye-only control were resuspended in a minimal amount of UltraPure water and characterized by NanoFCM. The final concentration of Ats DyL800-labeled PMPs was $1.14 \times 10^{11}$ PMPs/mL.

c) Uptake of DyL800-Labeled Ats PMPs by *Arabidopsis thaliana* and Alfalfa

To assess whether PMPs can be taken up and transported systemically in planta, *Arabidopsis* seedlings were germinated in liquid culture as described in Example 11 (a) on top of a mesh filter, to allow the roots to grow through the mesh, and to allow partial exposure of At seedlings to a PMP solution. Alfalfa sprouts were obtained from a local supermarket. 9 day-old *Arabidopsis* seedlings and Alfalfa sprouts were treated with a 0.5 ml solution of water (negative control), DyL800 dye only (dye control) DyL800-labeled Ats ($2.2 \times 10^{10}$ PMPs/ml) in 0.5×MS medium by partial root exposure (*A. thaliana* seedlings in a mesh floating in a PMP solution, or Alfalfa sprouts by partial root exposure in a 1.5 ml Eppendorf tube) for 22 or 24 hours, respectively, at 23° C. Plants where then washed 3 times in MS medium and imaged using an Odyssey® CLx infrared imager (Li-Cor).

Figure 2:
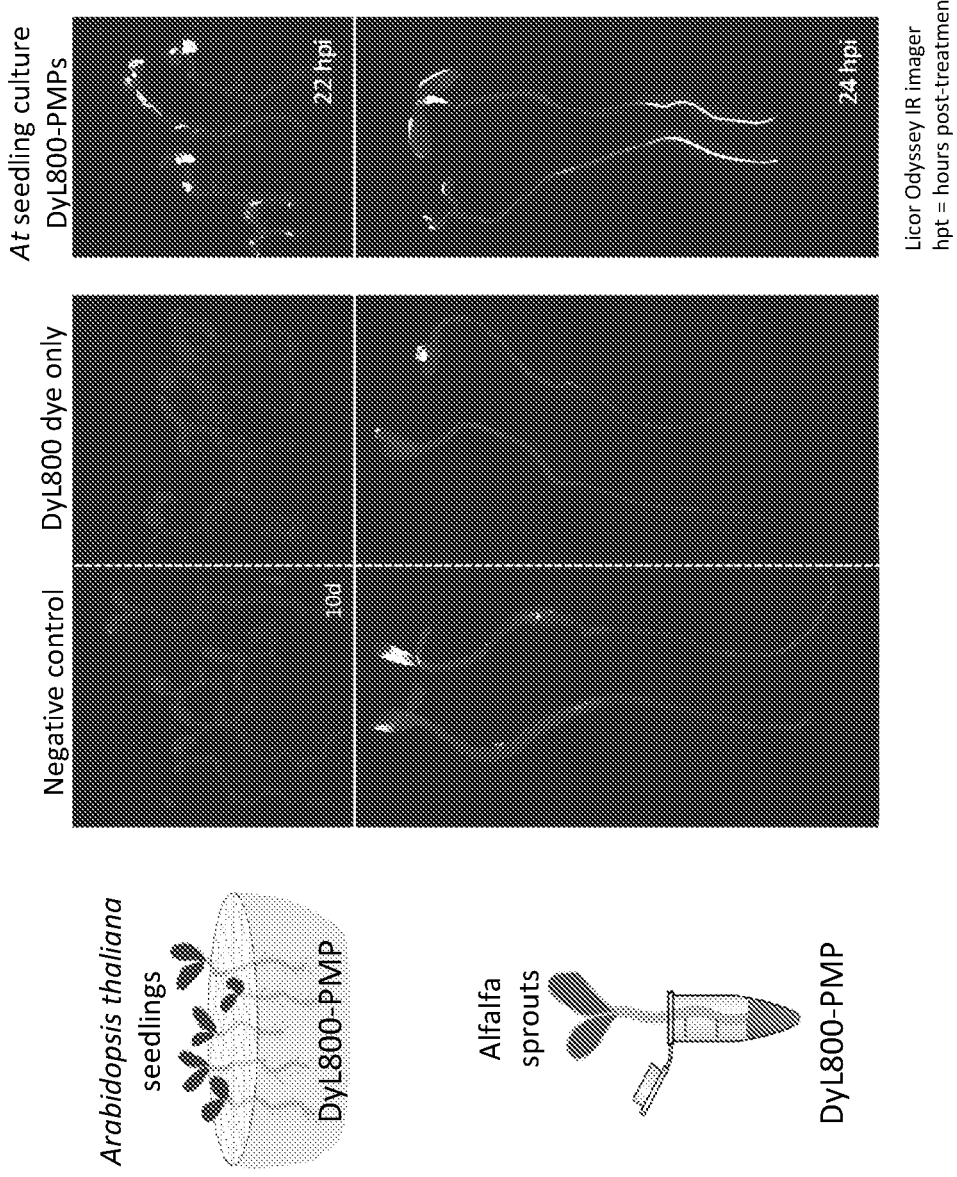
FIG. 2 is a pair of diagrams and a set of photomicrographs showing uptake of *Arabidopsis thaliana* (At) seedling culture PMPs labeled with DL800 by *Arabidopsis thaliana* seedlings (upper panels) and alfalfa sprouts (lower panels). Intensity of fluorescence of DL800 dye is displayed. Intensity of fluorescence was measured at 22 hpi (hours post-treatment) for *Arabidopsis thaliana* seedlings and at 24 hpi for alfalfa sprouts. Seedlings incubated with no dye ("negative control") and with free DL800 dye ("DL800 dye only") are shown as controls.

Compared to the negative (some autofluorescence in Alfalfa sprout leafs) and dye only control, all PMP sources showed a fluorescence signal (white is high fluorescent signal, black is no signal) in both *Arabidopsis* seedlings and Alfalfa sprouts, indicating that PMPs are taken up by both plants (FIG. 2). The presence of fluorescence signal in *Arabidopsis* leafs or alfalfa stem areas that were not exposed to the PMP solution indicates active transport of the PMPs in planta.

These data show that secreted PMPs can be taken up and transported in planta.

Example 12: PMP Production from Crucifer Plant Hydroponic Culture

This example demonstrates that PMPs can be produced from plant hydroponic culture. In this example, *Arabidopsis thaliana* seedlings are used as model plants.

a) Production of *Arabidopsis thaliana* Hydroponic Seedling Culture PMPs

Wild-type *Arabidopsis thaliana* Col-0 seeds were obtained from the *Arabidopsis* Biological Resource Center (ABRC). Seeds were surface sterilized with 70% ethanol followed by incubation with 50% bleach/0.1% Triton™ X-100 for 10 minutes, and 4 sterile ddH$_2$O washes to remove the bleach solution. Seeds were stratified for 3d at 4° C. in the dark. Approximately 200-220 seeds were germinated per 100 cm$^2$ plate (pre-coated with 0.5% fetal calf serum in water), containing 20 mL 0.5×MS medium (2.15 g/L Murashige and Skoog salts, 1% sucrose, pH 5.8), sealed with 3M surgical tape, and were grown in an incubator with a photoperiod of 16 h light at 23° C./8 h dark at 21° C. Seven day-old seedling culture medium was collected from 11 culture plates. A total of 150 mL culture medium was collected, and plates were washed with a 350 ml MES buffer (20 mM MES, 100 mM NaCL, PH 6). Medium was passed through a 0.45 µm filter to remove debris, and filtered medium was concentrated and washed (600 mL MES buffer) by TFF to 200 mL (2.5×). Concentrated medium was dialyzed overnight at 4° C. in MES buffer, using a 300 kDa dialysis membrane to remove contaminants. Subsequently, the dialyzed medium was further concentrated by TFF to a final volume of 26.5 mL (20× concentrated relative to starting material).

Figure 3E:
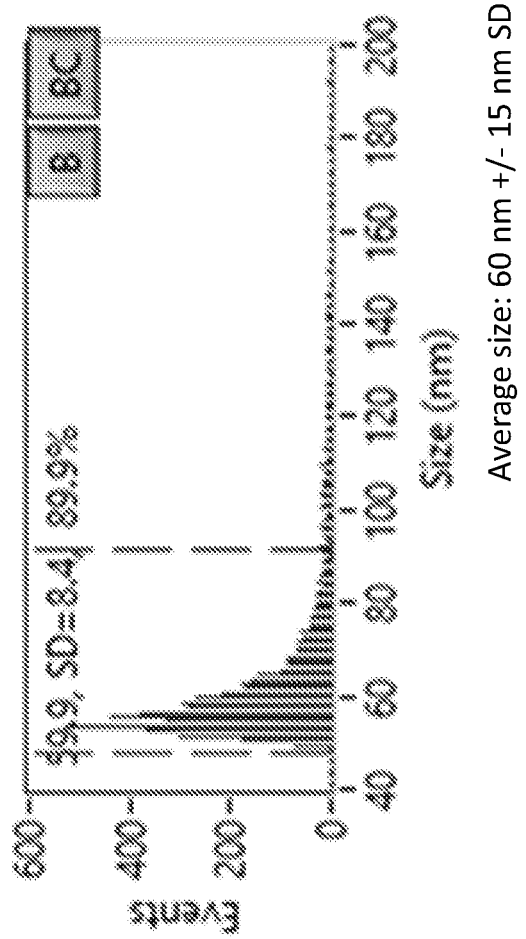
FIG. 3E is a graph showing the size distribution of Ats PMPs (nm) for the gated particles (background subtracted) of FIG. 3D. Median PMP size (nm) was determined using Exo bead standards according to NanoFCM's instructions.

Next, size exclusion chromatography was employed to elute the PMP-containing fractions, which were analyzed by NanoFCM for PMP concentration, absorbance at 280 nm (SpectraMax®), and protein concentration (Pierce™ BCA assay) to verify the PMP-containing fractions and late fractions containing contaminants (FIGS. 3A-3C). SEC fractions 4-6 contained purified PMPs (fractions 8-15 contained contaminants) and were pooled together. The final PMP concentration ($6.96 \times 10^9$ PMPs/ml) and PMP size (60 nm+/−15 nm SD) in the combined sterilized PMP-containing fractions were determined by NanoFCM, using concentration and size standards provided by the manufacturer (FIGS. 3D and 3E).

These data demonstrated that plants grown in hydroponic culture secreted PMPs into the media (secreted PMPs), which were isolated, purified and concentrated to produce a PMP composition comprising secreted PMPs.

Example 13: PMP Production from Crucifer Plant Root Culture

This example demonstrates that PMPs can be produced from plant root cultures. In this example, *Arabidopsis thaliana* is used as model plant.

a) Production of *Arabidopsis thaliana* Root Culture PMPs

Seeds of *Arabidopsis thaliana* (*Arabidopsis*) ecotype Columbia (Col-0) were sterilized as follows: 70% ethanol for 1 min, 50% household bleach with 0.1% Triton X-100 (Sigma) for 10 min, three washes with sterile deionized water. Sterilized seeds were resuspended in sterile 0.1% agarose and stratified at 4° C. for three days in the dark. Seeds were then placed on ½ MS plates (Murashige & Skoog basal salt mixture (Sigma) 2.15 g/L, sucrose 10 g/L, MES (Sigma) 0.5 g/L, phytoagar (Duchefa) 5 g/L, pH 5.8 adjusted with KOH) sealed with medical tape (3M) and placed in plant growth incubator (16 hr light, 23C/21C day/night) for seven days. Seedlings were transferred from plates to sterile 125 mL Erlenmeyer flask (Thermo Fisher; vented, non-baffled) containing 25 mL *Arabidopsis* Root Culture (ARC) medium (Murashige & Skoog basal salt mixture (Sigma) 4.3 g/L, 6% KH$_2$PO$_4$ 3 ml/L, 1000×Gamborg's vitamin stock (Sigma) 1 ml/L, biotin 1 mg/L, glycine 2 mg/L, sucrose 30 g/L, pH 5.8 adjusted with KOH) and grown with continuous light at 23° C. on an orbital shaker (Thermo Fisher) at 80 revolutions per minute (rpm) for two weeks. The root system was then excised from seedlings and transferred to fresh ARC medium (25 mL in new 125 mL flask). The plant hormone indole-3-acetic acid (IAA, an auxin, Sigma) was added at 0.05 mg/L for two days to stimulate root branching. The medium was then replaced with fresh ARC medium and the root culture grown for two weeks at 23° C. at 80 rpm in the dark. Culture medium was collected and centrifuged at 4,000×g for 30 min to pellet debris. Supernatant was filtered through 1 µM and 0.45 µM polyethersulfone (PES) filters (Whatman). Filtrate was subjected to ultracentrifugation at 100,000×g for 45 min to pellet PMPs. The pellet was resuspended in 1×PBS, pH 7.4 and analyzed using NanoFCM. PMP concentration (4.09×

Figure 4:
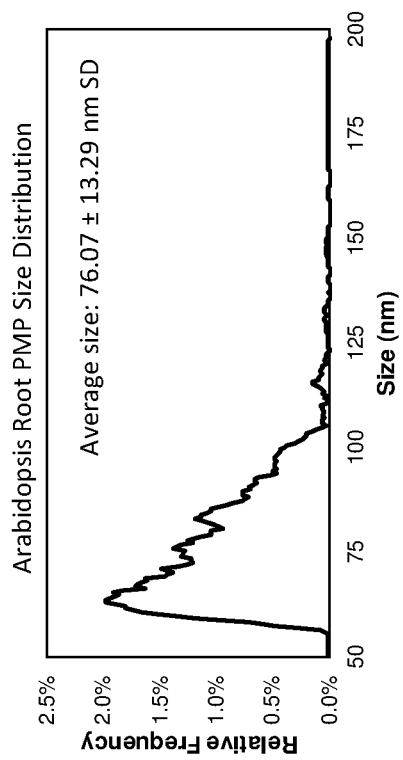
FIG. 4 is a graph showing the relative frequency of particles of a given size (nm) in *Arabidopsis thaliana* root culture PMPs as measured using NanoFCM over the size range of the instrument (50-200 nm). Data are presented as Mean±SD.

10$^9$ PMPs/mL) and PMP size (76±13 nm SD) were determined by NanoFCM using concentration and size standards provided by the manufacturer (FIG. 4). The resulting PMPs were additionally purified using Zeba spin desalting columns (MWCO 40 kDa, Thermo Fisher) equilibrated with 1×PBS, pH 7.4. The protein concentrations before and after Zeba column purification were 0.75 mg/ml and 0.65 mg/mL, respectively, as detected by Pierce™ BCA protein assay (Thermo Fisher).

These data demonstrate that PMPs can be isolated, purified, and concentrated from root cultures.

Example 14: Enhanced Production of PMPs from Plant Cell Culture Using Abiotic, Biotic, and Chemical Stimulants This example demonstrates that PMP production from plant cell culture can be elicited by abiotic and biotic stimuli. Zea mays, Black Mexican sweet (BMS) cell culture is used as model plant cell line, sodium chloride and salicylic acid are used as model abiotic stimuli, and flagellin 22 (flg22) is used as a model biotic stimulus.

a) Zea mays, Black Mexican Sweet (BMS) Cell Culture Conditions

Zea mays, Black Mexican Sweet (BMS) cells were purchased from the ABRC. BMS cells were grown in Murashige and Skoog basal medium pH 5.8, containing 4.3 g/L Murashige and Skoog Basal Salt Mixture (Sigma M5524), 2% sucrose (S0389, Millipore Sigma), 2 mg/L 2,4-dichlorophenoxyacetic acid (D7299, Millipore Sigma), 250 ug/L thiamine HCL (V-014, Millipore Sigma) and a 1× MS vitamin mix solution in ddH$_2$O. The 1× vitamin mix solution contained niacin (N0761-100G, Millipore Sigma), pyroxidine hydrochloride (P6280-25G, Millipore Sigma), D-pantothenic acid hemicalcium salt (P5155-100G, Millipore Sigma), L-Asparagine (A4159-25G, Millipore Sigma), and myo-inositol (I7508-100G, Millipore Sigma) at respective final concentrations of 1.3 mg/L, 250 µg/L, 250 µg/L, 130 mg/L, and 200 mg/L. Cells were grown in 1 L vented conical sterile flasks in dark conditions at 24° C. with agitation (110 rpm). For experiments, BMS cells were grown until cells were at a packed cell volume (PCV) of 20%. The PCV estimates cell density and is defined as the volume of cells divided by the total volume of the cell culture aliquot. The Packed Cell Volume is expressed as a percentage. The PCV was determined as follows: 5 mL of BMS cell suspension was centrifuged for 5 min at 3900 rpm, and the volume of the cell pellet was determined.

c) Increased PMP Production by Zea mays BMS Cells by Flagellin 22 Elicitation

To determine the effect of the flagellin peptide flg22 (QRLSTGSRINSAKDDAAGLQIA (SEQ ID NO: 14) (AnaSpec AS-62633) on PMP production by Zea mays BMS cells, 200 mL of BMS cell culture were prepared as described above. A cytotoxicity assay was carried out to determine the range of concentrations of flg22 that would not affect apparent BMS cell growth, and the flg22 concentration of 1 µM was determined to be compatible with cell growth. 30 mL of BMS cell suspension was distributed in individual 125 ml conical culture vented-flasks. In parallel, 89.55 mL of fresh media was mixed with 450 µL of 400 µM flg22 peptide suspension prepared in ultrapure sterile water to a final concentration of 2 µM. For the control conditions, 450 µL of ultrapure sterile water was added instead of flg22. Then, 30 ml of the media/flg22 or media/water mix was added to each flask containing 30 mL cell suspension (1:1 v/v) to a flg22 final concentration of 1 µM. Biological triplicates were performed for both flg22 treatment and control conditions. Control cells and cells treated with flg22 were grown at 24° C. with agitation (110 rpm) for 96 hours.

Figure 5C:
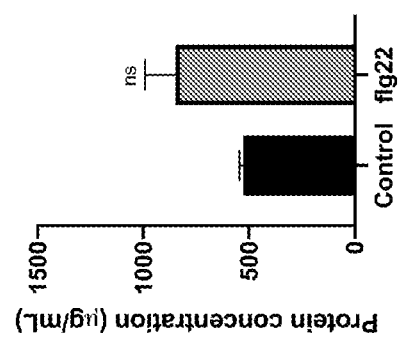
FIG. 5C is is a graph showing protein concentration in control BMS cell culture and BMS cell culture treated with 1 μM flg22 as measured using a BCA assay.
Figure 5B:
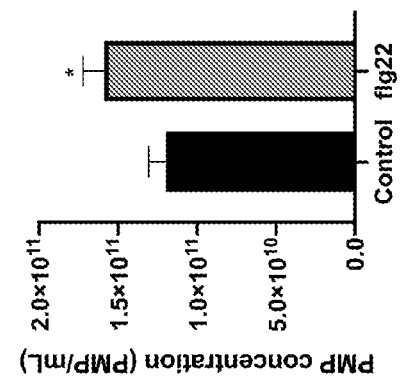
FIG. 5B is a graph showing concentration of PMPs in control BMS cell culture and BMS cell culture treated with 1 μM flg22 as measured using NanoFCM.
Figure 5A:
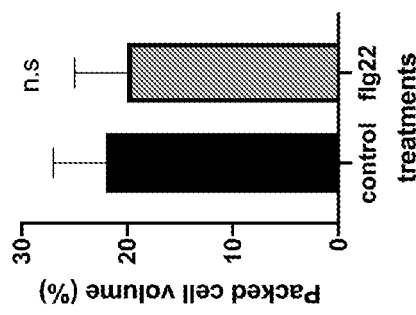
FIG. 5A is a graph showing packed cell volume (PCV; expressed in percentage) in control *Zea mays* Black Mexican Sweet (BMS) cell culture and BMS cell culture treated with 1 μM flagellin peptide flg22.

After 96 hours of incubation, flg22-treated and control cell cultures were processed in identical conditions as follows. 1 mL of cell culture sample was used to determine PCV as described above (FIG. 5A). Cells were sedimented to the bottom of the flasks to collect 30 mL of medium and were centrifuged for 15 min at 4000× g prior to 1 µm and 0.45 µm filtration. Then, 20 mL of the resulting medium was concentrated by ultracentrifugation (45 min, 100,000×g, 4'° C.). The final PMP pellets were resuspended in 200 µL of sterile PBS, pH 7.4. PMP concentration and PMP size were determined by NanoFCM using concentration and size standards provided by the manufacturer, and the protein concentration was determined by Pierce™ BCA protein assay (Thermo Fisher) (FIGS. 5B and 5C). The control conditions, perfomed in triplicates, presented an average PMP concentration of 1.2×10$^{11}$ PMPs/mL, whereas the PMP concentration was on average 1.59×10$^{11}$ PMP/mL in the flagellin-stimulated conditions done in triplicates. The mean PMP size was 88.7±15 nm for the control treatment and 86.6±15 nm for the flg22 treatment. These data indicated that the flg22 peptide stimulates the production of PMPs by BMS cells in culture.

d) Increased PMP Production by Zea mays BMS Cells by Salicylic Acid Elicitation

To determine the effect of salicylic acid (SA) on PMP production by Zea mays BMS cells, 200 ml of BMS cell culture were prepared as described above. A cytotoxicity assay was carried out to determine the range of concentrations of SA that would not affect apparent BMS cell growth, and a concentration of 100 µM was found to be compatible with cell growth. 30 mL of BMS cell suspension was distributed into individual 125 ml conical culture vented-flasks. In parallel, 89.82 mL fresh media was mixed with 180 µL of 100 mM salicylic acid solution prepared in dimethyl sulfoxide (DMSO) to a final concentration of 200 µM. For the control conditions, 180 µL of DMSO was added instead of salicylic acid. Then, 30 mL of the media/SA or media/water mix was added to each flask containing 30 mL cell suspension (1:1 v/v) to a final SA concentration of 100 µM. Biological triplicates were performed for both SA treatment and control conditions. SA treatment and control cell cultures were grown at 24° C. with agitation (110 rpm) for 96 hours.

After 96 hours of incubation, both SA-treated and control cell cultures were processed in identical conditions as follows. 1 mL of cell culture sample was used to determine their PCV as described above (FIG. 6A). Cells were sedimented to the bottom of the flasks to collect 30 ml of medium, and wre centrifuged for 15 min at 4000× g prior to 1 µm and 0.45 µm filtration. Then, 20 mL of the resulting medium was concentrated by ultracentrifugation (45 min, 100,000×g, 4° C.). The final PMP pellets were resuspended in 200 µL of sterile PBS, pH 7.4. PMP concentration and PMP size were determined by NanoFCM using concentration and size standards provided by the manufacturer, and protein concentration was determined by Pierce™ BCA protein assay (ThermoFisher Scientific) (FIGS. 6B and 6C). The resulting PMPs were additionally purified using Zeba spin desalting columns (MWCO 40 kDa, ThermoFisher) equilibrated with 1×PBS, pH 7.4. The control conditions, performed in triplicates, presented an average PMP concentration of 1.47×10$^{11}$ PMP/mL, while the PMP concentration was on average 1.84×10$^{11}$ PMP/mL in the salicylic acid-stimulated conditions performed in triplicates. The protein concentration following purification was reduced by about 3-fold for SA-treated PMPs and about 2-fold for control PMPs (e.g. for control: 0.55 mg/mL vs. 0.26 mg/mL), while 95-98% of particles were retained after purification. The mean PMP size was 87±15 nm for control PMPs and 86.5±15 nm for PMPs from the SA treatment. These data demonstrated that salicylic acid stimulates the production of PMPs by BMS cells in culture.

Example 15: Large-Scale PMP Production from Plant Cell Culture Medium Using a Bioreactor This example demonstrates that PMPs can be produced from large-scale plant cell culture. In this example, the *Zea mays* Black Mexican Sweet (BMS) cell line is used as a model plant cell line for PMP production.

a) Production of *Zea mays* BMS Cell Line PMPs

*Zea mays* BMS cells were cultured as described in Example 12 (a). BMS cells were passaged at a PCV of approximatively 30% every 7 days. PCV was determined as described in Example 12 (a).

b) Scaled PMP Production from Plant Cell Culture Medium Using a Bioreactor

Figure 7A:
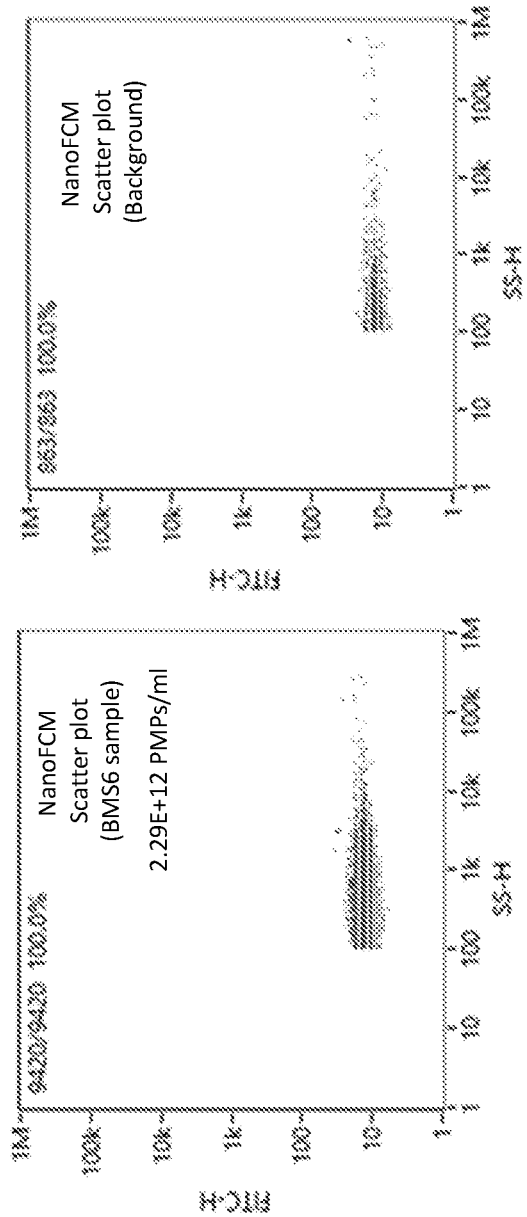
FIG. 7A is a scatter plot showing particles in the BMS cell culture PMP-containing SEC fractions purified from a 4 L culture as measured by NanoFCM. The left panel shows BMS PMPs, and the right panel shows the BMS buffer background. PMP concentration (particles/mL) was determined using a bead standard according to NanoFCM's instructions.
Figure 7C:
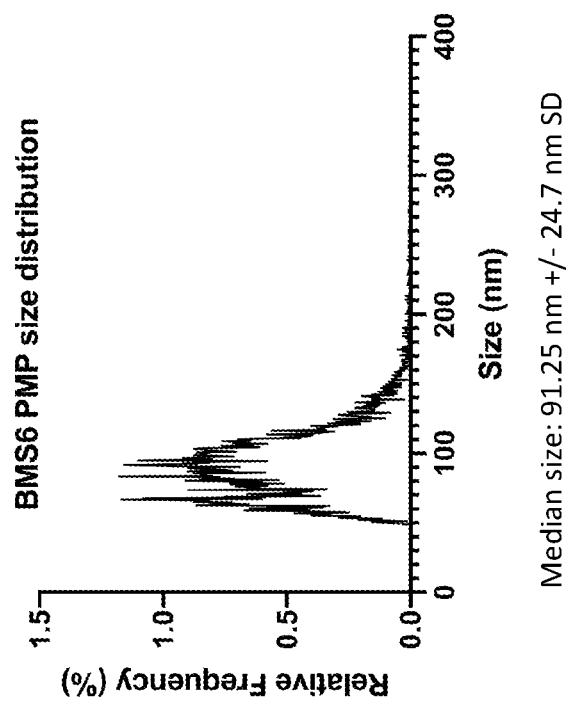
FIG. 7C is a graph showing the size distribution of BMS cell culture PMPs (nm) for the gated particles (background subtracted) of FIG. 7A. Median PMP size (nm) was determined using Exo bead standards according to NanoFCM's instructions.
Figure 7B:
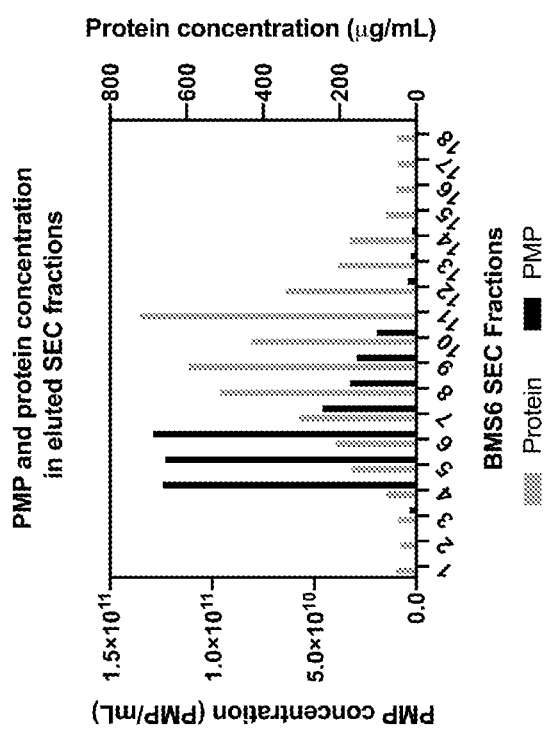
FIG. 7B is is a graph showing PMP concentration protein concentration (particles/mL, as measured using NanoFCM) and protein concentration (μg/mL, as determined by BCA analysis) in eluted BMS cell culture SEC fractions. PMPs were eluted in fractions 3-8.

For PMP production, BMS cells were grown until cells were at a PCV of 25%. Then, 4 L of cells were allowed to sediment and 3 L of the upper BMS medium was collected and spun down at 3000× g for 20 min and 10,000×g for 40 min to remove large debris. EDTA was added to a final concentration of 50 mM and pH was adjusted to 7.5. Medium was filtered through a 11 µm, 1 µm, and 0.45 µm filter to remove large particles and aggregates. The resulting filtered medium was concentrated 10 times, washed with 10× volume (v/v, 3.3 L PBS 1×, pH 7.4), and concentrated to 60 mL (50×) using a tangential flow filtration (TFF) system (300 kDa pore size, Repligen). Next, we used size exclusion chromatography (SEC) to elute the PMP-containing fractions, which were analyzed by NanoFCM for PMP concentration and size (FIGS. 7A and 7B). The protein concentration in fractions was detected by Pierce™ BCA protein assay (FIG. 7B). Analyses of number of particles and protein concentration analyses were carried out to verify the PMP-containing fractions and contaminants-containing fractions (FIGS. 7A and 78). SEC fractions 3-8 contained purified PMPs (fractions 9-18 contained contaminants) and were pooled together. The final PMP concentration (2.29× $10^{12}$ PMPs/mL) and median PMP size (91.25 nm+/−24.7 nm SD) in the combined concentrated PMP-containing fractions were determined by NanoFCM using concentration and size standards provided by the manufacturer (FIGS. 7A and 7C). Scaling up production from 160 mL to 4 L in bioreactors scaled up PMP concentration from 2.84×$10^{10}$ PMP/mL (Example 10) to 2.29×$10^{12}$ PMP/mL.

These data demonstrated that cultured plant cells secrete PMPs into the media and that they can be isolated, purified and concentrated from bioreactors in scaled production.

Example 16: Isolation of PMPs from Roots of Tomato Grown in Hydroponic Culture and Enhancement of PMP Production Using Chemical Stimuli This example demonstrates that PMPs can be produced from plant hydroponic cultures. In this example, tomato is used as a model plant. Furthermore, this example demonstrates that PMP production from plant hydroponic culture can be elicited by chemical stimuli. Salicylic acid is used as a model chemical stimulus.

a) Growth of Tomato Plants in Hydroponic Cultures

Figure 8B:
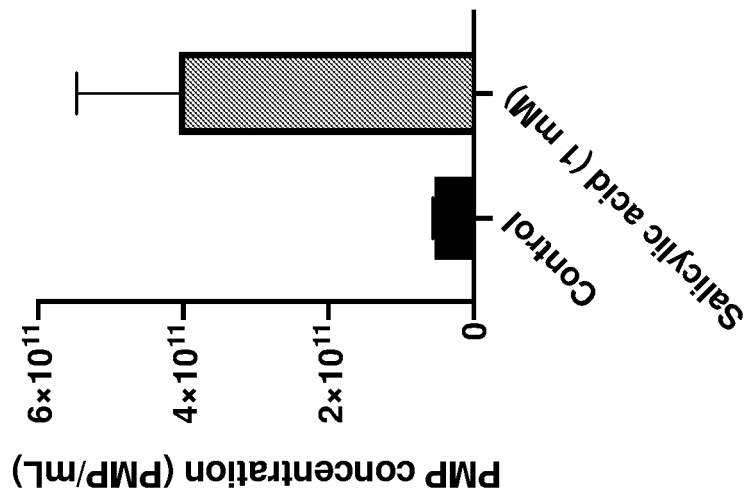
FIG. 8B is a graph showing PMP concentration (PMPs/mL, as measured using NanoFCM) for PMPs isolated from roots of tomato plants grown in hydroponic culture. Graph shows mean±SEM, n=2.
Figure 8A:
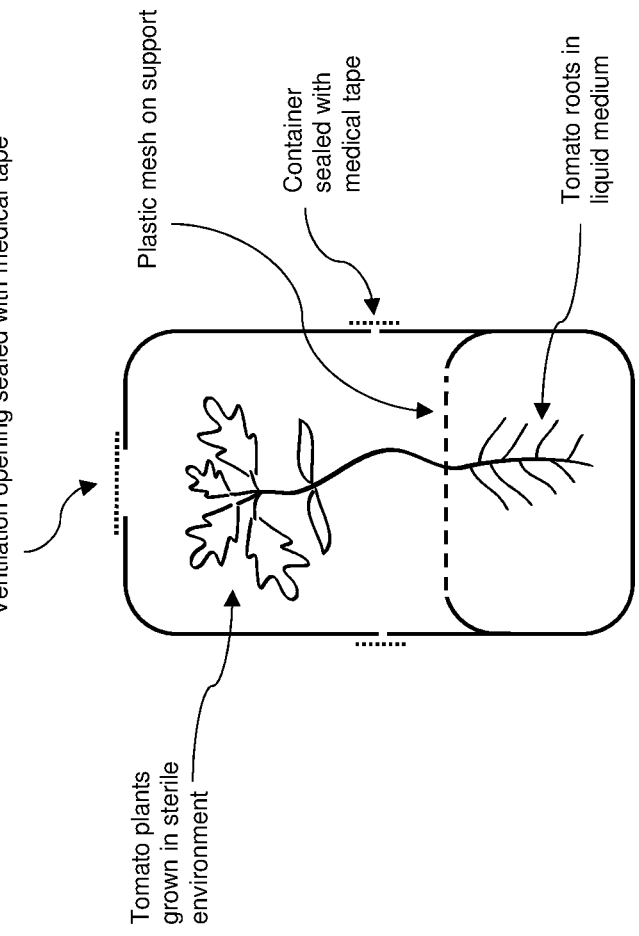
FIG. 8A is a schematic diagram showing a sterile hydroponic plant growth chamber.

Seeds of tomato (*Solanum lycopersicum*) cultivar Moneymaker were sterilized as follows: 70% ethanol for 3 min, 50% household bleach with 0.1% Triton X-100 (Sigma) for 20 min, washed three times with sterile deionized water. Sterilized seeds were germinated on moistened filter paper (Whatman®) in sterile Petri dishes sealed with medical tape (3M) and placed in a plant growth incubator (16 hr light, 23C/21C day/night) for seven days. Clear, square, presterilized plastic containers (PhytoTech Labs) were assembled into hydroponic containers similar to what was previously described (Alatorre-Cobos et al., BMC Plant Biol., 14: Article No.: 69, 2014; FIG. 8A). Two containers were cut with sterile scalpels to assemble a support for a sterile polytetrafluoroethylene (PTFE) plastic mesh (McMaster-Carr). Plastic mesh was fixed to plastic supports with sterile staples. Small openings were cut into the plastic mesh and germinated seedlings threaded through the openings using sterile forceps. Each mesh supported five seedlings. 200 mL 1×MS growth medium (Murashige & Skoog basal salt mixture (Sigma) 4.3 g/L, sucrose 10 g/L, MES (Sigma) 0.5 g/L, pH 5.8 adjusted with KOH) was added to a whole plastic container serving as the base. Plastic support with mesh and threaded seedlings was placed into the base container. A second whole plastic container with a cut 2 cm² opening and sealed with medical tape was used as the lid. The two halves were sealed with medical tape and the containers transferred to a plant incubator (16 hr light, 23° C./21° C. day/night) for three weeks.

b) Stimulation of PMP Production Using Salicylic Acid

To determine the effect of salicylic acid on PMP production by tomato plants grown in hydroponic culture, three-week-old plants were treated with 1 mM salicylic acid for three days by addition to the liquid growth medium. Salicylic acid (Sigma) was prepared as a 1M stock in DMSO (Sigma). Sterile 200 µL salicylic acid or sterile 200 µL DMSO were added to the treatment and control plants, respectively, the growth containers resealed with medical tape, and the plants were placed back into the growth incubator.

c) Isolation of PMPs Produced by Tomato Roots Grown in Hydroponic Cultures

Culture medium (180 mL per container) was collected and centrifuged at 4,000×g for 30 min to pellet debris. Supernatant was filtered through 1 µM and 0.45 µM PES filters (Whatman®). Filtrate was concentrated to 20 mL using tangential flow filtration (TFF-Easy columns, HansaBioMed). Concentrated culture medium was subjected to ultracentrifugation at 100,000×g for 45 min to pellet PMPs. Pellets were resuspended in 200 µL 1×PBS, pH 7.4 and analyzed using nano flow-cytometry (NanoFCM). PMP concentration (treatment: 4.06×$10^{11}$±1.41×$10^{11}$ PMP/mL (SEM); control: 5.44×$10^{10}$±2.49×$10^{10}$ PMP/mL (SEM)) and PMP size (treatment: 97±25 nm (SD); control: 82±27 nm (SD)) were determined by NanoFCM using concentration and size standards provided by the manufacturer (FIG. 8B). Our data shows that plants can be grown in hydroponic culture and that PMPs secreted by the plant roots can be isolated from the medium. Our data further shows that hydroponically grown tomato plants can be elicited with chemical stimulants, in this example salicylic acid, to enhance secretion of PMPs from the plant roots.

OTHER EMBODIMENTS

Some embodiments of the invention are within the following numbered paragraphs.

1. A method for producing plant messenger packs (PMPs), the method comprising:
   (a) obtaining a culture medium in which a plant, a plant part, or a plant cell has been cultured; and
   (b) purifying PMPs from the culture medium.
2. A method for producing plant PMPs, the method comprising:
   (a) culturing a plant, a plant part, or a plant cell in a culture medium;
   (b) harvesting the culture medium or a portion thereof; and
   (c) purifying PMPs from the culture medium.
3. The method of paragraph 1 or 2, wherein the culture medium is a liquid culture medium.
4. The method of paragraph 3, wherein the liquid culture medium is in a hydroponic system.
5. The method of paragraph 1 or 2, wherein the culture medium is a gel culture medium.
6. The method of paragraph 5, wherein the gel culture medium is agar or agarose.
7. The method of paragraph 1 or 2, wherein the culture medium is a semi-solid or solid culture medium.
8. The method of paragraph 7, wherein the semi-solid or solid culture medium is a sterile natural soil or a sterile synthetic soil.
9. The method of any one of paragraphs 1-8, wherein the culture medium comprises one or more of a macronutrient, a micronutrient, a salt, an enzyme, an antibiotic, an antifungal agent, or a plant growth factor.
10. The method of any one of paragraphs 1-9, wherein the culturing is performed in a bioreactor.
11. The method of paragraph 10, wherein the bioreactor is a vessel having a capacity of at least 1 L, 10 L, 50 L, 100 L, or 500 L.
12. The method of any one of paragraphs 1-11, wherein the harvesting comprises separating the plant, plant part, or plant cell and the plant culture medium.
13. The method of any one of paragraphs 1-12, wherein the harvesting does not comprise disruption of the plant, plant part, or plant cell.
14. The method of paragraph 12 or 13, wherein the separating comprises one or more of gravity sedimentation, centrifugation, a spin filter, and a membrane system.
15. The method of paragraph 14, wherein the harvesting comprises centrifugation of the plant, plant part, or plant cell and the culture medium.
16. The method of any one of paragraphs 1-13, wherein the harvesting comprises juicing the culture medium.
17. The method of any one of paragraphs 1-13, wherein the harvesting comprises washing the culture medium.
18. The method of any one of paragraphs 1-17, wherein the culture medium is periodically harvested and replaced.
19. The method of any one of paragraphs 1-18, wherein the culture medium is provided at a volume of at least 1 L.
20. The method of any one of paragraphs 1-19, wherein the plant is a seedling.
21. The method of paragraph 20, wherein the seedling is germinated in the culture medium.
22. The method of any one of paragraphs 1-19, wherein the plant part is a radicle or a root.
23. The method of paragraph 22, wherein the root is not attached to a plant shoot.
24. The method of any one of paragraphs 1-19, wherein the plant part is a pollen grain.
25. The method of any one of paragraphs 1-19, wherein the plant part is a callus.
26. The method of any one of paragraphs 1-25, wherein the plant is a dicot or a monocot or the plant part is a part of a dicot or a monocot.
27. The method of any one of paragraphs 1-26, wherein the plant or plant part is a soybean plant or a part thereof, a fava bean plant or a part thereof, an *Arabidopsis* plant or a part thereof, a tomato plant or a part thereof, a barley plant or a part thereof, or an oat plant or a part thereof.
28. The method of any one of paragraphs 1-19, wherein the plant cell is a tobacco BY-2 cell.
29. The method of any one of paragraphs 1-28, wherein the plant, plant part, or plant cell has been grown for at least 24 hours.
30. The method of paragraph 29, wherein the plant, plant part, or plant cell has been grown for at least 1 week.
31. The method of any one of paragraphs 1-30, wherein the plant, plant part, or plant cell is genetically modified.
32. The method of paragraph 31, wherein the genetically modified plant, plant part, or plant cell contains a genetic modification that is effective to increase the production of PMPs from the plant, plant part, or plant cell relative to an unmodified plant, plant part, or plant cell.
33. The method of paragraph 31 or 32, wherein the genetically modified plant, plant part, or plant cell contains a genetic modification that is effective to increase expression of EXO70a1 or EXO84 in the plant, plant part, or plant cell relative to an unmodified plant, plant part, or plant cell.
34. The method of paragraph 33, wherein the genetic modification is stable integration of an EXO70a1 or an EXO84 transgene.
35. The method of any one of paragraphs 1-34, further comprising exposing the plant, plant part, or plant cell to an effective amount of a stimulant to increase PMP production.
36. The method of paragraph 35, wherein the stimulant is a biotic stimulant.
37. The method of paragraph 36, wherein the biotic stimulant is a microbial stimulant.
38. The method of paragraph 37, wherein the microbial stimulant is a bacterial polypeptide, a bacterial saccharide, a bacterial nucleic acid, or a bacterial small molecule.
39. The method of paragraph 38, wherein the bacterial polypeptide is Elongation Factor Tu 18 (EFT18).
40. The method of paragraph 37, wherein the microbial stimulant is a fungal polypeptide, a fungal saccharide, a fungal nucleic acid, or a fungal small molecule.
41. The method of paragraph 40, wherein the fungal polypeptide is Flagellin2.
42. The method of paragraph 37, wherein the microbial stimulant is a microorganism.
43. The method of paragraph 42, wherein the microorganism is a bacterium.
44. The method of paragraph 42, wherein the microorganism is a virus or a protozoan.
45. The method of paragraph 42, wherein the microorganism is a fungus.
46. The method of paragraph 36, wherein the plant stimulant is an abiotic stimulant.
47. The method of paragraph 46, wherein the abiotic stimulant is osmotic stress, drought, water deprivation, flood, high light intensity, very high light intensity, high temperature, low temperature, salinity, heavy metal toxicity, anaerobiosis, nutrient deficiency, nutrient excess, UV irradiation, atmospheric pollution, or a chemical that induces production of reactive oxygen species (ROS).

48. The method of paragraph 36, wherein the plant stimulant is a chemical elicitor.

49. The method of paragraph 48, wherein the chemical elicitor is salicylic acid.

50. The method of paragraph 48, wherein the chemical elicitor is benzothiadiazole.

51. The method of paragraph 48, wherein the chemical elicitor is 2,6-dichloroisonicotinic acid.

52. The method of paragraph 36, wherein the stimulant is a heterologous nucleic acid that increases gene expression of EXO70a1 or EXO84.

53. The method of any one of paragraphs 36-52, wherein the stimulant is added at least 24 hours before the harvesting of the culture medium.

54. The method of any one of paragraphs 1-53, wherein the purifying step comprises isolating a crude PMP fraction, wherein the crude PMP fraction has a decreased level of at least one contaminant or undesired component from the plant or part thereof relative to a level in an initial sample.

55. The method of paragraph 54, wherein the purifying step further comprises purifying the crude PMP fraction, thereby producing a plurality of pure PMPs, wherein the plurality of pure PMPs have a decreased level of at least one contaminant or undesired component from the plant or part thereof relative to a level in the crude PMP fraction.

56. The method of any one of paragraphs 1-55, wherein the method further comprises determining the purity of the PMPs and collecting PMPs identified as pure.

57. The method of any one of paragraphs 1-56, further comprising formulating the PMPs with a carrier, thereby generating a PMP composition.

58. The method of paragraph 57, wherein the carrier is an agriculturally acceptable carrier.

59. The method of paragraph 58, wherein the PMP composition is formulated for delivery to a plant.

60. The method of paragraph 57, wherein the carrier is a pharmaceutically acceptable carrier.

61. The method of paragraph 60, wherein the PMP composition is formulated for administration to a human.

62. The method of any one of paragraphs 57-61, wherein the composition is formulated as a liquid, a solid, an aerosol, a paste, a gel, or a gas composition.

63. The method of any one of paragraphs 57-62, wherein the PMP composition is stable for at least 24 hours, 48 hours, seven days, or 30 days.

64. The method of any one of paragraphs 57-63, wherein the PMP composition is stable at a temperature of at least 4° C., 20° C., 24° C., or 37° C.

65. The method of any one of paragraphs 1-64, further comprising loading the PMPs with a heterologous functional agent.

66. The method of paragraph 65, wherein the heterologous functional agent is a heterologous agricultural agent.

67. The method of paragraph 66, wherein the heterologous agricultural agent is a pesticidal agent.

68. The method of paragraph 66, wherein the heterologous agricultural agent is a fertilizing agent.

69. The method of paragraph 66, wherein the heterologous agricultural agent is an herbicidal agent.

70. The method of paragraph 66, wherein the heterologous agricultural agent is a plant-modifying agent.

71. The method of paragraph 65, wherein the heterologous functional agent is a heterologous therapeutic agent.

72. The method of paragraph 71, wherein the heterologous therapeutic agent comprises an antifungal agent, an antibacterial agent, a virucidal agent, an anti-viral agent, an insecticidal agent, a nematicidal agent, an antiparasitic agent, or an insect repellent.

73. A method for producing PMPs, the method comprising:
(a) culturing a plant, plant part, or a plant cell in a bioreactor;
(b) exposing the plant, plant part, or plant cell to an effective amount of a stimulant to increase PMP production;
(c) harvesting the culture medium; and
(d) purifying PMPs from the culture medium.

74. A PMP composition comprising a plurality of PMPs, wherein the PMPs are produced by a process comprising the steps of:
(a) obtaining a culture medium in which a plant, a plant part, or a plant cell has been cultured; and
(b) purifying PMPs from the culture medium.

75. A PMP composition comprising a plurality of PMPs, wherein the PMPs are produced by a process comprising the steps of:
(a) culturing a plant, a plant part, or a plant cell in a culture medium;
(b) harvesting the culture medium; and
(c) purifying PMPs from the culture medium.

76. The PMP composition of paragraph 74 or 75, further comprising exposing the plant, plant part, or plant cell to an effective amount of a stimulant to increase PMP production.

77. The PMP composition of any one of paragraphs 74-76, wherein the stimulant is a biotic stimulant, an abiotic stimulant, or a chemical elicitor.

78. The PMP composition of any one of paragraphs 74-77, wherein the purifying step comprises isolating a crude PMP fraction, wherein the crude PMP fraction has a decreased level of at least one contaminant or undesired component from the plant or part thereof relative to a level in an initial sample.

79. The PMP composition of paragraph 78, wherein the purifying step further comprises purifying the crude PMP fraction, thereby producing a plurality of pure PMPs, wherein the plurality of pure PMPs have a decreased level of at least one contaminant or undesired component from the plant or part thereof relative to a level in the crude PMP fraction.

80. The PMP composition of any one of paragraphs 74-79, wherein the PMP composition further comprises formulating the PMPs with a carrier.

81. The PMP composition of paragraph 80, wherein the carrier is an agriculturally acceptable carrier.

82. The PMP composition of paragraph 81, wherein the PMP composition is formulated for delivery to a plant.

83. The PMP composition of paragraph 80, wherein the carrier is a pharmaceutically acceptable carrier.

84. The PMP composition of paragraph 83, wherein the PMP composition is formulated for administration to a human.

85. The PMP composition of any one of paragraphs 74-84, wherein the composition is formulated as a liquid, a solid, an aerosol, a paste, a gel, or a gas composition.

86. The PMP composition of any one of paragraphs 74-85, wherein the PMP composition is stable for at least 24 hours, 48 hours, seven days, or 30 days.

87. The PMP composition of any one of paragraphs 74-86, wherein the PMP composition is stable at a temperature of at least 4° C., 20° C., 24° C., or 37° C.

88. A PMP bioreactor comprising a bioreactor containing a plant culture and optionally containing an effective amount of a stimulant to increase PMP production.

89. The PMP bioreactor of paragraph 88, wherein the plant culture is a culture comprising entire plants, plant parts, or plant cells.

90. The PMP bioreactor of paragraph 89, wherein the plant is a seedling.

91. The PMP bioreactor of paragraph 89, wherein the plant part is a radicle or a root.

92. The PMP bioreactor of paragraph 91, wherein the root is not attached to a plant shoot.

93. The PMP bioreactor of paragraph 89, wherein the plant part is a pollen grain.

94. The PMP bioreactor of paragraph 89, wherein the plant part is a callus.

95. The PMP bioreactor of any one of paragraphs 88-94, wherein the plant is a dicot or a monocot or the plant part is a part of a dicot or a monocot.

96. The PMP bioreactor of any one of paragraphs 88-95, wherein the plant or plant part is a soybean plant or a part thereof, a fava bean plant or a part thereof, an *Arabidopsis* plant or a part thereof, a tomato plant or a part thereof, a barley plant or a part thereof, or an oat plant or a part thereof.

97. The PMP bioreactor of paragraph 89, wherein the plant cell is a tobacco BY-2 cell.

98. The PMP bioreactor of any one of paragraphs 88-97, wherein the plant, plant part, or plant cell has been grown for at least 24 hours.

99. The PMP bioreactor of paragraph 29, wherein the plant, plant part, or plant cell has been grown for at least 1 week.

100. The PMP bioreactor of any one of paragraphs 88-99, wherein the plant, plant part, or plant cell is genetically modified.

101. The PMP bioreactor of paragraph 100, wherein the genetically modified plant, plant part, or plant cell contains a genetic modification that is effective to increase the production of PMPs from the plant, plant part, or plant cell relative to an unmodified plant, plant part, or plant cell.

102. The PMP bioreactor of paragraph 100 or 101, wherein the genetically modified plant, plant part, or plant cell contains a genetic modification that is effective to increase expression of EXO70a1 or EXO84 in the plant, plant part, or plant cell relative to an unmodified plant, plant part, or plant cell.

103. The PMP bioreactor of paragraph 102, wherein the genetic modification is stable integration of an EXO70a1 or an EXO84 transgene.

104. The PMP bioreactor of any one of paragraphs 88-103, wherein the stimulant is a biotic stimulant.

105. The PMP bioreactor of paragraph 104, wherein the biotic stimulant is a microbial stimulant.

106. The PMP bioreactor of paragraph 105, wherein the microbial stimulant is a bacterial polypeptide, a bacterial saccharide, a bacterial nucleic acid, or a bacterial small molecule.

107. The PMP bioreactor of paragraph 106, wherein the bacterial polypeptide is Elongation Factor Tu 18 (EFT18).

108. The PMP bioreactor of paragraph 105, wherein the microbial stimulant is a fungal polypeptide, a fungal saccharide, a fungal nucleic acid, or a fungal small molecule.

109. The PMP bioreactor of paragraph 108, wherein the fungal polypeptide is Flagellin2.

110. The PMP bioreactor of paragraph 105, wherein the microbial stimulant is a microorganism.

111. The PMP bioreactor of paragraph 110, wherein the microorganism is a bacterium.

112. The PMP bioreactor of paragraph 110, wherein the microorganism is a virus or a protozoan.

113. The PMP bioreactor of paragraph 110, wherein the microorganism is a fungus.

114. The PMP bioreactor of any one of paragraphs 88-103, wherein the plant stimulant is an abiotic stimulant.

115. The PMP bioreactor of paragraph 114, wherein the abiotic stimulant is osmotic stress, drought, water deprivation, flood, high light intensity, very high light intensity, high temperature, low temperature, salinity, heavy metal toxicity, anaerobiosis, nutrient deficiency, nutrient excess, UV irradiation, atmospheric pollution, or a chemical that induces production of reactive oxygen species (ROS).

116. The PMP bioreactor of any one of paragraphs 88-103, wherein the plant stimulant is a chemical elicitor.

117. The PMP bioreactor of paragraph 116, wherein the chemical elicitor is salicylic acid.

118. The PMP bioreactor of paragraph 116, wherein the chemical elicitor is benzothiadiazole.

119. The PMP bioreactor of paragraph 116, wherein the chemical elicitor is 2,6-dichloroisonicotinic acid.

120. The PMP bioreactor of any one of paragraphs 88-103, wherein the stimulant is a heterologous nucleic acid that increases gene expression of EXO70a1 or EXO84.

121. The PMP bioreactor of any one of paragraphs 88-120, wherein the stimulant is added at least 24 hours before the harvesting of the culture medium.

122. A method of increasing the fitness of a plant, the method comprising delivering to the plant an effective amount of the PMP composition of any one of paragraphs 74-87, wherein the method increases the fitness of the plant relative to an untreated plant.

123. A method of decreasing the fitness of a plant pest, the method comprising delivering to the plant pest an effective amount of the PMP composition of any one of paragraphs 74-87, wherein the method decreases the fitness of the plant pest relative to an untreated plant pest.

124. A method of treating an infection in an animal in need thereof, the method comprising administering to the animal an effective amount of the PMP composition of any one of paragraphs 74-87.

125. A method of decreasing the fitness of a pathogen, the method comprising delivering to the pathogen an effective amount of the PMP composition of any one of paragraphs 74-87, wherein the method is effective to decrease the fitness of the pathogen relative to an untreated pathogen.

126. A method of decreasing the fitness of an animal pathogen vector, the method comprising delivering to the vector an effective amount of the PMP composition of any one of paragraphs 74-87, wherein the method decreases the fitness of the vector relative to an untreated vector.

127. A method for producing plant messenger packs (PMPs), the method comprising:
  (a) culturing a plant or plant part in a culture medium in a hydroponic system;
  (b) harvesting the culture medium; and
  (c) purifying PMPs from the culture medium.

128. The method of paragraph 127, wherein the plant or plant part is a tomato plant or a tomato plant part.

129. The method of paragraph 127, wherein the plant is a seedling.

130. The method of paragraph 127, wherein the plant part is a root.

131. The method of paragraph 127, wherein the culture medium is a liquid culture medium.

132. The method of paragraph 127, wherein the culture medium is a gel culture medium.

133. The method of paragraph 127, wherein the culture medium comprises one or more of a macronutrient, a micronutrient, a salt, an enzyme, an antibiotic, an antifungal agent, or a plant growth factor.

134. The method of paragraph 127, wherein the hydroponic system has a capacity of at least 1 L.

135. The method of paragraph 127, wherein the hydroponic system has a capacity of at least 100 L.

136. The method of paragraph 127, wherein the hydroponic system has a capacity of at least 500 L.

137. The method of paragraph 127, wherein the harvesting comprises separating the culture medium from the plant or plant part.

138. The method of paragraph 127, wherein the harvesting does not comprise disruption of the plant or plant part.

139. The method of paragraph 127, wherein the culturing is performed for at least 1 week.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Other embodiments are within the claims.

TABLE 1

| Plant EV-Markers | | |
| --- | --- | --- |
| Example Species | Accession No. | Protein Name |
| Arabidopsis thaliana | C0LGG8 | Probable LRR receptor-like serine/threonine-protein kinase At1g53430 (EC 2.7.11.1) |
| Arabidopsis thaliana | F4HQT8 | Uncharacterized protein |
| Arabidopsis thaliana | F4HWU0 | Protein kinase superfamily protein |
| Arabidopsis thaliana | F4I082 | Bifunctional inhibitor/lipid-transfer protein/seed storage 2S albumin superfamily protein |
| Arabidopsis thaliana | F4I3M3 | Kinase with tetratricopeptide repeat domain-containing protein |
| Arabidopsis thaliana | F4IB62 | Leucine-rich repeat protein kinase family protein |
| Arabidopsis thaliana | O03042 | Ribulose bisphosphate carboxylase large chain (RuBisCO large subunit) (EC 4.1.1.39) |
| Arabidopsis thaliana | O03986 | Heat shock protein 90-4 (AtHSP90.4) (AtHsp90-4) (Heat shock protein 81-4) (Hsp81-4) |
| Arabidopsis thaliana | O04023 | Protein SRC2 homolog (AtSRC2) |
| Arabidopsis thaliana | O04309 | Jacalin-related lectin 35 (JA-responsive protein 1) (Myrosinase-binding protein-like At3g16470) |
| Arabidopsis thaliana | O04314 | PYK10-binding protein 1 (Jacalin-related lectin 30) (Jasmonic acid-induced protein) |
| Arabidopsis thaliana | O04922 | Probable glutathione peroxidase 2 (EC 1.11.1.9) |
| Arabidopsis thaliana | O22126 | Fasciclin-like arabinogalactan protein 8 (AtAGP8) |
| Arabidopsis thaliana | O23179 | Patatin-like protein 1 (AtPLP1 (EC 3.1.1.—) (Patatin-related phospholipase A IIgamma) (pPLAIIg) (Phospholipase A IVA) (AtPLAIVA) |
| Arabidopsis thaliana | O23207 | Probable NAD(P)H dehydrogenase (quinone) FQR1-like 2 (EC 1.6.5.2) |
| Arabidopsis thaliana | O23255 | Adenosylhomocysteinase 1 (AdoHcyase 1) (EC 3.3.1.1) (Protein EMBRYO DEFECTIVE 1395) (Protein HOMOLOGY-DEPENDENT GENE SILENCING 1) (S-adenosyl-L-homocysteine hydrolase 1) (SAH hydrolase 1) |
| Arabidopsis thaliana | O23482 | Oligopeptide transporter 3 (AtOPT3) |
| Arabidopsis thaliana | O23654 | V-type proton ATPase catalytic subunit A (V-ATPase subunit A) (EC 3.6.3.14) (V-ATPase 69 kDa subunit) (Vacuolar H(+)-ATPase subunit A) (Vacuolar proton pump subunit alpha) |
| Arabidopsis thaliana | O48788 | Probable inactive receptor kinase At2g26730 |
| Arabidopsis thaliana | O48963 | Phototropin-1 (EC 2.7.11.1) (Non-phototropic hypocotyl protein 1) (Root phototropism protein 1) |
| Arabidopsis thaliana | O49195 | Vegetative storage protein 1 |
| Arabidopsis thaliana | O50008 | 5-methyltetrahydropteroyltriglutamate--homocysteine methyltransferase 1 (EC 2.1.1.14) (Cobalamin-independent methionine synthase 1) (AtMS1) (Vitamin-B12-independent methionine synthase 1) |
| Arabidopsis thaliana | O64696 | Putative uncharacterized protein At2g34510 |
| Arabidopsis thaliana | O65572 | Carotenoid 9,10(9',10')-cleavage dioxygenase 1 (EC 1.14.99.n4) (AtCCD1) (Neoxanthin cleavage enzyme NC1) (AtNCED1) |
| Arabidopsis thaliana | O65660 | PLAT domain-containing protein 1 (AtPLAT1) (PLAT domain protein 1) |
| Arabidopsis thaliana | O65719 | Heat shock 70 kDa protein 3 (Heat shock cognate 70 kDa protein 3) (Heat shock cognate protein 70-3) (AtHsc70-3) (Heat shock protein 70-3) (AtHsp70-3) |
| Arabidopsis thaliana | O80517 | Uclacyanin-2 (Blue copper-binding protein II) (BCB II) (Phytocyanin 2) (Uclacyanin-II) |
| Arabidopsis thaliana | O80576 | At2g44060 (Late embryogenesis abundant protein, group 2) (Similar to late embryogenesis abundant proteins) |
| Arabidopsis thaliana | O80725 | ABC transporter B family member 4 (ABC transporter ABCB.4) (AtABCB4) (Multidrug resistance protein 4) (P-glycoprotein 4) |

TABLE 1-continued

Plant EV-Markers

| | | |
|---|---|---|
| *Arabidopsis thaliana* | O80837 | Remorin (DNA-binding protein) |
| *Arabidopsis thaliana* | O80852 | Glutathione S-transferase F9 (AtGSTF9) (EC 2.5.1.18) (AtGSTF7) (GST class-phi member 9) |
| *Arabidopsis thaliana* | O80858 | Expressed protein (Putative uncharacterized protein At2g30930) (Putative uncharacterized protein At2g30930; F7F1.14) |
| *Arabidopsis thaliana* | O80939 | L-type lectin-domain containing receptor kinase IV.1 (Arabidopsis thaliana lectin-receptor kinase e) (AthlecRK-e) (LecRK-IV.1) (EC 2.7.11.1) (Lectin Receptor Kinase 1) |
| *Arabidopsis thaliana* | O80948 | Jacalin-related lectin 23 (Myrosinase-binding protein-like At2g39330) |
| *Arabidopsis thaliana* | O82628 | V-type proton ATPase subunit G1 (V-ATPase subunit G1) (Vacuolar H(+)-ATPase subunit G isoform 1) (Vacuolar proton pump subunit G1) |
| *Arabidopsis thaliana* | P10795 | Ribulose bisphosphate carboxylase small chain 1A, chloroplastic (RuBisCO small subunit 1A) (EC 4.1.1.39) |
| *Arabidopsis thaliana* | P10896 | Ribulose bisphosphate carboxylase/oxygenase activase, chloroplastic (RA) (RuBisCO activase) |
| *Arabidopsis thaliana* | P17094 | 60S ribosomal protein L3-1 (Protein EMBRYO DEFECTIVE 2207) |
| *Arabidopsis thaliana* | P19456 | ATPase 2, plasma membrane-type (EC 3.6.3.6) (Proton pump 2) |
| *Arabidopsis thaliana* | P20649 | ATPase 1, plasma membrane-type (EC 3.6.3.6) (Proton pump 1) |
| *Arabidopsis thaliana* | P22953 | Probable mediator of RNA polymerase II transcription subunit 37e (Heat shock 70 kDa protein 1) (Heat shock cognate 70 kDa protein 1) (Heat shock cognate protein 70-1) (AtHsc70-1) (Heat shock protein 70-1) (AtHsp70-1) (Protein EARLY-RESPONSIVE TO DEHYDRATION 2) |
| *Arabidopsis thaliana* | P23586 | Sugar transport protein 1 (Glucose transporter) (Hexose transporter 1) |
| *Arabidopsis thaliana* | P24636 | Tubulin beta-4 chain (Beta-4-tubulin) |
| *Arabidopsis thaliana* | P25696 | Bifunctional enolase 2/transcriptional activator (EC 4.2.1.11) (2-phospho-D-glycerate hydro-lyase 2) (2-phosphoglycerate dehydratase 2) (LOW EXPRESSION OF OSMOTICALLY RESPONSIVE GENES 1) |
| *Arabidopsis thaliana* | P25856 | Glyceraldehyde-3-phosphate dehydrogenase GAPA1, chloroplastic (EC 1.2.1.13) (NADP-dependent glyceraldehydephosphate dehydrogenase A subunit 1) |
| *Arabidopsis thaliana* | P28186 | Ras-related protein RABE1c (AtRABE1c) (Ras-related protein Ara-3) (Ras-related protein Rab8A) (AtRab8A) |
| *Arabidopsis thaliana* | P30302 | Aquaporin PIP2-3 (Plasma membrane intrinsic protein 2-3) (AtPIP2; 3) (Plasma membrane intrinsic protein 2c) (PIP2c) (RD28-PIP) (TMP2C) (Water stress-induced tonoplast intrinsic protein) (WSI-TIP) [Cleaved into: Aquaporin PIP2-3, N-terminally processed] |
| *Arabidopsis thaliana* | P31414 | Pyrophosphate-energized vacuolar membrane proton pump 1 (EC 3.6.1.1) (Pyrophosphate-energized inorganic pyrophosphatase 1) (H(+)-PPase 1) (Vacuolar proton pyrophosphatase 1) (Vacuolar proton pyrophosphatase 3) |
| *Arabidopsis thaliana* | P32961 | Nitrilase 1 (EC 3.5.5.1) |
| *Arabidopsis thaliana* | P38666 | 60S ribosomal protein L24-2 (Protein SHORT VALVE 1) |
| *Arabidopsis thaliana* | P39207 | Nucleoside diphosphate kinase 1 (EC 2.7.4.6) (Nucleoside diphosphate kinase I) (NDK I) (NDP kinase I) (NDPK I) |
| *Arabidopsis thaliana* | P42643 | 14-3-3-like protein GF14 chi (General regulatory factor 1) |
| *Arabidopsis thaliana* | P42737 | Beta carbonic anhydrase 2, chloroplastic (AtbCA2) (AtbetaCA2) (EC 4.2.1.1) (Beta carbonate dehydratase 2) |
| *Arabidopsis thaliana* | P42759 | Dehydrin ERD10 (Low-temperature-induced protein LTI45) |
| *Arabidopsis thaliana* | P42761 | Glutathione S-transferase F10 (AtGSTF10) (EC 2.5.1.18) (AtGSTF4) (GST class-phi member 10) (Protein EARLY RESPONSE TO DEHYDRATION 13) |
| *Arabidopsis thaliana* | P42763 | Dehydrin ERD14 |
| *Arabidopsis thaliana* | P42791 | 60S ribosomal protein L18-2 |
| *Arabidopsis thaliana* | P43286 | Aquaporin PIP2-1 (Plasma membrane intrinsic protein 2-1) (AtPIP2; 1) (Plasma membrane intrinsic protein 2a) (PIP2a) [Cleaved into: Aquaporin PIP2-1, N-terminally processed] |
| *Arabidopsis thaliana* | P46286 | 60S ribosomal protein L8-1 (60S ribosomal protein L2) (Protein EMBRYO DEFECTIVE 2296) |
| *Arabidopsis thaliana* | P46422 | Glutathione S-transferase F2 (AtGSTF2) (EC 2.5.1.18) (24 kDa auxin-binding protein) (AtPM24) (GST class-phi member 2) |
| *Arabidopsis thaliana* | P47998 | Cysteine synthase 1 (EC 2.5.1.47) (At.OAS.5-8) (Beta-substituted Ala synthase 1; 1) (ARAth-Bsas1; 1) (CSase A) (AtCS-A) (Cys-3A) (O-acetylserine (thiol)-lyase 1) (OAS-TL A) (O-acetylserine sulfhydrylase) (Protein ONSET OF LEAF DEATH 3) |
| *Arabidopsis thaliana* | P48347 | 14-3-3-like protein GF14 epsilon (General regulatory factor 10) |

TABLE 1-continued

| | | Plant EV-Markers |
|---|---|---|
| *Arabidopsis thaliana* | P48491 | Triosephosphate isomerase, cytosolic (TIM) (Triose-phosphate isomerase) (EC 5.3.1.1) |
| *Arabidopsis thaliana* | P50318 | Phosphoglycerate kinase 2, chloroplastic (EC 2.7.2.3) |
| *Arabidopsis thaliana* | P53492 | Actin-7 (Actin-2) |
| *Arabidopsis thaliana* | P54144 | Ammonium transporter 1 member 1 (AtAMT1; 1) |
| *Arabidopsis thaliana* | P92963 | Ras-related protein RABB1c (AtRABB1c) (Ras-related protein Rab2A) (AtRab2A) |
| *Arabidopsis thaliana* | P93004 | Aquaporin PIP2-7 (Plasma membrane intrinsic protein 2-7) (AtPIP2; 7) (Plasma membrane intrinsic protein 3) (Salt stress-induced major intrinsic protein) [Cleaved into: Aquaporin PIP2-7, N-terminally processed] |
| *Arabidopsis thaliana* | P93025 | Phototropin-2 (EC 2.7.11.1) (Defective in chloroplast avoidance protein 1) (Non-phototropic hypocotyl 1-like protein 1) (AtKin7) (NPH1-like protein 1) |
| *Arabidopsis thaliana* | P93819 | Malate dehydrogenase 1, cytoplasmic (EC 1.1.1.37) (Cytosolic NAD-dependent malate dehydrogenase 1) (cNAD-MDH1) (Cytosolic malate dehydrogenase 1) (Cytosolic MDH1) |
| *Arabidopsis thaliana* | Q03250 | Glycine-rich RNA-binding protein 7 (AtGR-RBP7) (AtRBG7) (Glycine-rich protein 7) (AtGRP7) (Protein COLD, CIRCADIAN RHYTHM, AND RNA BINDING 2) (Protein CCR2) |
| *Arabidopsis thaliana* | Q05431 | L-ascorbate peroxidase 1, cytosolic (AP) (AtAPx01) (EC 1.11.1.11) |
| *Arabidopsis thaliana* | Q06611 | Aquaporin PIP1-2 (AtPIP1; 2) (Plasma membrane intrinsic protein 1b) (PIP1b) (Transmembrane protein A) (AthH2) (TMP-A) |
| *Arabidopsis thaliana* | Q07488 | Blue copper protein (Blue copper-binding protein) (AtBCB) (Phytocyanin 1) (Stellacyanin) |
| *Arabidopsis thaliana* | Q0WLB5 | Clathrin heavy chain 2 |
| *Arabidopsis thaliana* | Q0WNJ6 | Clathrin heavy chain 1 |
| *Arabidopsis thaliana* | Q1ECE0 | Vesicle-associated protein 4-1 (Plant VAP homolog 4-1) (AtPVA41) (Protein MEMBRANE-ASSOCIATED MANNITOL-INDUCED) (AtMAMI) (VAMP-associated protein 4-1) |
| *Arabidopsis thaliana* | Q38882 | Phospholipase D alpha 1 (AtPLDalpha1) (PLD alpha 1) (EC 3.1.4.4) (Choline phosphatase 1) (PLDalpha) (Phosphatidylcholine-hydrolyzing phospholipase D 1) |
| *Arabidopsis thaliana* | Q38900 | Peptidyl-prolyl cis-trans isomerase CYP19-1 (PPIase CYP19-1) (EC 5.2.1.8) (Cyclophilin of 19 kDa 1) (Rotamase cyclophilin-3) |
| *Arabidopsis thaliana* | Q39033 | Phosphoinositide phospholipase C 2 (EC 3.1.4.11) (Phosphoinositide phospholipase PLC2) (AtPLC2) (PI-PLC2) |
| *Arabidopsis thaliana* | Q39085 | Delta(24)-sterol reductase (EC 1.3.1.72) (Cell elongation protein DIMINUTO) (Cell elongation protein Dwarf1) (Protein CABBAGE1) (Protein ENHANCED VERY-LOW-FLUENCE RESPONSE 1) |
| *Arabidopsis thaliana* | Q39228 | Sugar transport protein 4 (Hexose transporter 4) |
| *Arabidopsis thaliana* | Q39241 | Thioredoxin H5 (AtTrxh5) (Protein LOCUS OF INSENSITIVITY TO VICTORIN 1) (Thioredoxin 5) (AtTRX5) |
| *Arabidopsis thaliana* | Q39258 | V-type proton ATPase subunit E1 (V-ATPase subunit E1) (Protein EMBRYO DEFECTIVE 2448) (Vacuolar H(+)-ATPase subunit E isoform 1) (Vacuolar proton pump subunit E1) |
| *Arabidopsis thaliana* | Q42112 | 60S acidic ribosomal protein PO-2 |
| *Arabidopsis thaliana* | Q42403 | Thioredoxin H3 (AtTrxh3) (Thioredoxin 3) (AtTRX3) |
| *Arabidopsis thaliana* | Q42479 | Calcium-dependent protein kinase 3 (EC 2.7.11.1) (Calcium-dependent protein kinase isoform CDPK6) (AtCDPK6) |
| *Arabidopsis thaliana* | Q42547 | Catalase-3 (EC 1.11.1.6) |
| *Arabidopsis thaliana* | Q56WH1 | Tubulin alpha-3 chain |
| *Arabidopsis thaliana* | Q56WK6 | Patellin-1 |
| *Arabidopsis thaliana* | Q56X75 | CASP-like protein 4D2 (AtCASPL4D2) |
| *Arabidopsis thaliana* | Q56ZI2 | Patellin-2 |
| *Arabidopsis thaliana* | Q7Y208 | Glycerophosphodiester phosphodiesterase GDPDL1 (EC 3.1.4.46) (Glycerophosphodiester phosphodiesterase-like 1) (ATGDPDL1) (Glycerophosphodiesterase-like 3) (Protein SHV3-LIKE 2) |
| *Arabidopsis thaliana* | Q84VZ5 | Uncharacterized GPI-anchored protein At5g19240 |
| *Arabidopsis thaliana* | Q84WU7 | Eukaryotic aspartyl protease family protein (Putative uncharacterized protein At3g51330) |
| *Arabidopsis thaliana* | Q8GUL8 | Uncharacterized GPI-anchored protein At5g19230 |
| *Arabidopsis thaliana* | Q8GYA4 | Cysteine-rich receptor-like protein kinase 10 (Cysteine-rich RLK10) (EC 2.7.11.—) (Receptor-like protein kinase 4) |
| *Arabidopsis thaliana* | Q8GYN5 | RPM1-interacting protein 4 |
| *Arabidopsis thaliana* | Q8GZ99 | At5g49760 (Leucine-rich repeat protein kinase family protein) (Leucine-rich repeat receptor-like protein kinase) (Putative receptor protein kinase) |
| *Arabidopsis thaliana* | Q8L636 | Sodium/calcium exchanger NCL (Na(+)/Ca(2+)-exchange protein NCL) (Protein NCX-like) (AtNCL) |

TABLE 1-continued

Plant EV-Markers

| | | |
|---|---|---|
| *Arabidopsis thaliana* | Q8L7S1 | At1g45200 (At1g45200/At1g45200) (Triacylglycerol lipase-like 1) |
| *Arabidopsis thaliana* | Q8LAA6 | Probable aquaporin PIP1-5 (AtPIP1; 5) (Plasma membrane intrinsic protein 1d) (PIP1d) |
| *Arabidopsis thaliana* | Q8LCP6 | Endoglucanase 10 (EC 3.2.1.4) (Endo-1,4-beta glucanase 10) |
| *Arabidopsis thaliana* | Q8RWV0 | Transketolase-1, chloroplastic (TK) (EC 2.2.1.1) |
| *Arabidopsis thaliana* | Q8S8Q6 | Tetraspanin-8 |
| *Arabidopsis thaliana* | Q8VZG8 | MDIS1-interacting receptor like kinase 2 (AtMIK2) (Probable LRR receptor-like serine/threonine-protein kinase At4g08850) (EC 2.7.11.1) |
| *Arabidopsis thaliana* | Q8VZU2 | Syntaxin-132 (AtSYP132) |
| *Arabidopsis thaliana* | Q8W4E2 | V-type proton ATPase subunit B3 (V-ATPase subunit B3) (Vacuolar H(+)-ATPase subunit B isoform 3) (Vacuolar proton pump subunit B3) |
| *Arabidopsis thaliana* | Q8W4S4 | V-type proton ATPase subunit a3 (V-ATPase subunit a3) (V-type proton ATPase 95 kDa subunit a isoform 3) (V-ATPase 95 kDa isoform a3) (Vacuolar H(+)-ATPase subunit a isoform 3) (Vacuolar proton pump subunit a3) (Vacuolar proton translocating ATPase 95 kDa subunit a isoform 3) |
| *Arabidopsis thaliana* | Q93VG5 | 40S ribosomal protein S8-1 |
| *Arabidopsis thaliana* | Q93XY5 | Tetraspanin-18 (TOM2A homologous protein 2) |
| *Arabidopsis thaliana* | Q93YS4 | ABC transporter G family member 22 (ABC transporter ABCG.22) (AtABCG22) (White-brown complex homolog protein 23) (AtWBC23) |
| *Arabidopsis thaliana* | Q93Z08 | Glucan endo-1,3-beta-glucosidase 6 (EC 3.2.1.39) ((1 -> 3)-beta-glucan endohydrolase 6) ((1 -> 3)-beta-glucanase 6) (Beta-1,3-endoglucanase 6) (Beta-1,3-glucanase 6) |
| *Arabidopsis thaliana* | Q940M8 | 3-oxo-5-alpha-steroid 4-dehydrogenase (DUF1295) (At1g73650/F25P22_7) |
| *Arabidopsis thaliana* | Q944A7 | Probable serine/threonine-protein kinase At4g35230 (EC 2.7.11.1) |
| *Arabidopsis thaliana* | Q944G5 | Protein NRT1/PTR FAMILY 2.10 (AtNPF2.10) (Protein GLUCOSINOLATE TRANSPORTER-1) |
| *Arabidopsis thaliana* | Q94AZ2 | Sugar transport protein 13 (Hexose transporter 13) (Multicopy suppressor of snf4 deficiency protein 1) |
| *Arabidopsis thaliana* | Q94BT2 | Auxin-induced in root cultures protein 12 |
| *Arabidopsis thaliana* | Q94CE4 | Beta carbonic anhydrase 4 (AtbCA4) (AtbetaCA4) (EC 4.2.1.1) (Beta carbonate dehydratase 4) |
| *Arabidopsis thaliana* | Q94KI8 | Two pore calcium channel protein 1 (Calcium channel protein 1) (AtCCH1) (Fatty acid oxygenation up-regulated protein 2) (Voltage-dependent calcium channel protein TPC1) (AtTPC1) |
| *Arabidopsis thaliana* | Q96262 | Plasma membrane-associated cation-binding protein 1 (AtPCAP1) (Microtubule-destabilizing protein 25) |
| *Arabidopsis thaliana* | Q9C5Y0 | Phospholipase D delta (AtPLDdelta) (PLD delta) (EC 3.1.4.4) |
| *Arabidopsis thaliana* | Q9C7F7 | Non-specific lipid transfer protein GPI-anchored 1 (AtLTPG-1) (Protein LTP-GPI-ANCHORED 1) |
| *Arabidopsis thaliana* | Q9C821 | Proline-rich receptor-like protein kinase PERK15 (EC 2.7.11.1) (Proline-rich extensin-like receptor kinase 15) (AtPERK15) |
| *Arabidopsis thaliana* | Q9C8G5 | CSC1-like protein ERD4 (Protein EARLY-RESPONSIVE TO DEHYDRATION STRESS 4) |
| *Arabidopsis thaliana* | Q9C9C5 | 60S ribosomal protein L6-3 |
| *Arabidopsis thaliana* | Q9CAR7 | Hypersensitive-induced response protein 2 (AtHIR2) |
| *Arabidopsis thaliana* | Q9FFH6 | Fasciclin-like arabinogalactan protein 13 |
| *Arabidopsis thaliana* | Q9FGT8 | Temperature-induced lipocalin-1 (AtTIL1) |
| *Arabidopsis thaliana* | Q9FJ62 | Glycerophosphodiester phosphodiesterase GDPDL4 (EC 3.1.4.46) (Glycerophosphodiester phosphodiesterase-like 4) (ATGDPDL4) (Glycerophosphodiesterase-like 1) (Protein SHV3-LIKE 1) |
| *Arabidopsis thaliana* | Q9FK68 | Ras-related protein RABA1c (AtRABA1c) |
| *Arabidopsis thaliana* | Q9FKS8 | Lysine histidine transporter 1 |
| *Arabidopsis thaliana* | Q9FM65 | Fasciclin-like arabinogalactan protein 1 |
| *Arabidopsis thaliana* | Q9FNH6 | NDR1/HIN1-like protein 3 |
| *Arabidopsis thaliana* | Q9FRL3 | Sugar transporter ERD6-like 6 |
| *Arabidopsis thaliana* | Q9FWR4 | Glutathione S-transferase DHAR1, mitochondrial (EC 2.5.1.18) (Chloride intracellular channel homolog 1) (CLIC homolog 1) (Glutathione-dependent dehydroascorbate reductase 1) (AtDHAR1) (GSH-dependent dehydroascorbate reductase 1) (mtDHAR) |
| *Arabidopsis thaliana* | Q9FX54 | Glyceraldehyde-3-phosphate dehydrogenase GAPC2, cytosolic (EC 1.2.1.12) (NAD-dependent glyceraldehydephosphate dehydrogenase C subunit 2) |
| *Arabidopsis thaliana* | Q9LE22 | Probable calcium-binding protein CML27 (Calmodulin-like protein 27) |
| *Arabidopsis thaliana* | Q9LEX1 | At3g61050 (CaLB protein) (Calcium-dependent lipid-binding (CaLB domain) family protein) |

TABLE 1-continued

Plant EV-Markers

| | | |
|---|---|---|
| *Arabidopsis thaliana* | Q9LF79 | Calcium-transporting ATPase 8, plasma membrane-type (EC 3.6.3.8) (Ca(2+)-ATPase isoform 8) |
| *Arabidopsis thaliana* | Q9LJG3 | GDSL esterase/lipase ESM1 (EC 3.1.1.—) (Extracellular lipase ESM1) (Protein EPITHIOSPECIFIER MODIFIER 1) (AtESM1) |
| *Arabidopsis thaliana* | Q9LJI5 | V-type proton ATPase subunit d1 (V-ATPase subunit d1) (Vacuolar H(+)-ATPase subunit d isoform 1) (Vacuolar proton pump subunit d1) |
| *Arabidopsis thaliana* | Q9LME4 | Probable protein phosphatase 2C 9 (AtPP2C09) (EC 3.1.3.16) (Phytochrome-associated protein phosphatase 2C) (PAPP2C) |
| *Arabidopsis thaliana* | Q9LNP3 | At1g17620/F11A6_23 (F1L3.32) (Late embryogenesis abundant (LEA) hydroxyproline-rich glycoprotein family) (Putative uncharacterized protein At1g17620) |
| *Arabidopsis thaliana* | Q9LNW1 | Ras-related protein RABA2b (AtRABA2b) |
| *Arabidopsis thaliana* | Q9LQU2 | Protein PLANT CADMIUM RESISTANCE 1 (AtPCR1) |
| *Arabidopsis thaliana* | Q9LQU4 | Protein PLANT CADMIUM RESISTANCE 2 (AtPCR2) |
| *Arabidopsis thaliana* | Q9LR30 | Glutamate--glyoxylate aminotransferase 1 (AtGGT2) (EC 2.6.1.4) (Alanine aminotransferase GGT1) (EC 2.6.1.2) (Alanine--glyoxylate aminotransferase GGT1) (EC 2.6.1.44) (Alanine-2-oxoglutarate aminotransferase 1) (EC 2.6.1.—) |
| *Arabidopsis thaliana* | Q9LSI9 | Inactive LRR receptor-like serine/threonine-protein kinase BIR2 (Protein BAK1-INTERACTING RECEPTOR-LIKE KINASE 2) |
| *Arabidopsis thaliana* | Q9LSQ5 | NAD(P)H dehydrogenase (quinone) FQR1 (EC 1.6.5.2) (Flavodoxin-like quinone reductase 1) |
| *Arabidopsis thaliana* | Q9LUT0 | Protein kinase superfamily protein (Putative uncharacterized protein At3g17410) (Serine/threonine protein kinase-like protein) |
| *Arabidopsis thaliana* | Q9LV48 | Proline-rich receptor-like protein kinase PERK1 (EC 2.7.11.1) (Proline-rich extensin-like receptor kinase 1) (AtPERK1) |
| *Arabidopsis thaliana* | Q9LX65 | V-type proton ATPase subunit H (V-ATPase subunit H) (Vacuolar H(+)-ATPase subunit H) (Vacuolar proton pump subunit H) |
| *Arabidopsis thaliana* | Q9LYG3 | NADP-dependent malic enzyme 2 (AtNADP-ME2) (NADP-malic enzyme 2) (EC 1.1.1.40) |
| *Arabidopsis thaliana* | Q9M088 | Glucan endo-1,3-beta-glucosidase 5 (EC 3.2.1.39) ((1 -> 3)-beta-glucan endohydrolase 5) ((1 -> 3)-beta-glucanase 5) (Beta-1,3-endoglucanase 5) (Beta-1,3-glucanase 5) |
| *Arabidopsis thaliana* | Q9M2D8 | Uncharacterized protein At3g61260 |
| *Arabidopsis thaliana* | Q9M386 | Late embryogenesis abundant (LEA) hydroxyproline-rich glycoprotein family (Putative uncharacterized protein At3g54200) (Putative uncharacterized protein F24B22.160) |
| *Arabidopsis thaliana* | Q9M390 | Protein NRT1/PTR FAMILY 8.1 (AtNPF8.1) (Peptide transporter PTR1) |
| *Arabidopsis thaliana* | Q9M5P2 | Secretory carrier-associated membrane protein 3 (AtSC3) (Secretory carrier membrane protein 3) |
| *Arabidopsis thaliana* | Q9M8T0 | Probable inactive receptor kinase At3g02880 |
| *Arabidopsis thaliana* | Q9SDS7 | V-type proton ATPase subunit C (V-ATPase subunit C) (Vacuolar H(+)-ATPase subunit C) (Vacuolar proton pump subunit C) |
| *Arabidopsis thaliana* | Q9SEL6 | Vesicle transport v-SNARE 11 (AtVTI11) (Protein SHOOT GRAVITROPISM 4) (Vesicle soluble NSF attachment protein receptor VTI1a) (AtVTI1a) (Vesicle transport v-SNARE protein VTI1a) |
| *Arabidopsis thaliana* | Q9SF29 | Syntaxin-71 (AtSYP71) |
| *Arabidopsis thaliana* | Q9SF85 | Adenosine kinase 1 (AK 1) (EC 2.7.1.20) (Adenosine 5'-phosphotransferase 1) |
| *Arabidopsis thaliana* | Q9SIE7 | PLAT domain-containing protein 2 (AtPLAT2) (PLAT domain protein 2) |
| *Arabidopsis thaliana* | Q9SIM4 | 60S ribosomal protein L14-1 |
| *Arabidopsis thaliana* | Q9SIU8 | Probable protein phosphatase 2C 20 (AtPP2C20) (EC 3.1.3.16) (AtPPC3; 1.2) |
| *Arabidopsis thaliana* | Q9SJ81 | Fasciclin-like arabinogalactan protein 7 |
| *Arabidopsis thaliana* | Q9SKB2 | Leucine-rich repeat receptor-like serine/threonine/tyrosine-protein kinase SOBIR1 (EC 2.7.10.1) (EC 2.7.11.1) (Protein EVERSHED) (Protein SUPPRESSOR OF BIR1-1) |
| *Arabidopsis thaliana* | Q9SKR2 | Synaptotagmin-1 (NTMC2T1.1) (Synaptotagmin A) |
| *Arabidopsis thaliana* | Q9SLF7 | 60S acidic ribosomal protein P2-2 |
| *Arabidopsis thaliana* | Q9SPE6 | Alpha-soluble NSF attachment protein 2 (Alpha-SNAP2) (N-ethylmaleimide-sensitive factor attachment protein alpha 2) |
| *Arabidopsis thaliana* | Q9SRH6 | Hypersensitive-induced response protein 3 (AtHIR3) |
| *Arabidopsis thaliana* | Q9SRY5 | Glutathione S-transferase F7 (EC 2.5.1.18) (AtGSTF8) (GST class-phi member 7) (Glutathione S-transferase 11) |
| *Arabidopsis thaliana* | Q9SRZ6 | Cytosolic isocitrate dehydrogenase [NADP] (EC 1.1.1.42) |
| *Arabidopsis thaliana* | Q9SSK5 | MLP-like protein 43 |
| *Arabidopsis thaliana* | Q9SU13 | Fasciclin-like arabinogalactan protein 2 |

TABLE 1-continued

Plant EV-Markers

| | | |
|---|---|---|
| *Arabidopsis thaliana* | Q9SU40 | Monocopper oxidase-like protein SKU5 (Skewed roots) |
| *Arabidopsis thaliana* | Q9SUR6 | Cystine lyase CORI3 (EC 4.4.1.35) (Protein CORONATINE INDUCED 3) (Protein JASMONIC ACID RESPONSIVE 2) (Tyrosine aminotransferase CORI3) |
| *Arabidopsis thaliana* | Q9SVC2 | Syntaxin-122 (AtSYP122) (Synt4) |
| *Arabidopsis thaliana* | Q9SVF0 | Putative uncharacterized protein AT4g38350 (Putative uncharacterized protein F22I13.120) |
| *Arabidopsis thaliana* | Q9SW40 | Major facilitator superfamily protein (Putative uncharacterized protein AT4g34950) (Putative uncharacterized protein T11I11.190) |
| *Arabidopsis thaliana* | Q9SYT0 | Annexin D1 (AnnAt1) (Annexin A1) |
| *Arabidopsis thaliana* | Q9SZ11 | Glycerophosphodiester phosphodiesterase GDPDL3 (EC 3.1.4.46) (Glycerophosphodiester phosphodiesterase-like 3) (ATGDPDL3) (Glycerophosphodiesterase-like 2) (Protein MUTANT ROOT HAIR 5) (Protein SHAVEN 3) |
| *Arabidopsis thaliana* | Q9SZN1 | V-type proton ATPase subunit B2 (V-ATPase subunit B2) (Vacuolar H(+)-ATPase subunit B isoform 2) (Vacuolar proton pump subunit B2) |
| *Arabidopsis thaliana* | Q9SZP6 | AT4g38690/F20M13_250 (PLC-like phosphodiesterases superfamily protein) (Putative uncharacterized protein AT4g38690) (Putative uncharacterized protein F20M13.250) |
| *Arabidopsis thaliana* | Q9SZR1 | Calcium-transporting ATPase 10, plasma membrane-type (EC 3.6.3.8) (Ca(2+)-ATPase isoform 10) |
| *Arabidopsis thaliana* | Q9T053 | Phospholipase D gamma 1 (AtPLDgamma1) (PLD gamma 1) (EC 3.1.4.4) (Choline phosphatase) (Lecithinase D) (Lipophosphodiesterase II) |
| *Arabidopsis thaliana* | Q9T076 | Early nodulin-like protein 2 (Phytocyanin-like protein) |
| *Arabidopsis thaliana* | Q9T0A0 | Long chain acyl-CoA synthetase 4 (EC 6.2.1.3) |
| *Arabidopsis thaliana* | Q9T0G4 | Putative uncharacterized protein AT4g10060 (Putative uncharacterized protein T5L19.190) |
| *Arabidopsis thaliana* | Q9XEE2 | Annexin D2 (AnnAt2) |
| *Arabidopsis thaliana* | Q9XGM1 | V-type proton ATPase subunit D (V-ATPase subunit D) (Vacuolar H(+)-ATPase subunit D) (Vacuolar proton pump subunit D) |
| *Arabidopsis thaliana* | Q9XI93 | At1g13930/F16A14.27 (F16A14.14) (F7A19.2 protein) (Oleosin-B3-like protein) |
| *Arabidopsis thaliana* | Q9XIE2 | ABC transporter G family member 36 (ABC transporter ABCG.36) (AtABCG36) (Pleiotropic drug resistance protein 8) (Protein PENETRATION 3) |
| *Arabidopsis thaliana* | Q9ZPZ4 | Putative uncharacterized protein (Putative uncharacterized protein At1g09310) (T31J12.3 protein) |
| *Arabidopsis thaliana* | Q9ZQX4 | V-type proton ATPase subunit F (V-ATPase subunit F) (V-ATPase 14 kDa subunit) (Vacuolar H(+)-ATPase subunit F) (Vacuolar proton pump subunit F) |
| *Arabidopsis thaliana* | Q9ZSA2 | Calcium-dependent protein kinase 21 (EC 2.7.11.1) |
| *Arabidopsis thaliana* | Q9ZSD4 | Syntaxin-121 (AtSYP121) (Syntaxin-related protein At-Syr1) |
| *Arabidopsis thaliana* | Q9ZV07 | Probable aquaporin PIP2-6 (Plasma membrane intrinsic protein 2-6) (AtPIP2; 6) (Plasma membrane intrinsic protein 2e) (PIP2e) [Cleaved into: Probable aquaporin PIP2-6, N-terminally processed] |
| *Arabidopsis thaliana* | Q9ZVF3 | MLP-like protein 328 |
| *Arabidopsis thaliana* | Q9ZWA8 | Fasciclin-like arabinogalactan protein 9 |
| *Arabidopsis thaliana* | Q9ZSD4 | SYR1, Syntaxin Related Protein 1, also known as SYP121, PENETRATION1/PEN1 (Protein PENETRATION 1) |
| *Citrus lemon* | A1ECK0 | Putative glutaredoxin |
| *Citrus lemon* | A9YVC9 | Pyrophosphate--fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |
| *Citrus lemon* | B2YGY1 | Glycosyltransferase (EC 2.4.1.—) |
| *Citrus lemon* | B6DZD3 | Glutathione S-transferase Tau2 (Glutathione transferase Tau2) |
| *Citrus lemon* | C3VIC2 | Translation elongation factor |
| *Citrus lemon* | C8CPS0 | Importin subunit alpha |
| *Citrus lemon* | D3JWB5 | Flavanone 3-hydroxylase |
| *Citrus lemon* | E0ADY2 | Putative caffeic acid O-methyltransferase |
| *Citrus lemon* | E5DK62 | ATP synthase subunit alpha (Fragment) |
| *Citrus lemon* | E9M5S3 | Putative L-galactose-1-phosphate phosphatase |
| *Citrus lemon* | F1CGQ9 | Heat shock protein 90 |
| *Citrus lemon* | F8WL79 | Aminopeptidase (EC 3.4.11.—) |
| *Citrus lemon* | F8WL86 | Heat shock protein |
| *Citrus lemon* | K9JG59 | Abscisic acid stress ripening-related protein |
| *Citrus lemon* | Q000W4 | Fe(lll)-chelate reductase |
| *Citrus lemon* | Q39538 | Heat shock protein (Fragment) |
| *Citrus lemon* | Q5UEN6 | Putative signal recognition particle protein |
| *Citrus lemon* | Q8GV08 | Dehydrin |
| *Citrus lemon* | Q8L893 | Cytosolic phosphoglucomutase (Fragment) |
| *Citrus lemon* | Q8S990 | Polygalacturonase-inhibiting protein |

TABLE 1-continued

| | | Plant EV-Markers |
|---|---|---|
| Citrus lemon | Q8W3U6 | Polygalacturonase-inhibitor protein |
| Citrus lemon | Q93XL8 | Dehydrin COR15 |
| Citrus lemon | Q941Q1 | Non-symbiotic hemoglobin class 1 |
| Citrus lemon | Q9MBF3 | Glycine-rich RNA-binding protein |
| Citrus lemon | Q9SP55 | V-type proton ATPase subunit G (V-ATPase subunit G) (Vacuolar proton pump subunit G) |
| Citrus lemon | Q9THJ8 | Ribulose bisphosphate carboxylase large chain (EC 4.1.1.39) (Fragment) |
| Citrus lemon | Q9ZST2 | Pyrophosphate--fructose 6-phosphate 1-phosphotransferase subunit alpha (PFP) (6-phosphofructokinase, pyrophosphate dependent) (PPi-PFK) (Pyrophosphate-dependent 6-phosphofructose-1-kinase) |
| Citrus lemon | Q9ZWH6 | Polygalacturonase inhibitor |
| Citrus lemon | S5DXI9 | Nucleocapsid protein |
| Citrus lemon | S5NFC6 | GTP cyclohydrolase |
| Citrus lemon | V4RG42 | Uncharacterized protein |
| Citrus lemon | V4RGP4 | Uncharacterized protein |
| Citrus lemon | V4RHN8 | Uncharacterized protein |
| Citrus lemon | V4RJ07 | Uncharacterized protein |
| Citrus lemon | V4RJK9 | Adenosylhomocysteinase (EC 3.3.1.1) |
| Citrus lemon | V4RJM1 | Uncharacterized protein |
| Citrus lemon | V4RJX1 | 40S ribosomal protein S6 |
| Citrus lemon | V4RLB2 | Uncharacterized protein |
| Citrus lemon | V4RMX8 | Uncharacterized protein |
| Citrus lemon | V4RNA5 | Uncharacterized protein |
| Citrus lemon | V4RP81 | Glycosyltransferase (EC 2.4.1.—) |
| Citrus lemon | V4RPZ5 | Adenylyl cyclase-associated protein |
| Citrus lemon | V4RTN9 | Histone H4 |
| Citrus lemon | V4RUZ4 | Phosphoserine aminotransferase (EC 2.6.1.52) |
| Citrus lemon | V4RVF6 | Uncharacterized protein |
| Citrus lemon | V4RXD4 | Uncharacterized protein |
| Citrus lemon | V4RXG2 | Uncharacterized protein |
| Citrus lemon | V4RYA0 | Uncharacterized protein |
| Citrus lemon | V4RYE3 | Uncharacterized protein |
| Citrus lemon | V4RYH3 | Uncharacterized protein |
| Citrus lemon | V4RYX8 | Uncharacterized protein |
| Citrus lemon | V4RZ12 | Coatomer subunit beta' |
| Citrus lemon | V4RZ89 | Uncharacterized protein |
| Citrus lemon | V4RZE3 | Uncharacterized protein |
| Citrus lemon | V4RZF3 | 1,2-dihydroxy-3-keto-5-methylthiopentene dioxygenase (EC 1.13.11.54) (Acireductone dioxygenase (Fe(2+)-requiring)) (ARD) (Fe-ARD) |
| Citrus lemon | V4RZM7 | Uncharacterized protein |
| Citrus lemon | V4RZX6 | Uncharacterized protein |
| Citrus lemon | V4S1V0 | Uncharacterized protein |
| Citrus lemon | V4S2B6 | Uncharacterized protein |
| Citrus lemon | V4S2N1 | Uncharacterized protein |
| Citrus lemon | V4S2S5 | Uncharacterized protein (Fragment) |
| Citrus lemon | V4S346 | Uncharacterized protein |
| Citrus lemon | V4S3T8 | Uncharacterized protein |
| Citrus lemon | V4S409 | Cyanate hydratase (Cyanase) (EC 4.2.1.104) (Cyanate hydrolase) (Cyanate lyase) |
| Citrus lemon | V4S4E4 | Histone H2B |
| Citrus lemon | V4S4F6 | Flavin-containing monooxygenase (EC 1.—.—.—) |
| Citrus lemon | V4S4J1 | Uncharacterized protein |
| Citrus lemon | V4S4K9 | Uncharacterized protein |
| Citrus lemon | V4S535 | Proteasome subunit alpha type (EC 3.4.25.1) |
| Citrus lemon | V4S5A8 | Isocitrate dehydrogenase [NADP] (EC 1.1.1.42) |
| Citrus lemon | V4S5G8 | Uncharacterized protein |
| Citrus lemon | V4S5I6 | Uncharacterized protein |
| Citrus lemon | V4S5N4 | Uncharacterized protein (Fragment) |
| Citrus lemon | V4S5Q3 | Uncharacterized protein |
| Citrus lemon | V4S5X8 | Uncharacterized protein |
| Citrus lemon | V4S5Y1 | Uncharacterized protein |
| Citrus lemon | V4S6P4 | Calcium-transporting ATPase (EC 3.6.3.8) |
| Citrus lemon | V4S6W0 | Uncharacterized protein |
| Citrus lemon | V4S6W7 | Uncharacterized protein (Fragment) |
| Citrus lemon | V4S6Y4 | Uncharacterized protein |
| Citrus lemon | V4S773 | Ribosomal protein L19 |
| Citrus lemon | V4S7U0 | Uncharacterized protein |
| Citrus lemon | V4S7U5 | Uncharacterized protein |
| Citrus lemon | V4S7W4 | Pyruvate kinase (EC 2.7.1.40) |
| Citrus lemon | V4S885 | Uncharacterized protein |
| Citrus lemon | V4S8T3 | Peptidyl-prolyl cis-trans isomerase (PPIase) (EC 5.2.1.8) |
| Citrus lemon | V4S920 | Uncharacterized protein |
| Citrus lemon | V4S999 | Uncharacterized protein |
| Citrus lemon | V4S9G5 | Phosphoglycerate kinase (EC 2.7.2.3) |
| Citrus lemon | V4S9Q6 | Beta-amylase (EC 3.2.1.2) |

TABLE 1-continued

Plant EV-Markers

| | | |
|---|---|---|
| Citrus lemon | V4SA44 | Serine/threonine-protein phosphatase (EC 3.1.3.16) |
| Citrus lemon | V4SAE0 | Alpha-1,4 glucan phosphorylase (EC 2.4.1.1) |
| Citrus lemon | V4SAF6 | Uncharacterized protein |
| Citrus lemon | V4SAI9 | Eukaryotic translation initiation factor 3 subunit M (eIF3m) |
| Citrus lemon | V4SAJ5 | Ribosomal protein |
| Citrus lemon | V4SAR3 | Uncharacterized protein |
| Citrus lemon | V4SB37 | Uncharacterized protein |
| Citrus lemon | V4SBI0 | Elongation factor 1-alpha |
| Citrus lemon | V4SBI8 | D-3-phosphoglycerate dehydrogenase (EC 1.1.1.95) |
| Citrus lemon | V4SBL9 | Polyadenylate-binding protein (PABP) |
| Citrus lemon | V4SBR1 | S-formylglutathione hydrolase (EC 3.1.2.12) |
| Citrus lemon | V4SBR6 | Uncharacterized protein |
| Citrus lemon | V4SCG7 | Uncharacterized protein |
| Citrus lemon | V4SCJ2 | Uncharacterized protein |
| Citrus lemon | V4SCQ6 | Peptidyl-prolyl cis-trans isomerase (PPIase) (EC 5.2.1.8) |
| Citrus lemon | V4SDJ8 | Uncharacterized protein |
| Citrus lemon | V4SE41 | Protein DETOXIFICATION (Multidrug and toxic compound extrusion protein) |
| Citrus lemon | V4SE90 | Uncharacterized protein |
| Citrus lemon | V4SED1 | Succinate dehydrogenase [ubiquinone] flavoprotein subunit, mitochondrial (EC 1.3.5.1) |
| Citrus lemon | V4SEI1 | Uncharacterized protein |
| Citrus lemon | V4SEN9 | Uncharacterized protein |
| Citrus lemon | V4SEX8 | Uncharacterized protein |
| Citrus lemon | V4SF31 | Uncharacterized protein |
| Citrus lemon | V4SF69 | 40S ribosomal protein S24 |
| Citrus lemon | V4SF76 | Cysteine synthase (EC 2.5.1.47) |
| Citrus lemon | V4SFK3 | Uncharacterized protein |
| Citrus lemon | V4SFL4 | Uncharacterized protein |
| Citrus lemon | V4SFW2 | Uncharacterized protein |
| Citrus lemon | V4SGC9 | Uncharacterized protein |
| Citrus lemon | V4SGJ4 | Uncharacterized protein |
| Citrus lemon | V4SGN4 | Uncharacterized protein |
| Citrus lemon | V4SGV6 | Uncharacterized protein |
| Citrus lemon | V4SGV7 | Uncharacterized protein |
| Citrus lemon | V4SHH1 | Plasma membrane ATPase (EC 3.6.3.6) (Fragment) |
| Citrus lemon | V4SHI2 | Uncharacterized protein |
| Citrus lemon | V4SHJ3 | Uncharacterized protein |
| Citrus lemon | V4SI86 | Uncharacterized protein |
| Citrus lemon | V4SI88 | Uncharacterized protein |
| Citrus lemon | V4SIA2 | Uncharacterized protein |
| Citrus lemon | V4SIC1 | Phospholipase D (EC 3.1.4.4) |
| Citrus lemon | V4SJ14 | Uncharacterized protein |
| Citrus lemon | V4SJ48 | Uncharacterized protein |
| Citrus lemon | V4SJ69 | Uncharacterized protein |
| Citrus lemon | V4SJD9 | Uncharacterized protein |
| Citrus lemon | V4SJS7 | Uncharacterized protein |
| Citrus lemon | V4SJT5 | Uncharacterized protein |
| Citrus lemon | V4SKA2 | Uncharacterized protein |
| Citrus lemon | V4SKG4 | Glucose-6-phosphate isomerase (EC 5.3.1.9) |
| Citrus lemon | V4SKJ1 | Uncharacterized protein |
| Citrus lemon | V4SL90 | Uncharacterized protein |
| Citrus lemon | V4SLC6 | Proteasome subunit beta type (EC 3.4.25.1) |
| Citrus lemon | V4SLI7 | Uncharacterized protein |
| Citrus lemon | V4SLQ6 | Uncharacterized protein |
| Citrus lemon | V4SMD8 | Uncharacterized protein |
| Citrus lemon | V4SMN7 | Uncharacterized protein |
| Citrus lemon | V4SMV5 | Uncharacterized protein |
| Citrus lemon | V4SN00 | Uncharacterized protein |
| Citrus lemon | V4SNA9 | Uncharacterized protein |
| Citrus lemon | V4SNC1 | Uncharacterized protein |
| Citrus lemon | V4SNC4 | Aconitate hydratase (Aconitase) (EC 4.2.1.3) |
| Citrus lemon | V4SNZ3 | Uncharacterized protein |
| Citrus lemon | V4SP86 | Uncharacterized protein |
| Citrus lemon | V4SPM1 | 40S ribosomal protein S12 |
| Citrus lemon | V4SPW4 | 40S ribosomal protein S4 |
| Citrus lemon | V4SQ71 | Uncharacterized protein |
| Citrus lemon | V4SQ89 | Uncharacterized protein |
| Citrus lemon | V4SQ92 | Uncharacterized protein |
| Citrus lemon | V4SQC7 | Peroxidase (EC 1.11.1.7) |
| Citrus lemon | V4SQG3 | Uncharacterized protein |
| Citrus lemon | V4SR15 | Uncharacterized protein |
| Citrus lemon | V4SRN3 | Transmembrane 9 superfamily member |
| Citrus lemon | V4SS09 | Uncharacterized protein |
| Citrus lemon | V4SS11 | Uncharacterized protein |
| Citrus lemon | V4SS50 | Uncharacterized protein |
| Citrus lemon | V4SSB6 | Uncharacterized protein |
| Citrus lemon | V4SSB8 | Proteasome subunit alpha type (EC 3.4.25.1) |

TABLE 1-continued

| | Plant EV-Markers | |
|---|---|---|
| Citrus lemon | V4SSL7 | Uncharacterized protein |
| Citrus lemon | V4SSQ1 | Uncharacterized protein |
| Citrus lemon | V4SST6 | Uncharacterized protein |
| Citrus lemon | V4SSW9 | Uncharacterized protein |
| Citrus lemon | V4SSX5 | Uncharacterized protein |
| Citrus lemon | V4SU82 | Uncharacterized protein |
| Citrus lemon | V4SUD3 | Uncharacterized protein |
| Citrus lemon | V4SUL7 | Uncharacterized protein |
| Citrus lemon | V4SUP3 | Uncharacterized protein |
| Citrus lemon | V4SUT4 | UDP-glucose 6-dehydrogenase (EC 1.1.1.22) |
| Citrus lemon | V4SUY5 | Uncharacterized protein |
| Citrus lemon | V4SV60 | Serine/threonine-protein phosphatase (EC 3.1.3.16) |
| Citrus lemon | V4SV61 | Uncharacterized protein |
| Citrus lemon | V4SVI5 | Proteasome subunit alpha type (EC 3.4.25.1) |
| Citrus lemon | V4SVI6 | Uncharacterized protein |
| Citrus lemon | V4SW04 | Uncharacterized protein (Fragment) |
| Citrus lemon | V4SWD9 | Uncharacterized protein |
| Citrus lemon | V4SWJ0 | 40S ribosomal protein S3a |
| Citrus lemon | V4SWQ9 | Uncharacterized protein |
| Citrus lemon | V4SWR9 | Uncharacterized protein |
| Citrus lemon | V4SWU9 | Fructose-bisphosphate aldolase (EC 4.1.2.13) |
| Citrus lemon | V4SX11 | Uncharacterized protein |
| Citrus lemon | V4SX99 | Uncharacterized protein |
| Citrus lemon | V4SXC7 | Proteasome subunit alpha type (EC 3.4.25.1) |
| Citrus lemon | V4SXQ5 | Uncharacterized protein |
| Citrus lemon | V4SXW1 | Beta-adaptin-like protein |
| Citrus lemon | V4SXY9 | Uncharacterized protein |
| Citrus lemon | V4SY74 | Uncharacterized protein |
| Citrus lemon | V4SY90 | Uncharacterized protein |
| Citrus lemon | V4SY93 | Uncharacterized protein |
| Citrus lemon | V4SYH9 | Uncharacterized protein |
| Citrus lemon | V4SYK6 | Uncharacterized protein |
| Citrus lemon | V4SZ03 | Uncharacterized protein |
| Citrus lemon | V4SZ73 | Uncharacterized protein |
| Citrus lemon | V4SZI9 | Uncharacterized protein |
| Citrus lemon | V4SZX7 | Uncharacterized protein |
| Citrus lemon | V4T057 | Ribosomal protein L15 |
| Citrus lemon | V4T0V5 | Eukaryotic translation initiation factor 3 subunit A (eIF3a) (Eukaryotic translation initiation factor 3 subunit 10) |
| Citrus lemon | V4T0Y1 | Uncharacterized protein |
| Citrus lemon | V4T1Q6 | Uncharacterized protein |
| Citrus lemon | V4T1U7 | Uncharacterized protein |
| Citrus lemon | V4T2D9 | Uncharacterized protein |
| Citrus lemon | V4T2M6 | Tubulin beta chain |
| Citrus lemon | V4T3G2 | Uncharacterized protein |
| Citrus lemon | V4T3P3 | 6-phosphogluconate dehydrogenase, decarboxylating (EC 1.1.1.44) |
| Citrus lemon | V4T3V9 | Uncharacterized protein |
| Citrus lemon | V4T3Y6 | Uncharacterized protein |
| Citrus lemon | V4T4H3 | Uncharacterized protein |
| Citrus lemon | V4T4I7 | Uncharacterized protein |
| Citrus lemon | V4T4M7 | Superoxide dismutase [Cu—Zn] (EC 1.15.1.1) |
| Citrus lemon | V4T539 | Uncharacterized protein |
| Citrus lemon | V4T541 | Uncharacterized protein |
| Citrus lemon | V4T576 | Uncharacterized protein |
| Citrus lemon | V4T5E1 | Uncharacterized protein |
| Citrus lemon | V4T5I3 | Uncharacterized protein |
| Citrus lemon | V4T5W7 | Uncharacterized protein |
| Citrus lemon | V4T6T5 | 60S acidic ribosomal protein P0 |
| Citrus lemon | V4T722 | Uncharacterized protein |
| Citrus lemon | V4T785 | Uncharacterized protein |
| Citrus lemon | V4T7E2 | Uncharacterized protein |
| Citrus lemon | V4T7I7 | Uncharacterized protein |
| Citrus lemon | V4T7N0 | Proteasome subunit beta type (EC 3.4.25.1) |
| Citrus lemon | V4T7N4 | Uncharacterized protein |
| Citrus lemon | V4T7T2 | Uncharacterized protein |
| Citrus lemon | V4T7W5 | Uncharacterized protein |
| Citrus lemon | V4T825 | Uncharacterized protein |
| Citrus lemon | V4T846 | Uncharacterized protein |
| Citrus lemon | V4T8E9 | S-acyltransferase (EC 2.3.1.225) (Palmitoyltransferase) |
| Citrus lemon | V4T8G2 | Uncharacterized protein |
| Citrus lemon | V4T8G9 | Chorismate synthase (EC 4.2.3.5) |
| Citrus lemon | V4T8Y6 | Uncharacterized protein |
| Citrus lemon | V4T8Y8 | Uncharacterized protein |
| Citrus lemon | V4T939 | Carboxypeptidase (EC 3.4.16.—) |
| Citrus lemon | V4T957 | Uncharacterized protein |
| Citrus lemon | V4T998 | Uncharacterized protein |
| Citrus lemon | V4T9B9 | Uncharacterized protein |

TABLE 1-continued

Plant EV-Markers

| | | |
|---|---|---|
| Citrus lemon | V4T9Y7 | Uncharacterized protein |
| Citrus lemon | V4TA70 | Uncharacterized protein |
| Citrus lemon | V4TAF6 | Uncharacterized protein |
| Citrus lemon | V4TB09 | Uncharacterized protein |
| Citrus lemon | V4TB32 | Uncharacterized protein |
| Citrus lemon | V4TB89 | Uncharacterized protein |
| Citrus lemon | V4TBN7 | Phosphoinositide phospholipase C (EC 3.1.4.11) |
| Citrus lemon | V4TBQ3 | Uncharacterized protein |
| Citrus lemon | V4TBS4 | Uncharacterized protein |
| Citrus lemon | V4TBU3 | Uncharacterized protein |
| Citrus lemon | V4TCA6 | Uncharacterized protein |
| Citrus lemon | V4TCL3 | Uncharacterized protein |
| Citrus lemon | V4TCS5 | Pectate lyase (EC 4.2.2.2) |
| Citrus lemon | V4TD99 | Uncharacterized protein |
| Citrus lemon | V4TDB5 | Uncharacterized protein |
| Citrus lemon | V4TDI2 | Uncharacterized protein |
| Citrus lemon | V4TDY3 | Serine/threonine-protein kinase (EC 2.7.11.1) |
| Citrus lemon | V4TE72 | Uncharacterized protein |
| Citrus lemon | V4TE95 | Uncharacterized protein |
| Citrus lemon | V4TEC0 | Uncharacterized protein |
| Citrus lemon | V4TED8 | Uncharacterized protein |
| Citrus lemon | V4TES4 | Uncharacterized protein |
| Citrus lemon | V4TEY9 | Uncharacterized protein |
| Citrus lemon | V4TF24 | Proteasome subunit alpha type (EC 3.4.25.1) |
| Citrus lemon | V4TF52 | Uricase (EC 1.7.3.3) (Urate oxidase) |
| Citrus lemon | V4TFV8 | Catalase (EC 1.11.1.6) |
| Citrus lemon | V4TGU1 | Uncharacterized protein |
| Citrus lemon | V4TH28 | Uncharacterized protein |
| Citrus lemon | V4TH78 | Reticulon-like protein |
| Citrus lemon | V4THM9 | Uncharacterized protein |
| Citrus lemon | V4TIU2 | Ribulose-phosphate 3-epimerase (EC 5.1.3.1) |
| Citrus lemon | V4TIW6 | Uncharacterized protein |
| Citrus lemon | V4TIY6 | Uncharacterized protein |
| Citrus lemon | V4TIZ5 | Uncharacterized protein |
| Citrus lemon | V4TJ75 | Uncharacterized protein |
| Citrus lemon | V4TJC3 | Uncharacterized protein |
| Citrus lemon | V4TJQ9 | Uncharacterized protein |
| Citrus lemon | V4TK29 | NEDD8-activating enzyme E1 regulatory subunit |
| Citrus lemon | V4TL04 | Uncharacterized protein |
| Citrus lemon | V4TLL5 | Uncharacterized protein |
| Citrus lemon | V4TLP6 | Uncharacterized protein |
| Citrus lemon | V4TM00 | Uncharacterized protein |
| Citrus lemon | V4TM19 | Uncharacterized protein |
| Citrus lemon | V4TMB7 | Uncharacterized protein (Fragment) |
| Citrus lemon | V4TMD1 | Uncharacterized protein |
| Citrus lemon | V4TMD6 | Uncharacterized protein |
| Citrus lemon | V4TMV4 | Uncharacterized protein |
| Citrus lemon | V4TN30 | Uncharacterized protein |
| Citrus lemon | V4TN38 | Uncharacterized protein |
| Citrus lemon | V4TNY8 | Uncharacterized protein |
| Citrus lemon | V4TP87 | Carbonic anhydrase (EC 4.2.1.1) (Carbonate dehydratase) |
| Citrus lemon | V4TPM1 | Homoserine dehydrogenase (HDH) (EC 1.1.1.3) |
| Citrus lemon | V4TQB6 | Uncharacterized protein |
| Citrus lemon | V4TQM7 | Uncharacterized protein |
| Citrus lemon | V4TQR2 | Uncharacterized protein |
| Citrus lemon | V4TQV9 | Uncharacterized protein |
| Citrus lemon | V4TS21 | Proteasome subunit beta type (EC 3.4.25.1) |
| Citrus lemon | V4TS28 | Annexin |
| Citrus lemon | V4TSD8 | Uncharacterized protein (Fragment) |
| Citrus lemon | V4TSF8 | Uncharacterized protein |
| Citrus lemon | V4TSI9 | Uncharacterized protein |
| Citrus lemon | V4TT89 | Uncharacterized protein |
| Citrus lemon | V4TTA0 | Uncharacterized protein |
| Citrus lemon | V4TTR8 | Uncharacterized protein |
| Citrus lemon | V4TTV4 | Uncharacterized protein |
| Citrus lemon | V4TTZ7 | Uncharacterized protein |
| Citrus lemon | V4TU54 | Uncharacterized protein |
| Citrus lemon | V4TVB6 | Uncharacterized protein |
| Citrus lemon | V4TVG1 | Eukaryotic translation initiation factor 5A (eIF-5A) |
| Citrus lemon | V4TVJ4 | Profilin |
| Citrus lemon | V4TVM6 | Uncharacterized protein |
| Citrus lemon | V4TVM9 | Uncharacterized protein |
| Citrus lemon | V4TVP7 | Uncharacterized protein |
| Citrus lemon | V4TVT8 | Uncharacterized protein |
| Citrus lemon | V4TW14 | Uncharacterized protein |
| Citrus lemon | V4TWG9 | T-complex protein 1 subunit delta |
| Citrus lemon | V4TWU1 | Probable bifunctional methylthioribulose-1-phosphate dehydratase/enolase-phosphatase E1 [Includes: Enolase-phosphatase |

TABLE 1-continued

| | Plant EV-Markers | |
|---|---|---|
| | | E1 (EC 3.1.3.77) (2,3-diketo-5-methylthio-1-phosphopentane phosphatase); Methylthioribulose-1-phosphate dehydratase (MTRu-1-P dehydratase) (EC 4.2.1.109)] |
| Citrus lemon | V4TWX8 | Uncharacterized protein |
| Citrus lemon | V4TXH0 | Glutamate decarboxylase (EC 4.1.1.15) |
| Citrus lemon | V4TXK9 | Uncharacterized protein |
| Citrus lemon | V4TXU9 | Thiamine thiazole synthase, chloroplastic (Thiazole biosynthetic enzyme) |
| Citrus lemon | V4TY40 | Uncharacterized protein |
| Citrus lemon | V4TYJ6 | Uncharacterized protein |
| Citrus lemon | V4TYP5 | 60S ribosomal protein L13 |
| Citrus lemon | V4TYP6 | Uncharacterized protein |
| Citrus lemon | V4TYR6 | Uncharacterized protein |
| Citrus lemon | V4TYZ8 | Tubulin alpha chain |
| Citrus lemon | V4TZ91 | Guanosine nucleotide diphosphate dissociation inhibitor |
| Citrus lemon | V4TZA8 | Uncharacterized protein |
| Citrus lemon | V4TZJ1 | Uncharacterized protein |
| Citrus lemon | V4TZK5 | Uncharacterized protein |
| Citrus lemon | V4TZP2 | Uncharacterized protein |
| Citrus lemon | V4TZT8 | Uncharacterized protein |
| Citrus lemon | V4TZU3 | Mitogen-activated protein kinase (EC 2.7.11.24) |
| Citrus lemon | V4TZU5 | Dihydrolipoyl dehydrogenase (EC 1.8.1.4) |
| Citrus lemon | V4TZZ0 | Uncharacterized protein |
| Citrus lemon | V4U003 | Eukaryotic translation initiation factor 3 subunit K (eIF3k) (eIF-3 p25) |
| Citrus lemon | V4U068 | Uncharacterized protein |
| Citrus lemon | V4U088 | Uncharacterized protein |
| Citrus lemon | V4U0J7 | Uncharacterized protein |
| Citrus lemon | V4U133 | Uncharacterized protein |
| Citrus lemon | V4U1A8 | Uncharacterized protein |
| Citrus lemon | V4U1K1 | Xylose isomerase (EC 5.3.1.5) |
| Citrus lemon | V4U1M1 | Uncharacterized protein |
| Citrus lemon | V4U1V0 | Uncharacterized protein |
| Citrus lemon | V4U1X7 | Uncharacterized protein |
| Citrus lemon | V4U1X9 | Proteasome subunit beta type (EC 3.4.25.1) |
| Citrus lemon | V4U251 | Uncharacterized protein |
| Citrus lemon | V4U283 | Uncharacterized protein |
| Citrus lemon | V4U2E4 | Uncharacterized protein |
| Citrus lemon | V4U2F7 | Uncharacterized protein |
| Citrus lemon | V4U2H8 | Uncharacterized protein |
| Citrus lemon | V4U2L0 | Malate dehydrogenase (EC 1.1.1.37) |
| Citrus lemon | V4U2L2 | Uncharacterized protein |
| Citrus lemon | V4U2W4 | V-type proton ATPase subunit C |
| Citrus lemon | V4U3L2 | Uncharacterized protein |
| Citrus lemon | V4U3W8 | Uncharacterized protein |
| Citrus lemon | V4U412 | Uncharacterized protein |
| Citrus lemon | V4U4K2 | Uncharacterized protein |
| Citrus lemon | V4U4M4 | Uncharacterized protein |
| Citrus lemon | V4U4N5 | Eukaryotic translation initiation factor 6 (eIF-6) |
| Citrus lemon | V4U4S9 | Uncharacterized protein |
| Citrus lemon | V4U4X3 | Serine hydroxymethyltransferase (EC 2.1.2.1) |
| Citrus lemon | V4U4Z9 | Uncharacterized protein |
| Citrus lemon | V4U500 | Uncharacterized protein |
| Citrus lemon | V4U5B0 | Eukaryotic translation initiation factor 3 subunit E (eIF3e) (Eukaryotic translation initiation factor 3 subunit 6) |
| Citrus lemon | V4U5B8 | Glutathione peroxidase |
| Citrus lemon | V4U5R5 | Citrate synthase |
| Citrus lemon | V4U5Y8 | Uncharacterized protein |
| Citrus lemon | V4U6I5 | ATP synthase subunit beta (EC 3.6.3.14) |
| Citrus lemon | V4U6Q8 | Uncharacterized protein |
| Citrus lemon | V4U706 | Uncharacterized protein |
| Citrus lemon | V4U717 | Uncharacterized protein |
| Citrus lemon | V4U726 | Uncharacterized protein |
| Citrus lemon | V4U729 | Uncharacterized protein |
| Citrus lemon | V4U734 | Serine/threonine-protein phosphatase (EC 3.1.3.16) |
| Citrus lemon | V4U7G7 | Uncharacterized protein |
| Citrus lemon | V4U7H5 | Uncharacterized protein |
| Citrus lemon | V4U7R1 | Potassium transporter |
| Citrus lemon | V4U7R7 | Mitogen-activated protein kinase (EC 2.7.11.24) |
| Citrus lemon | V4U833 | Malic enzyme |
| Citrus lemon | V4U840 | Uncharacterized protein |
| Citrus lemon | V4U8C3 | Uncharacterized protein |
| Citrus lemon | V4U8J1 | 3-phosphoshikimate 1-carboxyvinyltransferase (EC 2.5.1.19) |
| Citrus lemon | V4U8J8 | T-complex protein 1 subunit gamma |
| Citrus lemon | V4U995 | Uncharacterized protein |
| Citrus lemon | V4U999 | Uncharacterized protein |
| Citrus lemon | V4U9C7 | Eukaryotic translation initiation factor 3 subunit D (eIF3d) (Eukaryotic translation initiation factor 3 subunit 7) (eIF-3-zeta) |

TABLE 1-continued

| | Plant EV-Markers | |
|---|---|---|
| Citrus lemon | V4U9G8 | Proline iminopeptidase (EC 3.4.11.5) |
| Citrus lemon | V4U9L1 | Uncharacterized protein |
| Citrus lemon | V4UA63 | Phytochrome |
| Citrus lemon | V4UAC8 | Uncharacterized protein |
| Citrus lemon | V4UAR4 | Uncharacterized protein |
| Citrus lemon | V4UB30 | Uncharacterized protein |
| Citrus lemon | V4UBK8 | V-type proton ATPase subunit a |
| Citrus lemon | V4UBL3 | Coatomer subunit alpha |
| Citrus lemon | V4UBL5 | Uncharacterized protein (Fragment) |
| Citrus lemon | V4UBM0 | Uncharacterized protein |
| Citrus lemon | V4UBZ8 | Aspartate aminotransferase (EC 2.6.1.1) |
| Citrus lemon | V4UC72 | Uncharacterized protein |
| Citrus lemon | V4UC97 | Beta-glucosidase (EC 3.2.1.21) |
| Citrus lemon | V4UCE2 | Uncharacterized protein |
| Citrus lemon | V4UCT9 | Acetyl-coenzyme A synthetase (EC 6.2.1.1) |
| Citrus lemon | V4UCZ1 | Uncharacterized protein |
| Citrus lemon | V4UE34 | Uncharacterized protein |
| Citrus lemon | V4UE78 | Uncharacterized protein |
| Citrus lemon | V4UER3 | Uncharacterized protein |
| Citrus lemon | V4UET6 | Uncharacterized protein |
| Citrus lemon | V4UEZ6 | Uncharacterized protein |
| Citrus lemon | V4UFD0 | Uncharacterized protein |
| Citrus lemon | V4UFG8 | Uncharacterized protein |
| Citrus lemon | V4UFK1 | Uncharacterized protein |
| Citrus lemon | V4UG68 | Eukaryotic translation initiation factor 3 subunit I (eIF3i) |
| Citrus lemon | V4UGB0 | Uncharacterized protein |
| Citrus lemon | V4UGH4 | Uncharacterized protein |
| Citrus lemon | V4UGL9 | Uncharacterized protein |
| Citrus lemon | V4UGQ0 | Ubiquitinyl hydrolase 1 (EC 3.4.19.12) |
| Citrus lemon | V4UH00 | Uncharacterized protein |
| Citrus lemon | V4UH48 | Uncharacterized protein |
| Citrus lemon | V4UH77 | Proteasome subunit alpha type (EC 3.4.25.1) |
| Citrus lemon | V4UHD8 | Uncharacterized protein |
| Citrus lemon | V4UHD9 | Uncharacterized protein |
| Citrus lemon | V4UHF1 | Uncharacterized protein |
| Citrus lemon | V4UHZ5 | Uncharacterized protein |
| Citrus lemon | V4UI07 | 40S ribosomal protein S8 |
| Citrus lemon | V4UI34 | Eukaryotic translation initiation factor 3 subunit L (eIF3I) |
| Citrus lemon | V4UIF1 | Uncharacterized protein |
| Citrus lemon | V4UIN5 | Uncharacterized protein |
| Citrus lemon | V4UIX8 | Uncharacterized protein |
| Citrus lemon | V4UJ12 | Uncharacterized protein |
| Citrus lemon | V4UJ42 | Uncharacterized protein |
| Citrus lemon | V4UJ63 | Uncharacterized protein |
| Citrus lemon | V4UJB7 | Uncharacterized protein (Fragment) |
| Citrus lemon | V4UJC4 | Uncharacterized protein |
| Citrus lemon | V4UJX0 | Phosphotransferase (EC 2.7.1.—) |
| Citrus lemon | V4UJY5 | Uncharacterized protein |
| Citrus lemon | V4UK18 | Uncharacterized protein |
| Citrus lemon | V4UK52 | Uncharacterized protein |
| Citrus lemon | V4UKM9 | Uncharacterized protein |
| Citrus lemon | V4UKS4 | Uncharacterized protein |
| Citrus lemon | V4UKV6 | 40S ribosomal protein SA |
| Citrus lemon | V4UL30 | Pyrophosphate-fructose 6-phosphate 1-phosphotransferase subunit beta (PFP) (EC 2.7.1.90) (6-phosphofructokinase, pyrophosphate dependent) (PPi-PFK) (Pyrophosphate-dependent 6-phosphofructose-1-kinase) |
| Citrus lemon | V4UL39 | Uncharacterized protein |
| Citrus lemon | V4ULH9 | Uncharacterized protein |
| Citrus lemon | V4ULL2 | Uncharacterized protein |
| Citrus lemon | V4ULS0 | Uncharacterized protein |
| Citrus lemon | V4UMU7 | Uncharacterized protein |
| Citrus lemon | V4UN36 | Uncharacterized protein |
| Citrus lemon | V4UNT5 | Uncharacterized protein |
| Citrus lemon | V4UNW1 | Uncharacterized protein |
| Citrus lemon | V4UP89 | Uncharacterized protein |
| Citrus lemon | V4UPE4 | Uncharacterized protein |
| Citrus lemon | V4UPF7 | Uncharacterized protein |
| Citrus lemon | V4UPK0 | Uncharacterized protein |
| Citrus lemon | V4UPX5 | Uncharacterized protein |
| Citrus lemon | V4UQ58 | Uncharacterized protein |
| Citrus lemon | V4UQF6 | Uncharacterized protein |
| Citrus lemon | V4UR21 | Uncharacterized protein |
| Citrus lemon | V4UR80 | Uncharacterized protein |
| Citrus lemon | V4URK3 | Uncharacterized protein |
| Citrus lemon | V4URT3 | Uncharacterized protein |
| Citrus lemon | V4US96 | Uncharacterized protein |
| Citrus lemon | V4USQ8 | Uncharacterized protein |

TABLE 1-continued

| Plant EV-Markers | | |
|---|---|---|
| *Citrus lemon* | V4UT16 | Uncharacterized protein |
| *Citrus lemon* | V4UTC6 | Uncharacterized protein |
| *Citrus lemon* | V4UTC8 | Uncharacterized protein |
| *Citrus lemon* | V4UTP6 | Uncharacterized protein |
| *Citrus lemon* | V4UTY0 | Proteasome subunit alpha type (EC 3.4.25.1) |
| *Citrus lemon* | V4UU96 | Uncharacterized protein |
| *Citrus lemon* | V4UUB6 | Uncharacterized protein |
| *Citrus lemon* | V4UUJ9 | Aminopeptidase (EC 3.4.11.—) |
| *Citrus lemon* | V4UUK6 | Uncharacterized protein |
| *Citrus lemon* | V4UV09 | Uncharacterized protein |
| *Citrus lemon* | V4UV83 | Lysine--tRNA ligase (EC 6.1.1.6) (Lysyl-tRNA synthetase) |
| *Citrus lemon* | V4UVJ5 | Diacylglycerol kinase (DAG kinase) (EC 2.7.1.107) |
| *Citrus lemon* | V4UW03 | Uncharacterized protein |
| *Citrus lemon* | V4UW04 | Uncharacterized protein |
| *Citrus lemon* | V4UWR1 | Uncharacterized protein |
| *Citrus lemon* | V4UWV8 | Uncharacterized protein |
| *Citrus lemon* | V4UX36 | Uncharacterized protein |
| *Citrus lemon* | V4V003 | Uncharacterized protein |
| *Citrus lemon* | V4V0J0 | 40S ribosomal protein S26 |
| *Citrus lemon* | V4V1P8 | Uncharacterized protein |
| *Citrus lemon* | V4V4V0 | Uncharacterized protein |
| *Citrus lemon* | V4V5T8 | Ubiquitin-fold modifier 1 |
| *Citrus lemon* | V4V600 | Uncharacterized protein |
| *Citrus lemon* | V4V622 | Aldehyde dehydrogenase |
| *Citrus lemon* | V4V6W1 | Uncharacterized protein |
| *Citrus lemon* | V4V6Z2 | Uncharacterized protein |
| *Citrus lemon* | V4V738 | Uncharacterized protein |
| *Citrus lemon* | V4V8H5 | Vacuolar protein sorting-associated protein 35 |
| *Citrus lemon* | V4V9P6 | Eukaryotic translation initiation factor 3 subunit F (eIF3f) (eIF-3-epsilon) |
| *Citrus lemon* | V4V9V7 | Clathrin heavy chain |
| *Citrus lemon* | V4V9X3 | Uncharacterized protein |
| *Citrus lemon* | V4VAA3 | Superoxide dismutase (EC 1.15.1.1) |
| *Citrus lemon* | V4VAF3 | Uncharacterized protein |
| *Citrus lemon* | V4VBQ0 | Uncharacterized protein (Fragment) |
| *Citrus lemon* | V4VCL1 | Proteasome subunit beta type (EC 3.4.25.1) |
| *Citrus lemon* | V4VCZ9 | Uncharacterized protein |
| *Citrus lemon* | V4VDK1 | Peptidylprolyl isomerase (EC 5.2.1.8) |
| *Citrus lemon* | V4VEA1 | Uncharacterized protein |
| *Citrus lemon* | V4VEB3 | Alanine--tRNA ligase (EC 6.1.1.7) (Alanyl-tRNA synthetase) (AlaRS) |
| *Citrus lemon* | V4VEE3 | Glutamine synthetase (EC 6.3.1.2) |
| *Citrus lemon* | V4VFM3 | Uncharacterized protein |
| *Citrus lemon* | V4VFN5 | Proteasome subunit beta type (EC 3.4.25.1) |
| *Citrus lemon* | V4VGD6 | Uncharacterized protein |
| *Citrus lemon* | V4VGL9 | Uncharacterized protein |
| *Citrus lemon* | V4VHI6 | Uncharacterized protein |
| *Citrus lemon* | V4VIP4 | Uncharacterized protein |
| *Citrus lemon* | V4VJT4 | Uncharacterized protein |
| *Citrus lemon* | V4VK14 | Uncharacterized protein |
| *Citrus lemon* | V4VKI5 | Protein-L-isoaspartate O-methyltransferase (EC 2.1.1.77) |
| *Citrus lemon* | V4VKP2 | Glyceraldehyde-3-phosphate dehydrogenase (EC 1.2.1.—) |
| *Citrus lemon* | V4VL73 | Acyl-coenzyme A oxidase |
| *Citrus lemon* | V4VLL7 | Uncharacterized protein |
| *Citrus lemon* | V4VN43 | Uncharacterized protein (Fragment) |
| *Citrus lemon* | V4VQH3 | Methylenetetrahydrofolate reductase (EC 1.5.1.20) |
| *Citrus lemon* | V4VTC9 | Uncharacterized protein (Fragment) |
| *Citrus lemon* | V4VTT4 | Uncharacterized protein |
| *Citrus lemon* | V4VTY7 | Uncharacterized protein |
| *Citrus lemon* | V4VU14 | Uncharacterized protein |
| *Citrus lemon* | V4VU32 | Uncharacterized protein |
| *Citrus lemon* | V4VUK6 | S-(hydroxymethyl)glutathione dehydrogenase (EC 1.1.1.284) |
| *Citrus lemon* | V4VVR8 | Uncharacterized protein |
| *Citrus lemon* | V4VXE2 | Uncharacterized protein |
| *Citrus lemon* | V4VY37 | Phosphomannomutase (EC 5.4.2.8) |
| *Citrus lemon* | V4VYC0 | Uncharacterized protein |
| *Citrus lemon* | V4VYV1 | Uncharacterized protein |
| *Citrus lemon* | V4VZ80 | Uncharacterized protein |
| *Citrus lemon* | V4VZJ7 | Uncharacterized protein |
| *Citrus lemon* | V4W2P2 | Alpha-mannosidase (EC 3.2.1.—) |
| *Citrus lemon* | V4W2Z9 | Chloride channel protein |
| *Citrus lemon* | V4W378 | Uncharacterized protein |
| *Citrus lemon* | V4W4G3 | Uncharacterized protein |
| *Citrus lemon* | V4W5F1 | Uncharacterized protein |
| *Citrus lemon* | V4W5N8 | Uncharacterized protein |
| *Citrus lemon* | V4W5U2 | Uncharacterized protein |
| *Citrus lemon* | V4W6G1 | Uncharacterized protein |
| *Citrus lemon* | V4W730 | Uncharacterized protein |

TABLE 1-continued

Plant EV-Markers

| | | |
|---|---|---|
| Citrus lemon | V4W7J4 | Obg-like ATPase 1 |
| Citrus lemon | V4W7L5 | Uncharacterized protein |
| Citrus lemon | V4W8C5 | Uncharacterized protein |
| Citrus lemon | V4W8C9 | Uncharacterized protein |
| Citrus lemon | V4W8D3 | Uncharacterized protein |
| Citrus lemon | V4W9I1 | Uncharacterized protein |
| Citrus lemon | V4W9F6 | 60S ribosomal protein L18a |
| Citrus lemon | V4W9G2 | Uncharacterized protein (Fragment) |
| Citrus lemon | V4W9L3 | Uncharacterized protein |
| Citrus lemon | V4W9Y8 | Uncharacterized protein |
| Citrus lemon | V4WAP9 | Coatomer subunit beta (Beta-coat protein) |
| Citrus lemon | V4WBK6 | Cytochrome b-c1 complex subunit 7 |
| Citrus lemon | V4WC15 | Malic enzyme |
| Citrus lemon | V4WC19 | Uncharacterized protein |
| Citrus lemon | V4WC74 | Uncharacterized protein |
| Citrus lemon | V4WC86 | Serine/threonine-protein phosphatase 2A 55 kDa regulatory subunit B |
| Citrus lemon | V4WCS4 | GTP-binding nuclear protein |
| Citrus lemon | V4WD80 | Aspartate aminotransferase (EC 2.6.1.1) |
| Citrus lemon | V4WDK0 | Uncharacterized protein |
| Citrus lemon | V4WDK3 | ATP-dependent 6-phosphofructokinase (ATP-PFK) (Phosphofructokinase) (EC 2.7.1.11) (Phosphohexokinase) |
| Citrus lemon | V4WE00 | Uncharacterized protein |
| Citrus lemon | V4WEE3 | Uncharacterized protein |
| Citrus lemon | V4WEN2 | Uncharacterized protein |
| Citrus lemon | V4WG97 | Autophagy-related protein |
| Citrus lemon | V4WGV2 | Uncharacterized protein |
| Citrus lemon | V4WGW5 | Uridine kinase (EC 2.7.1.48) |
| Citrus lemon | V4WHD4 | Uncharacterized protein |
| Citrus lemon | V4WHF8 | Sucrose synthase (EC 2.4.1.13) |
| Citrus lemon | V4WHK2 | Pectinesterase (EC 3.1.1.11) |
| Citrus lemon | V4WHQ4 | Uncharacterized protein |
| Citrus lemon | V4WHT6 | Uncharacterized protein |
| Citrus lemon | V4WJ93 | Uncharacterized protein |
| Citrus lemon | V4WJA9 | Uncharacterized protein |
| Citrus lemon | V4WJB1 | Uncharacterized protein |
| Citrus lemon | V9HXG3 | Protein disulfide-isomerase (EC 5.3.4.1) |
| Citrus lemon | W8Q8K1 | Putative inorganic pyrophosphatase |
| Citrus lemon | W8QJL0 | Putative isopentenyl pyrophosphate isomerase |

| Grape | Accession Number | Identified Proteins |
|---|---|---|
| Grape | A5C5K3 (+2) | Adenosylhomocysteinase |
| Grape | Q9M6B5 | Alcohol dehydrogenase 6 |
| Grape | A3FA65 (+1) | Aquaporin PIP1; 3 |
| Grape | Q0MX13 (+2) | Aquaporin PIP2; 2 |
| Grape | A3FA69 (+4) | Aquaporin PIP2; 4 |
| Grape | A5AFS1 (+2) | Elongation factor 1-alpha |
| Grape | UPI0001985702 | elongation factor 2 |
| Grape | D7T227 | Enolase |
| Grape | D7TJ12 | Enolase |
| Grape | A5B118 (+1) | Fructose-bisphosphate aldolase |
| Grape | E0CQ39 | Glucose-6-phosphate isomerase |
| Grape | D7TW04 | Glutathione peroxidase |
| Grape | A1YW90 (+3) | Glutathione S-transferase |
| Grape | A5BEW0 | Histone H4 |
| Grape | UPI00015C9A6A | HSC70-1 (heat shock cognate 70 kDa protein 1); ATP binding isoform 1 |
| Grape | D7FBC0 (+1) | Malate dehydrogenase |
| Grape | D7TBH4 | Malic enzyme |
| Grape | A5ATB7 (+1) | Methylenetetrahydrofolate reductase |
| Grape | A5JPK7 (+1) | Monodehydroascorbate reductase |
| Grape | A5AKD8 | Peptidyl-prolyl cis-trans isomerase |
| Grape | A5BQN6 | Peptidyl-prolyl cis-trans isomerase |
| Grape | A5CAF6 | Phosphoglycerate kinase |
| Grape | Q09VU3 (+1) | Phospholipase D |
| Grape | D7SK33 | Phosphorylase |
| Grape | A5AQ89 | Profilin |
| Grape | C5DB50 (+2) | Putative 2,3-bisphosphoglycerate-independent phosphoglycerate mutase |
| Grape | D7TIZ5 | Pyruvate kinase |
| Grape | A5BV65 | Triosephosphate isomerase |
| Grapefruit | G8Z362 (+1) | (E)-beta-farnesene synthase |
| Grapefruit | Q5CD81 | (E)-beta-ocimene synthase |
| Grapefruit | D0UZK1 (+2) | 1,2 rhamnosyltransferase |
| Grapefruit | A7ISD3 | 1,6-rhamnosyltransferase |
| Grapefruit | Q80H98 | 280 kDa protein |
| Grapefruit | Q15GA4 (+2) | 286 kDa polyprotein |

TABLE 1-continued

| | Plant EV-Markers | |
|---|---|---|
| Grapefruit | D7NHW9 | 2-phospho-D-glycerate hydrolase |
| Grapefruit | D0EAL9 | 349 kDa polyprotein |
| Grapefruit | Q9DTG5 | 349-kDa polyprotein |
| Grapefruit | O22297 | Acidic cellulase |
| Grapefruit | Q8H986 | Acidic class I chitinase |
| Grapefruit | D3GQL0 | Aconitate hydratase 1 |
| Grapefruit | K7N8A0 | Actin |
| Grapefruit | A8W8Y0 | Alcohol acyl transferase |
| Grapefruit | Q84V85 | Allene oxide synthase |
| Grapefruit | F8WL79 | Aminopeptidase |
| Grapefruit | Q09MG5 | Apocytochrome f |
| Grapefruit | J7EIR8 | Ascorbate peroxidase |
| Grapefruit | B9VRH6 | Ascorbate peroxidase |
| Grapefruit | G9I820 | Auxin-response factor |
| Grapefruit | J7ICW8 | Beta-amylase |
| Grapefruit | Q8L5Q9 | Beta-galactosidase |
| Grapefruit | A7BG60 | Beta-pinene synthase |
| Grapefruit | C0KLD1 | Beta-tubulin |
| Grapefruit | Q91QZ1 | Capsid protein |
| Grapefruit | Q3SAK9 | Capsid protein |
| Grapefruit | D2U833 | Cation chloride cotransporter |
| Grapefruit | C3VPJ0 (+3) | Chalcone synthase |
| Grapefruit | D5LM39 | Chloride channel protein |
| Grapefruit | Q9M4U0 | Cinnamate 4-hydroxylase CYP73 |
| Grapefruit | Q39627 | Citrin |
| Grapefruit | G2XKD3 | Coat protein |
| Grapefruit | Q3L2I6 | Coat protein |
| Grapefruit | D5FV16 | CRT/DRE binding factor |
| Grapefruit | Q8H6S5 | CTV.2 |
| Grapefruit | Q8H6Q8 | CTV.20 |
| Grapefruit | Q8H6Q7 | CTV.22 |
| Grapefruit | Q1I1D7 | Cytochrome P450 |
| Grapefruit | Q7Y045 | Dehydrin |
| Grapefruit | F8WLD2 | DNA excision repair protein |
| Grapefruit | Q09MI8 | DNA-directed RNA polymerase subunit beta" |
| Grapefruit | D2WKC9 | Ethylene response 1 |
| Grapefruit | D2WKD2 | Ethylene response sensor 1 |
| Grapefruit | D7PVG7 | Ethylene-insensitive 3-like 1 protein |
| Grapefruit | G3CHK8 | Eukaryotic translation initiation factor 3 subunit E |
| Grapefruit | A9NJG4 (+3) | Fatty acid hydroperoxide lyase |
| Grapefruit | B8Y9B5 | F-box family protein |
| Grapefruit | Q000W4 | Fe(III)-chelate reductase |
| Grapefruit | Q6Q3H4 | Fructokinase |
| Grapefruit | F8WL95 | Gag-pol polyprotein |
| Grapefruit | Q8L5K4 | Gamma-terpinene synthase, chloroplastic |
| Grapefruit | Q9SP43 | Glucose-1-phosphate adenylyltransferase |
| Grapefruit | Q3HM93 | Glutathione S-transferase |
| Grapefruit | D0VEW6 | GRAS family transcription factor |
| Grapefruit | F8WL87 | Heat shock protein |
| Grapefruit | H9NHK0 | Hsp90 |
| Grapefruit | Q8H6R4 | Jp18 |
| Grapefruit | G3CHK6 | Leucine-rich repeat family protein |
| Grapefruit | B2YGX9 (+1) | Limonoid UDP-glucosyltransferase |
| Grapefruit | Q05KK0 | MADS-box protein |
| Grapefruit | F8WLB4 | Mechanosensitive ion channel domain-containing protein |
| Grapefruit | Q5CD82 | Monoterpene synthase |
| Grapefruit | F8WLC4 | MYB transcription factor |
| Grapefruit | A5YWA9 | NAC domain protein |
| Grapefruit | Q09MC9 | NAD(P)H-quinone oxidoreductase subunit 5, chloroplastic |
| Grapefruit | Q8H6R9 | NBS-LRR type disease resistance protein |
| Grapefruit | Q8H6S0 | NBS-LRR type disease resistance protein |
| Grapefruit | Q8H6R6 | NBS-LRR type disease resistance protein |
| Grapefruit | J9WR93 | p1a |
| Grapefruit | Q1X8V8 | P23 |
| Grapefruit | E7DSS0 (+4) | P23 |
| Grapefruit | G0Z9I6 | p27 |
| Grapefruit | I3XHN0 | p33 |
| Grapefruit | B8YDL3 | p33 protein |
| Grapefruit | B9VB22 | p33 protein |
| Grapefruit | P87587 | P346 |
| Grapefruit | B9VB56 | p349 protein |
| Grapefruit | I3RWW7 | p349 protein |
| Grapefruit | B9VB20 | p349 protein |
| Grapefruit | Q9WID7 | p349 protein |
| Grapefruit | Q2XP16 | P353 |
| Grapefruit | O04886 (+1) | Pectinesterase 1 |
| Grapefruit | F8WL74 | Peptidyl-prolyl cis-trans isomerase |
| Grapefruit | Q0ZA67 | Peroxidase |

TABLE 1-continued

| | | Plant EV-Markers |
|---|---|---|
| Grapefruit | F1CT41 | Phosphoenolpyruvate carboxylase |
| Grapefruit | B1PBV7 (+2) | Phytoene synthase |
| Grapefruit | Q9ZWQ8 | Plastid-lipid-associated protein, chloroplastic |
| Grapefruit | Q94FM1 | Pol polyprotein |
| Grapefruit | Q94FM0 | Pol polyprotein |
| Grapefruit | G9I825 | Poly C-binding protein |
| Grapefruit | O64460 (+7) | Polygalacturonase inhibitor |
| Grapefruit | I3XHM8 | Polyprotein |
| Grapefruit | C0STR9 | Polyprotein |
| Grapefruit | H6U1F0 | Polyprotein |
| Grapefruit | B8QHP8 | Polyprotein |
| Grapefruit | I3V6C0 | Polyprotein |
| Grapefruit | C0STS0 | Polyprotein |
| Grapefruit | K0FGH5 | Polyprotein |
| Grapefruit | Q3HWZ1 | Polyprotein |
| Grapefruit | F8WLA5 | PPR containing protein |
| Grapefruit | Q06652 (+1) | Probable phospholipid hydroperoxide glutathione peroxidase |
| Grapefruit | P84177 | Profilin |
| Grapefruit | Q09MB4 | Protein ycf2 |
| Grapefruit | A8C183 | PSI reaction center subunit II |
| Grapefruit | A5JVP6 | Putative 2b protein |
| Grapefruit | D0EFM2 | Putative eukaryotic translation initiation factor 1 |
| Grapefruit | Q18L98 | Putative gag-pol polyprotein |
| Grapefruit | B5AMI9 | Putative movement protein |
| Grapefruit | A1ECK5 | Putative multiple stress-responsive zinc-finger protein |
| Grapefruit | B5AMJ0 | Putative replicase polyprotein |
| Grapefruit | I7CYN5 | Putative RNA-dependent RNA polymerase |
| Grapefruit | Q8RVR2 | Putative terpene synthase |
| Grapefruit | B5TE89 | Putative uncharacterized protein |
| Grapefruit | Q8JVF3 | Putative uncharacterized protein |
| Grapefruit | F8WLB0 | Putative uncharacterized protein ORF43 |
| Grapefruit | A5JVP4 | Putative viral replicase |
| Grapefruit | M1JAW3 | Replicase |
| Grapefruit | H6VXK8 | Replicase polyprotein |
| Grapefruit | J9UF50 (+1) | Replicase protein 1a |
| Grapefruit | J9RV45 | Replicase protein 2a |
| Grapefruit | Q5EGG5 | Replicase-associated polyprotein |
| Grapefruit | G9I823 | RNA recognition motif protein 1 |
| Grapefruit | J7EPC0 | RNA-dependent RNA polymerase |
| Grapefruit | Q6DN67 | RNA-directed RNA polymerase L |
| Grapefruit | A9CQM4 | SEPALLATA1 homolog |
| Grapefruit | Q9SLS2 | Sucrose synthase |
| Grapefruit | Q9SLV8 (+1) | Sucrose synthase |
| Grapefruit | Q38JC1 | Temperature-induced lipocalin |
| Grapefruit | D0ELH6 | Tetratricopeptide domain-containing thioredoxin |
| Grapefruit | D2KU75 | Thaumatin-like protein |
| Grapefruit | C3VIC2 | Translation elongation factor |
| Grapefruit | D5LY07 | Ubiquitin/ribosomal fusion protein |
| Grapefruit | C6KI43 | UDP-glucosyltransferase family 1 protein |
| Grapefruit | A0FKR1 | Vacuolar citrate/H+ symporter |
| Grapefruit | Q944C8 | Vacuolar invertase |
| Grapefruit | Q9MB46 | V-type proton ATPase subunit E |
| Grapefruit | F8WL82 | WD-40 repeat family protein |
| Helianthuus annuus | HanXRQChr03g0080391 | Hsp90 |
| Helianthuus annuus | HanXRQChr13g0408351 | Hsp90 |
| Helianthuus annuus | HanXRQChr13g0408441 | Hsp90 |
| Helianthuus annuus | HanXRQChr14g0462551 | Hsp90 |
| Helianthuus annuus | HanXRQChr02g0044471 | Hsp70 |
| Helianthuus annuus | HanXRQChr02g0044481 | Hsp70 |
| Helianthuus annuus | HanXRQChr05g0132631 | Hsp70 |
| Helianthuus annuus | HanXRQChr05g0134631 | Hsp70 |
| Helianthuus annuus | HanXRQChr05g0134801 | Hsp70 |
| Helianthuus annuus | HanXRQChr10g0299441 | glutathione S-transferase |
| Helianthuus annuus | HanXRQChr16g0516291 | glutathione S-transferase |
| Helianthuus annuus | HanXRQChr03g0091431 | lactate/malate dehydrogenase |
| Helianthuus annuus | HanXRQChr13g0421951 | lactate/malate dehydrogenase |
| Helianthuus annuus | HanXRQChr10g0304821 | lactate/malate dehydrogenase |
| Helianthuus annuus | HanXRQChr12g0373491 | lactate/malate dehydrogenase |
| Helianthuus annuus | HanXRQChr01g0031071 | small GTPase superfamily, Rab type |
| Helianthuus annuus | HanXRQChr01g0031091 | small GTPase superfamily, Rab type |
| Helianthuus annuus | HanXRQChr02g0050791 | small GTPase superfamily, Rab type |
| Helianthuus annuus | HanXRQChr11g0353711 | small GTPase superfamily, Rab type |
| Helianthuus annuus | HanXRQChr13g0402771 | small GTPase superfamily, Rab type |
| Helianthuus annuus | HanXRQChr07g0190171 | isocitrate/isopropylmalate dehydrogenase |
| Helianthuus annuus | HanXRQChr16g0532251 | isocitrate/isopropylmalate dehydrogenase |
| Helianthuus annuus | HanXRQChr03g0079131 | phosphoenolpyruvate carboxylase |
| Helianthuus annuus | HanXRQChr15g0495261 | phosphoenolpyruvate carboxylase |

TABLE 1-continued

| | Plant EV-Markers | |
|---|---|---|
| Helianthuus annuus | HanXRQChr13g0388931 | phosphoenolpyruvate carboxylase |
| Helianthuus annuus | HanXRQChr14g0442731 | phosphoenolpyruvate carboxylase |
| Helianthuus annuus | HanXRQChr15g0482381 | UTP-glucose-1-phosphate uridylyltransferase |
| Helianthuus annuus | HanXRQChr16g0532261 | UTP-glucose-1-phosphate uridylyltransferase |
| Helianthuus annuus | HanXRQChr05g0135591 | tubulin |
| Helianthuus annuus | HanXRQChr06g0178921 | tubulin |
| Helianthuus annuus | HanXRQChr08g0237071 | tubulin |
| Helianthuus annuus | HanXRQChr11g0337991 | tubulin |
| Helianthuus annuus | HanXRQChr13g0407921 | tubulin |
| Helianthuus annuus | HanXRQChr05g0145191 | tubulin |
| Helianthuus annuus | HanXRQChr07g0187021 | tubulin |
| Helianthuus annuus | HanXRQChr07g0189811 | tubulin |
| Helianthuus annuus | HanXRQChr09g0253681 | tubulin |
| Helianthuus annuus | HanXRQChr10g0288911 | tubulin |
| Helianthuus annuus | HanXRQChr11g0322631 | tubulin |
| Helianthuus annuus | HanXRQChr12g0367231 | tubulin |
| Helianthuus annuus | HanXRQChr13g0386681 | tubulin |
| Helianthuus annuus | HanXRQChr13g0393261 | tubulin |
| Helianthuus annuus | HanXRQChr12g0371591 | ubiquitin |
| Helianthuus annuus | HanXRQChr12g0383641 | ubiquitin |
| Helianthuus annuus | HanXRQChr17g0569881 | ubiquitin |
| Helianthuus annuus | HanXRQChr06g0171511 | photosystem II HCF136, stability/assembly factor |
| Helianthuus annuus | HanXRQChr17g0544921 | photosystem II HCF136, stability/assembly factor |
| Helianthuus annuus | HanXRQChr16g0526461 | proteasome B-type subunit |
| Helianthuus annuus | HanXRQChr17g0565551 | proteasome B-type subunit |
| Helianthuus annuus | HanXRQChr05g0149801 | proteasome B-type subunit |
| Helianthuus annuus | HanXRQChr09g0241421 | proteasome B-type subunit |
| Helianthuus annuus | HanXRQChr11g0353161 | proteasome B-type subunit |
| Helianthuus annuus | HanXRQChr16g0506311 | proteinase inhibitor family I3 (Kunitz) |
| Helianthuus annuus | HanXRQChr16g0506331 | proteinase inhibitor family I3 (Kunitz) |
| Helianthuus annuus | HanXRQChr09g0265401 | metallopeptidase (M10 family) |
| Helianthuus annuus | HanXRQChr09g0265411 | metallopeptidase (M10 family) |
| Helianthuus annuus | HanXRQChr05g0154561 | ATPase, AAA-type |
| Helianthuus annuus | HanXRQChr08g0235061 | ATPase, AAA-type |
| Helianthuus annuus | HanXRQChr09g0273921 | ATPase, AAA-type |
| Helianthuus annuus | HanXRQChr16g0498881 | ATPase, AAA-type |
| Helianthuus annuus | HanXRQChr02g0058711 | oxoacid dehydrogenase acyltransferase |
| Helianthuus annuus | HanXRQChr08g0214191 | oxoacid dehydrogenase acyltransferase |
| Helianthuus annuus | HanXRQChr08g0208631 | small GTPase superfamily, SAR1-type |
| Helianthuus annuus | HanXRQChr11g0331441 | small GTPase superfamily, SAR1-type |
| Helianthuus annuus | HanXRQChr12g0371571 | small GTPase superfamily, SAR1-type |
| Helianthuus annuus | HanXRQChr12g0383571 | small GTPase superfamily, SAR1-type |
| Helianthuus annuus | HanXRQChr14g0446771 | small GTPase superfamily, SAR1-type |
| Helianthuus annuus | HanXRQChr17g0539461 | small GTPase superfamily, SAR1-type |
| Helianthuus annuus | HanXRQChr17g0548271 | small GTPase superfamily, SAR1-type |
| Helianthuus annuus | HanXRQChr17g0569871 | small GTPase superfamily, SAR1-type |
| Helianthuus annuus | HanXRQChr10g0311201 | ATPase, V1 complex, subunit A |
| Helianthuus annuus | HanXRQChr12g0359711 | ATPase, V1 complex, subunit A |
| Helianthuus annuus | HanXRQChr04g0124671 | fructose-1,6-bisphosphatase |
| Helianthuus annuus | HanXRQChr06g0176631 | fructose-1,6-bisphosphatase |
| Helianthuus annuus | HanXRQCPg0579861 | photosystem II PsbD/D2, reaction centre |
| Helianthuus annuus | HanXRQChr00c0439g0574731 | photosystem II PsbD/D2, reaction centre |
| Helianthuus annuus | HanXRQChr04g0099321 | photosystem II PsbD/D2, reaction centre |
| Helianthuus annuus | HanXRQChr08g0210231 | photosystem II PsbD/D2, reaction centre |
| Helianthuus annuus | HanXRQChr11g0326671 | photosystem II PsbD/D2, reaction centre |
| Helianthuus annuus | HanXRQChr17g0549121 | photosystem II PsbD/D2, reaction centre |
| Helianthuus annuus | HanXRQCPg0579731 | photosystem II protein D1 |
| Helianthuus annuus | HanXRQChr00c0126g0571821 | photosystem II protein D1 |
| Helianthuus annuus | HanXRQChr00c0165g0572191 | photosystem II protein D1 |
| Helianthuus annuus | HanXRQChr00c0368g0574171 | photosystem II protein D1 |
| Helianthuus annuus | HanXRQChr00c0454g0574931 | photosystem II protein D1 |
| Helianthuus annuus | HanXRQChr00c0524g0575441 | photosystem II protein D1 |
| Helianthuus annuus | HanXRQChr00c0572g0575941 | photosystem II protein D1 |
| Helianthuus annuus | HanXRQChr09g0257281 | photosystem II protein D1 |
| Helianthuus annuus | HanXRQChr11g0326571 | photosystem II protein D1 |
| Helianthuus annuus | HanXRQChr11g0327051 | photosystem II protein D1 |
| Helianthuus annuus | HanXRQChr16g0503941 | photosystem II protein D1 |
| Helianthuus annuus | HanXRQCPg0580061 | photosystem II cytochrome b559 |
| Helianthuus annuus | HanXRQChr01g0020331 | photosystem II cytochrome b559 |
| Helianthuus annuus | HanXRQChr10g0283581 | photosystem II cytochrome b559 |
| Helianthuus annuus | HanXRQChr10g0284271 | photosystem II cytochrome b559 |
| Helianthuus annuus | HanXRQChr10g0289291 | photosystem II cytochrome b559 |
| Helianthuus annuus | HanXRQChr10g0318171 | photosystem II cytochrome b559 |
| Helianthuus annuus | HanXRQChr11g0326851 | photosystem II cytochrome b559 |
| Helianthuus annuus | HanXRQChr16g0529011 | photosystem II cytochrome b559 |
| Helianthuus annuus | HanXRQChr08g0219051 | chlorophyll A-B binding protein |
| Helianthuus annuus | HanXRQChr12g0370841 | chlorophyll A-B binding protein |
| Helianthuus annuus | HanXRQChr02g0053151 | chlorophyll A-B binding protein |

TABLE 1-continued

Plant EV-Markers

| | | |
|---|---|---|
| Helianthuus annuus | HanXRQChr02g0053161 | chlorophyll A-B binding protein |
| Helianthuus annuus | HanXRQCPg0580051 | cytochrome f |
| Helianthuus annuus | HanXRQChr01g0020341 | cytochrome f |
| Helianthuus annuus | HanXRQChr10g0283571 | cytochrome f |
| Helianthuus annuus | HanXRQChr10g0284261 | cytochrome f |
| Helianthuus annuus | HanXRQChr10g0289281 | cytochrome f |
| Helianthuus annuus | HanXRQChr10g0318181 | cytochrome f |
| Helianthuus annuus | HanXRQChr11g0326841 | cytochrome f |
| Helianthuus annuus | HanXRQChr15g0497521 | cytochrome f |
| Helianthuus annuus | HanXRQChr06g0163851 | ribosomal protein |
| Helianthuus annuus | HanXRQChr09g0252071 | ribosomal protein |
| Helianthuus annuus | HanXRQChr12g0374041 | ribosomal protein |
| Helianthuus annuus | HanXRQChr04g0128141 | ribosomal protein |
| Helianthuus annuus | HanXRQChr05g0163131 | ribosomal protein |
| Helianthuus annuus | HanXRQChr03g0076971 | ribosomal protein |
| Helianthuus annuus | HanXRQChr05g0159851 | ribosomal protein |
| Helianthuus annuus | HanXRQChr05g0159971 | ribosomal protein |
| Helianthuus annuus | HanXRQChr11g0324631 | ribosomal protein |
| Helianthuus annuus | HanXRQChr13g0408051 | ribosomal protein |
| Helianthuus annuus | HanXRQChr03g0089331 | ribosomal protein |
| Helianthuus annuus | HanXRQChr13g0419951 | ribosomal protein |
| Helianthuus annuus | HanXRQChr15g0497041 | ribosomal protein |
| Helianthuus annuus | HanXRQChr16g0499761 | ribosomal protein |
| Helianthuus annuus | HanXRQChr04g0106961 | ribosomal protein |
| Helianthuus annuus | HanXRQChr06g0175811 | ribosomal protein |
| Helianthuus annuus | HanXRQChr04g0122771 | ribosomal protein |
| Helianthuus annuus | HanXRQChr09g0245691 | ribosomal protein |
| Helianthuus annuus | HanXRQChr16g0520021 | ribosomal protein |
| Helianthuus annuus | HanXRQChr03g0060471 | ribosomal protein |
| Helianthuus annuus | HanXRQChr14g0429531 | ribosomal protein |
| Helianthuus annuus | HanXRQChr06g0171911 | ribosomal protein |
| Helianthuus annuus | HanXRQChr15g0479091 | ribosomal protein |
| Helianthuus annuus | HanXRQChr15g0479101 | ribosomal protein |
| Helianthuus annuus | HanXRQChr17g0543641 | ribosomal protein |
| Helianthuus annuus | HanXRQChr17g0543661 | ribosomal protein |
| Helianthuus annuus | HanXRQChr04g0105831 | ribosomal protein |
| Helianthuus annuus | HanXRQChr09g0258341 | ribosomal protein |
| Helianthuus annuus | HanXRQChr10g0287141 | ribosomal protein |
| Helianthuus annuus | HanXRQChr15g0463911 | ribosomal protein |
| Helianthuus annuus | HanXRQChr03g0076171 | ribosomal protein |
| Helianthuus annuus | HanXRQChr05g0159291 | ribosomal protein |
| Helianthuus annuus | HanXRQChr13g0407551 | ribosomal protein |
| Helianthuus annuus | HanXRQChr12g0380701 | ribosomal protein |
| Helianthuus annuus | HanXRQChr15g0477271 | ribosomal protein |
| Helianthuus annuus | HanXRQChr17g0545211 | ribosomal protein |
| Helianthuus annuus | HanXRQChr17g0570741 | ribosomal protein |
| Helianthuus annuus | HanXRQChr17g0570761 | ribosomal protein |
| Helianthuus annuus | HanXRQChr02g0044021 | ribosomal protein |
| Helianthuus annuus | HanXRQChr05g0152871 | ribosomal protein |
| Helianthuus annuus | HanXRQChr01g0012781 | ribosomal protein |
| Helianthuus annuus | HanXRQChr08g0230861 | ribosomal protein |
| Helianthuus annuus | HanXRQChr13g0391831 | ribosomal protein |
| Helianthuus annuus | HanXRQChr11g0337791 | bifunctional trypsin/alpha-amylase inhibitor |
| Helianthuus annuus | HanXRQChr10g0312371 | 2-oxoacid dehydrogenase acyltransferase |
| Helianthuus annuus | HanXRQChr09g0276191 | acid phosphatase (class B) |
| Helianthuus annuus | HanXRQChr05g0142271 | aldose-1-epimerase |
| Helianthuus annuus | HanXRQChr14g0439791 | alpha-D-phosphohexomutase |
| Helianthuus annuus | HanXRQChr09g0251071 | alpha-L-fucosidase |
| Helianthuus annuus | HanXRQChr05g0147371 | annexin |
| Helianthuus annuus | HanXRQChr09g0247561 | Asp protease (Peptidase family A1) |
| Helianthuus annuus | HanXRQChr13g0409681 | berberine-bridge enzyme (S)-reticulin: oxygen oxido-reductase |
| Helianthuus annuus | HanXRQChr10g0295971 | beta-hydroxyacyl-(acyl-carrier-protein) dehydratase |
| Helianthuus annuus | HanXRQChr13g0412571 | carbohydrate esterase family 13 - CE13 (pectin acylesterase - PAE) |
| Helianthuus annuus | HanXRQChr12g0360101 | carbohydrate esterase family 8 - CE8 (pectin methylesterase - PME) |
| Helianthuus annuus | HanXRQChr01g0019231 | carbonic anhydrase |
| Helianthuus annuus | HanXRQChr02g0036611 | cellular retinaldehyde binding/alpha-tocopherol transport |
| Helianthuus annuus | HanXRQChr10g0313581 | chaperonin Cpn60 |
| Helianthuus annuus | HanXRQChr09g0251791 | chlathrin |
| Helianthuus annuus | HanXRQChr11g0329811 | chlorophyll A-B binding protein |
| Helianthuus annuus | HanXRQChr13g0398861 | cobalamin (vitamin B12)-independent methionine synthase |
| Helianthuus annuus | HanXRQChr10g0298981 | cyclophilin |
| Helianthuus annuus | HanXRQChr04g0103281 | Cys protease (papain family) |
| Helianthuus annuus | HanXRQChr09g0268361 | cytochrome P450 |
| Helianthuus annuus | HanXRQChr17g0535591 | dirigent protein |
| Helianthuus annuus | HanXRQChr03g0065901 | expansin |
| Helianthuus annuus | HanXRQChr11g0336761 | expressed protein (cupin domain, seed storage protein domain) |

TABLE 1-continued

| Plant EV-Markers | | |
|---|---|---|
| Helianthuus annuus | HanXRQChr10g0280931 | expressed protein (cupin domain, seed storage protein domain) |
| Helianthuus annuus | HanXRQChr10g0288971 | expressed protein (cupin domain, seed storage protein domain) |
| Helianthuus annuus | HanXRQChr12g0380361 | expressed protein (cupin domain, seed storage protein domain) |
| Helianthuus annuus | HanXRQChr09g0254381 | expressed protein (cupin domain, seed storage protein domain) |
| Helianthuus annuus | HanXRQChr04g0112711 | expressed protein (cupin domain, seed storage protein domain) |
| Helianthuus annuus | HanXRQChr07g0196131 | expressed protein (cupin domain, seed storage protein domain) |
| Helianthuus annuus | HanXRQChr10g0301281 | expressed protein (cupin domain, seed storage protein domain) |
| Helianthuus annuus | HanXRQChr10g0301931 | expressed protein (cupin domain, seed storage protein domain) |
| Helianthuus annuus | HanXRQChr13g0404461 | expressed protein (cupin domain) |
| Helianthuus annuus | HanXRQChr01g0015821 | expressed protein (DUF642) |
| Helianthuus annuus | HanXRQChr03g0065301 | expressed protein (Gnk2-homologous domain, antifungal protein of Ginkgo seeds) |
| Helianthuus annuus | HanXRQChr03g0068311 | expressed protein (LRR domains) |
| Helianthuus annuus | HanXRQChr10g0291371 | expressed protein (LRR domains) |
| Helianthuus annuus | HanXRQChr03g0075061 | fasciclin-like arabinogalactan protein (FLA) |
| Helianthuus annuus | HanXRQChr08g0221961 | ferritin |
| Helianthuus annuus | HanXRQChr09g0257521 | FMN-dependent dehydrogenase |
| Helianthuus annuus | HanXRQChr14g0441641 | fructose-bisphosphate aldolase |
| Helianthuus annuus | HanXRQChr10g0312621 | germin |
| Helianthuus annuus | HanXRQChr09g0244271 | glucose-methanol-choline oxidoreductase |
| Helianthuus annuus | HanXRQChr03g0061571 | glutamate synthase |
| Helianthuus annuus | HanXRQChr05g0144801 | glyceraldehyde 3-phosphate dehydrogenase |
| Helianthuus annuus | HanXRQChr17g0550211 | glycerophosphoryl diester phosphodiesterase |
| Helianthuus annuus | HanXRQChr06g0175391 | glycoside hydrolase family 16 - GH16 (endoxyloglucan transferase) |
| Helianthuus annuus | HanXRQChr11g0351571 | glycoside hydrolase family 17 - GH17 (beta-1,3-glucosidase) |
| Helianthuus annuus | HanXRQChr05g0141461 | glycoside hydrolase family 18 - GH18 |
| Helianthuus annuus | HanXRQChr09g0276721 | glycoside hydrolase family 19 - GH19 |
| Helianthuus annuus | HanXRQChr02g0046191 | glycoside hydrolase family 2 - GH2 |
| Helianthuus annuus | HanXRQChr16g0524981 | glycoside hydrolase family 20 - GH20 (N-acetyl-beta-glucosaminidase) |
| Helianthuus annuus | HanXRQChr11g0322851 | glycoside hydrolase family 27 - GH27 (alpha-galactosidase/melibiase) |
| Helianthuus annuus | HanXRQChr10g0293191 | glycoside hydrolase family 3 - GH3 |
| Helianthuus annuus | HanXRQChr16g0511881 | glycoside hydrolase family 31 - GH31 (alpha-xylosidase) |
| Helianthuus annuus | HanXRQChr14g0461441 | glycoside hydrolase family 32 - GH32 (vacuolar invertase) |
| Helianthuus annuus | HanXRQChr13g0423671 | glycoside hydrolase family 35 - GH35 (beta-galactosidase) |
| Helianthuus annuus | HanXRQChr10g0319301 | glycoside hydrolase family 35 - GH35 (beta-galactosidase) |
| Helianthuus annuus | HanXRQChr09g0256531 | glycoside hydrolase family 38 - GH38 (alpha-mannosidase) |
| Helianthuus annuus | HanXRQChr11g0320901 | glycoside hydrolase family 5 - GH5 (glucan-1,3-beta glucosidase) |
| Helianthuus annuus | HanXRQChr05g0130491 | glycoside hydrolase family 51 - GH51 (alpha-arabinofuranosidase) |
| Helianthuus annuus | HanXRQChr10g0314191 | glycoside hydrolase family 79 - GH79 (endo-beta-glucuronidase/heparanase |
| Helianthuus annuus | HanXRQChr13g0397411 | homologous to A. thaliana PMR5 (Powdery Mildew Resistant) (carbohydrate acylation) |
| Helianthuus annuus | HanXRQChr14g0444681 | inhibitor family I3 (Kunitz-P family) |
| Helianthuus annuus | HanXRQChr14g0445181 | lactate/malate dehydrogenase |
| Helianthuus annuus | HanXRQChr17g0564111 | lectin (D-mannose) |
| Helianthuus annuus | HanXRQChr17g0558861 | lectin (PAN-2 domain) |
| Helianthuus annuus | HanXRQChr02g0039251 | lipase acylhydrolase (GDSL family) |
| Helianthuus annuus | HanXRQChr01g0000161 | lipid transfer protein/trypsin-alpha amylase inhibitor |
| Helianthuus annuus | HanXRQChr02g0047121 | mannose-binding lectin |
| Helianthuus annuus | HanXRQChr10g0303361 | mitochondrial carrier protein |
| Helianthuus annuus | HanXRQChr15g0489551 | multicopper oxidase |
| Helianthuus annuus | HanXRQChr05g0135581 | neutral/alkaline nonlysosomal ceramidase |
| Helianthuus annuus | HanXRQChr01g0017621 | nucleoside diphosphate kinase |
| Helianthuus annuus | HanXRQChr10g0295991 | peroxidase |
| Helianthuus annuus | HanXRQChr13g0398251 | peroxiredoxin |
| Helianthuus annuus | HanXRQChr11g0333171 | phosphate-induced (phi) protein 1 |
| Helianthuus annuus | HanXRQChr03g0060421 | phosphodiesterase/nucleotide pyrophosphatase/phosphate transferase |
| Helianthuus annuus | HanXRQChr03g0078011 | phosphofructokinase |
| Helianthuus annuus | HanXRQChr13g0408831 | phosphoglycerate kinase |
| Helianthuus annuus | HanXRQChr10g0286701 | phosphoglycerate mutase |
| Helianthuus annuus | HanXRQChr06g0171591 | photosystem II PsbP, oxygen evolving complex |
| Helianthuus annuus | HanXRQChr14g0434951 | plastid lipid-associated protein/fibrillin conserved domain |
| Helianthuus annuus | HanXRQChr05g0146621 | plastocyanin (blue copper binding protein) |
| Helianthuus annuus | HanXRQChr11g0330251 | polyphenol oxidase |

TABLE 1-continued

Plant EV-Markers

| | | |
|---|---|---|
| Helianthuus annuus | HanXRQChr04g0094541 | proteasome A-type subunit |
| Helianthuus annuus | HanXRQChr03g0081271 | proteasome B-type subunit |
| Helianthuus annuus | HanXRQChr12g0356851 | purple acid phosphatase |
| Helianthuus annuus | HanXRQChr15g0485781 | pyridoxal phosphate-dependent transferase |
| Helianthuus annuus | HanXRQChr11g0336791 | ribosomal protein |
| Helianthuus annuus | HanXRQChr11g0330521 | ribosomal protein |
| Helianthuus annuus | HanXRQChr11g0326801 | ribulose bisphosphate carboxylase, large subunit |
| Helianthuus annuus | HanXRQChr16g0523951 | ribulose-1,5-bisphosphate carboxylase small subunit |
| Helianthuus annuus | HanXRQChr01g0022151 | S-adenosyl-L-homocysteine hydrolase |
| Helianthuus annuus | HanXRQChr14g0454811 | S-adenosylmethionine synthetase |
| Helianthuus annuus | HanXRQChr04g0109991 | SCP-like extracellular protein (PR-1) |
| Helianthuus annuus | HanXRQChr03g0072241 | Ser carboxypeptidase (Peptidase family S10) |
| Helianthuus annuus | HanXRQChr12g0377221 | Ser protease (subtilisin) (Peptidase family S8) |
| Helianthuus annuus | HanXRQChr02g0055581 | superoxide dismutase |
| Helianthuus annuus | HanXRQChr15g0493261 | thaumatin (PR5) |
| Helianthuus annuus | HanXRQChr16g0532531 | transketolase |
| Helianthuus annuus | HanXRQChr07g0197421 | translation elongation factor EFTu/EF1A |
| Helianthuus annuus | HanXRQChr06g0173951 | translationally controlled tumour protein |

What is claimed is:

1. A method of increasing the fitness of a plant, the method comprising delivering to the plant an effective amount of a PMP composition comprising a plurality of PMPs comprising a heterologous agricultural agent, wherein the PMPs are produced by a process comprising the steps of:
   (a) obtaining a culture medium in which a plant, a plant part, or a plant cell has been cultured;
   (b) purifying PMPs from the culture medium; and
   (c) loading the PMPs with a heterologous agricultural agent;
   wherein each of the PMPs comprises a purified plant extracellular vesicle (EV) or a segment, portion, or extract thereof; and
   wherein the PMP composition increases the fitness of the plant relative to an untreated plant.

2. A method of decreasing the fitness of a plant pest, the method comprising delivering to the plant pest an effective amount of a PMP composition comprising a plurality of PMPs comprising a heterologous agricultural agent, wherein the PMPs are produced by a process comprising the steps of:
   (a) obtaining a culture medium in which a plant, a plant part, or a plant cell has been cultured;
   (b) purifying PMPs from the culture medium; and
   (c) loading the PMPs with a heterologous agricultural agent;
   wherein each of the PMPs comprises a purified plant extracellular vesicle (EV) or a segment, portion, or extract thereof; and
   wherein the PMP composition decreases the fitness of the plant pest relative to an untreated plant pest.

3. The method of claim 1, wherein the heterologous agricultural agent comprises one or more of a pesticidal agent, a fertilizing agent, and a herbicidal agent.

4. The method of claim 3, wherein the heterologous agricultural agent incudes a pesticidal agent, and wherein the pesticidal agent includes at least one of an antifungal agent, an antibacterial agent, an insecticidal agent, a molluscicidal agent, a nematicidal agent, a virucidal agent, a peptide, a polypeptide, a nucleic acid, and a polynucleotide.

5. The method of claim 4, wherein:
   a. the antifungal agent includes at least one of azoxystrobin, mancozeb, prothioconazole, folpet, tebuconazole, difenoconazole, captan, bupirimate, fosetyl-Al, a strobilurin, dimoxystrobin, enestroburin, fluoxastrobin, kresoxim-methyl, metominostrobin, picoxystrobin, pyraclostrobin, trifloxystrobin, orysastrobin, a carboxamide, a carboxanilide, benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M, methfuroxam, metsulfovax, ofurace, oxadixyl, oxycarboxin, penthiopyrad, pyracarbolid, salicylanilide, tecloftalam, thifluzamide, tiadinil, an N-biphenylamide, bixafen, boscalid, a carboxylic acid morpholide, dimethomorph, flumorph, a benzamide, flumetover, fluopicolid, zoxamid, a carboxamide, carpropamid, diclocymet, mandipropamid, silthiofam, an azole, a triazole, bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, an imidazole, cyazofamid, imazalil, pefurazoate, prochloraz, triflumizole, a benzimidazole, benomyl, carbendazim, fuberidazole, thiabendazole, ethaboxam, etridiazole, hymexazol, a pyridine, fuazinam, pyrifenox, pyrimidines, bupirimate, cyprodinil, ferimzone, fenarimol, mepanipyrim, nuarimol, pyrimethanil, a piperazine, triforine, a pyrrole, fludioxonil, fenpiclonil, a morpholine, aldimorph, dodemorph, fenpropimorph, tridemorph, a dicarboximide, iprodione, procymidone, vinclozolin, acibenzolar-S-methyl, anilazine, captafol, dazomet, diclomezin, fenoxanil, folpet, fenpropidin, famoxadon, fenamidon, octhilinone, probenazole, proquinazid, pyroquilon, quinoxyfen, tricyclazole, a carbamate, a dithiocarbamate, ferbam, maneb, metiram, metam, propineb, thiram, zineb, ziram, diethofencarb, flubenthiavalicarb, iprovalicarb, propamocarb, a guanidine, dodine, iminoctadine, guazatine, kasugamycin, a polyoxin, streptomycin, validamycin A, a fentin salt, a sulfur-containing heterocyclyl compound, isoprothiolane, dithianone, an organophosphorous compound, edifenphos, fosetyl, fosetyl-aluminum, iprobenfos, pyrazophos, tolclofos-methyl, an organochlorine compound, thiophanate-methyl, chlorothalonil, dichlofluanid, tolylfluanid, flusulfamide, phthalide, hexachlorobenzene, pencycuron, quintozene, nitrophenyl derivatives, binapacryl, dinocap, dinobuton, spiroxamine, cyflufenamid, cymoxanil, metrafenon, N-2-cyanophenyl-3,4-dichloroisothiazol-5-carboxamide, N-(3',4',5'-trifluorobiphenyl-2-yl)-3-difluoromethyl-1-methylpyrazole-4-carboxamide, 3-[5-(4-chlorophenyl)-2,3-dimethylisoxazolidin-3-yl]-pyridine, N-(3',4'-dichloro-4-fluorobiphenyl-2-yl)-3-difluoromethyl-1-methylpyrazol-e-4-carboxamide, 5-chloro-7-(4-methylpiperidin-1-yl)-6-(2,4,6-trifluorophenyl)-[1,2,4]tria-zolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazo-le-1-sulfonamide, methyl-(2-chloro-5-[1-(3-methylbenzyloxyimino)-ethyl]benzyl) carbamate, methyl-(2-chloro-5-[1-(6-methylpyridin-2-ylmethoxyimino)ethyl]benzyl) carbamate, methyl 3-(4-chloro-phenyl)-3-(2-isopropoxycarbonylamino-3-methylbutyryl-amino) propionate, 4-fluorophenyl N-(1-(1-(4-cyanophenyl) ethanesulfonyl) but-2-yl) carbamate, N-(2-(4-[3-(4-chlorophenyl) prop-2-ynyloxy]-3-methoxyphenyl)ethyl)-2-metha-nesulfonylamino-3-methylbutyramide, N-(2-(4-[3-(4-chlorophenyl) prop-2-ynyloxy]-3-methoxyphenyl)ethyl)-2-ethan-esulfonylamino-3-methylbutyramide, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylt-hiazol-5-carboxamide, methyl 2-(ortho-((2,5-dimethylphenyloxy-methylene)phenyl)-3-methoxyacrylate, and esters and salts thereof;

b. the antibacterial agent includes at least one of a hypochlorite, sodium hypochlorite, a chloramine, dichloroisocyanurate, trichloroisocyanurate, wet chlorine, chlorine dioxide, a peroxide, peracetic acid, potassium persulfate, sodium perborate, sodium percarbonate, urea perhydrate, iodine, iodpovidone, ethanol, 1-propanol, 2-propanol, 2-phenoxyethanol, phenol, a cresol, a halogenated phenol, hexachlorophene, triclosan, trichlorophenol, tribromophenol, pentachlorophenol, a cationic surfactant, benzalkonium chloride, cetyl trimethylammonium bromide, cetyl trimethylammonium chloride, didecyldimethylammonium chloride, cetylpyridinium chloride, benzethonium chloride, chlorhexidine, glucoprotamine, octenidine dihydrochloride, an ozone solution, colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, phosphoric acid, nitric acid, sulfuric acid, amidosulfuric acid, toluenesulfonic acid, sodium hydroxide, potassium hydroxide, calcium hydroxide, sorbic acid, benzoic acid, lactic acid, salicylic acid, a penicillin, a cephalosporin, vancomycin, a polymyxin, a rifamycin, a lipiarmycin, a quinolone, a sulfonamide, an aminoglycoside, kasugamycin, a macrolide, a lincosamide, a tetracycline, a cyclic lipopeptide, daptomycin, a glycylcycline, tigecycline, an oxazolidinone, linezolid, a lipiarmycin, fidaxomicin, rifampicin, ciprofloxacin, doxycycline, ampicillin, polymyxin B, gramicidin, isoniazid, rifampicin, pyrazinamide, ethambutol, myambutol, streptomycin, and esters and salts thereof;

c. the insecticidal agent includes at least one of a chloronicotinyl, a neonicotinoid, acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, an acetylcholinesterase (AChE) inhibitor, a carbamate, alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb, an organophosphate, acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, a pyrethroid, acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, a pyrethrin, pyrethrum, an oxadiazine, indoxacarb, an acetylcholine receptor modulator, a spinosyn, Spinosad, a cyclodiene, camphechlor, chlordane, endosulfan, gamma-HCH, HCH, heptachlor, an organochlorine, lindane, methoxychlor, a fiprole, acetoprole, ethiprole, vaniliprole, fipronil, a mectin, abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene, a diacylhydrazine, chromafenozide, halofenozide, methoxyfenozide, tebufenozide, a benzoylurea, bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron, an organotin, azocyclotin, cyhexatin, fenbutatin oxide, a pyrrole, chlorfenapyr, a dinitrophenol, binapacyrl, dinobuton, dinocap, DNOC, a METI, fenazaquin, fenpyroximate, pyrimidifen, pyridaben, tebufenpyrad, tolfenpyrad, rotenone, acequinocyl, fluacrypyrim, a microbial disrupter of the intestinal membrane of insects, a *Bacillus thuringiensis* strain, an inhibitor of lipid synthesis, a tetronic acid, a tetramic acid, spirodiclofen, spiromesifen, spirotetramat, cis-3-(2,5-dimethylphenyl)-8-methoxy-2-oxo-1-azaspiro[4.5]dec-3-en-4-yl ethyl carbonate, a carboxamide, flonicamid, an octopaminergic agonist, amitraz, an inhibitor of the magnesium-stimulated ATPase, propargite, a ryanodin receptor agonist, a phthalamide, rynaxapyr, N2-[1,1-dimethyl-2-(methylsulphonyl)ethyl]-3-iodo-N1-[2-methyl-4-[1,2,2,2-tetrafluoro-1-(trifluoromethyl)ethyl]phenyl]-1,2-benzenedi-carboxamide, and esters and salts thereof;

d. the molluscicidal agent includes at least one of a metal salt, iron phosphate, aluminium sulfate, ferric sodium EDTA, metaldehyde, methiocarb, and an acetylcholinesterase inhibitor; or e. the nematicidal agent includes at least one of a fumigant, D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, a carbamate, Aldicarb, Aldoxycarb, Carbofuran, Oxamyl, Cleothocarb, an organophosphate, Ethoprophos, Fenamiphos, Cadusafos, Fosthiazate, Fensulfothion, Thionazin, Isazofos, and a biochemical.

6. The method of claim 4, wherein the heterologous agricultural agent incudes an herbicidal agent.

7. The method of claim 6, wherein the herbicidal agent includes at least one of glufosinate, propaquizafop, metamitron, metazachlor, pendimethalin, flufenacet, diflufenican, clomazone, nicosulfuron, mesotrione, pinoxaden, sulcotrione, prosulfocarb, sulfentrazone, bifenox, quinmerac, triallate, terbuthylazine, atrazine, oxyfluorfen, diuron, trifluralin, chlorotoluron, a benzoic acid herbicide, dicamba, a phenoxyalkanoic acid herbicide, 2,4-D, MCPA, a 2,4-DB ester, an aryloxyphenoxypropionic acid herbicide, clodinafop, cyhalofop, fenoxaprop, fluazifop, haloxyfop, a quizalofop ester, a pyridinecarboxylic acid herbicide, aminopyralid, picloram, a clopyralid ester, a pyrimidinecarboxylic acid herbicide, an aminocyclopyrachlor ester, a pyridyloxyalkanoic acid herbicide, fluoroxypyr, triclopyr, a hydroxybenzonitrile herbicide, bromoxynil, ioxynil, an arylpyridine carboxylic acid, an arylpyrimidine carboxylic acid, acetochlor, acifluorfen, alachlor, ametryn, amitrole, asulam, atrazine, azafenidin, benefin, bensulfuron, bensulide, bentazon, bromacil, bromoxynil, butylate, carfentrazone, chloramben, chlorimuron, chlorproham, chlorsulfuron, clethodim, clomazone, clopyralid, cloransulam, cyanazine, cycloate, DCPA, desmedipham, dichlobenil, diclofop, diclosulam, diethatyl, difenzoquat, diflufenzopyr, dimethenamid-p, diquat, diuron, DSMA, endothall, EPTC, ethalfluralin, ethametsulfuron, ethofumesate, fenoxaprop, fluazifop-P, flucarbazone, flufenacet, flumetsulam, flumiclorac, flumioxazin, fluometuron, fluroxypyr, fluthiacet, fomesafen, foramsulfuron, glyphosate, halosulfuron, haloxyfop, hexazinone, imazamethabenz, imazamox, imazapic, imazaquin, imazethapyr, isoxaben, isoxaflutole, lactofen, linuron, MCPB, methazole, metolachlor-s, metribuzin, metsulfuron, molinate, MSMA, napropamide, naptalam, nicosulfuron, norflurazon, oryzalin, oxadiazon, oxasulfuron, oxyfluorfen, paraquat, pebulate, pelargonic acid, pendimethalin, phenmedipham, picloram, primisulfuron, prodiamine, prometryn, pronamide, propachlor, propanil, prosulfuron, pyrazon, pyridate, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, vernolate, and esters and salts thereof.

8. The method of claim 2, wherein the heterologous agricultural agent comprises one or more of a pesticidal agent, a fertilizing agent, and a herbicidal agent.

9. The method of claim 8, wherein the heterologous agricultural agent incudes a pesticidal agent, and wherein the pesticidal agent includes at least one of an antifungal agent, an antibacterial agent, an insecticidal agent, a molluscicidal agent, a nematicidal agent, a virucidal agent, a peptide, a polypeptide, a nucleic acid, and a polynucleotide.

10. The method of claim 9, wherein:

a. the antifungal agent includes at least one of azoxystrobin, mancozeb, prothioconazole, folpet, tebuconazole, difenoconazole, captan, bupirimate, fosetyl-Al, a strobilurin, dimoxystrobin, enestroburin, fluoxastrobin, kresoxim-methyl, metominostrobin, picoxystrobin, pyraclostrobin, trifloxystrobin, orysastrobin, a carboxamide, a carboxanilide, benalaxyl, benalaxyl-M, benodanil, carboxin, mebenil, mepronil, fenfuram, fenhexamid, flutolanil, furalaxyl, furcarbanil, furametpyr, metalaxyl, metalaxyl-M, methfuroxam, metsulfovax, ofurace, oxadixyl, oxycarboxin, penthiopyrad, pyracarbolid, salicylanilide, tecloftalam, thifluzamide, tiadinil, an N-biphenylamide, bixafen, boscalid, a carboxylic acid morpholide, dimethomorph, flumorph, a benzamide, flumetover, fluopicolid, zoxamid, a carboxamide, carpropamid, diclocymet, mandipropamid, silthiofam, an azole, a triazole, bitertanol, bromuconazole, cyproconazole, difenoconazole, diniconazole, enilconazole, epoxiconazole, fenbuconazole, flusilazol, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, an imidazole, cyazofamid, imazalil, pefurazoate, prochloraz, triflumizole, a benzimidazole, benomyl, carbendazim, fuberidazole, thiabendazole, ethaboxam, etridiazole, hymexazol, a pyridine, fuazinam, pyrifenox, pyrimidines, bupirimate, cyprodinil, ferimzone, fenarimol, mepanipyrim, nuarimol, pyrimethanil, a piperazine, triforine, a pyrrole, fludioxonil, fenpiclonil, a morpholine, aldimorph, dodemorph, fenpropimorph, tridemorph, a dicarboximide, iprodione, procymidone, vinclozolin, acibenzolar-S-methyl, anilazine, captafol, dazomet, diclomezin, fenoxanil, folpet, fenpropidin, famoxadon, fenamidon, octhilinone, probenazole, proquinazid, pyroquilon, quinoxyfen, tricyclazole, a carbamate, a dithiocarbamate, ferbam, maneb, metiram, metam, propineb, thiram, zineb, ziram, diethofencarb, flubenthiavalicarb, iprovalicarb, propamocarb, a guanidine, dodine, iminoctadine, guazatine, kasugamycin, a polyoxin, streptomycin, validamycin A, a fentin salt, a sulfur-containing heterocyclyl compound, isoprothiolane, dithianone, an organophosphorous compound, edifenphos, fosetyl, fosetyl-aluminum, iprobenfos, pyrazophos, tolclofos-methyl, an organochlorine compound, thiophanate-methyl, chlorothalonil, dichlofluanid, tolylfluanid, flusulfamide, phthalide, hexachlorobenzene, pencycuron, quintozene, nitrophenyl derivatives, binapacryl, dinocap, dinobuton, spiroxamine, cyflufenamid, cymoxanil, metrafenon, N-2-cyanophenyl-3,4-dichloroisothiazol-5-carboxamide, N-(3',4',5'-trifluorobiphenyl-2-yl)-3-difluoromethyl-1-methylpyrazole-4-carboxamide, 3-[5-(4-chlorophenyl)-2,3-dimethylisoxazolidin-3-yl]-pyridine, N-(3',4'-dichloro-4-fluorobiphenyl-2-yl)-3-difluoromethyl-1-methylpyrazol-e-4-carboxamide, 5-chloro-7-(4-methylpiperidin-1-yl)-6-(2,4,6-trifluorophenyl)-[1,2,4]tria-zolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazo-le-1-sulfonamide, methyl-(2-chloro-5-[1-(3-methylbenzyloxyimino)-ethyl]benzyl) carbamate, methyl-(2-chloro-5-[1-(6-methylpyridin-2-ylmethoxyimino)ethyl]benzyl) carbamate, methyl 3-(4-chloro-phenyl)-3-(2-isopropoxycarbonylamino-3-methylbutyryl-amino) propionate, 4-fluorophenyl N-(1-(1-(4-cyanophenyl) ethanesulfonyl) but-2-yl) carbamate, N-(2-(4-[3-(4-chlorophenyl) prop-2-ynyloxy]-3-methoxyphenyl)ethyl)-2-metha-nesulfonylamino-3-methylbutyramide, N-(2-(4-[3-(4-chlorophenyl) prop-2-ynyloxy]-3-methoxyphenyl)ethyl)-2-ethan-esulfonylamino-3-methylbutyramide, N-(4'-bromobiphenyl-2-yl)-4-difluoromethyl-2-methylthiazol-5-carboxamide, N-(4'-trifluoromethylbiphenyl-2-yl)-4-difluoromethyl-2-methylthiazol-5-carboxamide, N-(4'-chloro-3'-fluorobiphenyl-2-yl)-4-difluoromethyl-2-methylt-hiazol-5-carboxamide, methyl 2-(ortho-((2,5-dimethylphenyloxy-methylene)phenyl)-3-methoxyacrylate, and esters and salts thereof;

b. the antibacterial agent includes at least one of a hypochlorite, sodium hypochlorite, a chloramine, dichloroisocyanurate, trichloroisocyanurate, wet chlorine, chlorine dioxide, a peroxide, peracetic acid, potassium persulfate, sodium perborate, sodium percarbonate, urea perhydrate, iodine, iodpovidone, ethanol, 1-propanol, 2-propanol, 2-phenoxyethanol, phenol, a cresol, a halogenated phenol, hexachlorophene, triclosan, trichlorophenol, tribromophenol, pentachlorophenol, a cationic surfactant, benzalkonium chloride, cetyl trimethylammonium bromide, cetyl trimethylammonium chloride, didecyldimethylammonium chloride, cetylpyridinium chloride, benzethonium chloride, chlorhexidine, glucoprotamine, octenidine dihydrochloride, an ozone solution, colloidal silver, silver nitrate, mercury chloride, phenylmercury salts, copper sulfate, copper oxide-chloride, copper hydroxide, copper octanoate, copper oxychloride sulfate, copper sulfate, copper sulfate pentahydrate, phosphoric acid, nitric acid, sulfuric acid, amidosulfuric acid, toluenesulfonic acid, sodium hydroxide, potassium hydroxide, calcium hydroxide, sorbic acid, benzoic acid, lactic acid, salicylic acid, a penicillin, a cephalosporin, vancomycin, a polymyxin, a rifamycin, a lipiarmycin, a quinolone, a sulfonamide, an aminoglycoside, kasugamycin, a macrolide, a lincosamide, a tetracycline, a cyclic lipopeptide, daptomycin, a glycylcycline, tigecycline, an oxazolidinone, linezolid, a lipiarmycin, fidaxomicin, rifampicin, ciprofloxacin, doxycycline, ampicillin, polymyxin B, gramicidin, isoniazid, rifampicin, pyrazinamide, ethambutol, myambutol, streptomycin, and esters and salts thereof;

c. the insecticidal agent includes at least one of a chloronicotinyl, a neonicotinoid, acetamiprid, clothianidin, dinotefuran, imidacloprid, nitenpyram, nithiazine, thiacloprid, thiamethoxam, imidaclothiz, (2E)-1-[(2-chloro-1,3-thiazol-5-yl)methyl]-3,5-dimethyl-N-nitro-1,3,5-tri-azinan-2-imine, an acetylcholinesterase (AChE) inhibitor, a carbamate, alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb, an organophosphate, acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, a pyrethroid, acrinathrin, allethrin (d-cis-trans, d-trans), cypermethrin (alpha-, beta-, theta-, zeta-), permethrin (cis-, trans-), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda, cyhalothrin, metofluthrin, phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, a pyrethrin, pyrethrum, an oxadiazine, indoxacarb, an acetylcholine receptor modulator, a spinosyn, Spinosad, a cyclodiene, camphechlor, chlordane, endosulfan, gamma-HCH, HCH, heptachlor, an organochlorine, lindane, methoxychlor, a fiprole, acetoprole, ethiprole, vaniliprole, fipronil, a mectin, abamectin, avermectin, emamectin, emamectin-benzoate, fenoxycarb, hydroprene, kinoprene, methoprene, ivermectin, lepimectin, epofenonane, pyriproxifen, milbemectin, milbemycin, triprene, a diacylhydrazine, chromafenozide, halofenozide, methoxyfenozide, tebufenozide, a benzoylurea, bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron, an organotin, azocyclotin, cyhexatin, fenbutatin oxide, a pyrrole, chlorfenapyr, a dinitrophenol, binapacyrl, dinobuton, dinocap, DNOC, a METI, fenazaquin, fenpyroximate, pyrimidifen, pyridaben, tebufenpyrad, tolfenpyrad, rotenone, acequinocyl, fluacrypyrim, a microbial disrupter of the intestinal membrane of insects, a *Bacillus thuringiensis* strain, an inhibitor of lipid synthesis, a tetronic acid, a tetramic acid, spirodiclofen, spiromesifen, spirotetramat, cis-3-(2,5-dimethylphenyl)-8-methoxy-2-oxo-1-azaspiro[4.5]dec-3-en-4-yl ethyl carbonate, a carboxamide, flonicamid, an octopaminergic agonist, amitraz, an inhibitor of the magnesium-stimulated ATPase, propargite, a ryanodin receptor agonist, a phthalamide, rynaxapyr, N2-[1,1-dimethyl-2-(methylsulphonyl)ethyl]-3-iodo-N1-[2-methyl-4-[1,2,2,2-tetrafluoro-1-(trifluoromethyl)ethyl]phenyl]-1,2-benzenedi-carboxamide, and esters and salts thereof;
d. the molluscicidal agent includes at least one of a metal salt, iron phosphate, aluminium sulfate, ferric sodium EDTA, metaldehyde, methiocarb, and an acetylcholinesterase inhibitor; or
e. the nematicidal agent includes at least one of a fumigant, D-D, 1,3-Dichloropropene, Ethylene Dibromide, 1,2-Dibromo-3-Chloropropane, Methyl Bromide, Chloropicrin, Metam Sodium, Dazomet, Methyl Isothiocyanate (MITC), Sodium Tetrathiocarbonate, a carbamate, Aldicarb, Aldoxycarb, Carbofuran, Oxamyl, Cleothocarb, an organophosphate, Ethoprophos, Fenamiphos, Cadusafos, Fosthiazate, Fensulfothion, Thionazin, Isazofos, and a biochemical.

11. The method of claim 8, wherein the heterologous agricultural agent incudes an herbicidal agent.

12. The composition of claim 11, wherein the herbicidal agent includes at least one of glufosinate, propaquizafop, metamitron, metazachlor, pendimethalin, flufenacet, diflufenican, clomazone, nicosulfuron, mesotrione, pinoxaden, sulcotrione, prosulfocarb, sulfentrazone, bifenox, quinmerac, triallate, terbuthylazine, atrazine, oxyfluorfen, diuron, trifluralin, chlorotoluron, a benzoic acid herbicide, dicamba, a phenoxyalkanoic acid herbicide, 2,4-D, MCPA, a 2,4-DB ester, an aryloxyphenoxypropionic acid herbicide, clodinafop, cyhalofop, fenoxaprop, fluazifop, haloxyfop, a quizalofop ester, a pyridinecarboxylic acid herbicide, aminopyralid, picloram, a clopyralid ester, a pyrimidinecarboxylic acid herbicide, an aminocyclopyrachlor ester, a pyridyloxyalkanoic acid herbicide, fluoroxypyr, triclopyr, a hydroxybenzonitrile herbicide, bromoxynil, ioxynil, an arylpyridine carboxylic acid, an arylpyrimidine carboxylic acid, acetochlor, acifluorfen, alachlor, ametryn, amitrole, asulam, atrazine, azafenidin, benefin, bensulfuron, bensulide, bentazon, bromacil, bromoxynil, butylate, carfentrazone, chloramben, chlorimuron, chlorproham, chlorsulfuron, clethodim, clomazone, clopyralid, cloransulam, cyanazine, cycloate, DCPA, desmedipham, dichlobenil, diclofop, diclosulam, diethatyl, difenzoquat, diflufenzopyr, dimethenamid-p, diquat, diuron, DSMA, endothall, EPTC, ethalfluralin, ethametsulfuron, ethofumesate, fenoxaprop, fluazifop-P, flucarbazone, flufenacet, flumetsulam, flumiclorac, flumioxazin, fluometuron, fluroxypyr, fluthiacet, fomesafen, foramsulfuron, glyphosate, halosulfuron, haloxyfop, hexazinone, imazamethabenz, imazamox, imazapic, imazaquin, imazethapyr, isoxaben, isoxaflutole, lactofen, linuron, MCPB, methazole, metolachlor-s, metribuzin, metsulfuron, molinate, MSMA, napropamide, naptalam, nicosulfuron, norflurazon, oryzalin, oxadiazon, oxasulfuron, oxyfluorfen, paraquat, pebulate, pelargonic acid, pendimethalin, phenmedipham, picloram, primisulfuron, prodiamine, prometryn, pronamide, propachlor, propanil, prosulfuron, pyrazon, pyridate, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, vernolate, and esters and salts thereof.

* * * * *